United States Patent
Moloney et al.

(10) Patent No.: US 6,750,046 B2
(45) Date of Patent: *Jun. 15, 2004

(54) PREPARATION OF THIOREDOXIN AND THIOREDOXIN REDUCTASE PROTEINS ON OIL BODIES

(75) Inventors: Maurice M. Moloney, Calgary (CA); Bipin K. Dalmia, San Diego, CA (US)

(73) Assignee: Sembiosys Genetics, Inc., Calgary (CA)

(*) Notice: Subject to any disclaimer, the term of this patent is extended or adjusted under 35 U.S.C. 154(b) by 0 days.

This patent is subject to a terminal disclaimer.

(21) Appl. No.: 09/897,425

(22) Filed: Jul. 3, 2001

(65) Prior Publication Data

US 2002/0088025 A1 Jul. 4, 2002

Related U.S. Application Data

(63) Continuation-in-part of application No. 09/210,843, filed on Dec. 15, 1998, now Pat. No. 6,288,304, which is a continuation-in-part of application No. 08/846,021, filed on Apr. 25, 1997, now Pat. No. 5,948,682, which is a continuation-in-part of application No. 08/366,783, filed on Dec. 30, 1994, now Pat. No. 5,650,554, which is a continuation-in-part of application No. 08/142,418, filed on Nov. 16, 1993, now abandoned, which is a continuation-in-part of application No. 07/659,835, filed on Feb. 22, 1991, now abandoned.

(51) Int. Cl.$^7$ .................. C12N 15/62; C12N 15/82; C12N 15/53; A01H 5/00; A01H 5/10

(52) U.S. Cl. ............. 435/69.7; 435/69.8; 435/320.1; 435/419; 435/189; 800/278; 800/281; 536/23.4

(58) Field of Search .................. 800/278, 281; 435/69.7, 69.8, 320.1, 419, 189; 536/23.4

(56) References Cited

U.S. PATENT DOCUMENTS 5,650,554 A 7/1997 Moloney .................. 800/205

FOREIGN PATENT DOCUMENTS

| EP | 0 193 259 | 9/1986 |
|---|---|---|
| WO | WO 93/07278 | 4/1993 |
| WO | WO 97/02352 | 1/1997 |
| WO | WO 00/36126 | 6/2000 |
| WO | WO 00/58352 | 10/2000 |

OTHER PUBLICATIONS

Radke, et al., "Transformation of *Brassica napus* L. using *Agrobacterium tumefaciens*: Developmentally Regulated Expression of a Reintroduced Napin Gene", Theor. Appln. Genet., Springer–Verlag, vol. 75, pp. 685–694, (1988).

Taylor, et al., "Storage–protein Regulation and Lipid Accumulation in Microspore embryos of *Brassica napus* L.", Planta, Springer–Verlag, vol. 181, pp. 18–26, (1990).

Sijmons, et al., "Production of Correctly Processed Human Serum Albumin in Transgenic Plants", Bio/Technology, vol. 8, pp. 217–221, (1990).

Huang, "Lipid Bodies", Modern Methods Plant Analysis, vol. 1, pp. 145–151, (1985).

Misra, et al., "Heavy Metal Tolerant Transgenic *Brassica napus* L. and *Nicotiana tabacum* L. Plants", Theor. Appl. Genet., Springer–Verlag, vol. 78, pp. 161–168, (1989).

Hatzopoulos, et al., "Interaction of Nuclear Factors with Upstream Sequences of Lipid Body Membrane Protein Gene from Carrot", The Plant Cell, American Society of Plant Physiologists, vol. 2, pp. 457–467, (1990).

Lee, et al., "Maize Oleosin is Correctly Targeted to Seed Oil Bodies in *Brassica napus* Transformed with the Maize Oleosin Gene", Biology, Proc. Natl. Acad. Sci. USA, vol. 88, pp. 6181–6185, (1991).

Vance, et al., "Expression of Lipid Body Protein Gene during Maize Seed Development", The Journal of Biological Chemistry, The American Society for Biochemistry and Molecular Biology, Inc., vol. 263, No. 3, pp. 1476–1481, (1988).

Vance, et al., "The Major Protein from Lipid Bodies of Maize", The Journal of Biological Chemistry, The American Society for Biochemistry and Molecular Biology, Inc., vol. 262, pp. 11275–11279, (1987).

Qu, et al., "Oleosin KD 18 on the Surface of Oil Bodies in Maize", The Journal of Biological Chemistry, The American Society for Biochemistry and Molecular Biology, Inc., vol. 265, No. 4, pp. 2238–2243, (1990).

Sengupta–Gopalan, et al., "Developmentally Regulated Expression of the Bean β–Phaseolin Gene in Tobacco Seed", Developmental Biology, Proc. Natl. Acad. Sci, USA, vol. 82, pp. 3320–3324, (1985).

Fraley, et al., "Expression of Bacterial Genes in Plant Cells", Genetics, Proc. Natl. Acad. Sci, USA, vol. 80, pp. 4803–4807, (1983).

Vanderkerckhove, et al., "Enkephalins Produced in transgenic Plants using Modified 2S Seed Storage Proteins", Bio/Technology, vol. 7, pp. 929–932, (1989).

Murphy, et al., "Synthesis of the Major Oil–body Membrane Protein in Developing Rapeseed (*Brassica napus*) Embryos", Biochem. J., vol. 258, pp. 285–293, (1989).

Qu, et al., "Characteristics and Biosynthesis of Membrane Proteins of Lipid Bodies in the Scutella of Maize (*Zea mays* L.)", Biochem. J., vol. 235, pp. 57–65, (1986).

(List continued on next page.)

*Primary Examiner*—David T. Fox
(74) *Attorney, Agent, or Firm*—Foley & Lardner

(57) ABSTRACT

The present invention relates to the use of a class of genes called oil body protein genes that have unique features. The discovery of these features allowed the invention of methods for the production of recombinant proteins wherein a protein of interest can be easily separated from other host cell components. The invention is further exemplified by methods for exploitation of the unique characteristics of the oil body proteins and oil body genes for expression of polypeptides of interest in many organisms, particularly plant seeds. Said polypeptides include thioredoxin and/or thioredoxin reductase. The invention can also be modified to recover recombinant polypeptides fused to oil body proteins from non-plant host cells.

21 Claims, 38 Drawing Sheets

OTHER PUBLICATIONS

Josefsson, et al. "Structure of a Gene Encoding the 1.7 S Storage Protein Napin, from *Brassica napus*", The Journal of Biological Chemistry, vol. 262, No. 25, pp. 12196–12201, (1987).

Scofield, et al., "Nucleotide Sequence of A Member of the Napin Storage Protein Family From *Brassica napus*", Journal of Biological Chemistry, The American Society for Biochemistry and Molecular Biology, Inc., vol. 262, No. 25, pp. 12202–12208, (1987).

Fujikawa, et al., "Bovine Factor X1 (Stuart Factor), Mechanism of Activation by a Protein from Russell's Viper Venom", Biochemistry, vol. 11, pp. 4892–4899, (1972).

Nagai, et al., "Oxygen Binding Properties of Human Mutant Hemoglobins Synthesized in *Escherichia coli*", Biochemistry, Proc. Natl. Acad. Sci. USA, vol. 82, pp. 7252–7255, (1985).

Scholtissek, et al., "A Plasmid Vector System for the Expression of a Triprotein Consisting of Betagalactosidase, a Collagenase Recognition Site and a Foreign Gene Product", Gene, Elsevier, vol. 62 pp. 55–64 (1988).

Bevan, "Binary Agrobacterium Vectors for Plant Transformation", Nucleic Acids Research, IRL Press Limited, vol. 12, No. 22, pp. 8711–8721, (1984).

Murphy, et al., "A class of Amphipathic Proteins Associated with Lipid Storage Bodies in Plants", Biochem. Biophys. Acta, Elsevier Science Publishers, vol. 1088, pp. 86–94, (1991).

Antoni, et al., "A Short Synthetic Peptide Fragment of Human Interleukin 1 with Immunostimulatory But not Inflammatory Activity", The Journal of Immunology, The American Association of Immunologists, vol. 137, pp. 3201–3204, (1986).

An, et al., "New Cloning Vehicles for Transformation of Higher Plants", Embo J., IRL Press Limited, vol. 4, pp. 277–284, (1985).

Hood, et al., "The Hypervirulence of *Agrobacterium tumefaciens* A281 is encoded in a Region of pTiBo542 outside of T–DNA", Journal of Bacteriology, American Society for Microbiology, vol. 168, No. 1, pp. 1291–1301, (1986).

Holbrook, et al., "Oilbody Proteins in Microspore–Derived Embryos of *Brassica napus*", Plant Physiol. vol. 97, pp. 1051–1058, (1991).

Kalinski, et al., "Molecular Cloning of a Protein Associated with Soybean Seed Oil Bodies that is Similar to Thiol Proteases of the Papain Family", The Journal of Biological Chemistry, vol. 265, pp. 13843–13848, (1990).

Bosch, et al., "A Trout Growth Hormone is Expressed, Correctly Folded and Partially Glycosylated in the Leaves but not the Seeds of Transgenic Plants", Transgenic Research, Chapman & Hall, vol. 3, pp. 304–310, (1994).

Koren, et al., "Carp Growth Hormone: Molecular Cloning and Sequencing of cDNA", Cell, vol. 77, pp. 309–315, (1989).

Bower, et al., "Two members of the Thioredoxin–h Family Interact with the Kinase Domain of a Brassica S Locus Receptor Kinase", Plant Cell, American Society of Plant Physiologist, vol. 8, pp. 1641–1650, (1996).

Carugo, et al., "NADP–Dependent Enzymes. I: Conserved Stereochemistry of Cofactor Binding", Proteins, Wiley–Liss, Inc., vol. 28, pp. 10–28, (1997).

Del Val, et al., "Thioredoxin Treatment Increases Digestibility and Lowers Allergenicity of Milk", J. Allerg. Clin. Immunol., vol. 103, pp. 690–697, (1999).

Galkin, et al., "Construction of a New Leucine Dehydrogenase with Preferred Specificity for NADP$^+$ by Site–Directed Mutagenesis of the Strictly NAD+–Specific Enzyme", Protein Engineering, Oxford University Press, vol. 10, pp. 687–690, (1997).

Gautier, et al., "Characterization of Wheat Thioredoxin h cDNA and Production of an Active Triticum Aestivum Protein in *Escherichia coli*", Eur. J. Biochem., FEBS, vol., 252, pp. 314–324, (1998).

Höög, et al., "Nucleotide Sequence of the Thioredoxin Gene from *Escherichia coli*", Bioscience Reports, vol. 4, pp. 917–923, (1984).

Holmberg, et al., "Redesign of the Coenzyme Specificity in L–Lactate Dehydrogenase from *Bacillus stearothermophilus* Using Site–Directed Mutagenesis and Media Engineering", Protein Engineering, Oxford University Press, vol. 12, pp. 851–856, (1999).

Hurley, et al., "Determinants of Cofacto; Specificity in Isocitrate Dehydrogenase: Structure of an Engineered NADP+–NAD+ Specificity–Reversal Mutant", Biochemistry, vol. 35, pp. 5670–5678, (1996).

Ishiwatari, et al., "Thioredoxin h is one of the Major Proteins in Rice Phloem sap", Planta, vol. 195, pp. 456–463, (1995).

Johnson, et al., "Thioredoxin System of the Photosynthetic Anaerobe *Chromatium vinosum*", Journal of Bacteriology, American Society for Microbiology, vol. 158, No. 3, pp. 1061–1069, (1984).

Luthman, et al., "Rat Liver Thioredoxin and Thioredoxin Reductase: Purification and Characterization", Biochemistry, vol. 21, No 26, pp. 6628–6633, (1982).

Marty, et al., "Nucleotide Sequence of a cDNA Encoding a Tobacco Thioredoxin", Plant Mol. Biol., vol. 17, pp. 143–148, (1991).

Rivera–Madrid, "Evidence for Five Divergent Thioredoxin h Sequences in *Arabidopsis thaliana*", Proc. Natl. Acad. Sci., vol. 92, pp. 5620–5624, (1995).

Russel, et al., "Sequence of Thioredoxin Reductase from *Escherichia coli*", J. Bio. Chem., vol. 263, pp. 9015–9019, (1988).

Shi, et al., "A Novel Plasma Membrane–Bound Thioredoxin From Soybean", Plant Mol. Biol., vol. 32, pp. 653–662, (1996).

Shiraishi, et al., "Engineering of Pyridine Nucleotide Specificity of Nitrate Reductase: Mutagenesis of Recombinant Cytochrome b Reductase Fragment of *Neurospora crassa* NADPH: Nitrate Reductase", Archives of Biochemistry and Biophysics, Academic Press, vol. 358, No. 1, pp. 104–115, (1998).

Terashima, et al., "Short Communication cDNA Sequence of Bovine Thioredoxin", DNA Seq., vol. 10, No. 3, pp. 203–205, (1999).

```
              NcoI
-867  CCATGGCTATACCCAACCTCGGTCTTGGTCACACCAGGAACTCTCTGGTAAGCTAGCTCCACTCCCCAGAAACAACCGGCGCCAAATTGC

-777  CGGAATTGCTGACCTGAAGACGGAACATCATCGTCGGGTCCTTGGGCGATTGCGGCGGAAGATGGGTCAGCTTGGGCTTGAGGACGAGAC

-687  CCGAATCGAGTCTGTTGAAAGGTTGTTCATTGGGATTTGTATACGGAGATTGGTCGTCGAGAGGTTTGAGGGAAAGGACAAATGGGTTTG
                                                         R1

-597  GCTCTGGAGAAAGAGAGTGCGGCTTTAGAGAGAGAATTGAGAGGTTTAGAGAGAGATGCGGCGGCGATGACGGGAGGAGAGACGACGAGG
             R2                        R2
                                    R1
-507  ACCTGCATTATCAAAGCAGTGACGTGGTGAAATTTGGAACTTTTAAGAGGCAGATAGATTTATTATTTGTATCCATTTTCTTCATTGTTC

-417  TAGAATGTCGCGGAACAAATTTTAAAAACTAAATCCTAAATTTTTCTAATTTTGTTGCCAATAGTGGATATGTGGGCCGTATAGAAGGAAT

-327  CTATTGAAGGCCCAAACCCATACTGACGAGCCCAAAGGTTCGTTTTGCGTTTTATGTTTCGGTTCGATGCCAACGCCACATTCTGAGCTA
                    T
-237  GGCAAAAAACAAACGTGTCTTTGAATAGACTCCTCTCGTTAACACATGCAGCGGCTGCATGGTGACGCCATTAACACGTGGCCTACAATT

-147  GCATGATGTCTCCATTGACACGTGACTTCTCGTCTCCTTTCTTAATATATCTAACAAACACTCCTACCTCTTCCAAAATATATACACATC
                                                                       M  A  D  T  A  R  G  T  H  H  D
-57   TTTTTGATCAATCTCTCATTCAAAATCTCATTCTCTCTAGTAAACAAGAACAAAAAAATGGCGGATACAGCTAGAGGAACCCATCACGAT

I  I  G  R  D  Q  Y  P  M  M  G  R  D  R  D  Q  Y  Q  M  S  G  R  G  S  D  Y  S  K  S  R
34    ATCATCGGCAGAGACCAGTACCCGATCATGGGCCGAGACCGAGACCAGTACCAGATGTCCGGACGAGGATCTGACTACTCCAAGTCTAGG

Q  I  A  K  A  A  T  A  V  T  A  G  G  S  L  L  V  L  S  S  L  T  L  V  G  T  V  I  A  L
124   CAGATTGCTAAAGCTGCAACTGCTGTCACAGCTGGTGGTTCCCTCCTTGTTCTCTCCAGCCTTACCCTTGTTGGAACTGTCATAGCTTTG

T  V  A  T  P  L  L  V  I  F  S  P  I  L  V  P  A  L  I  T  V  A  L  L  I  T  G  F  L  S
214   ACTGTTGCAACACCTCTGCTCGTTATCTTCAGCCCAATCCTTGTCCCGGCTCTCATCACAGTTGCACTCCTCATCACCGGTTTTCTTTCC

S  G  G  F  G  I  A  A  I  T  V  F  S  W  I  Y  K
304   TCTGGAGGGTTTGGCATTGCCGCTATAACCGTTTTCTCTTGGATTTACAAgtaagcacacatttatcatcttacttcataattttgtgca 394   atatgtgcatgcatgtgttgagccagtagctttggatcaattttttggtcgaataacaaatgtaacaataagaaattgcaaattctagg 484   gaacatttggttaactaaatacgaaatttgacctagctagcttgaatgtgtctgtgtatatcatctatataggtaaaatgcttggtatga Y  A  T  G  E  H  P  Q  G  S  D  K  L  D  S  A  R  M  K  L  G  S  K
574   tacctattgattgtgaatagGTACGCAACGGGAGAGCACCCACAGGGATCAGACAAGTTGGACAGTGCAAGGATGAAGTTGGGAAGCAAA A  Q  D  L  K  D  R  A  Q  Y  Y  G  Q  Q  H  T  G  G  E  H  D  R  D  R  T  R  G  G  Q  H
664   GCTCAGGATCTGAAAGACAGAGCTCAGTACTACGGACAGCAACATACTGGTGGGGAACATGACCGTGACCGTACTCGTGGTGGCCAGCAC
        T  T  *
754   ACTACTTAAGTTACCCCACTGATGTCATCGTCATAGTCCAATAACTCCAATGTCGGGGAGTTAGTTTATGAGGAATAAAGTGTTTAGAAT
                                                                                      KpnI
844   TTGATCAGGGGGAGATAATAAAAGCCGAGTTTGAATCTTTTTGTTATAAGTAATGTTTATGTGTGTTTCTATATGTTGTCAAATGGTACC
```

FIG. 2

```
  1 ATG GCG GAT ACA GCT AGA ACC CAT CAC GAT GTC ACA AGT CGA GAT CAG TAT CCC CGA GAC  60
  1  M   A   D   T   A   R   T   H   H   D   V   T   S   R   D   Q   Y   P   R   D   20

61 CGA GAC CAG TAT TCT ATG ATC GGT CGA GAC CGT GAC CAG TAC TCT ATG ATG GGC CGA GAC 120
 21  R   D   Q   Y   S   M   I   G   R   D   R   D   Q   Y   S   M   M   G   R   D   40

121 CGA GAC CAG TAC AAC ATG TAT GGT CGA GAC TAC TCC AAG TCT AGA CAG ATT GCT AAG GCT 180
 41  R   D   Q   Y   N   M   Y   G   R   D   Y   S   K   S   R   Q   I   A   K   A   60

181 GTT ACC GCA GTC ACG GCG GGT GGG TCC CTC CTT GTC CTC TCC AGT CTC ACC CTT GTT GGT 240
 61  V   T   A   V   T   A   G   G   S   L   L   V   L   S   S   L   T   L   V   G   80

241 ACT GTC ATT GCT TTG ACT GTT GCC ACT CCA CTC CTC GTT ATC TTT AGC CCA ATC CTC GTG 300
 81  T   V   I   A   L   T   V   A   T   P   L   L   V   I   F   S   P   I   L   V  100

301 CCG GCT CTC ATC ACC GTA GCA CTT CTC ATC ACT GGC TTT CTC TCC TCT GGT GGG TTT GCC 360
101  P   A   L   I   T   V   A   L   L   I   T   G   F   L   S   S   G   G   F   A  120

361 ATT GCA GCT ATA ACC GTC TTC TCC TGG ATC TAT AAG TAC GCA ACG GGA GAG CAC CCA CAG 420
121  I   A   A   I   T   V   F   S   W   I   Y   K   Y   A   T   G   E   H   P   Q  140

421 GGG TCA GAT AAG TTG GAC AGT GCA AGG ATG AAG CTG GGA ACC AAA GCT CAG GAT ATT AAA 480
141  G   S   D   K   L   D   S   A   R   M   K   L   G   T   K   A   Q   D   I   K  160

481 GAC AGA GCT CAA TAC TAC GGA CAG CAA CAT ACA GGT GGT GAG CAT GAC CGT GAC CGT ACT 540
161  D   R   A   Q   Y   Y   G   Q   Q   H   T   G   G   E   H   D   R   D   R   T  180

541 CGT GGT GGC CAG CAC ACT ACT TAA                                                  564
181  R   G   G   Q   H   T   T   *                                                  188
```

FIG. 4

HindIII
```
   1 ATAAGCTTGCATGCCTGCGGAACTCTCTGGTAAGCTAGCTCCACTCCCCAGAAACAACCG   60
  61 GCGCCAAATTGCCGGAATTGCTGACCTGAAGACGGAACATCATCGTCGGGTCCTTGGGCG  120
 121 ATTGCGGCGGAAGATGGGTCAGCTTGGGCTTGAGGACGAGACCCGAATCGAGTCTGTTGA  180
 181 AAGGTTGTTCATTGGGATTTGTATACGGAGATTGGTCGTCGAGAGGTTTGAGGGAAAGGA  240
 241 CAAATGGGTTTGGCTCTGGAGAAAGAGAGTGCGGCTTTAGAGAGAGAATTGAGAGGTTTA  300
 301 GAGAGAGATGCGGCGGCGATGACGGGAGGAGAGACGACGAGGACCTGCATTATCAAAGCA  360
 361 GTGACGTGGTGAAATTTGGAACTTTTAAGAGGCAGATAGATTTATTATTTGTATCCATTT  420
 421 TCTTCATTGTTCTAGAATGTCGCGGAACAAATTTTAAAAGTAAATGGTAAATTTTTCTAA  480
 481 TTTTGTTGCCAATAGTGGATATGTGGGCCGTATAGAAGGAATCTATTGAAGGCCCAAACC  540
 541 CATACTGACGAGCCCAAAGGTTCGTTTTGCGTTTTATGTTTCGGTTCGATGCCAACGCCA  600
 601 CATTCTGAGCTAGGCAAAAAACAAACGTGTCTTTGAATAGACTCCTCTCGTTAACACATG  660
 661 CAGCGGCTGCATGGTGACGCCATTAACACGTGGCCTACAATTGCATGATGTCTCCATTGA  720
 721 CACGTGACTTCTCGTCTCCTTTCTTAATATATCTAACAAACACTCCTACCTCTTCCAAAA  780
 781 TATATACACATCTTTTTGATCAATCTCTCATTCAAAATCTCATTCTCTCTAGTAAACAAG  840
         M A D T A R G T H H D I I G R D Q
 841 AACAAAAAAATGGCGGATACAGCTAGAGGAACCCATCACGATATCATCGGCAGAGACCAG  900
       Y P M M G R D R D Q Y Q M S G R G S D Y
 901 TACCCGATGATGGGCCGAGACCGAGACCAGTACCAGATGTCCGGACGAGGATCTGACTAC  960
       S K S R Q I A K A A T A V T A G G S L L
 961 TCCAAGTCTAGGCAGATTGCTAAAGCTGCAACTGCTGTCACAGCTGGTGGTTCCCTCCTT 1020
       V L S S L T L V G T V I A L T V A T P L
1021 GTTCTCTCCAGCCTTACCCTTGTTGGAACTGTCATAGCTTTGACTGTTGCAACACCTCTG 1080
       L V I F S P I L V P A L I T V A L L I T
1081 CTCGTTATCTTCAGCCCAATCCTTGTCCCGGCTCTCATCACAGTTGCACTCCTCATCACC 1140
       G F L S S G G F G I A A I T V F S W I Y
1141 GGTTTTCTTTCCTCTGGAGGGTTTGGCATTGCCGCTATAACCGTTTTCTCTTGGATTTAC 1200
       K
1201 AAGTAAGCACACATTTATCATCTTACTTCATAATTTTGTGCAATATGTGCATGCATGTGT 1260
1261 TGAGCCAGTAGCTTTGGATCAATTTTTTTGGTCGAATAACAAATGTAACAATAAGAAATT 1320
1321 GCAAATTCTAGGGAACATTTGGTTAACTAAATACGAAATTTGACCTAGCTAGCTTGAATG 1380
1381 TGTCTGTGTATATCATCTATATAGGTAAAATGCTTGGTATGATACCTATTGATTGTGAAT 1440
       Y A T G E H P Q G S D K L D S A R M K
1441 AGGTACGCAACGGGAGAGCACCCACAGGGATCAGACAAGTTGGACAGTGCAAGGATGAAG 1500
       L G S K A Q D L K D R A Q Y Y G Q Q H T
1501 TTGGGAAGCAAAGCTCAGGATCTGAAAGACAGAGCTCAGTACTACGGACAGCAACATACT 1560
       G G E H D R D R T R G G Q H T T L V P R
1561 GGTGGGAACATGACCGTGACCGTACTCGTGGTGGCCAGCACACTACTCTCGTTCCACGA  1620
       G S M A E I T R I P L Y K G K S L R K A
1621 GGATCCATGGCTGAGATCACCAGGATGGGTCTGTACAAAGGCAAGTCTCTGAGGAAGGCG 1680
       L K E H G L L E D F L Q K Q Q Y G I S S
1681 CTGAAGGAGCATGGGCTTCTGGAGGACTTCCTGCAGAAACAGCAGTATGGCATCAGCAGC 1740
       K Y S G F G E V A S V P L T N Y L D S Q
1742 AAGTACTCCGGCTTCGGGGAGGTGGCCAGCGTGCCCCTGACCAACTACCTGGATAGTCAG 1800
```

FIG. 6

```
              Y  F  G  K  I  Y  L  G  T  P  P  Q  E  F  T  V  L  F  D  T
1801 TACTTTGGAAGATCTACCTCGGGACCCCGCCCCAGGAGTTCACCGTGCTGTTTGACACT 1860
        G  S  S  D  F  W  V  P  S  I  Y  C  K  S  N  A  C  K  N  H
1861 GGCTCCTCTGACTTCTGGGTACCCTCTATCTACTGCAAGAGCAATGCCTGCAAAAACCAC 1920
        Q  R  F  D  P  R  K  S  S  T  F  Q  N  L  G  K  P  L  S  I
1921 CAGCGCTTCGACCCGAGAAAGTCGTCCACCTTCCAGAACCTGGGCAAGCCCCTGTCTATC 1980
        H  Y  G  T  G  S  M  Q  G  I  L  G  Y  D  T  V  T  V  S  N
1981 CACTACGGGACAGGCAGCATGCAGGGCATCCTGGGCTATGACACCGTCACTGTCTCCAAC 2040
        I  V  D  I  Q  Q  T  V  G  L  S  T  Q  E  P  G  D  V  F  T
2041 ATTGTGGACATCCAGCAGACAGTAGGCCTGAGCACCCAGGAGCCCGGGGACGTCTTCACC 2100
        Y  A  E  F  D  G  I  L  G  M  A  Y  P  S  L  A  S  E  Y  S
2101 TATGCCGAATTCGACGGGATCCTGGGGATGGCCTACCCCTCGCTCGCCTCAGAGTACTCG 2160
        I  P  V  F  D  N  M  M  N  R  H  L  V  A  Q  D  L  F  S  V
2161 ATACCCGTGTTTGACAACATGATGAACAGGCACCTGGTGGCCCAAGACCTGTTCTCGGTT 2220
        Y  M  D  R  N  G  Q  E  S  M  L  T  L  G  A  I  D  P  S  Y
2221 TACACAGGGTCCCTGCACTGGGTGCCCGTGACAGTGCAGCAGTACTGGCAGTTCACTGTG 2280
        D  S  V  T  I  S  G  V  V  V  A  C  E  G  G  C  Q  A  I  L
2281 GACAGTGTCACCATCAGCGGTGTGGTTGTGGCCTGTGAGGGTGGCTGTCAGGCCATCTTG 2340
        D  T  G  T  S  K  L  V  G  P  S  S  D  I  L  N  I  Q  Q  A
2341 GACACGGGCACCTCCAAGCTGGTCGGGCCCAGCAGCGACATCCTCAACATCCAGCAGGCC 2400
        I  G  A  T  Q  N  Q  Y  G  E  F  D  I  D  C  D  N  L  S  Y
2401 GACACGGGCACCTCCAAGCTGGTCGGGCCCAGCAGCGACATCCTCAACATCCAGCAGGCC 2460
        M  P  T  V  V  F  E  I  N  G  K  M  Y  P  L  T  P  S  A  Y
2461 ATTGGAGCCACACAGAACCAGTACGGTGAGTTTGACATCGACTGCGACAACCTGAGCTAC 2520
        T  S  Q  D  Q  G  F  C  T  S  G  F  Q  S  E  N  H  S  Q  K
2521 ATGCCCACTGTGGTCTTTGAGATCAATGGCAAAATGTACCCACTGACCCCCTCCGCCTAT 2580
        W  I  L  G  D  V  F  I  R  E  Y  Y  S  V  F  D  R  A  N  N
2581 ACCAGCCAAGACCAGGGCTTCTGTACCAGTGGCTTCCAGAGTGAAAATCATTCCCAGAAA 2640
        L  V  G  L  A  K  A  I  *
2641 TGGATCCTGGGGGATGTTTTCATCCGAGAGTATTACAGCGTCTTTGACAGGGCCAACAAC 2700
2701 CTCGTGGGGCTGGCCAAAGCCATCTGAAAGCTT                            2733
                                     HindIII
```

FIG. 6A

|  | 10 | 20 | 30 | 40 | 50 | 60 |
|---|---|---|---|---|---|---|
| TR | ATGAATGGTCTCGAAACTCACAACACAAGGCTCTGTATCGTAGGAAGTGGCCCAGCGGCA |
| ATTHIREDB | ATGAATGGTCTCGAAACTCACAACACAAGGCTCTGTATCGTAGGAAGTGGCCCAGCGGCA |

|  | 70 | 80 | 90 | 100 | 110 | 120 |
|---|---|---|---|---|---|---|
| TR | CACACGGCGGCGATTTACGCAGCTAGGGCTGAACTTAAACCTCTTCTCTTCGAAGGATGG |
| ATTHIREDB | CACACGGCGGCGATTTACGCAGCTAGGGCTGAACTTAAACCTCTTCTCTTCGAAGGATGG |

|  | 130 | 140 | 150 | 160 | 170 | 180 |
|---|---|---|---|---|---|---|
| TR | ATGGCTAACGACATCGCTCCCGGTGGTCAACTAACAACCACCACCGACGTCGAGAATTTC |
| ATTHIREDB | ATGGCTAACGACATCGCTCCCGGTGGTCAACT--CAACCAACCACCGCGT-GAGAATTTC |

|  | 190 | 200 | 210 | 220 | 230 | 240 |
|---|---|---|---|---|---|---|
| TR | CCCGGATTTCCAGAAGGTATTCTCGGAGTAGAGCTCACTGACAAATTCCGTAAACAATCG |
| ATTHIREDB | CCCGGATTTCCAGAAGGTATTCTCGGAGTAGAGCTCACTGACAAATTCCGTAAACAATCG |

|  | 250 | 260 | 270 | 280 | 290 | 300 |
|---|---|---|---|---|---|---|
| TR | GAGCGATTCGGTACTACGATATTTACAGAGACGGTGACGAAAGTCGATTTCTCTTCGAAA |
| ATTHIREDB | GAGCGATTCGGTACTACGATATTTACAGAGACGGTGACGAAAGTCGATTTCTCTTCGAAA |

|  | 310 | 320 | 330 | 340 | 350 | 360 |
|---|---|---|---|---|---|---|
| TR | CCGTTTAAGCTATTCACAGATTCAAAAGCCATTCTCGCTGACGCTGTGATTCTCGCTACT |
| ATTHIREDB | CCGTTTAAGCTATTCACAGATTCAAAAGCCATTCTCGCTGACGCTGTGATTCTCGCTATC |

|  | 370 | 380 | 390 | 400 | 410 | 420 |
|---|---|---|---|---|---|---|
| TR | GGAGCTGTGGCTAAGCGGCTTAGCTTCGTTGGATCTGGTGAAGGTTCTGGAGGTTTCTGG |
| ATTHIREDB | GGAGCTGTGGCTAAGTGGCTTAGCTTCGTTGGATCTGGTGAAGTTCTCGGAGGTTTGTGG |

|  | 430 | 440 | 450 | 460 | 470 | 480 |
|---|---|---|---|---|---|---|
| TR | AACCGTGGAATCTCCGCTTGTGCTGTTTGCGACGGAGCTGCTCCGATATTCCGTAACAAA |
| ATTHIREDB | AACCGTGGAATCTCCGCTTGTGCTGTTTGCGACGGAGCTGCTCCGATATTCCGCAACAAA |

|  | 490 | 500 | 510 | 520 | 530 | 540 |
|---|---|---|---|---|---|---|
| TR | CCTCTTGCGGTGATCGGTGGAGGCGATTCAGCAATGGAAGAAGCAAACTTTCTTACAAAA |
| ATTHIREDB | CCTCTTGCGGTGATCGGTGGAGGCGATTCTGCAATGGAAGAAGCAAACTTTCTTACAAAA |

|  | 550 | 560 | 570 | 580 | 590 | 600 |
|---|---|---|---|---|---|---|
| TR | TATGGATCTAAAGTGTATATAATCCATAGGAGAGATGCTTTTAGAGCGTCTAAGATTATG |
| ATTHIREDB | TATGGATCTAAAGTGTATATAATCGATAGGAGAGATGCTTTTAGAGCGTCTAAGATTATG |

|  | 610 | 620 | 630 | 640 | 650 | 660 |
|---|---|---|---|---|---|---|
| TR | CAGCAGCGAGCTTTGTCTAATCCTAAGATTGATGTGATTTGGAACTCGTCTGTTGTGGAA |
| ATTHIREDB | CAGCAGCGAGCTTTGTCTAATCCTAAGATTGATGTGATTTGGAACTCGTCTGTTGTGGAA |

|  | 670 | 680 | 690 | 700 | 710 | 720 |
|---|---|---|---|---|---|---|
| TR | GCTTATGGAGATGGAGAAAGAGATGTGCTTGGAGGATTGAAAGTGAAGAATGTGGTTACC |
| ATTHIREDB | GCTTATGGAGATGGAGAAAGAGATGTGCTTGGAGGATTGAAAGTGAAGAATGTGGTTACC |

|  | 730 | 740 | 750 | 760 | 770 | 780 |
|---|---|---|---|---|---|---|
| TR | GGAGATGTTTCTGATTTAAAAGTTTCTGGATTGTTCTTTGCTATTGGTCATGAGCCAGCT |
| ATTHIREDB | GGAGATGTTTCTGATTTAAAAGTTTCTGGATTGTTCTTTGCTATTGGTCATGAGCCAGCT |

|  | 790 | 800 | 810 | 820 | 830 | 840 |
|---|---|---|---|---|---|---|
| TR | ACCAAGTTTTTGGATGGTGGTGTTGAGTTAGATTCGGATGGTTATGTTGTCACGAAGCCT |
| ATTHIREDB | ACCAAGTTTTTGGATGGTGGTGTTGAGTTAGATTCGGATGGTTATGTTGTCACGAAGCCT |

|  | 850 | 860 | 870 | 880 | 890 | 900 |
|---|---|---|---|---|---|---|
| TR | GGTACTACACAGACTAGCGTTCCCGGAGTTTTCGCTGCGGGTGATGTTCAGGATAAGAAG |
| ATTHIREDB | GGTACTACACAGACTAGCGTTCCCGGAGTTTTCGCTGCGGGTGATGTTCAGGATAAGAAG |

|  | 910 | 920 | 930 | 940 | 950 | 960 |
|---|---|---|---|---|---|---|
| TR | TATAGGCAAGCCATCACTGCTGCAGGAACTGGGTGCATGGCAGCTTTGGATGCAGAGCAT |
| ATTHIREDB | TATAGGCAAGCCATCACTGCTGCAGGAACTGGGTGCATGGCAGCTTTGGATGCAGAGCAT |

|  | 970 | 980 | 990 | 1000 | 1010 | 1020 |
|---|---|---|---|---|---|---|
| TR | TACTTACAAGAGATTGGATCTCAGCAAGGTAAGAGTGATTGA |
| ATTHIREDB | TACTTACAAGAGATTGGATCTCAGCAAGGTAAGAGTGATTGA |

FIG. 9

```
  1 ATG AAT GGT CTC GAA ACT CAC AAC ACA AGG CTC TGT ATC GTA GGA AGT GGC CCA GCG GCA   60
  1  M   N   G   L   E   T   H   N   T   R   L   C   I   V   G   S   G   P   A   A   20

61 CAC AGC GCG GCG ATT TAC CGA GCT AGG GCT GAA CTT AAA CCT CTT CTC TTC GAA GGA TGG  120
 21  H   T   A   A   I   Y   A   R   A   E   L   K   P   L   L   F   E   G   W       40

121 ATG GCT AAC GAC ATC GCT CCC GGT GGT CAA CTA ACA ACC ACC ACC GAC GTC GAG AAT TTC  180
 41  M   A   N   D   I   A   P   G   G   Q   L   T   T   T   T   D   V   E   N   F   60

181 CCC GGA TTT CCA GAA GGT ATT CAC GGA GTA GAG CTC ACT GAC AAA TTC CGT AAA CAA TCG  240
 61  P   G   F   P   E   G   I   L   G   V   E   L   T   D   K   F   R   K   Q   S   80

241 GAG CGA TTC GGT ACT ACG ATA TTT ACA GAG ACG GTG ACG AAA GTC GAT TTC TCT TCG AAA  300
 81  E   R   F   G   T   T   I   F   T   E   T   V   T   K   V   D   F   S   S   K  100

301 CCG TTT AAG CTA TTC ACA GAT TCA AAA GCC ATT CTC GCT GAC GCT GTG ATT CTC GCT ACT  360
101  P   F   K   L   F   T   D   S   K   A   I   L   A   D   A   V   I   L   A   T  120

361 GGA GCT GTG GCT AAG CGG CTT AGC TTC GTT GGA TCT GGT GAA GGT TCT GGA GGT TTC TGG  420
121  G   A   V   A   K   R   L   S   F   V   G   S   G   E   G   S   G   G   F   W  140

421 AAC CGT GGA ATC TCC GCT TGT GCT GTT TGC GAC GGA GCT GCT CCG ATA TTC CGT AAC AAA  480
141  N   R   G   I   S   A   C   A   V   C   D   G   A   A   P   I   F   R   N   K  160

481 CCT CTT GCG GTG ATC GGT GGA GGC GAT TCA GCA ATG GAA GAA GCA AAC TTT CTT ACA AAA  540
161  P   L   A   V   I   G   G   G   D   S   A   M   E   E   A   N   F   L   T   K  180

541 TAT GGA TCT AAA GTG TAT ATA ATC CAT AGG AGA GAT GCT TTT AGA GCG TCT AAG ATT ATG  600
181  Y   G   S   K   V   Y   I   I   H   R   R   D   A   F   R   A   S   K   I   M  200

601 CAG CAG CGA GCT TTG TCT AAT CCT AAG ATT GAT GTG ATT TGG AAC TCG TCT GTT GTG GAA  660
201  Q   Q   R   A   L   S   N   P   K   I   D   V   I   W   N   S   S   V   V   E  220

661 GCT TAT GGA GAT GGA GAA AGA GAT GTG CTT GGA GGA TTG AAA GTG AAG AAT GTG GTT ACC  720
221  A   Y   G   D   G   E   R   D   V   L   G   G   L   K   V   K   N   V   V   T  240

721 GGA GAT GTT TCT GAT TTA AAA GTT TCT GGA TTG TTC TTT GCT ATT GGT CAT GAG CCA GCT  780
241  G   D   V   S   D   L   K   V   S   G   L   F   F   A   I   G   H   E   P   A  260

781 ACC AAG TTT TTG GAT GGT GGT GTT GAG TTA GAT TCG GAT GGT TAT GTT GTC ACG AAG CCT  840
261  T   K   F   L   D   G   G   V   E   L   D   S   D   G   Y   V   V   T   K   P  280

841 GGT ACT ACA CAG ACT AGC GTT CCC GGA GTT TTC GCT GCG GGT GAT GTT CAG GAT AAG AAG  900
281  G   T   T   Q   T   S   V   P   G   V   F   A   A   G   D   V   Q   D   K   K  300

901 TAT AGG CAA GCC ATC ACT GCT GCA GGA ACT GGG TGC ATG GCA GCT TTG GAT GCA GAG CAT  960
301  Y   R   Q   A   I   T   A   A   G   T   G   C   M   A   A   L   D   A   E   H  320

961 TAC TTA CAA GAG ATT GGA TCT CAG CAA GGT AAG AGT GAT TGA                          1002
321  Y   L   Q   E   I   G   S   Q   Q   G   K   S   D   *                           334
```

FIG. 10

|  | 10 | 20 | 30 | 40 | 50 | 60 |
|---|---|---|---|---|---|---|

TRANSLATION OF ATTHIREDB  MNGLETHNTRLCIVGSGPAAHTAAIYAARAELKPLLFEGWMANDIAPGGQLNQPP-RENF
TRANSLATION OF TR       MNGLETHNTRLCIVGSGPAAHTAAIYAARAELKPLLFEGWMANDIAPGGQLITTTDVENF 70      80      90     100     110     120

TRANSLATION OF ATTHIREDB  PGFPEGILGVELTDKFRKQSERFGTTIFTETVTKVDFSSKPFKLFTDSKAILADAVILAI
TRANSLATION OF TR       PGFPEGILGVELTDKFRKQSERFGTTIFTETVTKVDFSSKPFKLFTDSKAILADAVILAT 130     140     150     160     170     180

TRANSLATION OF ATTHIREDB  GAVAKWLSFVGSGEVLGGLWNRGISACAVCDGAAPIFRNKPLAVIGGGDSAMEEANFLTK
TRANSLATION OF TR       GAVAKRLSFVGSGEGSGGFWNRGISACAVCDGAAPIFRNKPLAVIGGGDSAMEEANFLTK 190     200     210     220     230     240

TRANSLATION OF ATTHIREDB  YGSKVYIIDRRDAFRASKIMQQRALSNPKIDVIWNSSVVEAYGDGERDVLGGLKVKNVVT
TRANSLATION OF TR       YGSKVYIIHRRDAFRASKIMQQRALSNPKIDVIWNSSVVEAYGDGERDVLGGLKVKNVVT 250     260     270     280     290     300

TRANSLATION OF ATTHIREDB  GDVSDLKVSGLFFAIGHEPATKFLDGGVELDSDGYVVTKPGTTQTSVPGVFAAGDVQDKK
TRANSLATION OF TR       GDVSDLKVSGLFFAIGHEPATKFLDGGVELDSDGYVVTKPGTTQTSVPGVFAAGDVQDKK 310     320     330     340     350     360

TRANSLATION OF ATTHIREDB  YRQAITAAGTGCMAALDAEHYLQEIGSQQGKSD
TRANSLATION OF TR       YRQAITAAGTGCMAALDAEHYLQEIGSQQGKSD

FIG. 11

PstI
1 ctgcaggaattcattgtactcccagtatcattatagtgaaagttttggctctctcgccggtggtttttacctctattta 80

81 aagggtttccacctaaaaattctggtatcattctcactttacttgttactttaatttctcataatctttggttgaaat 160

161 tatcacgcttccgcacacgatatccctacaaatttattatttgttaaacattttcaaaccgcataaaattttatgaagtc 240

241 ccgtctatctttaatgtagtctaacattttcatattgaaatatataatttacttaattttagcgttggtagaaagcataa 320

321 tgatttattcttattcttcttcatataaatgtttaatatacaatataaacaaattctttaccttaagaaggatttcccat 400

401 tttatattttaaaaatatatttatcaaatattttttcaaccacgtaaatctcataataataagttgtttcaaaagtaataa 480

481 aatttaactccataattttttttattcgactgatcttaaagcaacacccagtgacacaactagccattttttttctttgaat 560

561 aaaaaaatccaattatcattgtatttttttttatacaatgaaaatttcaccaaacaatcatttgtggtatttctgaagcaa 640

641 gtcatgttatgcaaaattctataattcccatttgacactacggaagtaactgaagatctgcttttacatgcgagacacat 720

721 cttctaaagtaattttaataatagttactatattcaagatttcatatatcaaatactcaatattacttctaaaaaattaa 800

801 ttagatataattaaaatattacttttttaattttaagtttaattgttgaatttgtgactattgatttattattctactat 880

881 gtttaaattgttttatagatagtttaaagtaaatataagtaatgtagtagagtgttagagtgttaccctaaaccataaac 960

961 tataagatttatggtggactaattttcatatatttcttattgcttttacctttcttggtatgtaagtccgtaactggaa 1040

1041 ttactgtgggttgccatggcactctgtggtcttttggttcatgcatggatgcttgcgcaagaaaaagacaaagaacaaag 1120

1121 aaaaaagacaaaacagagagacaaaacgcaatcacacaaccaactcaaattagtcactggctgatcaagatcgccgcgtc 1200

1201 catgtatgtctaaatgccatgcaaagcaacacgtgcttaacatgcactttaaatggctcacccatctcaacccacacaca 1280

1281 aacacattgcctttttcttcatcatcaccacaaccacctgtatatattcattctcttccgccacctcaatttcttcactt 1360

1361 caacacacgtcaacctgcatatgcgtgtcatcccatgcccaaatctccatgcatgttccaaccaccttctctcttatata 1440

1441 atacctataaatacctctaatatcactcacttctttcatcatccatccatccagagtactactactctactactataata 1520

```
1521 ccccaacccaactcatattcaatactactctact ATG GCT TCG GAA GAA GGA CAA GTG ATC GCC TGC 1587
                                   1   M   A   S   E   E   G   Q   V   I   A   C   11
1588 CAC ACC GTT GAG ACA TGG AAC GAG CAG CTT CAG AAG GCT AAT GAA TCC AAA ACT CTT GTG 1647
     12  H   T   V   E   T   W   N   E   Q   L   Q   K   A   N   E   S   K   T   L   V   31
1648 GTG GTT GAT TTC ACG GCT TCT TGG TGT GGA CCA TGT CGT TTC ATC GCT CCA TTC TTT GCT 1707
     32  V   V   D   F   T   A   S   W   C   G   P   C   R   F   I   A   P   F   F   A   51
1708 GAT TTG GCT AAG AAA CTT CCT AAC GTG CTT TTC CTC AAG GTT GAT ACT GAT GAA TTG AAG 1767
     52  D   L   A   K   K   L   P   N   V   L   F   L   K   V   D   T   D   E   L   K
```

FIG. 12

```
1768 TCG GTG GCA AGT GAT TGG GCG ATA CAG GCG ATG CCA ACC TTC ATG TTT TTG AAG GAA GGG 1827
  72 S   V   A   S   D   W   A   I   Q   A   M   P   T   F   M   F   L   K   E   G    91
1828 AAG ATT TTG GAC AAA GTT GTT GGA GCC AAG AAA GAT GAG CTT CAG TCT ACC ATT GCC AAA 1887
  92 K   I   L   D   K   V   V   G   A   K   K   D   E   L   Q   S   T   I   A   K   111
                    HindIII
1888 CAC TTG GCT TAA gcttaataagtatgaactaaaatgcatgtaggtgtaagagctcatggagagcatggaatattgt 1963
 112 H   L   A   *                                                                    115

1964 atccgaccatgtaacagtataataactgagctccatctcacttcttctatgaataaacaaaggatgttatgatatattaa 2043

2044 cactctatctatgcaccttattgttctatgataaatttcctcttattattataaatcatctgaatcgtgacggcttatgg 2123

2124 aatgcttcaaatagtacaaaaacaaatgtgtactataagactttctaaacaattctaactttagcattgtgaacgagaca 2203

2204 taagtgttaagaagacataacaattataatggaagaagtttgtctccatttatatattatatattacccacttatgtatt 2283

2284 atattaggatgttaaggagacataacaattataaagagagaagtttgtatccatttatatattatatactacccatttat 2363

2364 atattatacttatccacttatttaatgtctttataaggtttgatccatgatatttctaatattttagttgatatgtatat 2443

2444 gaaagggtactatttgaactctcttactctgtataaaggttggatcatccttaaagtgggtctatttaattttattgctt 2523

2524 cttacagataaaaaaaaaattatgagttggtttgataaaatattgaaggatttaaaataataataaataataaataacat 2603

2604 ataatatatgtatataaatttattataatataacatttatctataaaaaagtaaatattgtcataaatctatacaatcgt 2683

2684 ttagccttgctggacgactctcaattatttaaacgagagtaaacatatttgacttttggttatttaacaaattattatt 2763

2764 taacactatatgaaatttttttttttatcggcaaggaaataaaattaaattaggagggacaatggtgtgtcccaatcct 2843

2844 tatacaaccaacttccacaggaaggtcaggtcggggacaacaaaaaaacaggcaagggaaattttttaatttgggttgtc 2923

2924 ttgtttgctgcataatttatgcagtaaaacactacacataaccctttagcagtagagcaatggttgaccgtgtgcttag 3003

3004 cttcttttattttattttttttatcagcaaagaataaataaaataaaatgagacacttcagggatgtttcaacccttatac 3083

3084 aaaaccccaaaaacaagtttcctagcaccctaccaactaaggtacc                                    3129
                                                KpnI
```

FIG. 12A

PstI
1 ctgcaggaattcattgtactcccagtatcattatagtgaaagttttggctctctcgccggtggttttttacctctattta 80

81 aagggggttttccacctaaaaattctggtatcattctcactttacttgttactttaatttctcataatctttggttgaaat 160

161 tatcacgcttccgcacacgatatccctacaaatttattatttgttaaacattttcaaaccgcataaaattttatgaagtc 240

241 ccgtctatctttaatgtagtctaacattttcatattgaaatatataatttacttaattttagcgttggtagaaagcataa 320

321 tgatttattcttattcttcttcatataaatgtttaatatacaatataaacaaattctttaccttaagaaggatttcccat 400

401 tttatattttaaaaatatatttatcaaatatttttcaaccacgtaaatctcataataataagttgtttcaaaagtaataa 480

481 aatttaactccataatttttttattcgactgatcttaaagcaacacccagtgacacaactagccattttttttctttgaat 560

561 aaaaaaatccaattatcattgtatttttttttatacaatgaaaatttcaccaaacaatcatttgtggtatttctgaagcaa 640

641 gtcatgttatgcaaaattctataattcccatttgacactacggaagtaactgaagatctgcttttacatgcgagacacat 720

721 cttctaaagtaattttaataatagttactatattcaagatttcatatatcaaatactcaatattacttctaaaaaattaa 800

801 ttagatataattaaaatattactttttttaatttttaagtttaattgttgaatttgtgactattgatttattattctactat 880

881 gtttaaattgttttatagatagtttaaagtaaatataagtaatgtagtagagtgttagagtgttaccctaaaccataaac 960

961 tataagatttatggtggactaattttcatatatttcttattgcttttacctttttcttggtatgtaagtccgtaactggaa 1040

1041 ttactgtgggttgccatggcactctgtggtcttttggttcatgcatggatgcttgcgcaagaaaaagacaaagaacaaag 1120

1121 aaaaaagacaaaacagagagacaaaacgcaatcacacaaccaactcaaattagtcactggctgatcaagatcgccgcgtc 1200

1201 catgtatgtctaaatgccatgcaaagcaacacgtgcttaacatgcactttaaatggctcacccatctcaacccacacaca 1280

1281 aacacattgccttttcttcatcatcaccacaaccacctgtatatattcattctcttccgccacctcaatttcttcactt 1360

1361 caacacacgtcaacctgcatatgcgtgtcatcccatgcccaaatctccatgcatgttccaaccaccttctctcttatata 1440

1441 atacctataaatacctctaatatcactcacttctttcatcatccatccatccagagtactactactctactactataata 1520

```
1521 ccccaacccaactcatattcaatactactctact ATG GCG GAT ACA GCT AGA GGA ACC CAT CAC GAT 1587
                                    1   M   A   D   T   A   R   G   T   H   H   D   11

1588 ATC ATC GGC AGA GAC CAG TAC CCG ATG ATG GGC CGA GAC CGA GAC CAG TAC CAG ATG TCC 1647
     12  I   I   G   R   D   Q   Y   P   M   M   G   R   D   R   D   Q   Y   Q   M   S   31

1648 GGA CGA GGA TCT GAC TAC TCC AAG TCT AGG CAG ATT GCT AAA GCT GCA ACT GCT GTC ACA 1707
     32  G   R   G   S   D   Y   S   K   S   R   Q   I   A   K   A   A   T   A   V   T   51

1708 GCT GGT GGT TCC CTC CTT GTT CTC TCC AGC CTT ACC CTT GTT GGA ACT GTC ATA GCT TTG 1767
     52  A   G   G   S   L   L   V   L   S   S   L   T   L   V   G   T   V   I   A   L   71
```

FIG. 13

```
1768 ACT GTT GCA ACA CCT CTG CTC GTT ATC TTC AGC CCA ATC CTT GTC CCG GCT CTC ATC ACA 1827
  72  T   V   A   T   P   L   L   V   I   F   S   P   I   L   V   P   A   L   I   T   91
1828 GTT GCA CTC CTC ATC ACC GGT TTT CTT TCC TCT GGA GGG TTT GGC ATT GCC GCT ATA ACC 1887
  92  V   A   L   L   I   T   G   F   L   S   S   G   G   F   G   I   A   A   I   T  111
1888 GTT TTC TCT TGG ATT TAC AA gtaagcacacatttatcatcttacttcataattttgtgcaatatgtgcatgca 1960
 112  V   F   S   W   I   Y   K                                                       118
1961 tgtgttgagccagtagctttggatcaattttttggtcgaataacaaatgtaacaataagaaattgcaaattctagggaa 2040

2041 catttggttaactaaatacgaaatttgacctagctagcttgaatgtgtctgtgtatatcatctatataggtaaaatgctt 2120

2121 ggtatgatacctattgattgtgaatag G TAC GCA ACG GGA GAG CAC CCA CAG GGA TCA GAC AAG      2184
 119                               Y   A   T   G   E   H   P   Q   G   S   D   K      130
2185 TTG GAC AGT GCA AGG ATG AAG TTG GGA AGC AAA GCT CAG GAT CTG AAA GAC AGA GCT CAG 2244
 131  L   D   S   A   R   M   K   L   G   S   K   A   Q   D   L   K   D   R   A   Q  150
2245 TAC TAC GGA CAG CAA CAT ACT GGT GGG GAA CAT GAC CGT GAC CGT ACT CGT GGT GGC CAG 2304
 151  Y   Y   G   Q   Q   H   T   G   G   E   H   D   R   D   R   T   R   G   G   Q  170
              NcoI
2305 CAC ACT ACC ATG GCT TCG GAA GAA GGA CAA GTG ATC GCC TGC CAC ACC GTT GAG ACA TGG 2364
 171  H   T   T   M   A   S   E   E   G   Q   V   I   A   C   H   T   V   E   T   W  190
2365 AAC GAG CAG CTT CAG AAG GCT AAT GAA TCC AAA ACT CTT GTG GTG GTT GAT TTC ACG GCT 2424
 191  N   E   Q   L   Q   K   A   N   E   S   K   T   L   V   V   V   D   F   T   A  210
2425 TCT TGG TGT GGA CCA TGT CGT TTC ATC GCT CCA TTC TTT GCT GAT TTG GCT AAG AAA CTT 2484
 211  S   W   C   G   P   C   R   F   I   A   P   F   F   A   D   L   A   K   K   L  230
2485 CCT AAC GTG CTT TTC CTC AAG GTT GAT ACT GAT GAA TTG AAG TCG GTG GCA AGT GAT TGG 2544
 231  P   N   V   L   F   L   K   V   D   T   D   E   L   K   S   V   A   S   D   W  250
2545 GCG ATA CAG GCG ATG CCA ACC TTC ATG TTT TTG AAG GAA GGG AAG ATT TTG GAC AAA GTT 2604
 251  A   I   Q   A   M   P   T   F   M   F   L   K   E   G   K   I   L   D   K   V  270
2605 GTT GGA GCC AAG AAA GAT GAG CTT CAG TCT ACC ATT GCC AAA CAC TTG GCT TAA gcttaata 2666
 271  V   G   A   K   K   D   E   L   Q   S   T   I   A   K   H   L   A   *           288
2667 agtatgaactaaaatgcatgtaggtgtaagagctcatggagagcatggaatattgtatccgaccatgtaacagtataata 2746

2747 actgagctccatctcacttcttctatgaataaacaaaggatgttatgatatattaacactctatctatgcaccttattgt 2826

2827 tctatgataaatttcctcttattattataaatcatctgaatcgtgacggcttatggaatgcttcaaatagtacaaaaaca 2906

2907 aatgtgtactataagactttctaaacaattctaactttagcattgtgaacgagacataagtgttaagaagacataacaat 2986

2987 tataatggaagaagtttgtctccatttatatattatatattacccacttatgtattatattaggatgttaaggagacata 3066
```

FIG. 13A

```
3067 acaattataaagagagaagtttgtatccatttatatattatatactacccatttatatattatacttatccacttattta 3146
3147 atgtctttataaggtttgatccatgatatttctaatattttagttgatatgtatatgaaagggtactatttgaactctct 3226
3227 tactctgtataaaggttggatcatccttaaagtgggtctatttaattttattgcttcttacagataaaaaaaaaattatg 3306
3307 agttggtttgataaaatattgaaggatttaaaataataataaataataaataacatataatatatgtatataaatttatt 3386
3387 ataatataacatttatctataaaaaagtaaatattgtcataaatctatacaatcgtttagccttgctggacgactctcaa 3466
3467 ttatttaaacgagagtaaacatatttgacttttTggttatttaacaaattattatttaacactatatgaaattttttttt 3546
3547 tttatcggcaaggaaataaaattaaattaggagggacaatggtgtgtcccaatccttatacaaccaacttccacaggaag 3626
3627 gtcaggtcggggacaacaaaaaaacaggcaagggaaattttttaatttgggttgtcttgtttgctgcataatttatgcag 3706
3707 taaaacactacacataaccctttTagcagtagagcaatggttgaccgtgtgcttagcttcttttatttTattttTttatc 3786
3787 agcaaagaataaataaaataaaatgagacacttcagggatgtttcaacccttatacaaaaccccaaaaacaagtttccta 3866
3867 gcaccctaccaactaaggtacc                                                      3888
                         KpnI
```

FIG. 13B

PstI
1 ctgcaggaattcattgtactcccagtatcattatagtgaaagttttggctctctcgccggtggttttttacctctattta 80

81 aaggggttttccacctaaaaattctggtatcattctcactttacttgttactttaatttctcataatctttggttgaaat 160

161 tatcacgcttccgcacacgatatccctacaaatttattatttgttaaacattttcaaaccgcataaaattttatgaagtc 240

241 ccgtctatctttaatgtagtctaacattttcatattgaaatatataatttacttaattttagcgttggtagaaagcataa 320

321 tgatttattcttattcttcttcatataaatgtttaatatacaatataaacaaattctttaccttaagaaggatttcccat 400

401 tttatattttaaaaatatatttatcaaatattttcaaccacgtaaatctcataataataagttgtttcaaaagtaataa 480

481 aatttaactccataatttttttattcgactgatcttaaagcaacacccagtgacacaactagccatttttttctttgaat 560

561 aaaaaaatccaattatcattgtatttttttttatacaatgaaaatttcaccaaacaatcatttgtggtatttctgaagcaa 640

641 gtcatgttatgcaaaattctataattcccatttgacactacggaagtaactgaagatctgcttttacatgcgagacacat 720

721 cttctaaagtaattttaataatagttactatattcaagatttcatatatcaaatactcaatattacttctaaaaaattaa 800

801 ttagatataattaaaatattacttttttaattttaagtttaattgttgaatttgtgactattgatttattattctactat 880

881 gtttaaattgttttatagatagtttaaagtaaatataagtaatgtagtagagtgttagagtgttaccctaaaccataaac 960

961 tataagatttatggtggactaattttcatatatttcttattgcttttaccttttcttggtatgtaagtccgtaactggaa 1040

1041 ttactgtgggttgccatggcactctgtggtctttggttcatgcatggatgcttgcgcaagaaaaagacaaagaacaaag 1120

1121 aaaaaagacaaaacagagagacaaaacgcaatcacacaaccaactcaaattagtcactggctgatcaagatcgccgcgtc 1200

1201 catgtatgtctaaatgccatgcaaagcaacacgtgcttaacatgcactttaaatggctcacccatctcaacccacacaca 1280

1281 aacacattgccttttcttcatcatcaccacaaccacctgtatatattcattctcttccgccacctcaatttcttcactt 1360

1361 caacacacgtcaacctgcatatgcgtgtcatcccatgcccaaatctccatgcatgttccaaccaccttctctcttatata 1440

1441 ataccatataaatacctctaatatcactcacttctttcatcatccatccatccagagtactactactctactactataata 1520

1521 ccccaacccaactcatattcaatactactctact ATG GCT TCG GAA GAA GGA CAA GTG ATC GCC TGC 1587
                                       1   M   A   S   E   E   G   Q   V   I   A   C   11

1588 CAC ACC GTT GAG ACA TGG AAC GAG CAG CTT CAG AAG GCT AAT GAA TCC AAA ACT CTT GTG 1647
  12 H   T   V   E   T   W   N   E   Q   L   Q   K   A   N   E   S   K   T   L   V   31

1648 GTG GTT GAT TTC ACG GCT TCT TGG TGT GGA CCA TGT CGT TTC ATC GCT CCA TTC TTT GCT 1707
  32 V   V   D   F   T   A   S   W   C   G   P   C   R   F   I   A   P   F   F   A   51

1708 GAT TTG GCT AAG AAA CTT CCT AAC GTG CTT TTC CTC AAG GTT GAT ACT GAT GAA TTG AAG 1767
  52 D   L   A   K   K   L   P   N   V   L   F   L   K   V   D   T   D   E   L   K   71

FIG. 14

```
1768 TCG GTG GCA AGT GAT TGG GCG ATA CAG GCG ATG CCA ACC TTC ATG TTT TTG AAG GAA GGG 1827
 72 S   V   A   S   D   W   A   I   Q   A   M   P   T   F   M   F   L   K   E   G    91
1828 AAG ATT TTG GAC AAA GTT GTT GGA GCC AAG AAA GAT GAG CTT CAG TCT ACC ATT GCC AAA 1887
 92 K   I   L   D   K   V   V   G   A   K   K   D   E   L   Q   S   T   I   A   K   111
1888 CAC TTG GCT ATG GCG GAT ACA GCT AGA GGA ACC CAT CAC GAT ATC ATC GGC AGA GAC CAG 1947
112 H   L   A   M   A   D   T   A   R   G   T   H   H   D   I   I   G   R   D   Q   131
1948 TAC CCG ATG ATG GGC CGA GAC CGA GAC CAG TAC CAG ATG TCC GGA CGA GGA TCT GAC TAC 2007
132 Y   P   M   M   G   R   D   R   D   Q   Y   Q   M   S   G   R   G   S   D   Y   151
2008 TCC AAG TCT AGG CAG ATT GCT AAA GCT GCA ACT GCT GTC ACA GCT GGT GGT TCC CTC CTT 2067
152 S   K   S   R   Q   I   A   K   A   A   T   A   V   T   A   G   G   S   L   L   171
2068 GTT CTC TCC AGC CTT ACC CTT GTT GGA ACT GTC ATA GCT TTG ACT GTT GCA ACA CCT CTG 2127
172 V   L   S   S   L   T   L   V   G   T   V   I   A   L   T   V   A   T   P   L   191
2128 CTC GTT ATC TTC AGC CCA ATC CTT GTC CCG GCT CTC ATC ACA GTT GCA CTC CTC ATC ACC 2187
192 L   V   I   F   S   P   I   L   V   P   A   L   I   T   V   A   L   L   I   T   211
2188 GGT TTT CTT TCC TCT GGA GGG TTT GGC ATT GCC GCT ATA ACC GTT TTC TCT TGG ATT TAC 2247
212 G   F   L   S   S   G   G   F   G   I   A   A   I   T   V   F   S   W   I   Y   231
2248 AA gtaagcacacatttatcatcttacttcataattttgtgcaatatgtgcatgcatgtgttgagccagtagctttggat 2326
232 K                                                                                  232
2327 caatttttttggtcgaataacaaatgtaacaataagaaattgcaaattctagggaacatttggttaactaaatacgaaat 2406

2407 ttgacctagctagcttgaatgtgtctgtgtatatcatctatataggtaaaatgcttggtatgatacctattgattgtgaa 2486

2487 tag G TAC GCA ACG GGA GAG CAC CCA CAG GGA TCA GAC AAG TTG GAC AGT GCA AGG ATG 2544
233      Y   A   T   G   E   H   P   Q   G   S   D   K   L   D   S   A   R   M   250
2545 AAG TTG GGA AGC AAA GCT CAG GAT CTG AAA GAC AGA GCT CAG TAC TAC GGA CAG CAA CAT 2604
251 K   L   G   S   K   A   Q   D   L   K   D   R   A   Q   Y   Y   G   Q   Q   H   270
                                                                                HindIII
2605 ACT GGT GGG GAA CAT GAC CGT GAC CGT ACT CGT GGT GGC CAG CAC ACT ACT TAA gcttaata 2666
271 T   G   G   E   H   D   R   D   R   T   R   G   G   Q   H   T   T   *           288
2667 agtatgaactaaaatgcatgtaggtgtaagagctcatggagagcatggaatattgtatccgaccatgtaacagtataata 2746

2747 actgagctccatctcacttcttctatgaataaacaaaggatgttatgatXattaacactctatctatgcaccttattgt 2826

2827 tctatgataaatttcctcttattattataaatcatctgaatcgtgacggcttatggaatgcttcaaatagtacaaaaaca 2906

2907 aatgtgtactataagactttctaaacaattctaactttagcattgtgaacgagacataagtgttaagaagacataacaat 2986

2987 tataatggaagaagtttgtctccatttatatattatatattacccacttatgtattatattaggatgttaaggagacata 3066
```

FIG. 14A

```
3067 acaattataaagagagaagtttgtatccatttatatattatatactacccatttatatattatacttatccacttattta 3146

3147 atgtctttataaggtttgatccatgatatttctaatattttagttgatatgtatatgaaagggtactatttgaactctct 3226

3227 tactctgtataaaggttggatcatccttaaagtgggtctatttaattttattgcttcttacagataaaaaaaaaattatg 3306

3307 agttggtttgataaaatattgaaggatttaaaataataataaataataaataacatataatatatgtatataaatttatt 3386

3387 ataatataacatttatctataaaaaagtaaatattgtcataaatctatacaatcgtttagccttgctggacgactctcaa 3466

3467 ttatttaaacgagagtaaacatatttgacttttggttatttaacaaattattatttaacactatatgaattttttttt 3546

3547 tttatcggcaaggaaataaaattaaattaggagggacaatggtgtgtcccaatccttatacaaccaacttccacaggaag 3626

3627 gtcaggtcggggacaacaaaaaaacaggcaagggaaatttttaatttgggttgtcttgtttgctgcataatttatgcag 3706

3707 taaaacactacacataaccctttagcagtagagcaatggttgaccgtgtgcttagcttcttttattttatttttttatc 3786

3787 agcaaagaataaataaaataaaatgagacacttcagggatgtttcaacccttatacaaaaccccaaaaacaagtttccta 3866

3867 gcaccctaccaactaaggtacc                                                         3888
              KpnI
```

FIG. 14B

PstI
1 ctgcaggaattcattgtactcccagtatcattatagtgaaagttttggctctctcgccggtggttttttacctctattta 80

81 aaggggttttccacctaaaaattctggtatcattctcactttacttgttactttaatttctcataatctttggttgaaat 160

161 tatcacgcttccgcacacgatatccctacaaatttattatttgttaaacattttcaaaccgcataaaattttatgaagtc 240

241 ccgtctatctttaatgtagtctaacattttcatattgaaatatataatttacttaattttagcgttggtagaaagcataa 320

321 tgatttattcttattcttcttcatataaatgtttaatatacaatataaacaaattctttaccttaagaaggatttcccat 400

401 tttatattttaaaaatatatttatcaaatattttcaaccacgtaaatctcataataataagttgtttcaaaagtaataa 480

481 aatttaactccataattttttttattcgactgatcttaaagcaacacccagtgacacaactagccattttttttctttgaat 560

561 aaaaaaatccaattatcattgtatttttttttatacaatgaaaatttcaccaaacaatcatttgtggtatttctgaagcaa 640

641 gtcatgttatgcaaaattctataattcccatttgacactacggaagtaactgaagatctgcttttacatgcgagacacat 720

721 cttctaaagtaattttaataatagttactatattcaagatttcatatatcaaatactcaatattacttctaaaaaattaa 800

801 ttagatataattaaaatattacttttttaattttaagtttaattgttgaatttgtgactattgatttattattctactat 880

881 gtttaaattgttttatagatagtttaaagtaaatataagtaatgtagtagagtgttagagtgttaccctaaaccataaac 960

961 tataagatttatggtggactaattttcatatatttcttattgcttttaccttttcttggtatgtaagtccgtaactggaa 1040

1041 ttactgtgggttgccatggcactctgtggtcttttggttcatgcatggatgcttgcgcaagaaaaagacaaagaacaaag 1120

1121 aaaaaagacaaaacagagagacaaaacgcaatcacacaaccaactcaaattagtcactggctgatcaagatcgccgcgtc 1200

1201 catgtatgtctaaatgccatgcaaagcaacacgtgcttaacatgcactttaaatggctcacccatctcaacccacacaca 1280

1281 aacacattgccttttctcttcatcatccaccaacccacctgtatatattcattctcttccgccacctcaatttcttcactt 1360

1361 caacacacgtcaacctgcatatgcgtgtcatcccatgcccaaatctccatgcatgttccaaccaccttctctcttatata 1440

1441 atacctataaataccctctaatatcactcacttctttcatcatccatccatccagagtactactactctactactataata 1520

1521 ccccaacccaactcatattcaatactactctact ATG AAT GGT CTC GAA ACT CAC AAC ACA AGG CTC 1587
                                       1  M   N   G   L   E   T   H   N   T   R   L   11

1588 TGT ATC GTA GGA AGT GGC CCA GCG GCA CAC ACG GCG GCG ATT TAC GCA GCT AGG GCT GAA 1647
     12  C   I   V   G   S   G   P   A   A   H   T   A   A   I   Y   A   A   R   A   E   31

1648 CTT AAA CCT CTT CTC TTC GAA GGA TGG ATG GCT AAC GAC ATC GCT CCC GGT GGT CAA CTA 1707
     32  L   K   P   L   L   F   E   G   W   M   A   N   D   I   A   P   G   G   Q   L   51

1708 ACA ACC ACC ACC GAC GTC GAG AAT TTC CCC GGA TTT CCA GAA GGT ATT CTC GGA GTA GAG 1767
     52  T   T   T   T   D   V   E   N   F   P   G   F   P   E   G   I   L   G   V   E   71

FIG. 15

```
1768 CTC ACT GAC AAA TTC CGT AAA CAA TCG GAG CGA TTC GGT ACT ACG ATA TTT ACA GAG ACG 1827
 72 L   T   D   K   F   R   K   Q   S   E   R   F   G   T   T   I   F   T   E   T    91
1828 GTG ACG AAA GTC GAT TTC TCT TCG AAA CCG TTT AAG CTA TTC ACA GAT TCA AAA GCC ATT 1887
 92 V   T   K   V   D   F   S   S   K   P   F   K   L   F   T   D   S   K   A   I   111
1888 CTC GCT GAC GCT GTG ATT CTC GCT ACT GGA GCT GTG GCT AAG CGG CTT AGC TTC GTT GGA 1947
112 L   A   D   A   V   I   L   A   T   G   A   V   A   K   R   L   S   F   V   G   131
1948 TCT GGT GAA GGT TCT GGA GGT TTC TGG AAC CGT GGA ATC TCC GCT TGT GCT GTT TGC GAC 2007
132 S   G   E   G   S   G   G   F   W   N   R   G   I   S   A   C   A   V   C   D   151
2008 GGA GCT GCT CCG ATA TTC CGT AAC AAA CCT CTT GCG GTG ATC GGT GGA GGC GAT TCA GCA 2067
152 G   A   A   P   I   F   R   N   K   P   L   A   V   I   G   G   G   D   S   A   171
2068 ATG GAA GAA GCA AAC TTT CTT ACA AAA TAT GGA TCT AAA GTG TAT ATA ATC CAT AGG AGA 2127
172 M   E   E   A   N   F   L   T   K   Y   G   S   K   V   Y   I   I   H   R   R   191
2128 GAT GCT TTT AGA GCG TCT AAG ATT ATG CAG CAG CGA GCT TTG TCT AAT CCT AAG ATT GAT 2187
 92 D   A   F   R   A   S   K   I   M   Q   Q   R   A   L   S   N   P   K   I   D   211
2188 GTG ATT TGG AAC TCG TCT GTT GTG GAA GCT TAT GGA GAT GGA GAA AGA GAT GTG CTT GGA 2247
212 V   I   W   N   S   S   V   V   E   A   Y   G   D   G   E   R   D   V   L   G   231
2248 GGA TTG AAA GTG AAG AAT GTG GTT ACC GGA GAT GTT TCT GAT TTA AAA GTT TCT GGA TTG 2307
232 G   L   K   V   K   N   V   V   T   G   D   V   S   D   L   K   V   S   G   L   251
2308 TTC TTT GCT ATT GGT CAT GAG CCA GCT ACC AAG TTT TTG GAT GGT GGT GTT GAG TTA GAT 2367
252 F   F   A   I   G   H   E   P   A   T   K   F   L   D   G   G   V   E   L   D   271
2368 TCG GAT GGT TAT GTT GTC ACG AAG CCT GGT ACT ACA CAG ACT AGC GTT CCC GGA GTT TTC 2427
272 S   D   G   Y   V   V   T   K   P   G   T   T   Q   T   S   V   P   G   V   F   291
2428 GCT GCG GGT GAT GTT CAG GAT AAG AAG TAT AGG CAA GCC ATC ACT GCT GCA GGA ACT GGG 2487
292 A   A   G   D   V   Q   D   K   K   Y   R   Q   A   I   T   A   A   G   T   G   311
2488 TGC ATG GCA GCT TTG GAT GCA GAG CAT TAC TTA CAA GAG ATT GGA TCT CAG CAA GGT AAG 2547
312 C   M   A   A   L   D   A   E   H   Y   L   Q   E   I   G   S   Q   Q   G   K   331
2548 AGT GAT TGA agcttaataagtatgaactaaaatgcatgtaggtgtaagagctcatggagagcatggaatattgtatc 2624
332 S   D   *   HindIII                                                                334
2625 cgaccatgtaacagtataataactgagctccatctcacttcttctatgaataaacaaaggatgttatgatatattaacac 2704

2705 tctatctatgcaccttattgttctatgataaatttcctcttattattataaatcatctgaatcgtgacggcttatggaat 2784

2785 gcttcaaatagtacaaaaacaaatgtgtactataagactttctaaacaattctaactttagcattgtgaacgagacataa 2864

2865 gtgttaagaagacataacaattataatggaagaagtttgtctccatttatatattatatattacccacttatgtattata 2944
```

FIG. 15A 2945 ttaggatgttaaggagacataacaattataaagagagaagtttgtatccatttatatattatatactacccatttatata 3024

3025 ttatacttatccacttatttaatgtctttataaggtttgatccatgatatttctaatattttagttgatatgtatatgaa 3104

3105 agggtactatttgaactctcttactctgtataaaggttggatcatccttaaagtgggtctatttaattttattgcttctt 3184

3185 acagataaaaaaaaaattatgagttggtttgataaaatattgaaggatttaaaataataataaataataaataacatata 3264

3265 atatatgtatataaatttattataatataacatttatctataaaaaagtaaatattgtcataaatctatacaatcgttta 3344

3345 gccttgctggacgactctcaattatttaaacgagagtaaacatatttgacttttggttatttaacaaattattatttaa 3424

3425 cactatatgaaatttttttttttatcggcaaggaaataaaattaaattaggagggacaatggtgtgtcccaatccttat 3504

3505 acaaccaacttccacaggaaggtcaggtcggggacaacaaaaaaacaggcaagggaaatttttaatttgggttgtcttg 3584

3585 tttgctgcataatttatgcagtaaaacactacacataaacccttttagcagtagagcaatggttgaccgtgtgcttagctt 3664

3665 cttttatttattttttttatcagcaaagaataaataaaataaaatgagacacttcagggatgtttcaacccttataaaa 3744

3745 accccaaaaacaagtttcctagcaccctaccaactaaggtacc                                      3787
                                                KpnI

FIG. 15B

```
      PstI
   1 ctgcaggaattcattgtactcccagtatcattatagtgaaagttttggctctctcgccggtggttttttacctctattta 80

81 aagggtttccacctaaaaattctggtatcattctcactttacttgttactttaatttctcataatctttggttgaaat 160

161 tatcacgcttccgcacacgatatccctacaaatttattatttgttaaacattttcaaaccgcataaaattttatgaagtc 240

241 ccgtctatctttaatgtagtctaacattttcatattgaaatatataatttacttaattttagcgttggtagaaagcataa 320

321 tgatttattcttattcttcttcatataaatgtttaatatacaatataaacaaattctttaccttaagaaggatttcccat 400

401 tttatattttaaaaatatatttatcaaatattttttcaaccacgtaaatctcataataataagttgtttcaaaagtaataa 480

481 aatttaactccataatttttttattcgactgatcttaaagcaacacccagtgacacaactagccatttttttctttgaat 560

561 aaaaaaatccaattatcattgtatttttttttatacaatgaaaatttcaccaaacaatcatttgtggtatttctgaagcaa 640

641 gtcatgttatgcaaaattctataattcccatttgacactacggaagtaactgaagatctgcttttacatgcgagacacat 720

721 cttctaaagtaattttaataatagttactatattcaagatttcatatatcaaatactcaatattacttctaaaaaattaa 800

801 ttagatataattaaaatattacttttttaattttaagtttaattgttgaatttgtgactattgatttattattctactat 880

881 gtttaaattgttttatagatagtttaaagtaaatataagtaatgtagtagagtgttagagtgttaccctaaaccataaac 960

961 tataagatttatggtggactaattttcatatatttcttattgcttttaccttttcttggtatgtaagtccgtaactggaa 1040

1041 ttactgtgggttgccatggcactctgtggtcttttggttcatgcatggatgcttgcgcaagaaaaagacaaagaacaaag 1120

1121 aaaaaagacaaaacagagagacaaaacgcaatcacacaaccaactcaaattagtcactggctgatcaagatcgccgcgtc 1200

1201 catgtatgtctaaatgccatgcaaagcaacacgtgcttaacatgcactttaaatggctcacccatctcaacccacacaca 1280

1281 aacacattgccttttcttcatcatcaccacaaccacctgtatatattcattctcttccgccacctcaatttcttcactt 1360

1361 caacacacgtcaacctgcatatgcgtgtcatcccatgcccaaatctccatgcatgttccaaccaccttctctcttatata 1440

1441 atacctataaatacctctaatatcactcacttctttcatcatccatccatccagagtactactactctactactataata 1520

1521 ccccaacccaactcatattcaatactactctact ATG GCG GAT ACA GCT AGA GGA ACC CAT CAC GAT 1587
   1                                    M   A   D   T   A   R   G   T   H   H   D   11

1588 ATC ATC GGC AGA GAC CAG TAC CCG ATG ATG GGC CGA GAC CGA GAC CAG TAC CAG ATG TCC 1647
  12  I   I   G   R   D   Q   Y   P   M   M   G   R   D   R   D   Q   Y   Q   M   S   31
1648 GGA CGA GGA TCT GAC TAC TCC AAG TCT AGG CAG ATT GCT AAA GCT GCA ACT GCT GTC ACA 1707
  32  G   R   G   S   D   Y   S   K   S   R   Q   I   A   K   A   A   T   A   V   T   51
1708 GCT GGT GGT TCC CTC CTT GTT CTC TCC AGC CTT ACC CTT GTT GGA ACT GTC ATA GCT TTG 1767
```

FIG. 16

```
 52 A   G   G   S   L   L   V   L   S   S   L   T   L   V   G   T   V   I   A   L   71
1768 ACT GTT GCA ACA CCT CTG CTC GTT ATC TTC AGC CCA ATC CTT GTC CCG GCT CTC ATC ACA 1827
 72 T   V   A   T   P   L   L   V   I   F   S   P   I   L   V   P   A   L   I   T   91
1828 GTT GCA CTC CTC ATC ACC GGT TTT CTT TCC TCT GGA GGG TTT GGC ATT GCC GCT ATA ACC 1887
 92 V   A   L   L   I   T   G   F   L   S   S   G   G   F   G   I   A   A   I   T   111
1888 GTT TTC TCT TGG ATT TAC AA gtaagcacacatttatcatcttacttcataattttgtgcaatatgtgcatgca 1960
112 V   F   S   W   I   Y   K                                                         118
1961 tgtgttgagccagtagctttggatcaattttttggtcgaataacaaatgtaacaataagaaattgcaaattctagggaa 2040

2041 catttggttaactaaatacgaaatttgacctagctagcttgaatgtgtctgtgtatatcatctatataggtaaaatgctt 2120

2121 ggtatgatacctattgattgtgaatag G TAC GCA ACG GGA GAG CAC CCA CAG GGA TCA GAC AAG 2184
119                               Y   A   T   G   E   H   P   Q   G   S   D   K   130
2185 TTG GAC AGT GCA AGG ATG AAG TTG GGA AGC AAA GCT CAG GAT CTG AAA GAC AGA GCT CAG 2244
131 L   D   S   A   R   M   K   L   G   S   K   A   Q   D   L   K   D   R   A   Q   150
2245 TAC TAC GGA CAG CAA CAT ACT GGT GGG GAA CAT GAC CGT GAC CGT ACT CGT GGT GGC CAG 2304
151 Y   Y   G   Q   Q   H   T   G   G   E   H   D   R   D   R   T   R   G   G   Q   170
2305 CAC ACT ACC ATG AAT GGT CTC GAA ACT CAC AAC ACA AGG CTC TGT ATC GTA GGA AGT GGC 2364
171 H   T   T   M   N   G   L   E   T   H   N   T   R   L   C   I   V   G   S   G   190
2365 CCA GCG GCA CAC ACG GCG GCG ATT TAC GCA GCT AGG GCT GAA CTT AAA CCT CTT CTC TTC 2424
191 P   A   A   H   T   A   A   I   Y   A   A   R   A   E   L   K   P   L   L   F   210
2425 GAA GGA TGG ATG GCT AAC GAC ATC GCT CCC GGT GGT CAA CTA ACA ACC ACC ACC GAC GTC 2484
211 E   G   W   M   A   N   D   I   A   P   G   G   Q   L   T   T   T   T   D   V   230
2485 GAG AAT TTC CCC GGA TTT CCA GAA GGT ATT CTC GGA GTA GAG CTC ACT GAC AAA TTC CGT 2544
231 E   N   F   P   G   F   P   E   G   I   L   G   V   E   L   T   D   K   F   R   250
2545 AAA CAA TCG GAG CGA TTC GGT ACT ACG ATA TTT ACA GAG ACG GTG ACG AAA GTC GAT TTC 2604
251 K   Q   S   E   R   F   G   T   T   I   F   T   E   T   V   T   K   V   D   F   270
2605 TCT TCG AAA CCG TTT AAG CTA TTC ACA GAT TCA AAA GCC ATT CTC GCT GAC GCT GTG ATT 2664
271 S   S   K   P   F   K   L   F   T   D   S   K   A   I   L   A   D   A   V   I   290
2665 CTC GCT ACT GGA GCT GTG GCT AAG CGG CTT AGC TTC GTT GGA TCT GGT GAA GGT TCT GGA 2724
291 L   A   T   G   A   V   A   K   R   L   S   F   V   G   S   G   E   G   S   G   310
2725 GGT TTC TGG AAC CGT GGA ATC TCC GCT TGT GCT GTT TGC GAC GGA GCT GCT CCG ATA TTC 2784
311 G   F   W   N   R   G   I   S   A   C   A   V   C   D   G   A   A   P   I   F   330
2785 CGT AAC AAA CCT CTT GCG GTG ATC GGT GGA GGC GAT TCA GCA ATG GAA GAA GCA AAC TTT 2844
331 R   N   K   P   L   A   V   I   G   G   G   D   S   A   M   E   E   A   N   F   350
```

FIG. 16A

```
2845 CTT ACA AAA TAT GGA TCT AAA GTG TAT ATA ATC CAT AGG AGA GAT GCT TTT AGA GCG TCT 2904
351  L   T   K   Y   G   S   K   V   Y   I   I   H   R   R   D   A   F   R   A   S  370
2905 AAG ATT ATG CAG CAG CGA GCT TTG TCT AAT CCT AAG ATT GAT GTG ATT TGG AAC TCG TCT 2964
371  K   I   M   Q   Q   R   A   L   S   N   P   K   I   D   V   I   W   N   S   S  390
2965 GTT GTG GAA GCT TAT GGA GAT GGA GAA AGA GAT GTG CTT GGA GGA TTG AAA GTG AAG AAT 3024
391  V   V   E   A   Y   G   D   G   E   R   D   V   L   G   G   L   K   V   K   N  410
3025 GTG GTT ACC GGA GAT GTT TCT GAT TTA AAA GTT TCT GGA TTG TTC TTT GCT ATT GGT CAT 3084
411  V   V   T   G   D   V   S   D   L   K   V   S   G   L   F   F   A   I   G   H  430
3085 GAG CCA GCT ACC AAG TTT TTG GAT GGT GGT GTT GAG TTA GAT TCG GAT GGT TAT GTT GTC 3144
431  E   P   A   T   K   F   L   D   G   G   V   E   L   D   S   D   G   Y   V   V  450
3145 ACG AAG CCT GGT ACT ACA CAG ACT AGC GTT CCC GGA GTT TTC GCT GCG GGT GAT GTT CAG 3204
451  T   K   P   G   T   T   Q   T   S   V   P   G   V   F   A   A   G   D   V   Q  470
3205 GAT AAG AAG TAT AGG CAA GCC ATC ACT GCT GCA GGA ACT GGG TGC ATG GCA GCT TTG GAT 3264
471  D   K   K   Y   R   Q   A   I   T   A   A   G   T   G   C   M   A   A   L   D  490
3265 GCA GAG CAT TAC TTA CAA GAG ATT GGA TCT CAG CAA GGT AAG AGT GAT TGA agcttaataagt 3327
491  A   E   H   Y   L   Q   E   I   G   S   Q   Q   G   K   S   D   *  HindIII    507
3328 atgaactaaaatgcatgtaggtgtaagagctcatggagagcatggaatattgtatccgaccatgtaacagtataataact 3407

3408 gagctccatctcacttcttctatgaataaacaaaggatgttatgatatattaacactctatctatgcaccttattgttct 3487

3488 atgataaatttcctcttattattataaatcatctgaatcgtgacggcttatggaatgcttcaaatagtacaaaaacaaat 3567

3568 gtgtactataagactttctaaacaattctaactttagcattgtgaacgagacataagtgttaagaagacataacaattat 3647

3648 aatggaagaagtttgtctccatttatatattatatattacccacttatgtattatattaggatgttaaggagacataaca 3727

3728 attataaagagagaagtttgtatccatttatatattatatactacccatttatatattatacttatccacttatttaatg 3807

3808 tctttataaggtttgatccatgatatttctaatattttagttgatatgtatatgaaagggtactatttgaactctcttac 3887

3888 tctgtataaaggttggatcatccttaaagtgggtctatttaattttattgcttcttacagataaaaaaaaaattatgagt 3967

3968 tggtttgataaaatattgaaggatttaaaataataataaataataaataacatataatatatgtatataaatttattata 4047

4048 atataacatttatctataaaaaagtaaatattgtcataaatctatacaatcgtttagccttgctggacgactctcaatta 4127

4128 tttaaacgagagtaaacatatttgacttttggttatttaacaaattattatttaacactatatgaaatttttttttttt 4207

4208 atcggcaaggaaataaaattaaattaggagggacaatggtgtgtcccaatccttatacaaccaacttccacaggaaggtc 4287
```

FIG. 16B

```
4288 aggtcggggacaacaaaaaaaacaggcaagggaaattttttaatttgggttgtcttgtttgctgcataatttatgcagtaa 4367

4368 aacactacacataaccctttttagcagtagagcaatggttgaccgtgtgcttagcttctttta ttttatttttttatcagc 4447

4448 aaagaataaataaaataaaatgagacacttcagggatgtttcaacccttatacaaaaccccaaaaacaagtttcctagca 4527

4528 ccctaccaactaaggtacc                                                              4546
                 KpnI
```

FIG. 16C

PstI
1 ctgcaggaattcattgtactcccagtatcattatagtgaaagttttggctctctcgccggtggttttttacctctattta 80

81 aaggggttttccacctaaaaattctggtatcattctcactttacttgttactttaatttctcataatctttggttgaaat 160

161 tatcacgcttccgcacacgatatccctacaaatttattatttgttaaacattttcaaaccgcataaaatttatgaagtc 240

241 ccgtctatctttaatgtagtctaacattttcatattgaaatatataatttacttaattttagcgttggtagaaagcataa 320

321 tgatttattcttattcttcttcatataaatgtttaatatacaatataaacaaattctttaccttaagaaggatttcccat 400

401 tttatattttaaaaatatatttatcaaatattttcaaccacgtaaatctcataataataagttgtttcaaaagtaataa 480

481 aatttaactccataatttttttattcgactgatcttaaagcaacacccagtgacacaactagccattttttttctttgaat 560

561 aaaaaaatccaattatcattgtatttttttatacaatgaaaatttcaccaaacaatcatttgtggtatttctgaagcaa 640

641 gtcatgttatgcaaaattctataattcccatttgacactacggaagtaactgaagatctgcttttacatgcgagacacat 720

721 cttctaaagtaattttaataatagttactatattcaagatttcatatatcaaatactcaatattacttctaaaaaattaa 800

801 ttagatataattaaaatattactttttttaattttaagtttaattgttgaatttgtgactattgatttattattctactat 880

881 gtttaaattgttttatagatagtttaaagtaaatataagtaatgtagtagagtgttagagtgttaccctaaaccataaac 960

961 tataagatttatggtggactaattttcatatatttcttattgcttttacctttcttggtatgtaagtccgtaactggaa 1040

1041 ttactgtgggttgccatggcactctgtggtcttttggttcatgcatggatgcttgcgcaagaaaaagacaaagaacaaag 1120

1121 aaaaaagacaaaacagagagacaaaacgcaatcacacaaccaactcaaattagtcactggctgatcaagatcgccgcgtc 1200

1201 catgtatgtctaaatgccatgcaaagcaacacgtgcttaacatgcactttaaatggctcacccatctcaacccacacaca 1280

1281 aacacattgcctttttcttcatcatcaccacaaccacctgtatatattcattctcttccgccacctcaatttcttcactt 1360

1361 caacacacgtcaacctgcatatgcgtgtcatcccatgcccaaatctccatgcatgttccaaccaccttctctcttatata 1440

1441 atacctataaatacctctaatatcactcacttctttcatcatccatccatccagagtactactactctactactataata 1520

1521 ccccaacccaactcatattcaatactactctact ATG AAT GGT CTC GAA ACT CAC AAC ACA AGG CTC 1587
                                      1  M   N   G   L   E   T   H   N   T   R   L  11

1588 TGT ATC GTA GGA AGT GGC CCA GCG GCA CAC ACG GCG GCG ATT TAC GCA GCT AGG GCT GAA 1647
     12  C   I   V   G   S   G   P   A   A   H   T   A   A   I   Y   A   A   R   A   E  31

1648 CTT AAA CCT CTT CTC TTC GAA GGA TGG ATG GCT AAC GAC ATC GCT CCC GGT GGT CAA CTA 1707
     32  L   K   P   L   L   F   E   G   W   M   A   N   D   I   A   P   G   G   Q   L  51

1708 ACA ACC ACC ACC GAC GTC GAG AAT TTC CCC GGA TTT CCA GAA GGT ATT CTC GGA GTA GAG 1767
     52  T   T   T   T   D   V   E   N   F   P   G   F   P   E   G   I   L   G   V   E  71

FIG. 17

```
1768 CTC ACT GAC AAA TTC CGT AAA CAA TCG GAG CGA TTC GGT ACT ACG ATA TTT ACA GAG ACG 1827
  72 L   T   D   K   F   R   K   Q   S   E   R   F   G   T   T   I   F   T   E   T    91
1828 GTG ACG AAA GTC GAT TTC TCT TCG AAA CCG TTT AAG CTA TTC ACA GAT TCA AAA GCC ATT 1887
  92 V   T   K   V   D   F   S   S   K   P   F   K   L   F   T   D   S   K   A   I   111
1888 CTC GCT GAC GCT GTG ATT CTC GCT ACT GGA GCT GTG GCT AAG CGG CTT AGC TTC GTT GGA 1947
 112 L   A   D   A   V   I   L   A   T   G   A   V   A   K   R   L   S   F   V   G   131
1948 TCT GGT GAA GGT TCT GGA GGT TTC TGG AAC CGT GGA ATC TCC GCT TGT GCT GTT TGC GAC 2007
 132 S   G   E   G   S   G   G   F   W   N   R   G   I   S   A   C   A   V   C   D   151
2008 GGA GCT GCT CCG ATA TTC CGT AAC AAA CCT CTT GCG GTG ATC GGT GGA GGC GAT TCA GCA 2067
 152 G   A   A   P   I   F   R   N   K   P   L   A   V   I   G   G   G   D   S   A   171
2068 ATG GAA GAA GCA AAC TTT CTT ACA AAA TAT GGA TCT AAA GTG TAT ATA ATC CAT AGG AGA 2127
 172 M   E   E   A   N   F   L   T   K   Y   G   S   K   V   Y   I   I   H   R   R   191
2128 GAT GCT TTT AGA GCG TCT AAG ATT ATG CAG CAG CGA GCT TTG TCT AAT CCT AAG ATT GAT 2187
 192 D   A   F   R   A   S   K   I   M   Q   Q   R   A   L   S   N   P   K   I   D   211
2188 GTG ATT TGG AAC TCG TCT GTT GTG GAA GCT TAT GGA GAT GGA GAA AGA GAT GTG CTT GGA 2247
 212 V   I   W   N   S   S   V   V   E   A   Y   G   D   G   E   R   D   V   L   G   231
2248 GGA TTG AAA GTG AAG AAT GTG GTT ACC GGA GAT GTT TCT GAT TTA AAA GTT TCT GGA TTG 2307
 232 G   L   K   V   K   N   V   V   T   G   D   V   S   D   L   K   V   S   G   L   251
2308 TTC TTT GCT ATT GGT CAT GAG CCA GCT ACC AAG TTT TTG GAT GGT GGT GTT GAG TTA GAT 2367
 252 F   F   A   I   G   H   E   P   A   T   K   F   L   D   G   G   V   E   L   D   271
2368 TCG GAT GGT TAT GTT GTC ACG AAG CCT GGT ACT ACA CAG ACT AGC GTT CCC GGA GTT TTC 2427
 272 S   D   G   Y   V   V   T   K   P   G   T   T   Q   T   S   V   P   G   V   F   291
2428 GCT GCG GGT GAT GTT CAG GAT AAG AAG TAT AGG CAA GCC ATC ACT GCT GCA GGA ACT GGG 2487
 292 A   A   G   D   V   Q   D   K   K   Y   R   Q   A   I   T   A   A   G   T   G   311
2488 TGC ATG GCA GCT TTG GAT GCA GAG CAT TAC TTA CAA GAG ATT GGA TCT CAG CAA GGT AAG 2547
 312 C   M   A   A   L   D   A   E   H   Y   L   Q   E   I   G   S   Q   Q   G   K   331
2548 AGT GAT ATG GCG GAT ACA GCT AGA GGA ACC CAT CAC GAT ATC ATC GGC AGA GAC CAG TAC 2607
 332 S   D   M   A   D   T   A   R   G   T   H   H   D   I   I   G   R   D   Q   Y   351
2608 CCG ATG ATG GGC CGA GAC CGA GAC CAG TAC CAG ATG TCC GGA CGA GGA TCT GAC TAC TCC 2667
 352 P   M   M   G   R   D   R   D   Q   Y   Q   M   S   G   R   G   S   D   Y   S   371
2668 AAG TCT AGG CAG ATT GCT AAA GCT GCA ACT GCT GTC ACA GCT GGT GGT TCC CTC CTT GTT 2727
 372 K   S   R   Q   I   A   K   A   A   T   A   V   T   A   G   G   S   L   L   V   391
```

FIG. 17A

```
2728 CTC TCC AGC CTT ACC CTT GTT GGA ACT GTC ATA GCT TTG ACT GTT GCA ACA CCT CTG CTC 2787
 392  L   S   S   L   T   L   V   G   T   V   I   A   L   T   V   A   T   P   L   L  411
2788 GTT ATC TTC AGC CCA ATC CTT GTC CCG GCT CTC ATC ACA GTT GCA CTC CTC ATC ACC GGT 2847
 412  V   I   F   S   P   I   L   V   P   A   L   I   T   V   A   L   L   I   T   G  431
2848 TTT CTT TCC TCT GGA GGG TTT GGC ATT GCC GCT ATA ACC GTT TTC TCT TGG ATT TAC AA g 2907
 432  F   L   S   S   G   G   F   G   I   A   A   I   T   V   F   S   W   I   Y   K  451
2908 taagcacacatttatcatcttacttcataattttgtgcaatatgtgcatgcatgtgttgagccagtagctttggatcaat 2987

2988 tttttggtcgaataacaaatgtaacaataagaaattgcaaattctagggaacatttggttaactaaatacgaaatttga 3067

3068 cctagctagcttgaatgtgtctgtgtatatcatctatataggtaaaatgcttggtatgatacctattgattgtgaatag 3146

3147 G TAC GCA ACG GGA GAG CAC CCA CAG GGA TCA GAC AAG TTG GAC AGT GCA AGG ATG AAG    3204
 452   Y   A   T   G   E   H   P   Q   G   S   D   K   L   D   S   A   R   M   K    470
3205 TTG GGA AGC AAA GCT CAG GAT CTG AAA GAC AGA GCT CAG TAC TAC GGA CAG CAA CAT ACT 3264
 471  L   G   S   K   A   Q   D   L   K   D   R   A   Q   Y   Y   G   Q   Q   H   T  490
3265 GGT GGG GAA CAT GAC CGT GAC CGT ACT CGT GGT GGC CAG CAC ACT ACT TAA gcttaataagta 3327
 491  G   G   E   H   D   R   D   R   T   R   G   G   Q   H   T   T   *   HindIII    507
3328 tgaactaaaatgcatgtaggtgtaagagctcatggagagcatggaatattgtatccgaccatgtaacagtataataactg 3407

3408 agctccatctcacttcttctatgaataaacaaaggatgttatgatatattaacactctatctatgcaccttattgttcta 3487

3488 tgataaatttcctcttattattataaatcatctgaatcgtgacggcttatggaatgcttcaaatagtacaaaaacaaatg 3567

3568 tgtactataagactttctaaacaattctaactttagcattgtgaacgagacataagtgttaagaagacataacaattata 3647

3648 atggaagaagtttgtctccatttatatattatatattacccacttatgtattatattaggatgttaaggagacataacaa 3727

3728 ttataaagagagaagtttgtatccatttatatattatatactacccatttatatattatacttatccacttatttaatgt 3807

3808 ctttataaggtttgatccatgatatttctaatattttagttgatatgtatatgaaagggtactatttgaactctcttact 3887

3888 ctgtataaaggttggatcatccttaaagtgggtctatttaattttattgcttcttacagataaaaaaaaaattatgagtt 3967

3968 ggtttgataaaatattgaaggatttaaaataataataaataataaataacatataatatatgtatataaatttattataa 4047

4048 tataacatttatctataaaaaagtaaatattgtcataaatctatacaatcgtttagccttgctggacgactctcaattat 4127

4128 ttaaacgagagtaaacatatttgacttttttggttatttaacaaattattatttaacactatatgaaatttttttttttta 4207

4208 tcggcaaggaaataaaattaaattaggagggacaatggtgtgtcccaatccttatacaaccaacttccacaggaaggtca 4287
```

FIG. 17B 4288 ggtcggggacaacaaaaaaaacaggcaagggaaatttttaatttgggttgtcttgtttgctgcataatttatgcagtaaa 4367

4368 acactacacataaccctttagcagtagagcaatggttgaccgtgtgcttagcttcttttattttatttttttatcagca 4447

4448 aagaataaataaaataaaatgagacacttcagggatgtttcaacccttatacaaaaccccaaaaacaagtttcctagcac 4527

4528 cctaccaactaa<u>ggtacc</u> 4545
                KpnI

FIG. 17C

SEQUENCE LISTING

```
<160> NUMBER OF SEQ ID NOS: 55

<210> SEQ ID NO 1
<211> LENGTH: 1800
<212> TYPE: DNA
<213> ORGANISM: Arabidopsis thaliana
<220> FEATURE:
<221> NAME/KEY: CDS
<222> LOCATION: (868)..(1221)
<221> NAME/KEY: CDS
<222> LOCATION: (1462)..(1626)

<400> SEQUENCE: 1
ccatggctat acccaacctc ggtcttggtc acaccaggaa ctctctggta agctagctcc     60
actccccaga aacaaccggc gccaaattgc cggaattgct gacctgaaga cggaacatca    120
tcgtcgggtc cttgggcgat tgcggcggaa gatgggtcag cttgggcttg aggacgagac    180
ccgaatcgag tctgttgaaa ggttgttcat tgggatttgt atacggagat tggtcgtcga    240
```

-continued

| | |
|---|---|
| gaggtttgag ggaaaggaca aatgggtttg gctctggaga aagagagtgc ggctttagag | 300 |
| agagaattga gaggtttaga gagagatgcg gcggcgatga cgggaggaga gacgacgagg | 360 |
| acctgcatta tcaaagcagt gacgtggtga aatttggaac ttttaagagg cagatagatt | 420 |
| tattatttgt atccattttc ttcattgttc tagaatgtcg cggaacaaat tttaaaacta | 480 |
| aatcctaaat ttttctaatt ttgttgccaa tagtggatat gtgggccgta tagaaggaat | 540 |
| ctattgaagg cccaaaccca tactgacgag cccaaaggtt cgttttgcgt tttatgtttc | 600 |
| ggttcgatgc caacgccaca ttctgagcta ggcaaaaaac aaacgtgtct ttgaatagac | 660 |
| tcctctcgtt aacacatgca gcggctgcat ggtgacgcca ttaacacgtg gcctacaatt | 720 |
| gcatgatgtc tccattgaca cgtgacttct cgtctccttt cttaatatat ctaacaaaca | 780 |
| ctcctacctc ttccaaaata tatacacatc tttttgatca atctctcatt caaaatctca | 840 |
| ttctctctag taaacaagaa caaaaaa atg gcg gat aca gct aga gga acc cat | 894 |
|                                                         Met Ala Asp Thr Ala Arg Gly Thr His<br>                                                         1                   5 | |
| cac gat atc atc ggc aga gac cag tac ccg atg atg ggc cga gac cga<br>His Asp Ile Ile Gly Arg Asp Gln Tyr Pro Met Met Gly Arg Asp Arg<br> 10                      15                    20                    25 | 942 |
| gac cag tac cag atg tcc gga cga gga tct gac tac tcc aag tct agg<br>Asp Gln Tyr Gln Met Ser Gly Arg Gly Ser Asp Tyr Ser Lys Ser Arg<br>                   30                    35                    40 | 990 |
| cag att gct aaa gct gca act gct gtc aca gct ggt ggt tcc ctc ctt<br>Gln Ile Ala Lys Ala Ala Thr Ala Val Thr Ala Gly Gly Ser Leu Leu<br>               45                    50                    55 | 1038 |
| gtt ctc tcc agc ctt acc ctt gtt gga act gtc ata gct ttg act gtt<br>Val Leu Ser Ser Leu Thr Leu Val Gly Thr Val Ile Ala Leu Thr Val<br>60                      65                    70 | 1086 |
| gca aca cct ctg ctc gtt atc ttc agc cca atc ctt gtc ccg gct ctc<br>Ala Thr Pro Leu Leu Val Ile Phe Ser Pro Ile Leu Val Pro Ala Leu<br> 75                      80                    85 | 1134 |
| atc aca gtt gca ctc ctc atc acc ggt ttt ctt tcc tct gga ggg ttt<br>Ile Thr Val Ala Leu Leu Ile Thr Gly Phe Leu Ser Ser Gly Gly Phe<br>90                      95                   100             105 | 1182 |
| ggc att gcc gct ata acc gtt ttc tct tgg att tac aag taagcacaca<br>Gly Ile Ala Ala Ile Thr Val Phe Ser Trp Ile Tyr Lys<br>                   110                   115 | 1231 |
| tttatcatct tacttcataa ttttgtgcaa tatgtgcatg catgtgttga gccagtagct | 1291 |
| ttggatcaat ttttttggtc gaataacaaa tgtaacaata agaaattgca aattctaggg | 1351 |
| aacatttggt taactaaata cgaaatttga cctagctagc ttgaatgtgt ctgtgtatat | 1411 |
| catctatata ggtaaaatgc ttggtatgat acctattgat tgtgaatagg tac gca<br>                                                                                                   Tyr Ala<br>                                                                                                   120 | 1467 |
| acg gga gag cac cca cag gga tca gac aag ttg gac agt gca agg atg<br>Thr Gly Glu His Pro Gln Gly Ser Asp Lys Leu Asp Ser Ala Arg Met<br>                   125                   130                   135 | 1515 |
| aag ttg gga agc aaa gct cag gat ctg aaa gac aga gct cag tac tac<br>Lys Leu Gly Ser Lys Ala Gln Asp Leu Lys Asp Arg Ala Gln Tyr Tyr<br>                140                   145                   150 | 1563 |
| gga cag caa cat act ggt ggg gaa cat gac cgt gac cgt act cgt ggt<br>Gly Gln Gln His Thr Gly Gly Glu His Asp Arg Asp Arg Thr Arg Gly<br>            155                   160                   165 | 1611 |
| ggc cag cac act act taagttaccc cactgatgtc atcgtcatag tccataact<br>Gly Gln His Thr Thr<br>     170 | 1666 |
| ccaatgtcgg ggagttagtt tatgaggaat aaagtgttta gaatttgatc agggggagat | 1726 |

-continued

```
aataaaagcc gagtttgaat cttttgtta taagtaatgt ttatgtgtgt ttctatatgt      1786
tgtcaaatgg tacc                                                       1800
```

<210> SEQ ID NO 2
<211> LENGTH: 118
<212> TYPE: PRT
<213> ORGANISM: Arabidopsis thaliana

<400> SEQUENCE: 2

```
Met Ala Asp Thr Ala Arg Gly Thr His His Asp Ile Ile Gly Arg Asp
 1               5                  10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys
        115
```

<210> SEQ ID NO 3
<211> LENGTH: 55
<212> TYPE: PRT
<213> ORGANISM: Arabidopsis thaliana

<400> SEQUENCE: 3

```
Tyr Ala Thr Gly Glu His Pro Gln Gly Ser Asp Lys Leu Asp Ser Ala
 1               5                  10                  15

Arg Met Lys Leu Gly Ser Lys Ala Gln Asp Leu Lys Asp Arg Ala Gln
            20                  25                  30

Tyr Tyr Gly Gln Gln His Thr Gly Gly Glu His Asp Arg Asp Arg Thr
        35                  40                  45

Arg Gly Gly Gln His Thr Thr
    50                  55
```

<210> SEQ ID NO 4
<211> LENGTH: 564
<212> TYPE: DNA
<213> ORGANISM: Brassica napus
<220> FEATURE:
<221> NAME/KEY: CDS
<222> LOCATION: (1)..(561)

<400> SEQUENCE: 4

```
atg gcg gat aca gct aga acc cat cac gat gtc aca agt cga gat cag    48
Met Ala Asp Thr Ala Arg Thr His His Asp Val Thr Ser Arg Asp Gln
 1               5                  10                  15 tat ccc cga gac cga gac cag tat tct atg atc ggt cga gac cgt gac    96
Tyr Pro Arg Asp Arg Asp Gln Tyr Ser Met Ile Gly Arg Asp Arg Asp
            20                  25                  30 cag tac tct atg atg ggc cga gac cga gac cag tac aac atg tat ggt   144
Gln Tyr Ser Met Met Gly Arg Asp Arg Asp Gln Tyr Asn Met Tyr Gly
        35                  40                  45
```

```
cga gac tac tcc aag tct aga cag att gct aag gct gtt acc gca gtc      192
Arg Asp Tyr Ser Lys Ser Arg Gln Ile Ala Lys Ala Val Thr Ala Val
    50                  55                  60 acg gcg ggt ggg tcc ctc ctt gtc ctc tcc agt ctc acc ctt gtt ggt      240
Thr Ala Gly Gly Ser Leu Leu Val Leu Ser Ser Leu Thr Leu Val Gly
65                  70                  75                  80 act gtc att gct ttg act gtt gcc act cca ctc ctc gtt atc ttt agc      288
Thr Val Ile Ala Leu Thr Val Ala Thr Pro Leu Leu Val Ile Phe Ser
                85                  90                  95 cca atc ctc gtg ccg gct ctc atc acc gta gca ctt ctc atc act ggc      336
Pro Ile Leu Val Pro Ala Leu Ile Thr Val Ala Leu Leu Ile Thr Gly
            100                 105                 110 ttt ctc tcc tct ggt ggg ttt gcc att gca gct ata acc gtc ttc tcc      384
Phe Leu Ser Ser Gly Gly Phe Ala Ile Ala Ala Ile Thr Val Phe Ser
        115                 120                 125 tgg atc tat aag tac gca acg gga gag cac cca cag ggg tca gat aag      432
Trp Ile Tyr Lys Tyr Ala Thr Gly Glu His Pro Gln Gly Ser Asp Lys
    130                 135                 140 ttg gac agt gca agg atg aag ctg gga acc aaa gct cag gat att aaa      480
Leu Asp Ser Ala Arg Met Lys Leu Gly Thr Lys Ala Gln Asp Ile Lys
145                 150                 155                 160 gac aga gct caa tac tac gga cag caa cat aca ggt ggt gag cat gac      528
Asp Arg Ala Gln Tyr Tyr Gly Gln Gln His Thr Gly Gly Glu His Asp
                165                 170                 175 cgt gac cgt act cgt ggt ggc cag cac act act taa                      564
Arg Asp Arg Thr Arg Gly Gly Gln His Thr Thr
            180                 185
```

<210> SEQ ID NO 5
<211> LENGTH: 187
<212> TYPE: PRT
<213> ORGANISM: Brassica napus

<400> SEQUENCE: 5

```
Met Ala Asp Thr Ala Arg Thr His His Asp Val Thr Ser Arg Asp Gln
1               5                   10                  15

Tyr Pro Arg Asp Arg Asp Gln Tyr Ser Met Ile Gly Arg Asp Arg Asp
                20                  25                  30

Gln Tyr Ser Met Met Gly Arg Asp Arg Asp Gln Tyr Asn Met Tyr Gly
            35                  40                  45

Arg Asp Tyr Ser Lys Ser Arg Gln Ile Ala Lys Ala Val Thr Ala Val
        50                  55                  60

Thr Ala Gly Gly Ser Leu Leu Val Leu Ser Ser Leu Thr Leu Val Gly
65                  70                  75                  80

Thr Val Ile Ala Leu Thr Val Ala Thr Pro Leu Leu Val Ile Phe Ser
                85                  90                  95

Pro Ile Leu Val Pro Ala Leu Ile Thr Val Ala Leu Leu Ile Thr Gly
            100                 105                 110

Phe Leu Ser Ser Gly Gly Phe Ala Ile Ala Ala Ile Thr Val Phe Ser
        115                 120                 125

Trp Ile Tyr Lys Tyr Ala Thr Gly Glu His Pro Gln Gly Ser Asp Lys
    130                 135                 140

Leu Asp Ser Ala Arg Met Lys Leu Gly Thr Lys Ala Gln Asp Ile Lys
145                 150                 155                 160

Asp Arg Ala Gln Tyr Tyr Gly Gln Gln His Thr Gly Gly Glu His Asp
                165                 170                 175
```

Arg Asp Arg Thr Arg Gly Gly Gln His Thr Thr
            180                 185

<210> SEQ ID NO 6
<211> LENGTH: 2733
<212> TYPE: DNA
<213> ORGANISM: Artificial Sequence
<220> FEATURE:
<223> OTHER INFORMATION: Description of Artificial Sequence: Fragment of
      pSBSOTPTNT containing the oleosin-chymosin fusion
      gene
<221> NAME/KEY: CDS
<222> LOCATION: (850)..(1203)
<221> NAME/KEY: CDS
<222> LOCATION: (1444)..(2724)

<400> SEQUENCE: 6

| ataagcttgc atgcctgcgg aactctctgg taagctagct ccactcccca gaaacaaccg | 60 |
|---|---|
| gcgccaaatt gccggaattg ctgacctgaa gacggaacat catcgtcggg tccttgggcg | 120 |
| attgcggcgg aagatgggtc agcttgggct tgaggacgag acccgaatcg agtctgttga | 180 |
| aaggttgttc attgggattt gtatacggag attggtcgtc gagaggtttg agggaaagga | 240 |
| caaatgggtt tggctctgga gaaagagagt gcggctttag agagagaatt gagaggttta | 300 |
| gagagagatg cggcggcgat gacgggagga gagacgacga ggacctgcat tatcaaagca | 360 |
| gtgacgtggt gaaatttgga acttttaaga ggcagataga tttattattt gtatccattt | 420 |
| tcttcattgt tctagaatgt cgcggaacaa attttaaaac taaatcctaa attttttctaa | 480 |
| ttttgttgcc aatagtggat atgtgggccg tatagaagga atctattgaa ggcccaaacc | 540 |
| catactgacg agcccaaagg ttcgttttgc gttttatgtt tcggttcgat gccaacgcca | 600 |
| cattctgagc taggcaaaaa acaaacgtgt ctttgaatag actcctctcg ttaacacatg | 660 |
| cagcggctgc atggtgacgc cattaacacg tggcctacaa ttgcatgatg tctccattga | 720 |
| cacgtgactt ctcgtctcct ttcttaatat atctaacaaa cactcctacc tcttccaaaa | 780 |
| tatatacaca tcttttttgat caatctctca ttcaaaatct cattctctct agtaaacaag | 840 | aacaaaaaa atg gcg gat aca gct aga gga acc cat cac gat atc atc ggc    891
           Met Ala Asp Thr Ala Arg Gly Thr His His Asp Ile Ile Gly
             1               5                  10 aga gac cag tac ccg atg atg ggc cga gac cga gac cag tac cag atg    939
Arg Asp Gln Tyr Pro Met Met Gly Arg Asp Arg Asp Gln Tyr Gln Met
 15                  20                  25                  30 tcc gga cga gga tct gac tac tcc aag tct agg cag att gct aaa gct    987
Ser Gly Arg Gly Ser Asp Tyr Ser Lys Ser Arg Gln Ile Ala Lys Ala
                 35                  40                  45 gca act gct gtc aca gct ggt ggt tcc ctc ctt gtt ctc tcc agc ctt    1035
Ala Thr Ala Val Thr Ala Gly Gly Ser Leu Leu Val Leu Ser Ser Leu
             50                  55                  60 acc ctt gtt gga act gtc ata gct ttg act gtt gca aca cct ctg ctc    1083
Thr Leu Val Gly Thr Val Ile Ala Leu Thr Val Ala Thr Pro Leu Leu
         65                  70                  75 gtt atc ttc agc cca atc ctt gtc ccg gct ctc atc aca gtt gca ctc    1131
Val Ile Phe Ser Pro Ile Leu Val Pro Ala Leu Ile Thr Val Ala Leu
     80                  85                  90 ctc atc acc ggt ttt ctt tcc tct gga ggg ttt ggc att gcc gct ata    1179
Leu Ile Thr Gly Phe Leu Ser Ser Gly Gly Phe Gly Ile Ala Ala Ile
 95                 100                 105                 110 acc gtt ttc tct tgg att tac aag taagcacaca tttatcatct tacttcataa    1233
Thr Val Phe Ser Trp Ile Tyr Lys
             115

-continued

```
tttgtgcaa tatgtgcatg catgtgttga gccagtagct ttggatcaat tttttggtc     1293 gaataacaaa tgtaacaata agaaattgca aattctaggg aacatttggt taactaaata    1353
cgaaatttga cctagctagc ttgaatgtgt ctgtgtatat catctatata ggtaaaatgc    1413
ttggtatgat acctattgat tgtgaatagg tac gca acg gga gag cac cca cag    1467
                                 Tyr Ala Thr Gly Glu His Pro Gln
                                                 120             125 gga tca gac aag ttg gac agt gca agg atg aag ttg gga agc aaa gct     1515
Gly Ser Asp Lys Leu Asp Ser Ala Arg Met Lys Leu Gly Ser Lys Ala
            130                 135                 140 cag gat ctg aaa gac aga gct cag tac tac gga cag caa cat act ggt     1563
Gln Asp Leu Lys Asp Arg Ala Gln Tyr Tyr Gly Gln Gln His Thr Gly
        145                 150                 155 ggg gaa cat gac cgt gac cgt act cgt ggt ggc cag cac act act ctc     1611
Gly Glu His Asp Arg Asp Arg Thr Arg Gly Gly Gln His Thr Thr Leu
    160                 165                 170 gtt cca cga gga tcc atg gct gag atc acc agg atc cct ctg tac aaa     1659
Val Pro Arg Gly Ser Met Ala Glu Ile Thr Arg Ile Pro Leu Tyr Lys
175                 180                 185                 190 ggc aag tct ctg agg aag gcg ctg aag gag cat ggg ctt ctg gag gac     1707
Gly Lys Ser Leu Arg Lys Ala Leu Lys Glu His Gly Leu Leu Glu Asp
                195                 200                 205 ttc ctg cag aaa cag cag tat ggc atc agc agc aag tac tcc ggc ttc     1755
Phe Leu Gln Lys Gln Gln Tyr Gly Ile Ser Ser Lys Tyr Ser Gly Phe
            210                 215                 220 ggg gag gtg gcc agc gtg ccc ctg acc aac tac ctg gat agt cag tac     1803
Gly Glu Val Ala Ser Val Pro Leu Thr Asn Tyr Leu Asp Ser Gln Tyr
        225                 230                 235 ttt ggg aag atc tac ctc ggg acc ccg ccc cag gag ttc acc gtg ctg     1851
Phe Gly Lys Ile Tyr Leu Gly Thr Pro Pro Gln Glu Phe Thr Val Leu
    240                 245                 250 ttt gac act ggc tcc tct gac ttc tgg gta ccc tct atc tac tgc aag     1899
Phe Asp Thr Gly Ser Ser Asp Phe Trp Val Pro Ser Ile Tyr Cys Lys
255                 260                 265                 270 agc aat gcc tgc aaa aac cac cag cgc ttc gac ccg aga aag tcg tcc     1947
Ser Asn Ala Cys Lys Asn His Gln Arg Phe Asp Pro Arg Lys Ser Ser
                275                 280                 285 acc ttc cag aac ctg ggc aag ccc ctg tct atc cac tac ggg aca ggc     1995
Thr Phe Gln Asn Leu Gly Lys Pro Leu Ser Ile His Tyr Gly Thr Gly
            290                 295                 300 agc atg cag ggc atc ctg ggc tat gac acc gtc act gtc tcc aac att     2043
Ser Met Gln Gly Ile Leu Gly Tyr Asp Thr Val Thr Val Ser Asn Ile
        305                 310                 315 gtg gac atc cag cag aca gta ggc ctg agc acc cag gag ccc ggg gac     2091
Val Asp Ile Gln Gln Thr Val Gly Leu Ser Thr Gln Glu Pro Gly Asp
    320                 325                 330 gtc ttc acc tat gcc gaa ttc gac ggg atc ctg ggg atg gcc tac ccc     2139
Val Phe Thr Tyr Ala Glu Phe Asp Gly Ile Leu Gly Met Ala Tyr Pro
335                 340                 345                 350 tcg ctc gcc tca gag tac tcg ata ccc gtg ttt gac aac atg atg aac     2187
Ser Leu Ala Ser Glu Tyr Ser Ile Pro Val Phe Asp Asn Met Met Asn
                355                 360                 365 agg cac ctg gtg gcc caa gac ctg ttc tcg gtt tac atg gac agg aat     2235
Arg His Leu Val Ala Gln Asp Leu Phe Ser Val Tyr Met Asp Arg Asn
            370                 375                 380 ggc cag gag agc atg ctc acg ctg ggg gcc atc gac ccg tcc tac tac     2283
Gly Gln Glu Ser Met Leu Thr Leu Gly Ala Ile Asp Pro Ser Tyr Tyr
        385                 390                 395 aca ggg tcc ctg cac tgg gtg ccc gtg aca gtg cag cag tac tgg cag     2331
```

```
Thr Gly Ser Leu His Trp Val Pro Val Thr Val Gln Gln Tyr Trp Gln
        400                 405                 410 ttc act gtg gac agt gtc acc atc agc ggt gtg gtt gtg gcc tgt gag    2379
Phe Thr Val Asp Ser Val Thr Ile Ser Gly Val Val Val Ala Cys Glu
415                 420                 425                 430 ggt ggc tgt cag gcc atc ttg gac acg ggc acc tcc aag ctg gtc ggg    2427
Gly Gly Cys Gln Ala Ile Leu Asp Thr Gly Thr Ser Lys Leu Val Gly
            435                 440                 445 ccc agc agc gac atc ctc aac atc cag cag gcc att gga gcc aca cag    2475
Pro Ser Ser Asp Ile Leu Asn Ile Gln Gln Ala Ile Gly Ala Thr Gln
        450                 455                 460 aac cag tac ggt gag ttt gac atc gac tgc gac aac ctg agc tac atg    2523
Asn Gln Tyr Gly Glu Phe Asp Ile Asp Cys Asp Asn Leu Ser Tyr Met
    465                 470                 475 ccc act gtg gtc ttt gag atc aat ggc aaa atg tac cca ctg acc ccc    2571
Pro Thr Val Val Phe Glu Ile Asn Gly Lys Met Tyr Pro Leu Thr Pro
480                 485                 490 tcc gcc tat acc agc caa gac cag ggc ttc tgt acc agt ggc ttc cag    2619
Ser Ala Tyr Thr Ser Gln Asp Gln Gly Phe Cys Thr Ser Gly Phe Gln
495                 500                 505                 510 agt gaa aat cat tcc cag aaa tgg atc ctg ggg gat gtt ttc atc cga    2667
Ser Glu Asn His Ser Gln Lys Trp Ile Leu Gly Asp Val Phe Ile Arg
            515                 520                 525 gag tat tac agc gtc ttt gac agg gcc aac aac ctc gtg ggg ctg gcc    2715
Glu Tyr Tyr Ser Val Phe Asp Arg Ala Asn Asn Leu Val Gly Leu Ala
        530                 535                 540 aaa gcc atc tgaaagctt                                              2733
Lys Ala Ile
        545

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Fragment of
      pSBSOTPTNT containing the oleosin-chymosin fusion
      gene

<400> SEQUENCE: 7

Met Ala Asp Thr Ala Arg Gly Thr His His Asp Ile Ile Gly Arg Asp
 1               5                  10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys
        115

<210> SEQ ID NO 8
<211> LENGTH: 427
<212> TYPE: PRT
```

<213> ORGANISM: Artificial Sequence
<220> FEATURE:
<223> OTHER INFORMATION: Description of Artificial Sequence: Fragment of
    pSBSOTPTNT containing the oleosin-chymosin fusion
    gene

<400> SEQUENCE: 8

```
Tyr Ala Thr Gly Glu His Pro Gln Gly Ser Asp Lys Leu Asp Ser Ala
 1               5                  10                  15

Arg Met Lys Leu Gly Ser Lys Ala Gln Asp Leu Lys Asp Arg Ala Gln
             20                  25                  30

Tyr Tyr Gly Gln Gln His Thr Gly Glu His Asp Arg Asp Arg Thr
         35                  40                  45

Arg Gly Gly Gln His Thr Thr Leu Val Pro Arg Gly Ser Met Ala Glu
         50                  55                  60

Ile Thr Arg Ile Pro Leu Tyr Lys Gly Lys Ser Leu Arg Lys Ala Leu
 65                  70                  75                  80

Lys Glu His Gly Leu Leu Glu Asp Phe Leu Gln Lys Gln Gln Tyr Gly
                 85                  90                  95

Ile Ser Ser Lys Tyr Ser Gly Phe Gly Glu Val Ala Ser Val Pro Leu
            100                 105                 110

Thr Asn Tyr Leu Asp Ser Gln Tyr Phe Gly Lys Ile Tyr Leu Gly Thr
            115                 120                 125

Pro Pro Gln Glu Phe Thr Val Leu Phe Asp Thr Gly Ser Ser Asp Phe
        130                 135                 140

Trp Val Pro Ser Ile Tyr Cys Lys Ser Asn Ala Cys Lys Asn His Gln
145                 150                 155                 160

Arg Phe Asp Pro Arg Lys Ser Ser Thr Phe Gln Asn Leu Gly Lys Pro
                165                 170                 175

Leu Ser Ile His Tyr Gly Thr Gly Ser Met Gln Gly Ile Leu Gly Tyr
            180                 185                 190

Asp Thr Val Thr Val Ser Asn Ile Val Asp Ile Gln Gln Thr Val Gly
        195                 200                 205

Leu Ser Thr Gln Glu Pro Gly Asp Val Phe Thr Tyr Ala Glu Phe Asp
210                 215                 220

Gly Ile Leu Gly Met Ala Tyr Pro Ser Leu Ala Ser Glu Tyr Ser Ile
225                 230                 235                 240

Pro Val Phe Asp Asn Met Met Asn Arg His Leu Val Ala Gln Asp Leu
                245                 250                 255

Phe Ser Val Tyr Met Asp Arg Asn Gly Gln Glu Ser Met Leu Thr Leu
            260                 265                 270

Gly Ala Ile Asp Pro Ser Tyr Tyr Thr Gly Ser Leu His Trp Val Pro
        275                 280                 285

Val Thr Val Gln Gln Tyr Trp Gln Phe Thr Val Asp Ser Val Thr Ile
    290                 295                 300

Ser Gly Val Val Val Ala Cys Glu Gly Cys Gln Ala Ile Leu Asp
305                 310                 315                 320

Thr Gly Thr Ser Lys Leu Val Gly Pro Ser Ser Asp Ile Leu Asn Ile
                325                 330                 335

Gln Gln Ala Ile Gly Ala Thr Gln Asn Gln Tyr Gly Glu Phe Asp Ile
            340                 345                 350

Asp Cys Asp Asn Leu Ser Tyr Met Pro Thr Val Val Phe Glu Ile Asn
        355                 360                 365

Gly Lys Met Tyr Pro Leu Thr Pro Ser Ala Tyr Thr Ser Gln Asp Gln
370                 375                 380
```

```
Gly Phe Cys Thr Ser Gly Phe Gln Ser Glu Asn His Ser Gln Lys Trp
385                 390                 395                 400

Ile Leu Gly Asp Val Phe Ile Arg Glu Tyr Tyr Ser Val Phe Asp Arg
            405                 410                 415

Ala Asn Asn Leu Val Gly Leu Ala Lys Ala Ile
            420                 425
```

```
<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Val Pro Arg Gly
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Glu Gly Arg
 1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Pro Leu Gly Pro
 1

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Asn Leu Tyr Phe Gln Gly
 1               5

<210> SEQ ID NO 13
<211> LENGTH: 14
<212> TYPE: DNA
<213> ORGANISM: Daucus carota

<400> SEQUENCE: 13
acggtaacaa ctct                                                    14

<210> SEQ ID NO 14
<211> LENGTH: 14
```

```
<212> TYPE: DNA
<213> ORGANISM: Zea mays

<400> SEQUENCE: 14
gcggtaacga cggc                                                        14

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 15
cactgcagga actctctggt aa                                               22

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 16
ctacccggga tcctgtttac tagagagaat g                                     31

<210> SEQ ID NO 17
<211> LENGTH: 62
<212> TYPE: DNA
<213> ORGANISM: Artificial Sequence
<220> FEATURE:
<223> OTHER INFORMATION: Description of Artificial Sequence: Primer

<400> SEQUENCE: 17
aatcccatgg atcctcgtgg aacgagagta gtgtgctggc caccacgagt acggtcacgg       60
tc                                                                     62

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
cactgcagga actctctggt aagc                                             24

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gaggatccat ggtacgtcct gtagaaacc                                        29

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 20
```
gtaaaacgac ggccagt                                                    17

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      oleosin/GUS fusion protein

<400> SEQUENCE: 21

Leu Val Pro Arg Gly Ser
 1               5

<210> SEQ ID NO 22
<211> LENGTH: 9
<212> TYPE: PRT
<213> ORGANISM: Homo sapiens

<400> SEQUENCE: 22

Val Gln Gly Glu Glu Ser Asn Asp Lys
 1               5

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 23
cgcggtacca tggctatacc caacctcg                                        28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 24
cgcatcgatg ttcttgttta ctagagag                                        28

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 25
gccatcgatc atatgttacg tcctgtagaa acccca                               36

<210> SEQ ID NO 26
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 26
cgcggatcct cttccttcga tttgtttgcc tccctgc                              37

<210> SEQ ID NO 27
<211> LENGTH: 27

```
<212> TYPE: DNA
<213> ORGANISM: Artificial Sequence
<220> FEATURE:
<223> OTHER INFORMATION: Description of Artificial Sequence: Primer

<400> SEQUENCE: 27
cgcggatcca tggcggatac agctaga                                      27

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 28
tgctctagac gatgacatca gtggggtaac ttaagt                            36

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      spacer sequence

<400> SEQUENCE: 29

Leu Val Pro Arg Gly Ser
 1               5

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 30
atctctagaa ttcaactact cttgctcaaa g                                 31

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 31
gggttgctcg agatttctaa tcaatttat                                    29

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 32
taccatggct tcggaagaag ga                                           22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 33
gaaagcttaa gccaagtgtt tg                                              22

<210> SEQ ID NO 34
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 34
ggccagcaca ctaccatgaa tggtctcgaa actcac                               36

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 35
ttaagcttca atcactctta ccttgctg                                        28

<210> SEQ ID NO 36
<211> LENGTH: 1002
<212> TYPE: DNA
<213> ORGANISM: Unknown Organism
<220> FEATURE:
<223> OTHER INFORMATION: Description of Unknown Organism: Published NADPH
      thioredoxin reductase sequence
<221> NAME/KEY: CDS
<222> LOCATION: (1)..(999)

<400> SEQUENCE: 36 atg aat ggt ctc gaa act cac aac aca agg ctc tgt atc gta gga agt       48
Met Asn Gly Leu Glu Thr His Asn Thr Arg Leu Cys Ile Val Gly Ser
 1               5                  10                  15 ggc cca gcg gca cac acg gcg gcg att tac gca gct agg gct gaa ctt       96
Gly Pro Ala Ala His Thr Ala Ala Ile Tyr Ala Ala Arg Ala Glu Leu
            20                  25                  30 aaa cct ctt ctc ttc gaa gga tgg atg gct aac gac atc gct ccc ggt      144
Lys Pro Leu Leu Phe Glu Gly Trp Met Ala Asn Asp Ile Ala Pro Gly
        35                  40                  45 ggt caa cta aca acc acc acc gac gtc gag aat ttc ccc gga ttt cca      192
Gly Gln Leu Thr Thr Thr Thr Asp Val Glu Asn Phe Pro Gly Phe Pro
    50                  55                  60 gaa ggt att ctc gga gta gag ctc act gac aaa ttc cgt aaa caa tcg      240
Glu Gly Ile Leu Gly Val Glu Leu Thr Asp Lys Phe Arg Lys Gln Ser
65                  70                  75                  80 gag cga ttc ggt act acg ata ttt aca gag acg gtg acg aaa gtc gat      288
Glu Arg Phe Gly Thr Thr Ile Phe Thr Glu Thr Val Thr Lys Val Asp
                85                  90                  95 ttc tct tcg aaa ccg ttt aag cta ttc aca gat tca aaa gcc att ctc      336
Phe Ser Ser Lys Pro Phe Lys Leu Phe Thr Asp Ser Lys Ala Ile Leu
            100                 105                 110 gct gac gct gtg att ctc gct act gga gct gtg gct aag cgg ctt agc      384
Ala Asp Ala Val Ile Leu Ala Thr Gly Ala Val Ala Lys Arg Leu Ser
        115                 120                 125 ttc gtt gga tct ggt gaa ggt tct gga ggt ttc tgg aac cgt gga atc      432
Phe Val Gly Ser Gly Glu Gly Ser Gly Gly Phe Trp Asn Arg Gly Ile
    130                 135                 140 tcc gct tgt gct gtt tgc gac gga gct gct ccg ata ttc cgt aac aaa      480
Ser Ala Cys Ala Val Cys Asp Gly Ala Ala Pro Ile Phe Arg Asn Lys
```

```
                                                                    -continued
145                      150                 155                 160 cct ctt gcg gtg atc ggt gga ggc gat tca gca atg gaa gaa gca aac      528
Pro Leu Ala Val Ile Gly Gly Gly Asp Ser Ala Met Glu Glu Ala Asn
                    165                 170                 175 ttt ctt aca aaa tat gga tct aaa gtg tat ata atc cat agg aga gat      576
Phe Leu Thr Lys Tyr Gly Ser Lys Val Tyr Ile Ile His Arg Arg Asp
                180                 185                 190 gct ttt aga gcg tct aag att atg cag cag cga gct ttg tct aat cct      624
Ala Phe Arg Ala Ser Lys Ile Met Gln Gln Arg Ala Leu Ser Asn Pro
            195                 200                 205 aag att gat gtg att tgg aac tcg tct gtt gtg gaa gct tat gga gat      672
Lys Ile Asp Val Ile Trp Asn Ser Ser Val Val Glu Ala Tyr Gly Asp
        210                 215                 220 gga gaa aga gat gtg ctt gga gga ttg aaa gtg aag aat gtg gtt acc      720
Gly Glu Arg Asp Val Leu Gly Gly Leu Lys Val Lys Asn Val Val Thr
225                 230                 235                 240 gga gat gtt tct gat tta aaa gtt tct gga ttg ttc ttt gct att ggt      768
Gly Asp Val Ser Asp Leu Lys Val Ser Gly Leu Phe Phe Ala Ile Gly
                    245                 250                 255 cat gag cca gct acc aag ttt ttg gat ggt ggt gtt gag tta gat tcg      816
His Glu Pro Ala Thr Lys Phe Leu Asp Gly Gly Val Glu Leu Asp Ser
                260                 265                 270 gat ggt tat gtt gtc acg aag cct ggt act aca cag act agc gtt ccc      864
Asp Gly Tyr Val Val Thr Lys Pro Gly Thr Thr Gln Thr Ser Val Pro
            275                 280                 285 gga gtt ttc gct gcg ggt gat gtt cag gat aag aag tat agg caa gcc      912
Gly Val Phe Ala Ala Gly Asp Val Gln Asp Lys Lys Tyr Arg Gln Ala
        290                 295                 300 atc act gct gca gga act ggg tgc atg gca gct ttg gat gca gag cat      960
Ile Thr Ala Ala Gly Thr Gly Cys Met Ala Ala Leu Asp Ala Glu His
305                 310                 315                 320 tac tta caa gag att gga tct cag caa ggt aag agt gat tga             1002
Tyr Leu Gln Glu Ile Gly Ser Gln Gln Gly Lys Ser Asp
                    325                 330

<210> SEQ ID NO 37
<211> LENGTH: 1002
<212> TYPE: DNA
<213> ORGANISM: Arabidopsis sp.
<220> FEATURE:
<221> NAME/KEY: CDS
<222> LOCATION: (1)..(999)

<400> SEQUENCE: 37 atg aat ggt ctc gaa act cac aac aca agg ctc tgt atc gta gga agt       48
Met Asn Gly Leu Glu Thr His Asn Thr Arg Leu Cys Ile Val Gly Ser
1               5                   10                  15 ggc cca gcg gca cac acg gcg gcg att tac gca gct agg gct gaa ctt       96
Gly Pro Ala Ala His Thr Ala Ala Ile Tyr Ala Ala Arg Ala Glu Leu
                20                  25                  30 aaa cct ctt ctc ttc gaa gga tgg atg gct aac gac atc gct ccc ggt      144
Lys Pro Leu Leu Phe Glu Gly Trp Met Ala Asn Asp Ile Ala Pro Gly
            35                  40                  45 ggt caa cta aca acc acc acc gac gtc gag aat ttc ccc gga ttt cca      192
Gly Gln Leu Thr Thr Thr Thr Asp Val Glu Asn Phe Pro Gly Phe Pro
        50                  55                  60 gaa ggt att ctc gga gta gag ctc act gac aaa ttc cgt aaa caa tcg      240
Glu Gly Ile Leu Gly Val Glu Leu Thr Asp Lys Phe Arg Lys Gln Ser
65                  70                  75                  80 gag cga ttc ggt act acg ata ttt aca gag acg gtg acg aaa gtc gat      288
```

```
Glu Arg Phe Gly Thr Thr Ile Phe Thr Glu Thr Val Thr Lys Val Asp
                85                  90                  95 ttc tct tcg aaa ccg ttt aag cta ttc aca gat tca aaa gcc att ctc        336
Phe Ser Ser Lys Pro Phe Lys Leu Phe Thr Asp Ser Lys Ala Ile Leu
            100                 105                 110 gct gac gct gtg att ctc gct act gga gct gtg gct aag cgg ctt agc        384
Ala Asp Ala Val Ile Leu Ala Thr Gly Ala Val Ala Lys Arg Leu Ser
        115                 120                 125 ttc gtt gga tct ggt gaa ggt tct gga ggt ttc tgg aac cgt gga atc        432
Phe Val Gly Ser Gly Glu Gly Ser Gly Gly Phe Trp Asn Arg Gly Ile
    130                 135                 140 tcc gct tgt gct gtt tgc gac gga gct gct ccg ata ttc cgt aac aaa        480
Ser Ala Cys Ala Val Cys Asp Gly Ala Ala Pro Ile Phe Arg Asn Lys
145                 150                 155                 160 cct ctt gcg gtg atc ggt gga ggc gat tca gca atg gaa gaa gca aac        528
Pro Leu Ala Val Ile Gly Gly Gly Asp Ser Ala Met Glu Glu Ala Asn
                165                 170                 175 ttt ctt aca aaa tat gga tct aaa gtg tat ata atc cat agg aga gat        576
Phe Leu Thr Lys Tyr Gly Ser Lys Val Tyr Ile Ile His Arg Arg Asp
            180                 185                 190 gct ttt aga gcg tct aag att atg cag cag cga gct ttg tct aat cct        624
Ala Phe Arg Ala Ser Lys Ile Met Gln Gln Arg Ala Leu Ser Asn Pro
        195                 200                 205 aag att gat gtg att tgg aac tcg tct gtt gtg gaa gct tat gga gat        672
Lys Ile Asp Val Ile Trp Asn Ser Ser Val Val Glu Ala Tyr Gly Asp
    210                 215                 220 gga gaa aga gat gtg ctt gga gga ttg aaa gtg aag aat gtg gtt acc        720
Gly Glu Arg Asp Val Leu Gly Gly Leu Lys Val Lys Asn Val Val Thr
225                 230                 235                 240 gga gat gtt tct gat tta aaa gtt tct gga ttg ttc ttt gct att ggt        768
Gly Asp Val Ser Asp Leu Lys Val Ser Gly Leu Phe Phe Ala Ile Gly
                245                 250                 255 cat gag cca gct acc aag ttt ttg gat ggt ggt gtt gag tta gat tcg        816
His Glu Pro Ala Thr Lys Phe Leu Asp Gly Gly Val Glu Leu Asp Ser
            260                 265                 270 gat ggt tat gtt gtc acg aag cct ggt act aca cag act agc gtt ccc        864
Asp Gly Tyr Val Val Thr Lys Pro Gly Thr Thr Gln Thr Ser Val Pro
        275                 280                 285 gga gtt ttc gct gcg ggt gat gtt cag gat aag aag tat agg caa gcc        912
Gly Val Phe Ala Ala Gly Asp Val Gln Asp Lys Lys Tyr Arg Gln Ala
    290                 295                 300 atc act gct gca gga act ggg tgc atg gca gct ttg gat gca gag cat        960
Ile Thr Ala Ala Gly Thr Gly Cys Met Ala Ala Leu Asp Ala Glu His
305                 310                 315                 320 tac tta caa gag att gga tct cag caa ggt aag agt gat tga                1002
Tyr Leu Gln Glu Ile Gly Ser Gln Gln Gly Lys Ser Asp
                325                 330
```

<210> SEQ ID NO 38
<211> LENGTH: 333
<212> TYPE: PRT
<213> ORGANISM: Arabidopsis sp.

<400> SEQUENCE: 38

```
Met Asn Gly Leu Glu Thr His Asn Thr Arg Leu Cys Ile Val Gly Ser
1               5                   10                  15

Gly Pro Ala Ala His Thr Ala Ala Ile Tyr Ala Ala Arg Ala Glu Leu
            20                  25                  30

Lys Pro Leu Leu Phe Glu Gly Trp Met Ala Asn Asp Ile Ala Pro Gly
        35                  40                  45
```

```
Gly Gln Leu Thr Thr Thr Thr Asp Val Glu Asn Phe Pro Gly Phe Pro
         50                  55                  60

Glu Gly Ile Leu Gly Val Glu Leu Thr Asp Lys Phe Arg Lys Gln Ser
 65                  70                  75                  80

Glu Arg Phe Gly Thr Thr Ile Phe Thr Glu Thr Val Thr Lys Val Asp
                 85                  90                  95

Phe Ser Ser Lys Pro Phe Lys Leu Phe Thr Asp Ser Lys Ala Ile Leu
                100                 105                 110

Ala Asp Ala Val Ile Leu Ala Thr Gly Ala Val Ala Lys Arg Leu Ser
                115                 120                 125

Phe Val Gly Ser Gly Glu Gly Ser Gly Gly Phe Trp Asn Arg Gly Ile
    130                 135                 140

Ser Ala Cys Ala Val Cys Asp Gly Ala Ala Pro Ile Phe Arg Asn Lys
145                 150                 155                 160

Pro Leu Ala Val Ile Gly Gly Gly Asp Ser Ala Met Glu Glu Ala Asn
                165                 170                 175

Phe Leu Thr Lys Tyr Gly Ser Lys Val Tyr Ile Ile His Arg Arg Asp
                180                 185                 190

Ala Phe Arg Ala Ser Lys Ile Met Gln Gln Arg Ala Leu Ser Asn Pro
    195                 200                 205

Lys Ile Asp Val Ile Trp Asn Ser Ser Val Val Glu Ala Tyr Gly Asp
210                 215                 220

Gly Glu Arg Asp Val Leu Gly Leu Lys Val Lys Asn Val Val Thr
225                 230                 235                 240

Gly Asp Val Ser Asp Leu Lys Val Ser Gly Leu Phe Phe Ala Ile Gly
                245                 250                 255

His Glu Pro Ala Thr Lys Phe Leu Asp Gly Val Glu Leu Asp Ser
                260                 265                 270

Asp Gly Tyr Val Val Thr Lys Pro Gly Thr Thr Gln Thr Ser Val Pro
    275                 280                 285

Gly Val Phe Ala Ala Gly Asp Val Gln Asp Lys Lys Tyr Arg Gln Ala
    290                 295                 300

Ile Thr Ala Ala Gly Thr Gly Cys Met Ala Ala Leu Asp Ala Glu His
305                 310                 315                 320

Tyr Leu Gln Glu Ile Gly Ser Gln Gln Gly Lys Ser Asp
                325                 330

<210> SEQ ID NO 39
<211> LENGTH: 333
<212> TYPE: PRT
<213> ORGANISM: Unknown Organism
<220> FEATURE:
<223> OTHER INFORMATION: Description of Unknown Organism: Published NADPH
      thioredoxin reductase sequence

<400> SEQUENCE: 39

Met Asn Gly Leu Glu Thr His Asn Thr Arg Leu Cys Ile Val Gly Ser
 1               5                  10                  15

Gly Pro Ala Ala His Thr Ala Ala Ile Tyr Ala Ala Arg Ala Glu Leu
                 20                  25                  30

Lys Pro Leu Leu Phe Glu Gly Trp Met Ala Asn Asp Ile Ala Pro Gly
             35                  40                  45

Gly Gln Leu Thr Thr Thr Thr Asp Val Glu Asn Phe Pro Gly Phe Pro
         50                  55                  60

Glu Gly Ile Leu Gly Val Glu Leu Thr Asp Lys Phe Arg Lys Gln Ser
```

```
                65                  70                  75                  80
Glu Arg Phe Gly Thr Thr Ile Phe Thr Glu Thr Val Thr Lys Val Asp
                    85                  90                  95
Phe Ser Ser Lys Pro Phe Lys Leu Phe Thr Asp Ser Lys Ala Ile Leu
                100                 105                 110
Ala Asp Ala Val Ile Leu Ala Thr Gly Ala Val Ala Lys Arg Leu Ser
                115                 120                 125
Phe Val Gly Ser Gly Glu Gly Ser Gly Gly Phe Trp Asn Arg Gly Ile
            130                 135                 140
Ser Ala Cys Ala Val Cys Asp Gly Ala Ala Pro Ile Phe Arg Asn Lys
145                 150                 155                 160
Pro Leu Ala Val Ile Gly Gly Gly Asp Ser Ala Met Glu Glu Ala Asn
                165                 170                 175
Phe Leu Thr Lys Tyr Gly Ser Lys Val Tyr Ile Ile His Arg Arg Asp
                180                 185                 190
Ala Phe Arg Ala Ser Lys Ile Met Gln Gln Arg Ala Leu Ser Asn Pro
                195                 200                 205
Lys Ile Asp Val Ile Trp Asn Ser Ser Val Val Glu Ala Tyr Gly Asp
                210                 215                 220
Gly Glu Arg Asp Val Leu Gly Gly Leu Lys Val Lys Asn Val Val Thr
225                 230                 235                 240
Gly Asp Val Ser Asp Leu Lys Val Ser Gly Leu Phe Ala Ile Gly
                245                 250                 255
His Glu Pro Ala Thr Lys Phe Leu Asp Gly Val Glu Leu Asp Ser
                260                 265                 270
Asp Gly Tyr Val Val Thr Lys Pro Gly Thr Thr Gln Thr Ser Val Pro
            275                 280                 285
Gly Val Phe Ala Ala Gly Asp Val Gln Asp Lys Lys Tyr Arg Gln Ala
            290                 295                 300
Ile Thr Ala Ala Gly Thr Gly Cys Met Ala Ala Leu Asp Ala Glu His
305                 310                 315                 320
Tyr Leu Gln Glu Ile Gly Ser Gln Gln Gly Lys Ser Asp
                325                 330

<210> SEQ ID NO 40
<211> LENGTH: 3129
<212> TYPE: DNA
<213> ORGANISM: Arabidopsis thaliana
<220> FEATURE:
<221> NAME/KEY: CDS
<222> LOCATION: (1555)..(1896)

<400> SEQUENCE: 40
ctgcaggaat tcattgtact cccagtatca ttatagtgaa agttttggct ctctcgccgg    60
tggtttttta cctctatttta aagggtttt ccacctaaaa attctggtat cattctcact   120
ttacttgtta ctttaatttc tcataatctt tggttgaaat tatcacgctt ccgcacacga   180
tatccctaca aatttattat ttgttaaaca ttttcaaacc gcataaaatt ttatgaagtc   240
ccgtctatct ttaatgtagt ctaacatttt catattgaaa tatataattt acttaatttt   300
agcgttggta gaaagcataa tgatttattc ttattcttct tcatataaat gtttaatata   360
caatataaac aaattcttta ccttaagaag gatttcccat tttatatttt aaaaatatat   420
ttatcaaata tttttcaacc acgtaaatct cataataata agttgtttca aaagtaataa   480
aatttaactc ataatttttt ttattcgact gatcttaaag caacacccag tgacacaact   540
```

```
                                                              -continued agccattttt ttctttgaat aaaaaaatcc aattatcatt gtatttttt tatacaatga      600 aaatttcacc aaacaatcat ttgtggtatt tctgaagcaa gtcatgttat gcaaaattct    660
ataattccca tttgacacta cggaagtaac tgaagatctg cttttacatg cgagacacat    720
cttctaaagt aatttttaata atagttacta tattcaagat ttcatatatc aaatactcaa   780
tattacttct aaaaaattaa ttagatataa ttaaaatatt acttttttaa ttttaagttt    840
aattgttgaa tttgtgacta ttgatttatt attctactat gtttaaattg ttttatagat   900
agtttaaagt aaatataagt aatgtagtag agtgttagag tgttacccta aaccataaac    960
tataagattt atggtggact aattttcata tatttcttat tgcttttacc ttttcttggt  1020
atgtaagtcc gtaactggaa ttactgtggg ttgccatggc actctgtggt cttttggttc   1080
atgcatggat gcttgcgcaa gaaaaagaca agaacaaag aaaaaagaca aaacagagag     1140
acaaaacgca atcacacaac caactcaaat tagtcactgg ctgatcaaga tcgccgcgtc   1200
catgtatgtc taaatgccat gcaaagcaac acgtgcttaa catgcacttt aaatggctca   1260
cccatctcaa cccacacaca aacacattgc cttttttcttc atcatcacca caaccacctg  1320
tatatattca ttctcttccg ccacctcaat ttcttcactt caacacacgt caacctgcat   1380
atgcgtgtca tcccatgccc aaatctccat gcatgttcca accaccttct ctcttatata   1440 ataccataa ataccctctaa tatcactcac ttctttcatc atccatccat ccagagtact  1500
actactctac tactataata ccccaaccca actcatattc aatactactc tact atg    1557
                                                              Met
                                                                1 gct tcg gaa gaa gga caa gtg atc gcc tgc cac acc gtt gag aca tgg    1605
Ala Ser Glu Glu Gly Gln Val Ile Ala Cys His Thr Val Glu Thr Trp
         5                  10                  15 aac gag cag ctt cag aag gct aat gaa tcc aaa act ctt gtg gtg gtt    1653
Asn Glu Gln Leu Gln Lys Ala Asn Glu Ser Lys Thr Leu Val Val Val
     20                  25                  30 gat ttc acg gct tct tgg tgt gga cca tgt cgt ttc atc gct cca ttc    1701
Asp Phe Thr Ala Ser Trp Cys Gly Pro Cys Arg Phe Ile Ala Pro Phe
 35                  40                  45 ttt gct gat ttg gct aag aaa ctt cct aac gtg ctt ttc ctc aag gtt    1749
Phe Ala Asp Leu Ala Lys Lys Leu Pro Asn Val Leu Phe Leu Lys Val
 50                  55                  60                  65 gat act gat gaa ttg aag tcg gtg gca agt gat tgg gcg ata cag gcg    1797
Asp Thr Asp Glu Leu Lys Ser Val Ala Ser Asp Trp Ala Ile Gln Ala
             70                  75                  80 atg cca acc ttc atg ttt ttg aag gaa ggg aag att ttg gac aaa gtt    1845
Met Pro Thr Phe Met Phe Leu Lys Glu Gly Lys Ile Leu Asp Lys Val
                 85                  90                  95 gtt gga gcc aag aaa gat gag ctt cag tct acc att gcc aaa cac ttg    1893
Val Gly Ala Lys Lys Asp Glu Leu Gln Ser Thr Ile Ala Lys His Leu
            100                 105                 110 gct taagcttaat aagtatgaac taaatgcat gtaggtgtaa gagctcatgg           1946
Ala agagcatgga atattgtatc cgaccatgta acagtataat aactgagctc catctcactt   2006
cttctatgaa taaacaaagg atgttatgat atattaacac tctatctatg cacccttattg  2066 ttctatgata aatttcctct tattattata aatcatctga atcgtgacgg cttatggaat   2126
gcttcaaata gtacaaaaac aaatgtgtac tataagactt tctaaacaat tctaactta    2186 gcattgtgaa cgagacataa gtgttaagaa gacataacaa ttataatgga agaagtttgt   2246
ctccatttat atattatata ttacccactt atgtattata ttaggatgtt aaggagacat   2306
```

-continued

```
aacaattata aagagagaag tttgtatcca tttatatatt atatactacc catttatata    2366
ttatacttat ccacttattt aatgtcttta taaggtttga tccatgatat ttctaatatt    2426
ttagttgata tgtatatgaa agggtactat ttgaactctc ttactctgta taaaggttgg    2486
atcatcctta aagtgggtct atttaatttt attgcttctt acagataaaa aaaaaattat    2546
gagttggttt gataaaatat tgaaggattt aaaataataa taataataa ataacatata    2606 atatatgtat ataaatttat tataatataa catttatcta taaaaagta aatattgtca    2666 taaatctata caatcgttta gccttgctgg acgactctca attatttaaa cgagagtaaa    2726
catatttgac tttttggtta tttaacaaat tattatttaa cactatatga aatttttttt    2786
ttttatcggc aaggaaataa aattaaatta ggagggacaa tggtgtgtcc caatccttat    2846
acaaccaact tccacaggaa ggtcaggtcg gggacaacaa aaaaacaggc aagggaaatt    2906
ttttaatttg ggttgtcttg tttgctgcat aatttatgca gtaaaacact acacataacc    2966
cttttagcag tagagcaatg gttgaccgtg tgcttagctt cttttatttt atttttttat    3026
cagcaaagaa taaataaaat aaaatgagac acttcaggga tgtttcaacc cttatacaaa    3086 acccccaaaaa caagtttcct agcaccctac caactaaggt acc                     3129
```

<210> SEQ ID NO 41
<211> LENGTH: 114
<212> TYPE: PRT
<213> ORGANISM: Arabidopsis thaliana

<400> SEQUENCE: 41

```
Met Ala Ser Glu Glu Gly Gln Val Ile Ala Cys His Thr Val Glu Thr
  1               5                  10                  15

Trp Asn Glu Gln Leu Gln Lys Ala Asn Glu Ser Lys Thr Leu Val Val
             20                  25                  30

Val Asp Phe Thr Ala Ser Trp Cys Gly Pro Cys Arg Phe Ile Ala Pro
         35                  40                  45

Phe Phe Ala Asp Leu Ala Lys Lys Leu Pro Asn Val Leu Phe Leu Lys
     50                  55                  60

Val Asp Thr Asp Glu Leu Lys Ser Val Ala Ser Asp Trp Ala Ile Gln
 65                  70                  75                  80

Ala Met Pro Thr Phe Met Phe Leu Lys Glu Gly Lys Ile Leu Asp Lys
                 85                  90                  95

Val Val Gly Ala Lys Lys Asp Glu Leu Gln Ser Thr Ile Ala Lys His
            100                 105                 110

Leu Ala
```

<210> SEQ ID NO 42
<211> LENGTH: 3888
<212> TYPE: DNA
<213> ORGANISM: Artificial Sequence
<220> FEATURE:
<221> NAME/KEY: CDS
<222> LOCATION: (1555)..(1908)
<221> NAME/KEY: CDS
<222> LOCATION: (2149)..(2655)
<223> OTHER INFORMATION: Description of Artificial Sequence: Phaseolin
      promoter-oleosin Trxh-phaseolin terminator

<400> SEQUENCE: 42

```
ctgcaggaat tcattgtact cccagtatca ttatagtgaa agttttggct ctctcgccgg      60
tggtttttta cctctatttta aagggggtttt ccacctaaaa attctggtat cattctcact    120
ttacttgtta ctttaatttc tcataatctt tggttgaaat tatcacgctt ccgcacacga     180
```

-continued

```
tatccctaca aatttattat ttgttaaaca ttttcaaacc gcataaaatt ttatgaagtc    240
ccgtctatct ttaatgtagt ctaacatttt catattgaaa tatataattt acttaatttt    300
agcgttggta gaaagcataa tgatttattc ttattcttct tcatataaat gtttaatata    360
caatataaac aaattcttta ccttaagaag gatttcccat tttatatttt aaaaatatat    420
ttatcaaata tttttcaacc acgtaaatct cataataata agttgtttca aaagtaataa    480
aatttaactc cataattttt ttattcgact gatcttaaag caacacccag tgacacaact    540
agccattttt ttctttgaat aaaaaaatcc aattatcatt gtattttttt tatacaatga    600
aaatttcacc aaacaatcat ttgtggtatt tctgaagcaa gtcatgttat gcaaaattct    660
ataattccca tttgacacta cggaagtaac tgaagatctg cttttacatg cgagacacat    720
cttctaaagt aatttttaata atagttacta tattcaagat ttcatatatc aaatactcaa    780
tattacttct aaaaaattaa ttagatataa ttaaaatatt acttttttaa ttttaagttt    840
aattgttgaa tttgtgacta ttgatttatt attctactat gtttaaattg ttttatagat    900
agtttaaagt aaatataagt aatgtagtag agtgttagag tgttaccctc aaccataaac    960
tataagattt atggtggact aattttcata tatttcttat tgcttttacc ttttcttggt   1020
atgtaagtcc gtaactggaa ttactgtggg ttgccatggc actctgtggt cttttggttc   1080
atgcatggat gcttgcgcaa gaaaaagaca agaacaaag aaaaagaca aacagagag     1140 acaaaacgca atcacacaac caactcaaat tagtcactgg ctgatcaaga tcgccgcgtc   1200
catgtatgtc taaatgccat gcaaagcaac acgtgcttaa catgcacttt aaatggctca   1260
cccatctcaa cccacacaca aacacattgc cttttttcttc atcatcacca caaccacctg   1320
tatatattca ttctcttccg ccacctcaat ttcttcactt caacacacgt caacctgcat   1380
atgcgtgtca tcccatgccc aaatctccat gcatgttcca accaccttct ctctttatata   1440 ataccctataa ataccctctaa tatcactcac ttctttcatc atccatccat ccagagtact   1500
actactctac tactataata ccccaaccca actcatattc aatactactc tact atg      1557
                                                                Met
                                                                 1 gcg gat aca gct aga gga acc cat cac gat atc atc ggc aga gac cag      1605
Ala Asp Thr Ala Arg Gly Thr His His Asp Ile Ile Gly Arg Asp Gln
           5                  10                  15 tac ccg atg atg ggc cga gac cga gac cag tac cag atg tcc gga cga      1653
Tyr Pro Met Met Gly Arg Asp Arg Asp Gln Tyr Gln Met Ser Gly Arg
       20                       25                  30 gga tct gac tac tcc aag tct agg cag att gct aaa gct gca act gct      1701
Gly Ser Asp Tyr Ser Lys Ser Arg Gln Ile Ala Lys Ala Ala Thr Ala
 35                      40                      45 gtc aca gct ggt ggt tcc ctc ctt gtt ctc tcc agc ctt acc ctt gtt      1749
Val Thr Ala Gly Gly Ser Leu Leu Val Leu Ser Ser Leu Thr Leu Val
 50                  55                      60                  65 gga act gtc ata gct ttg act gtt gca aca cct ctg ctc gtt atc ttc      1797
Gly Thr Val Ile Ala Leu Thr Val Ala Thr Pro Leu Leu Val Ile Phe
               70                  75                  80 agc cca atc ctt gtc ccg gct ctc atc aca gtt gca ctc ctc atc acc      1845
Ser Pro Ile Leu Val Pro Ala Leu Ile Thr Val Ala Leu Leu Ile Thr
           85                  90                  95 ggt ttt ctt tcc tct gga ggg ttt ggc att gcc gct ata acc gtt ttc      1893
Gly Phe Leu Ser Ser Gly Gly Phe Gly Ile Ala Ala Ile Thr Val Phe
       100                     105                     110 tct tgg att tac aag taagcacaca tttatcatct tacttcataa ttttgtgcaa      1948
Ser Trp Ile Tyr Lys
```

```
                 115
tatgtgcatg catgtgttga gccagtagct ttggatcaat ttttttggtc gaataacaaa    2008
tgtaacaata agaaattgca aattctaggg aacatttggt taactaaata cgaaatttga    2068
cctagctagc ttgaatgtgt ctgtgtatat catctatata ggtaaaatgc ttggtatgat    2128
acctattgat tgtgaatagg tac gca acg gga gag cac cca cag gga tca gac    2181
                      Tyr Ala Thr Gly Glu His Pro Gln Gly Ser Asp
                                              120                 125 aag ttg gac agt gca agg atg aag ttg gga agc aaa gct cag gat ctg    2229
Lys Leu Asp Ser Ala Arg Met Lys Leu Gly Ser Lys Ala Gln Asp Leu
130                 135                 140                 145 aaa gac aga gct cag tac tac gga cag caa cat act ggt ggg gaa cat    2277
Lys Asp Arg Ala Gln Tyr Tyr Gly Gln Gln His Thr Gly Gly Glu His
                150                 155                 160 gac cgt gac cgt act cgt ggt ggc cag cac act acc atg gct tcg gaa    2325
Asp Arg Asp Arg Thr Arg Gly Gly Gln His Thr Thr Met Ala Ser Glu
            165                 170                 175 gaa gga caa gtg atc gcc tgc cac acc gtt gag aca tgg aac gag cag    2373
Glu Gly Gln Val Ile Ala Cys His Thr Val Glu Thr Trp Asn Glu Gln
180                 185                 190 ctt cag aag gct aat gaa tcc aaa act ctt gtg gtg gtt gat ttc acg    2421
Leu Gln Lys Ala Asn Glu Ser Lys Thr Leu Val Val Val Asp Phe Thr
195                 200                 205 gct tct tgg tgt gga cca tgt cgt ttc atc gct cca ttc ttt gct gat    2469
Ala Ser Trp Cys Gly Pro Cys Arg Phe Ile Ala Pro Phe Phe Ala Asp
210                 215                 220                 225 ttg gct aag aaa ctt cct aac gtg ctt ttc ctc aag gtt gat act gat    2517
Leu Ala Lys Lys Leu Pro Asn Val Leu Phe Leu Lys Val Asp Thr Asp
                230                 235                 240 gaa ttg aag tcg gtg gca agt gat tgg gcg ata cag gcg atg cca acc    2565
Glu Leu Lys Ser Val Ala Ser Asp Trp Ala Ile Gln Ala Met Pro Thr
            245                 250                 255 ttc atg ttt ttg aag gaa ggg aag att ttg gac aaa gtt gtt gga gcc    2613
Phe Met Phe Leu Lys Glu Gly Lys Ile Leu Asp Lys Val Val Gly Ala
        260                 265                 270 aag aaa gat gag ctt cag tct acc att gcc aaa cac ttg gct              2655
Lys Lys Asp Glu Leu Gln Ser Thr Ile Ala Lys His Leu Ala
275                 280                 285 taagcttaat aagtatgaac taaaatgcat gtaggtgtaa gagctcatgg agagcatgga    2715
atattgtatc cgaccatgta acagtataat aactgagctc catctcactt cttctatgaa    2775
taaacaaagg atgttatgat atattaacac tctatctatg caccttattg ttctatgata    2835
aatttcctct tattattata aatcatctga atcgtgacgg cttatggaat gcttcaaata    2895
gtacaaaaac aaatgtgtac tataagactt tctaaacaat tctaacttta gcattgtgaa    2955
cgagacataa gtgttaagaa gacataacaa ttataatgga agaagtttgt ctccatttat    3015
atattatata ttacccactt atgtattata ttaggatgtt aaggagacat aacaattata    3075
aagagagaag tttgtatcca tttatatatt atatactacc catttatata ttatacttat    3135
ccacttattt aatgtcttta taaggtttga tccatgatat ttctaatatt ttagttgata    3195
tgtatatgaa agggtactat ttgaactctc ttactctgta taaaggttgg atcatcctta    3255
aagtgggtct atttaattttt attgcttctt acagataaaa aaaaaattat gagttggttt    3315
gataaaatat tgaaggattt aaaataataa taaataataa ataacatata atatatgtat    3375
ataaatttat tataatataa catttatcta taaaaaagta aatattgtca taaatctata    3435
caatcgttta gccttgctgg acgactctca attatttaaa cgagagtaaa catatttgac    3495
```

```
tttttggtta tttaacaaat tattatttaa cactatatga aatttttttt ttttatcggc    3555
aaggaaataa aattaaatta ggagggacaa tggtgtgtcc caatccttat acaaccaact    3615
tccacaggaa ggtcaggtcg gggacaacaa aaaaacaggc aagggaaatt ttttaatttg    3675
ggttgtcttg tttgctgcat aatttatgca gtaaaacact acacataacc cttttagcag    3735
tagagcaatg gttgaccgtg tgcttagctt cttttatttt atttttttat cagcaaagaa    3795
taaataaaat aaaatgagac acttcaggga tgtttcaacc cttatacaaa accccaaaaa    3855
caagtttcct agcaccctac caactaaggt acc                                 3888
```

<210> SEQ ID NO 43
<211> LENGTH: 118
<212> TYPE: PRT
<213> ORGANISM: Artificial Sequence
<220> FEATURE:
<223> OTHER INFORMATION: Description of Artificial Sequence: Phaseolin
      promoter-oleosin Trxh-phaseolin terminator

<400> SEQUENCE: 43

```
Met Ala Asp Thr Ala Arg Gly Thr His His Asp Ile Ile Gly Arg Asp
  1               5                  10                  15

Gln Tyr Pro Met Met Gly Arg Asp Arg Asp Gln Tyr Gln Met Ser Gly
             20                  25                  30

Arg Gly Ser Asp Tyr Ser Lys Ser Arg Gln Ile Ala Lys Ala Ala Thr
         35                  40                  45

Ala Val Thr Ala Gly Gly Ser Leu Leu Val Leu Ser Ser Leu Thr Leu
     50                  55                  60

Val Gly Thr Val Ile Ala Leu Thr Val Ala Thr Pro Leu Leu Val Ile
 65                  70                  75                  80

Phe Ser Pro Ile Leu Val Pro Ala Leu Ile Thr Val Ala Leu Leu Ile
                 85                  90                  95

Thr Gly Phe Leu Ser Ser Gly Gly Phe Gly Ile Ala Ala Ile Thr Val
            100                 105                 110

Phe Ser Trp Ile Tyr Lys
        115
```

<210> SEQ ID NO 44
<211> LENGTH: 169
<212> TYPE: PRT
<213> ORGANISM: Artificial Sequence
<220> FEATURE:
<223> OTHER INFORMATION: Description of Artificial Sequence: Phaseolin
      promoter-oleosin Trxh-phaseolin terminator

<400> SEQUENCE: 44

```
Tyr Ala Thr Gly Glu His Pro Gln Gly Ser Asp Lys Leu Asp Ser Ala
  1               5                  10                  15

Arg Met Lys Leu Gly Ser Lys Ala Gln Asp Leu Lys Asp Arg Ala Gln
             20                  25                  30

Tyr Tyr Gly Gln Gln His Thr Gly Gly Glu His Asp Arg Asp Arg Thr
         35                  40                  45

Arg Gly Gly Gln His Thr Thr Met Ala Ser Glu Glu Gly Gln Val Ile
     50                  55                  60

Ala Cys His Thr Val Glu Thr Trp Asn Glu Gln Leu Gln Lys Ala Asn
 65                  70                  75                  80

Glu Ser Lys Thr Leu Val Val Val Asp Phe Thr Ala Ser Trp Cys Gly
                 85                  90                  95
```

-continued

```
Pro Cys Arg Phe Ile Ala Pro Phe Phe Ala Asp Leu Ala Lys Lys Leu
            100                 105                 110
Pro Asn Val Leu Phe Leu Lys Val Asp Thr Asp Glu Leu Lys Ser Val
        115                 120                 125
Ala Ser Asp Trp Ala Ile Gln Ala Met Pro Thr Phe Met Phe Leu Lys
    130                 135                 140
Glu Gly Lys Ile Leu Asp Lys Val Val Gly Ala Lys Lys Asp Glu Leu
145                 150                 155                 160
Gln Ser Thr Ile Ala Lys His Leu Ala
                165

<210> SEQ ID NO 45
<211> LENGTH: 3888
<212> TYPE: DNA
<213> ORGANISM: Artificial Sequence
<220> FEATURE:
<223> OTHER INFORMATION: Description of Artificial Sequence: Phaseolin
      promoter-Trxh oleosin-phaseolin terminator
<221> NAME/KEY: CDS
<222> LOCATION: (1555)..(2250)
<221> NAME/KEY: CDS
<222> LOCATION: (2491)..(2655)

<400> SEQUENCE: 45
ctgcaggaat tcattgtact cccagtatca ttatagtgaa agttttggct ctctcgccgg      60
tggtttttta cctctatttta aagggttttt ccacctaaaa attctggtat cattctcact    120
ttacttgtta ctttaatttc tcataatctt tggttgaaat tatcacgctt ccgcacacga    180
tatccctaca aatttattat ttgttaaaca ttttcaaacc gcataaaatt ttatgaagtc    240
ccgtctatct ttaatgtagt ctaacatttt catattgaaa tatataattt acttaatttt    300
agcgttggta gaaagcataa tgatttattc ttattcttct tcatataaat gtttaatata    360
caatataaac aaattcttta ccttaagaag gatttcccat tttatatttt aaaaatatat    420
ttatcaaata tttttcaacc acgtaaatct cataataata agttgtttca aaagtaataa    480
aatttaactc cataattttt ttattcgact gatcttaaag caacacccag tgacacaact    540
agccattttt ttctttgaat aaaaaaatcc aattatcatt gtattttttt tatacaatga    600
aaatttcacc aaacaatcat ttgtggtatt tctgaagcaa gtcatgttat gcaaaattct    660
ataattccca tttgacacta cggaagtaac tgaagatctg cttttacatg cgagacacat    720
cttctaaagt aattttaata atagttacta tattcaagat ttcatatatc aaatactcaa    780
tattacttct aaaaaattaa ttagatataa ttaaaatatt acttttttaa ttttaagttt    840
aattgttgaa tttgtgacta ttgatttatt attctactat gtttaaattg ttttatagat    900
agtttaaagt aaatataagt aatgtagtag agtgttagag tgttacccta aaccataaac    960
tataagattt atggtggact aattttcata tatttcttat tgcttttacc ttttcttggt   1020
atgtaagtcc gtaactggaa ttactgtggg ttgccatggc actctgtggt cttttggttc   1080
atgcatggat gcttgcgcaa gaaaagaca aagaacaaag aaaaagaca aaacagagag       1140 acaaaacgca atcacacaac caactcaaat tagtcactgg ctgatcaaga tcgccgcgtc   1200
catgtatgtc taaatgccat gcaaagcaac acgtgcttaa catgcacttt aaatggctca   1260
cccatctcaa cccacacaca aacacattgc cttttcttc atcatcacca caaccacctg    1320
tatatattca ttctcttccg ccacctcaat ttcttcactt caacacacgt caacctgcat   1380
atgcgtgtca tcccatgccc aaatctccat gcatgttcca accaccttct ctcttatata   1440
atacctataa atacctctaa tatcactcac ttctttcatc atccatccat ccagagtact   1500
```

-continued

```
actactctac tactataata ccccaaccca actcatattc aatactactc tact atg      1557
                                                            Met
                                                             1 gct tcg gaa gaa gga caa gtg atc gcc tgc cac acc gtt gag aca tgg      1605
Ala Ser Glu Glu Gly Gln Val Ile Ala Cys His Thr Val Glu Thr Trp
          5                  10                 15 aac gag cag ctt cag aag gct aat gaa tcc aaa act ctt gtg gtg gtt      1653
Asn Glu Gln Leu Gln Lys Ala Asn Glu Ser Lys Thr Leu Val Val Val
     20                  25                  30 gat ttc acg gct tct tgg tgt gga cca tgt cgt ttc atc gct cca ttc      1701
Asp Phe Thr Ala Ser Trp Cys Gly Pro Cys Arg Phe Ile Ala Pro Phe
 35                  40                  45 ttt gct gat ttg gct aag aaa ctt cct aac gtg ctt ttc ctc aag gtt      1749
Phe Ala Asp Leu Ala Lys Lys Leu Pro Asn Val Leu Phe Leu Lys Val
 50                  55                  60                  65 gat act gat gaa ttg aag tcg gtg gca agt gat tgg gcg ata cag gcg      1797
Asp Thr Asp Glu Leu Lys Ser Val Ala Ser Asp Trp Ala Ile Gln Ala
         70                  75                  80 atg cca acc ttc atg ttt ttg aag gaa ggg aag att ttg gac aaa gtt      1845
Met Pro Thr Phe Met Phe Leu Lys Glu Gly Lys Ile Leu Asp Lys Val
             85                  90                  95 gtt gga gcc aag aaa gat gag ctt cag tct acc att gcc aaa cac ttg      1893
Val Gly Ala Lys Lys Asp Glu Leu Gln Ser Thr Ile Ala Lys His Leu
        100                 105                 110 gct atg gcg gat aca gct aga gga acc cat cac gat atc atc ggc aga      1941
Ala Met Ala Asp Thr Ala Arg Gly Thr His His Asp Ile Ile Gly Arg
    115                 120                 125 gac cag tac ccg atg atg ggc cga gac cga gac cag tac cag atg tcc      1989
Asp Gln Tyr Pro Met Met Gly Arg Asp Arg Asp Gln Tyr Gln Met Ser
130                 135                 140                 145 gga cga gga tct gac tac tcc aag tct agg cag att gct aaa gct gca      2037
Gly Arg Gly Ser Asp Tyr Ser Lys Ser Arg Gln Ile Ala Lys Ala Ala
                150                 155                 160 act gct gtc aca gct ggt ggt tcc ctc ctt gtt ctc tcc agc ctt acc      2085
Thr Ala Val Thr Ala Gly Gly Ser Leu Leu Val Leu Ser Ser Leu Thr
            165                 170                 175 ctt gtt gga act gtc ata gct ttg act gtt gca aca cct ctg ctc gtt      2133
Leu Val Gly Thr Val Ile Ala Leu Thr Val Ala Thr Pro Leu Leu Val
        180                 185                 190 atc ttc agc cca atc ctt gtc ccg gct ctc atc aca gtt gca ctc ctc      2181
Ile Phe Ser Pro Ile Leu Val Pro Ala Leu Ile Thr Val Ala Leu Leu
    195                 200                 205 atc acc ggt ttt ctt tcc tct gga ggg ttt ggc att gcc gct ata acc      2229
Ile Thr Gly Phe Leu Ser Ser Gly Gly Phe Gly Ile Ala Ala Ile Thr
210                 215                 220                 225 gtt ttc tct tgg att tac aag taagcacaca tttatcatct tacttcataa        2280
Val Phe Ser Trp Ile Tyr Lys
                230 ttttgtgcaa tatgtgcatg catgtgttga gccagtagct ttggatcaat ttttttggtc   2340 gaataacaaa tgtaacaata agaaattgca aattctaggg aacatttggt taactaaata   2400 cgaaatttga cctagctagc ttgaatgtgt ctgtgtatat catctatata ggtaaaatgc   2460 ttggtatgat acctattgat tgtgaatagg tac gca acg gga gag cac cca cag    2514
                                Tyr Ala Thr Gly Glu His Pro Gln
                                                235             240 gga tca gac aag ttg gac agt gca agg atg aag ttg gga agc aaa gct     2562
Gly Ser Asp Lys Leu Asp Ser Ala Arg Met Lys Leu Gly Ser Lys Ala
                245                 250                 255
```

-continued

```
cag gat ctg aaa gac aga gct cag tac tac gga cag caa cat act ggt      2610
Gln Asp Leu Lys Asp Arg Ala Gln Tyr Tyr Gly Gln Gln His Thr Gly
            260                 265                 270 ggg gaa cat gac cgt gac cgt act cgt ggt ggc cag cac act act          2655
Gly Glu His Asp Arg Asp Arg Thr Arg Gly Gly Gln His Thr Thr
        275                 280                 285 taagcttaat aagtatgaac taaaatgcat gtaggtgtaa gagctcatgg agagcatgga    2715
atattgtatc cgaccatgta acagtataat aactgagctc catctcactt cttctatgaa    2775
taaacaaagg atgttatgat atattaacac tctatctatg caccttattg ttctatgata    2835
aatttcctct tattattata aatcatctga atcgtgacgg cttatggaat gcttcaaata    2895
gtacaaaaac aaatgtgtac tataagactt tctaaacaat tctaacttta gcattgtgaa    2955
cgagacataa gtgttaagaa gacataacaa ttataatgga agaagtttgt ctccatttat    3015
atattatata ttacccactt atgtattata ttaggatgtt aaggagacat aacaattata    3075
aagagagaag tttgtatcca tttatatatt atatactacc catttatata ttatacttat    3135
ccacttattt aatgtcttta taaggtttga tccatgatat ttctaatatt ttagttgata    3195
tgtatatgaa agggtactat ttgaactctc ttactctgta taaggttgg atcatcctta     3255 aagtgggtct atttaatttt attgcttctt acagataaaa aaaaaattat gagttggttt    3315
gataaaatat tgaaggattt aaaataataa taaataataa ataacatata atatatgtat    3375
ataaatttat tataatataa catttatcta taaaaaagta aatattgtca taaatctata    3435
caatcgttta gccttgctgg acgactctca attatttaaa cgagagtaaa catatttgac    3495
tttttggtta tttaacaaat tattatttaa cactatatga aattttttt ttttatcggc     3555 aaggaaataa aattaaatta ggagggacaa tggtgtgtcc caatccttat acaaccaact    3615
tccacaggaa ggtcaggtcg gggacaacaa aaaacaggc aagggaaatt ttttaatttg     3675
ggttgtcttg tttgctgcat aatttatgca gtaaacact acacataacc cttttagcag     3735
tagagcaatg gttgaccgtg tgcttagctt cttttatttt attttttat cagcaaagaa     3795 taaataaaat aaaatgagac acttcaggga tgtttcaacc cttatacaaa accccaaaaa    3855
caagtttcct agcaccctac caactaaggt acc                                  3888
```

<210> SEQ ID NO 46
<211> LENGTH: 232
<212> TYPE: PRT
<213> ORGANISM: Artificial Sequence
<220> FEATURE:
<223> OTHER INFORMATION: Description of Artificial Sequence: Phaseolin
      promoter-Trxh oleosin-phaseolin terminator

<400> SEQUENCE: 46

```
Met Ala Ser Glu Glu Gly Gln Val Ile Ala Cys His Thr Val Glu Thr
 1               5                  10                  15

Trp Asn Glu Gln Leu Gln Lys Ala Asn Glu Ser Lys Thr Leu Val Val
            20                  25                  30

Val Asp Phe Thr Ala Ser Trp Cys Gly Pro Cys Arg Phe Ile Ala Pro
        35                  40                  45

Phe Phe Ala Asp Leu Ala Lys Lys Leu Pro Asn Val Leu Phe Leu Lys
    50                  55                  60

Val Asp Thr Asp Glu Leu Lys Ser Val Ala Ser Asp Trp Ala Ile Gln
65                  70                  75                  80

Ala Met Pro Thr Phe Met Phe Leu Lys Glu Gly Lys Ile Leu Asp Lys
                85                  90                  95
```

-continued

```
Val Val Gly Ala Lys Lys Asp Glu Leu Gln Ser Thr Ile Ala Lys His
            100                 105                 110

Leu Ala Met Ala Asp Thr Ala Arg Gly Thr His His Asp Ile Ile Gly
        115                 120                 125

Arg Asp Gln Tyr Pro Met Met Gly Arg Asp Arg Asp Gln Tyr Gln Met
    130                 135                 140

Ser Gly Arg Gly Ser Asp Tyr Ser Lys Ser Arg Gln Ile Ala Lys Ala
145                 150                 155                 160

Ala Thr Ala Val Thr Ala Gly Gly Ser Leu Leu Val Leu Ser Ser Leu
                165                 170                 175

Thr Leu Val Gly Thr Val Ile Ala Leu Thr Val Ala Thr Pro Leu Leu
            180                 185                 190

Val Ile Phe Ser Pro Ile Leu Val Pro Ala Leu Ile Thr Val Ala Leu
        195                 200                 205

Leu Ile Thr Gly Phe Leu Ser Ser Gly Gly Phe Gly Ile Ala Ala Ile
    210                 215                 220

Thr Val Phe Ser Trp Ile Tyr Lys
225                 230
```

<210> SEQ ID NO 47
<211> LENGTH: 55
<212> TYPE: PRT
<213> ORGANISM: Artificial Sequence
<220> FEATURE:
<223> OTHER INFORMATION: Description of Artificial Sequence: Phaseolin promoter-Trxh oleosin-phaseolin terminator

<400> SEQUENCE: 47

```
Tyr Ala Thr Gly Glu His Pro Gln Gly Ser Asp Lys Leu Asp Ser Ala
  1               5                  10                  15

Arg Met Lys Leu Gly Ser Lys Ala Gln Asp Leu Lys Asp Arg Ala Gln
            20                  25                  30

Tyr Tyr Gly Gln Gln His Thr Gly Gly Glu His Asp Arg Asp Arg Thr
        35                  40                  45

Arg Gly Gly Gln His Thr Thr
    50                  55
```

<210> SEQ ID NO 48
<211> LENGTH: 3787
<212> TYPE: DNA
<213> ORGANISM: Artificial Sequence
<220> FEATURE:
<223> OTHER INFORMATION: Description of Artificial Sequence: Phaseolin promoter-thioredoxin reductase-phaseolin terminator
<221> NAME/KEY: CDS
<222> LOCATION: (1555)..(2553)

<400> SEQUENCE: 48

```
ctgcaggaat tcattgtact cccagtatca ttatagtgaa agttttggct ctctcgccgg    60
tggtttttta cctctattta aagggtttt ccacctaaaa attctggtat cattctcact   120
ttacttgtta ctttaatttc tcataatctt tggttgaaat tatcacgctt ccgcacacga   180
tatccctaca aatttattat ttgttaaaca ttttcaaacc gcataaaatt ttatgaagtc   240
ccgtctatct ttaatgtagt ctaacatttt catattgaaa tatataattt acttaattt    300 agcgttggta gaaagcataa tgatttattc ttattcttct tcatataaat gtttaatata   360
caatataaac aaattcttta ccttaagaag gatttcccat tttatatttt aaaaatatat   420
ttatcaaata ttttcaacc acgtaaatct cataataata agttgtttca aaagtaataa   480
```

```
aatttaactc cataatttt ttattcgact gatcttaaag caacacccag tgacacaact      540 agccatttt ttctttgaat aaaaaaatcc aattatcatt gtatttttt tatacaatga      600 aaatttcacc aaacaatcat ttgtggtatt tctgaagcaa gtcatgttat gcaaaattct      660
ataattccca tttgacacta cggaagtaac tgaagatctg cttttacatg cgagacacat      720
cttctaaagt aattttaata atagttacta tattcaagat ttcatatatc aaatactcaa      780
tattacttct aaaaaattaa ttagatataa ttaaaatatt actttttaa ttttaagttt      840 aattgttgaa tttgtgacta ttgatttatt attctactat gtttaaattg ttttatagat      900
agtttaaagt aaatataagt aatgtagtag agtgttagag tgttaccta aaccataaac      960 tataagattt atggtggact aattttcata tatttcttat tgcttttacc ttttcttggt     1020
atgtaagtcc gtaactggaa ttactgtggg ttgccatggc actctgtggt cttttggttc     1080
atgcatggat gcttgcgcaa gaaaaagaca agaacaaag aaaaaagaca aaacagagag     1140
acaaaacgca atcacacaac caactcaaat tagtcactgg ctgatcaaga tcgccgcgtc     1200
catgtatgtc taaatgccat gcaaagcaac acgtgcttaa catgcacttt aaatggctca     1260
cccatctcaa cccacacaca aacacattgc ctttttcttc atcatcacca caaccacctg     1320
tatatattca ttctcttccg ccacctcaat ttcttcactt caacacacgt caacctgcat     1380
atgcgtgtca tcccatgccc aaatctccat gcatgttcca accaccttct ctcttatata     1440 ataccctataa ataccctctaa tatcactcac ttctttcatc atccatccat ccagagtact     1500
actactctac tactataata ccccaaccca actcatattc aatactactc tact atg       1557
                                                               Met
                                                                 1 aat ggt ctc gaa act cac aac aca agg ctc tgt atc gta gga agt ggc     1605
Asn Gly Leu Glu Thr His Asn Thr Arg Leu Cys Ile Val Gly Ser Gly
         5                  10                  15 cca gcg gca cac acg gcg gcg att tac gca gct agg gct gaa ctt aaa     1653
Pro Ala Ala His Thr Ala Ala Ile Tyr Ala Ala Arg Ala Glu Leu Lys
     20                  25                  30 cct ctt ctc ttc gaa gga tgg atg gct aac gac atc gct ccc ggt ggt     1701
Pro Leu Leu Phe Glu Gly Trp Met Ala Asn Asp Ile Ala Pro Gly Gly
 35                  40                  45 caa cta aca acc acc acc gac gtc gag aat ttc ccc gga ttt cca gaa     1749
Gln Leu Thr Thr Thr Thr Asp Val Glu Asn Phe Pro Gly Phe Pro Glu
 50                  55                  60                  65 ggt att ctc gga gta gag ctc act gac aaa ttc cgt aaa caa tcg gag     1797
Gly Ile Leu Gly Val Glu Leu Thr Asp Lys Phe Arg Lys Gln Ser Glu
                 70                  75                  80 cga ttc ggt act acg ata ttt aca gag acg gtg acg aaa gtc gat ttc     1845
Arg Phe Gly Thr Thr Ile Phe Thr Glu Thr Val Thr Lys Val Asp Phe
             85                  90                  95 tct tcg aaa ccg ttt aag cta ttc aca gat tca aaa gcc att ctc gct     1893
Ser Ser Lys Pro Phe Lys Leu Phe Thr Asp Ser Lys Ala Ile Leu Ala
        100                 105                 110 gac gct gtg att ctc gct act gga gct gtg gct aag cgg ctt agc ttc     1941
Asp Ala Val Ile Leu Ala Thr Gly Ala Val Ala Lys Arg Leu Ser Phe
    115                 120                 125 gtt gga tct ggt gaa ggt tct gga ggt ttc tgg aac cgt gga atc tcc     1989
Val Gly Ser Gly Glu Gly Ser Gly Gly Phe Trp Asn Arg Gly Ile Ser
130                 135                 140                 145 gct tgt gct gtt tgc gac gga gct gct ccg ata ttc cgt aac aaa cct     2037
Ala Cys Ala Val Cys Asp Gly Ala Ala Pro Ile Phe Arg Asn Lys Pro
                150                 155                 160
```

```
ctt gcg gtg atc ggt gga ggc gat tca gca atg gaa gaa gca aac ttt    2085
Leu Ala Val Ile Gly Gly Gly Asp Ser Ala Met Glu Glu Ala Asn Phe
            165                 170                 175 ctt aca aaa tat gga tct aaa gtg tat ata atc cat agg aga gat gct    2133
Leu Thr Lys Tyr Gly Ser Lys Val Tyr Ile Ile His Arg Arg Asp Ala
        180                 185                 190 ttt aga gcg tct aag att atg cag cag cga gct ttg tct aat cct aag    2181
Phe Arg Ala Ser Lys Ile Met Gln Gln Arg Ala Leu Ser Asn Pro Lys
    195                 200                 205 att gat gtg att tgg aac tcg tct gtt gtg gaa gct tat gga gat gga    2229
Ile Asp Val Ile Trp Asn Ser Ser Val Val Glu Ala Tyr Gly Asp Gly
210                 215                 220                 225 gaa aga gat gtg ctt gga gga ttg aaa gtg aag aat gtg gtt acc gga    2277
Glu Arg Asp Val Leu Gly Gly Leu Lys Val Lys Asn Val Val Thr Gly
            230                 235                 240 gat gtt tct gat tta aaa gtt tct gga ttg ttc ttt gct att ggt cat    2325
Asp Val Ser Asp Leu Lys Val Ser Gly Leu Phe Phe Ala Ile Gly His
        245                 250                 255 gag cca gct acc aag ttt ttg gat ggt ggt gtt gag tta gat tcg gat    2373
Glu Pro Ala Thr Lys Phe Leu Asp Gly Gly Val Glu Leu Asp Ser Asp
    260                 265                 270 ggt tat gtt gtc acg aag cct ggt act aca cag act agc gtt ccc gga    2421
Gly Tyr Val Val Thr Lys Pro Gly Thr Thr Gln Thr Ser Val Pro Gly
275                 280                 285 gtt ttc gct gcg ggt gat gtt cag gat aag aag tat agg caa gcc atc    2469
Val Phe Ala Ala Gly Asp Val Gln Asp Lys Lys Tyr Arg Gln Ala Ile
290                 295                 300                 305 act gct gca gga act ggg tgc atg gca gct ttg gat gca gag cat tac    2517
Thr Ala Ala Gly Thr Gly Cys Met Ala Ala Leu Asp Ala Glu His Tyr
            310                 315                 320 tta caa gag att gga tct cag caa ggt aag agt gat tgaagcttaa         2563
Leu Gln Glu Ile Gly Ser Gln Gln Gly Lys Ser Asp
        325                 330 taagtatgaa ctaaaatgca tgtaggtgta agagctcatg gagagcatgg aatattgtat    2623
ccgaccatgt aacagtataa taactgagct ccatctcact tcttctatga ataaacaaag    2683
gatgttatga tatattaaca ctctatctat gcaccttatt gttctatgat aaatttcctc    2743
ttattattat aaatcatctg aatcgtgacg gcttatggaa tgcttcaaat agtacaaaaa    2803
caaatgtgta ctataagact ttctaaacaa ttctaacttt agcattgtga acgagacata    2863
agtgttaaga agacataaca atttaatggg aagaagtttg tctccattta tatattatat    2923 attcccact tatgtattat attaggatgt taaggagaca taacaattat aaagagagaa    2983
gtttgtatcc atttatatat tatatactac ccatttatat attatactta tccacttatt    3043
taatgtcttt ataaggtttg atccatgata tttctaatat tttagttgat atgtatatga    3103
aagggtacta tttgaactct cttactctgt ataaaggttg gatcatcctt aaagtgggtc    3163
tatttaattt tattgcttct tacagataaa aaaaaaatta tgagttggtt tgataaaata    3223
ttgaaggatt taaataata ataaataata aataacatat aatatatgta tataaattta    3283
ttataatata acatttatct ataaaaaagt aaatattgtc ataaatctat acaatcgttt    3343
agccttgctg gacgactctc aatttattaa acgagagtaa acatatttga cttttttggtt   3403 atttaacaaa ttattattta acactatatg aaattttttt tttttatcgg caaggaaata    3463
aaattaaatt aggagggaca atggtgtgtc ccaatcctta acaaccaac ttccacagga     3523 aggtcaggtc ggggacaaca aaaaaacagg caagggaaat ttttaatttt ggggttgtctt   3583 gtttgctgca taatttatgc agtaaaacac tacacataac ccttttagca gtagagcaat    3643
```

-continued

```
ggttgaccgt gtgcttagct tcttttattt tattttttta tcagcaaaga ataaataaaa      3703
taaaatgaga cacttcaggg atgtttcaac ccttatacaa aaccccaaaa acaagtttcc      3763 tagcaccta ccaactaagg tacc                                             3787
```

<210> SEQ ID NO 49
<211> LENGTH: 333
<212> TYPE: PRT
<213> ORGANISM: Artificial Sequence
<220> FEATURE:
<223> OTHER INFORMATION: Description of Artificial Sequence: Phaseolin
     promoter-thioredoxin reductase-phaseolin
     terminator

<400> SEQUENCE: 49

```
Met Asn Gly Leu Glu Thr His Asn Thr Arg Leu Cys Ile Val Gly Ser
 1               5                  10                  15

Gly Pro Ala Ala His Thr Ala Ala Ile Tyr Ala Ala Arg Ala Glu Leu
            20                  25                  30

Lys Pro Leu Leu Phe Glu Gly Trp Met Ala Asn Asp Ile Ala Pro Gly
        35                  40                  45

Gly Gln Leu Thr Thr Thr Thr Asp Val Glu Asn Phe Pro Gly Phe Pro
    50                  55                  60

Glu Gly Ile Leu Gly Val Glu Leu Thr Asp Lys Phe Arg Lys Gln Ser
65                  70                  75                  80

Glu Arg Phe Gly Thr Thr Ile Phe Thr Glu Thr Val Thr Lys Val Asp
                85                  90                  95

Phe Ser Ser Lys Pro Phe Lys Leu Phe Thr Asp Ser Lys Ala Ile Leu
            100                 105                 110

Ala Asp Ala Val Ile Leu Ala Thr Gly Ala Val Ala Lys Arg Leu Ser
        115                 120                 125

Phe Val Gly Ser Gly Glu Gly Ser Gly Phe Trp Asn Arg Gly Ile
    130                 135                 140

Ser Ala Cys Ala Val Cys Asp Gly Ala Ala Pro Ile Phe Arg Asn Lys
145                 150                 155                 160

Pro Leu Ala Val Ile Gly Gly Gly Asp Ser Ala Met Glu Glu Ala Asn
                165                 170                 175

Phe Leu Thr Lys Tyr Gly Ser Lys Val Tyr Ile Ile His Arg Arg Asp
            180                 185                 190

Ala Phe Arg Ala Ser Lys Ile Met Gln Gln Arg Ala Leu Ser Asn Pro
        195                 200                 205

Lys Ile Asp Val Ile Trp Asn Ser Ser Val Val Glu Ala Tyr Gly Asp
    210                 215                 220

Gly Glu Arg Asp Val Leu Gly Gly Leu Lys Val Lys Asn Val Val Thr
225                 230                 235                 240

Gly Asp Val Ser Asp Leu Lys Val Ser Gly Leu Phe Phe Ala Ile Gly
                245                 250                 255

His Glu Pro Ala Thr Lys Phe Leu Asp Gly Gly Val Glu Leu Asp Ser
            260                 265                 270

Asp Gly Tyr Val Val Thr Lys Pro Gly Thr Thr Gln Thr Ser Val Pro
        275                 280                 285

Gly Val Phe Ala Ala Gly Asp Val Gln Asp Lys Lys Tyr Arg Gln Ala
    290                 295                 300

Ile Thr Ala Ala Gly Thr Gly Cys Met Ala Ala Leu Asp Ala Glu His
305                 310                 315                 320
```

Tyr Leu Gln Glu Ile Gly Ser Gln Gln Gly Lys Ser Asp
              325                 330

<210> SEQ ID NO 50
<211> LENGTH: 4546
<212> TYPE: DNA
<213> ORGANISM: Artificial Sequence
<220> FEATURE:
<223> OTHER INFORMATION: Description of Artificial Sequence: Phaseolin
      promoter-oleosin thioredoxin reducatse-phaseolin
      terminator
<221> NAME/KEY: CDS
<222> LOCATION: (1555)..(1908)
<221> NAME/KEY: CDS
<222> LOCATION: (2149)..(3312)

<400> SEQUENCE: 50

```
ctgcaggaat tcattgtact cccagtatca ttatagtgaa agttttggct ctctcgccgg      60
tggttttta cctctattta aaggggtttt ccacctaaaa attctggtat cattctcact     120
ttacttgtta ctttaatttc tcataatctt tggttgaaat tatcacgctt ccgcacacga    180
tatccctaca aatttattat ttgttaaaca ttttcaaacc gcataaaatt ttatgaagtc    240
ccgtctatct ttaatgtagt ctaacatttt catattgaaa tatataattt acttaatttt    300
agcgttggta gaaagcataa tgattttattc ttattcttct tcataaat gtttaatata     360
caatataaac aaattcttta ccttaagaag gatttcccat tttatatttt aaaaatatat    420
ttatcaaata tttttcaacc acgtaaatct cataataata agttgtttca aaagtaataa    480
aatttaactc cataattttt ttattcgact gatcttaaag caacacccag tgacacaact    540
agccattttt ttctttgaat aaaaaaatcc aattatcatt gtattttttt tatacaatga    600
aaatttcacc aaacaatcat ttgtggtatt tctgaagcaa gtcatgttat gcaaaattct    660
ataattccca tttgacacta cggaagtaac tgaagatctg cttttacatg cgagacacat    720
cttctaaagt aattttaata atagttacta tattcaagat ttcatatatc aaatactcaa    780
tattacttct aaaaaattaa ttagatataa ttaaaatatt acttttttaa ttttaagttt    840
aattgttgaa tttgtgacta ttgatttatt attctactat gtttaaattg ttttatagat    900
agtttaaagt aaatataagt aatgtagtag agtgttagag tgttacccta aaccataaac    960
tataagattt atggtggact aattttcata tatttcttat tgcttttacc ttttcttggt   1020
atgtaagtcc gtaactggaa ttactgtggg ttgccatggc actctgtggt cttttggttc   1080
atgcatggat gcttgcgcaa gaaaaagaca agaacaaag aaaaaagaca aacagagag    1140
acaaaacgca atcacacaac caactcaaat tagtcactgg ctgatcaaga tcgccgcgtc   1200
catgtatgtc taaatgccat gcaaagcaac acgtgcttaa catgcacttt aaatggctca   1260
cccatctcaa cccacacaca aacacattgc cttttttcttc atcatccaca caaccacctg   1320
tatatattca ttctcttccg ccacctcaat ttcttcactt caacacacgt caacctgcat   1380
atgcgtgtca tcccatgccc aaatctccat gcatgttcca accacttct ctcttatata    1440
ataccctataa atacctctaa tatcactcac ttctttcatc atccatccat ccagagtact   1500
actactctac tactataata ccccaaccca actcatattc aatactactc tact atg     1557
                                                              Met
                                                                1
gcg gat aca gct aga gga acc cat cac gat atc atc ggc aga gac cag   1605
Ala Asp Thr Ala Arg Gly Thr His His Asp Ile Ile Gly Arg Asp Gln
        5                   10                  15
tac ccg atg atg ggc cga gac cga gac cag tac cag atg tcc gga cga   1653
Tyr Pro Met Met Gly Arg Asp Arg Asp Gln Tyr Gln Met Ser Gly Arg
```

```
                    20                  25                  30
gga tct gac tac tcc aag tct agg cag att gct aaa gct gca act gct      1701
Gly Ser Asp Tyr Ser Lys Ser Arg Gln Ile Ala Lys Ala Ala Thr Ala
         35                  40                  45 gtc aca gct ggt ggt tcc ctc ctt gtt ctc tcc agc ctt acc ctt gtt      1749
Val Thr Ala Gly Gly Ser Leu Leu Val Leu Ser Ser Leu Thr Leu Val
 50                  55                  60                  65 gga act gtc ata gct ttg act gtt gca aca cct ctg ctc gtt atc ttc      1797
Gly Thr Val Ile Ala Leu Thr Val Ala Thr Pro Leu Leu Val Ile Phe
                 70                  75                  80 agc cca atc ctt gtc ccg gct ctc atc aca gtt gca ctc ctc atc acc      1845
Ser Pro Ile Leu Val Pro Ala Leu Ile Thr Val Ala Leu Leu Ile Thr
             85                  90                  95 ggt ttt ctt tcc tct gga ggg ttt ggc att gcc gct ata acc gtt ttc      1893
Gly Phe Leu Ser Ser Gly Gly Phe Gly Ile Ala Ala Ile Thr Val Phe
         100                 105                 110 tct tgg att tac aag taagcacaca tttatcatct tacttcataa ttttgtgcaa      1948
Ser Trp Ile Tyr Lys
     115 tatgtgcatg catgtgttga gccagtagct ttggatcaat ttttttggtc gaataacaaa    2008 tgtaacaata agaaattgca aattctaggg aacatttggt taactaaata cgaaatttga    2068 cctagctagc ttgaatgtgt ctgtgtatat catctatata ggtaaaatgc ttggtatgat    2128 acctattgat tgtgaatagg tac gca acg gga gag cac cca cag gga tca gac    2181
                      Tyr Ala Thr Gly Glu His Pro Gln Gly Ser Asp
                                          120                 125 aag ttg gac agt gca agg atg aag ttg gga agc aaa gct cag gat ctg      2229
Lys Leu Asp Ser Ala Arg Met Lys Leu Gly Ser Lys Ala Gln Asp Leu
130                 135                 140                 145 aaa gac aga gct cag tac tac gga cag caa cat act ggt ggg gaa cat      2277
Lys Asp Arg Ala Gln Tyr Tyr Gly Gln Gln His Thr Gly Gly Glu His
                 150                 155                 160 gac cgt gac cgt act cgt ggt ggc cag cac act acc atg aat ggt ctc      2325
Asp Arg Asp Arg Thr Arg Gly Gly Gln His Thr Thr Met Asn Gly Leu
             165                 170                 175 gaa act cac aac aca agg ctc tgt atc gta gga agt ggc cca gcg gca      2373
Glu Thr His Asn Thr Arg Leu Cys Ile Val Gly Ser Gly Pro Ala Ala
         180                 185                 190 cac acg gcg gcg att tac gca gct agg gct gaa ctt aaa cct ctt ctc      2421
His Thr Ala Ala Ile Tyr Ala Ala Arg Ala Glu Leu Lys Pro Leu Leu
     195                 200                 205 ttc gaa gga tgg atg gct aac gac atc gct ccc ggt ggt caa cta aca      2469
Phe Glu Gly Trp Met Ala Asn Asp Ile Ala Pro Gly Gly Gln Leu Thr
210                 215                 220                 225 acc acc acc gac gtc gag aat ttc ccc gga ttt cca gaa ggt att ctc      2517
Thr Thr Thr Asp Val Glu Asn Phe Pro Gly Phe Pro Glu Gly Ile Leu
                 230                 235                 240 gga gta gag ctc act gac aaa ttc cgt aaa caa tcg gag cga ttc ggt      2565
Gly Val Glu Leu Thr Asp Lys Phe Arg Lys Gln Ser Glu Arg Phe Gly
             245                 250                 255 act acg ata ttt aca gag acg gtg acg aaa gtc gat ttc tct tcg aaa      2613
Thr Thr Ile Phe Thr Glu Thr Val Thr Lys Val Asp Phe Ser Ser Lys
         260                 265                 270 ccg ttt aag cta ttc aca gat tca aaa gcc att ctc gct gac gct gtg      2661
Pro Phe Lys Leu Phe Thr Asp Ser Lys Ala Ile Leu Ala Asp Ala Val
     275                 280                 285 att ctc gct act gga gct gtg gct aag cgg ctt agc ttc gtt gga tct      2709
Ile Leu Ala Thr Gly Ala Val Ala Lys Arg Leu Ser Phe Val Gly Ser
290                 295                 300                 305
```

-continued

| | |
|---|---|
| ggt gaa ggt tct gga ggt ttc tgg aac cgt gga atc tcc gct tgt gct<br>Gly Glu Gly Ser Gly Gly Phe Trp Asn Arg Gly Ile Ser Ala Cys Ala<br>                          310                          315                    320 | 2757 |
| gtt tgc gac gga gct gct ccg ata ttc cgt aac aaa cct ctt gcg gtg<br>Val Cys Asp Gly Ala Ala Pro Ile Phe Arg Asn Lys Pro Leu Ala Val<br>                325                        330                    335 | 2805 |
| atc ggt gga ggc gat tca gca atg gaa gaa gca aac ttt ctt aca aaa<br>Ile Gly Gly Gly Asp Ser Ala Met Glu Glu Ala Asn Phe Leu Thr Lys<br>        340                        345                    350 | 2853 |
| tat gga tct aaa gtg tat ata atc cat agg aga gat gct ttt aga gcg<br>Tyr Gly Ser Lys Val Tyr Ile Ile His Arg Arg Asp Ala Phe Arg Ala<br>355                        360                        365 | 2901 |
| tct aag att atg cag cag cga gct ttg tct aat cct aag att gat gtg<br>Ser Lys Ile Met Gln Gln Arg Ala Leu Ser Asn Pro Lys Ile Asp Val<br>370                        375                        380                    385 | 2949 |
| att tgg aac tcg tct gtt gtg gaa gct tat gga gat gga gaa aga gat<br>Ile Trp Asn Ser Ser Val Val Glu Ala Tyr Gly Asp Gly Glu Arg Asp<br>                        390                        395                    400 | 2997 |
| gtg ctt gga gga ttg aaa gtg aag aat gtg gtt acc gga gat gtt tct<br>Val Leu Gly Gly Leu Lys Val Lys Asn Val Val Thr Gly Asp Val Ser<br>                  405                        410                    415 | 3045 |
| gat tta aaa gtt tct gga ttg ttc ttt gct att ggt cat gag cca gct<br>Asp Leu Lys Val Ser Gly Leu Phe Phe Ala Ile Gly His Glu Pro Ala<br>        420                        425                    430 | 3093 |
| acc aag ttt ttg gat ggt ggt gtt gag tta gat tcg gat ggt tat gtt<br>Thr Lys Phe Leu Asp Gly Gly Val Glu Leu Asp Ser Asp Gly Tyr Val<br>            435                        440                    445 | 3141 |
| gtc acg aag cct ggt act aca cag act agc gtt ccc gga gtt ttc gct<br>Val Thr Lys Pro Gly Thr Thr Gln Thr Ser Val Pro Gly Val Phe Ala<br>450                        455                        460                    465 | 3189 |
| gcg ggt gat gtt cag gat aag aag tat agg caa gcc atc act gct gca<br>Ala Gly Asp Val Gln Asp Lys Lys Tyr Arg Gln Ala Ile Thr Ala Ala<br>                        470                        475                    480 | 3237 |
| gga act ggg tgc atg gca gct ttg gat gca gag cat tac tta caa gag<br>Gly Thr Gly Cys Met Ala Ala Leu Asp Ala Glu His Tyr Leu Gln Glu<br>        485                        490                    495 | 3285 |
| att gga tct cag caa ggt aag agt gat tgaagcttaa taagtatgaa<br>Ile Gly Ser Gln Gln Gly Lys Ser Asp<br>            500                        505 | 3332 |
| ctaaaatgca tgtaggtgta agagctcatg gagagcatgg aatattgtat ccgaccatgt | 3392 |
| aacagtataa taactgagct ccatctcact tcttctatga ataaacaaag gatgttatga | 3452 |
| tatattaaca ctctatctat gcaccttatt gttctatgat aaatttcctc ttattattat | 3512 |
| aaatcatctg aatcgtgacg gcttatgaa tgcttcaaat agtacaaaaa caaatgtgta | 3572 |
| ctataagact ttctaaacaa ttctaacttt agcattgtga acgagacata agtgttaaga | 3632 |
| agacataaca attataatgg aagaagtttg tctccattta tatattatat attacccact | 3692 |
| tatgtattat attaggatgt taaggagaca taacaattat aaagagagaa gtttgtatcc | 3752 |
| atttatatat tatatactac ccatttatat attatactta tccacttatt taatgtcttt | 3812 |
| ataaggtttg atccatgata tttctaatat tttagttgat atgtatatga aagggtacta | 3872 |
| tttgaactct cttactctgt ataaggttg gatcatcctt aaagtgggtc tatttaattt | 3932 |
| tattgcttct tacagataaa aaaaaaatta tgagttggtt tgataaaata ttgaaggatt | 3992 |
| taaaataata ataataata aataacatat aatatatgta tataaattta ttataatata | 4052 |
| acatttatct ataaaaaagt aaatattgtc ataaatctat acaatcgttt agccttgctg | 4112 |

```
gacgactctc aattatttaa acgagagtaa acatatttga cttttttggtt atttaacaaa      4172 ttattattta acactatatg aaatttttttt tttttatcgg caaggaaata aaattaaatt      4232
aggagggaca atggtgtgtc ccaatcctta tacaaccaac ttccacagga aggtcaggtc      4292
ggggacaaca aaaaaacagg caagggaaat tttttaattt gggttgtctt gtttgctgca      4352
taatttatgc agtaaaacac tacacataac cctttagca gtagagcaat ggttgaccgt      4412
gtgcttagct tcttttattt tatttttta tcagcaaaga ataaataaaa taaaatgaga      4472
cacttcaggg atgtttcaac ccttatacaa aaccccaaaa acaagtttcc tagcacccta      4532
ccaactaagg tacc                                                      4546
```

<210> SEQ ID NO 51
<211> LENGTH: 118
<212> TYPE: PRT
<213> ORGANISM: Artificial Sequence
<220> FEATURE:
<223> OTHER INFORMATION: Description of Artificial Sequence: Phaseolin
      promoter-oleosin thioredoxin reducatse-phaseolin
      terminator

<400> SEQUENCE: 51

```
Met Ala Asp Thr Ala Arg Gly Thr His His Asp Ile Ile Gly Arg Asp
 1               5                  10                  15

Gln Tyr Pro Met Met Gly Arg Asp Arg Asp Gln Tyr Gln Met Ser Gly
                20                  25                  30

Arg Gly Ser Asp Tyr Ser Lys Ser Arg Gln Ile Ala Lys Ala Ala Thr
            35                  40                  45

Ala Val Thr Ala Gly Gly Ser Leu Leu Val Leu Ser Ser Leu Thr Leu
        50                  55                  60

Val Gly Thr Val Ile Ala Leu Thr Val Ala Thr Pro Leu Leu Val Ile
    65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
               100                 105                 110

Phe Ser Trp Ile Tyr Lys
            115
```

<210> SEQ ID NO 52
<211> LENGTH: 388
<212> TYPE: PRT
<213> ORGANISM: Artificial Sequence
<220> FEATURE:
<223> OTHER INFORMATION: Description of Artificial Sequence: Phaseolin
      promoter-oleosin thioredoxin reducatse-phaseolin
      terminator

<400> SEQUENCE: 52

```
Tyr Ala Thr Gly Glu His Pro Gln Gly Ser Asp Lys Leu Asp Ser Ala
 1               5                  10                  15

Arg Met Lys Leu Gly Ser Lys Ala Gln Asp Leu Lys Asp Arg Ala Gln
                20                  25                  30

Tyr Tyr Gly Gln Gln His Thr Gly Gly Glu His Asp Arg Asp Arg Thr
            35                  40                  45

Arg Gly Gly Gln His Thr Thr Met Asn Gly Leu Glu Thr His Asn Thr
        50                  55                  60

Arg Leu Cys Ile Val Gly Ser Gly Pro Ala Ala His Thr Ala Ala Ile
    65                  70                  75                  80
```

```
Tyr Ala Ala Arg Ala Glu Leu Lys Pro Leu Leu Phe Glu Gly Trp Met
                85                  90                  95

Ala Asn Asp Ile Ala Pro Gly Gly Gln Leu Thr Thr Thr Asp Val
            100                 105                 110

Glu Asn Phe Pro Gly Phe Pro Glu Gly Ile Leu Gly Val Glu Leu Thr
        115                 120                 125

Asp Lys Phe Arg Lys Gln Ser Glu Arg Phe Gly Thr Thr Ile Phe Thr
    130                 135                 140

Glu Thr Val Thr Lys Val Asp Phe Ser Ser Lys Pro Phe Lys Leu Phe
145                 150                 155                 160

Thr Asp Ser Lys Ala Ile Leu Ala Asp Ala Val Ile Leu Ala Thr Gly
                165                 170                 175

Ala Val Ala Lys Arg Leu Ser Phe Val Gly Ser Gly Glu Gly Ser Gly
                180                 185                 190

Gly Phe Trp Asn Arg Gly Ile Ser Ala Cys Ala Val Cys Asp Gly Ala
            195                 200                 205

Ala Pro Ile Phe Arg Asn Lys Pro Leu Ala Val Ile Gly Gly Gly Asp
    210                 215                 220

Ser Ala Met Glu Glu Ala Asn Phe Leu Thr Lys Tyr Gly Ser Lys Val
225                 230                 235                 240

Tyr Ile Ile His Arg Arg Asp Ala Phe Arg Ala Ser Lys Ile Met Gln
                245                 250                 255

Gln Arg Ala Leu Ser Asn Pro Lys Ile Asp Val Ile Trp Asn Ser Ser
            260                 265                 270

Val Val Glu Ala Tyr Gly Asp Gly Glu Arg Asp Val Leu Gly Gly Leu
    275                 280                 285

Lys Val Lys Asn Val Val Thr Gly Asp Val Ser Asp Leu Lys Val Ser
290                 295                 300

Gly Leu Phe Phe Ala Ile Gly His Glu Pro Ala Thr Lys Phe Leu Asp
305                 310                 315                 320

Gly Gly Val Glu Leu Asp Ser Asp Gly Tyr Val Val Thr Lys Pro Gly
                325                 330                 335

Thr Thr Gln Thr Ser Val Pro Gly Val Phe Ala Ala Gly Asp Val Gln
            340                 345                 350

Asp Lys Lys Tyr Arg Gln Ala Ile Thr Ala Ala Gly Thr Gly Cys Met
    355                 360                 365

Ala Ala Leu Asp Ala Glu His Tyr Leu Gln Glu Ile Gly Ser Gln Gln
370                 375                 380

Gly Lys Ser Asp
385

<210> SEQ ID NO 53
<211> LENGTH: 4545
<212> TYPE: DNA
<213> ORGANISM: Artificial Sequence
<220> FEATURE:
<223> OTHER INFORMATION: Description of Artificial Sequence: Phaseolin
      promoter-thioredoxin reductase oleosin-phaseolin
      terminator
<221> NAME/KEY: CDS
<222> LOCATION: (1555)..(2907)
<221> NAME/KEY: CDS
<222> LOCATION: (3148)..(3312)

<400> SEQUENCE: 53
ctgcaggaat tcattgtact cccagtatca ttatagtgaa agttttggct ctctcgccgg      60 tggttttta cctctatttta aagggggtttt ccacctaaaa attctggtat cattctcact   120
```

-continued

```
ttacttgtta ctttaatttc tcataatctt tggttgaaat tatcacgctt ccgcacacga      180
tatccctaca aatttattat ttgttaaaca ttttcaaacc gcataaaatt ttatgaagtc      240
ccgtctatct ttaatgtagt ctaacatttt catattgaaa tatataattt acttaatttt      300
agcgttggta gaaagcataa tgatttattc ttattcttct tcatataaat gtttaatata      360
caatataaac aaattcttta ccttaagaag gatttcccat tttatatttt aaaaatatat      420
ttatcaaata tttttcaacc acgtaaatct cataataata agttgtttca aaagtaataa      480
aatttaactc cataattttt ttattcgact gatcttaaag caacacccag tgacacaact      540
agccattttt ttctttgaat aaaaaaatcc aattatcatt gtattttttt tatacaatga      600
aaatttcacc aaacaatcat ttgtggtatt tctgaagcaa gtcatgttat gcaaaattct      660
ataattccca tttgacacta cggaagtaac tgaagatctg cttttacatg cgagacacat      720
cttctaaagt aattttaata atagttacta tattcaagat ttcatatatc aaatactcaa      780
tattacttct aaaaaattaa ttagatataa ttaaaatatt acttttttaa ttttaagttt      840
aattgttgaa tttgtgacta ttgatttatt attctactat gtttaaattg ttttatagat      900
agtttaaagt aaatataagt aatgtagtag agtgttagag tgttacccta aaccataaac      960
tataagattt atggtggact aattttcata tatttcttat tgcttttacc ttttcttggt     1020
atgtaagtcc gtaactggaa ttactgtggg ttgccatggc actctgtggt cttttggttc     1080
atgcatggat gcttgcgcaa gaaaaagaca agaacaaag aaaaaagaca aaacagagag      1140
acaaaacgca atcacacaac caactcaaat tagtcactgg ctgatcaaga tcgccgcgtc     1200
catgtatgtc taaatgccat gcaaagcaac acgtgcttaa catgcacttt aaatggctca     1260
cccatctcaa cccacacaca aacacattgc cttttttcttc atcatcacca caaccacctg     1320
tatatattca ttctcttccg ccacctcaat ttcttcactt caacacacgt caacctgcat     1380
atgcgtgtca tcccatgccc aaatctccat gcatgttcca accaccttct ctcttatata     1440
ataccctataa ataccctctaa tatcactcac ttctttcatc atccatccat ccagagtact     1500
actactctac tactataata ccccaaccca actcatattc aatactactc tact atg      1557
                                                                 Met
                                                                  1 aat ggt ctc gaa act cac aac aca agg ctc tgt atc gta gga agt ggc      1605
Asn Gly Leu Glu Thr His Asn Thr Arg Leu Cys Ile Val Gly Ser Gly
      5                  10                  15 cca gcg gca cac acg gcg gcg att tac gca gct agg gct gaa ctt aaa      1653
Pro Ala His Thr Ala Ala Ile Tyr Ala Ala Arg Ala Glu Leu Lys
 20                  25                  30 cct ctt ctc ttc gaa gga tgg atg gct aac gac atc gct ccc ggt ggt      1701
Pro Leu Leu Phe Glu Gly Trp Met Ala Asn Asp Ile Ala Pro Gly Gly
 35                  40                  45 caa cta aca acc acc acc gac gtc gag aat ttc ccc gga ttt cca gaa      1749
Gln Leu Thr Thr Thr Thr Asp Val Glu Asn Phe Pro Gly Phe Pro Glu
 50                  55                  60                  65 ggt att ctc gga gta gag ctc act gac aaa ttc cgt aaa caa tcg gag      1797
Gly Ile Leu Gly Val Glu Leu Thr Asp Lys Phe Arg Lys Gln Ser Glu
         70                  75                  80 cga ttc ggt act acg ata ttt aca gag acg gtg acg aaa gtc gat ttc      1845
Arg Phe Gly Thr Thr Ile Phe Thr Glu Thr Val Thr Lys Val Asp Phe
         85                  90                  95 tct tcg aaa ccg ttt aag cta ttc aca gat tca aaa gcc att ctc gct      1893
Ser Ser Lys Pro Phe Lys Leu Phe Thr Asp Ser Lys Ala Ile Leu Ala
        100                 105                 110
```

-continued

| | |
|---|---|
| gac gct gtg att ctc gct act gga gct gtg gct aag cgg ctt agc ttc<br>Asp Ala Val Ile Leu Ala Thr Gly Ala Val Ala Lys Arg Leu Ser Phe<br>115                          120                    125 | 1941 |
| gtt gga tct ggt gaa ggt tct gga ggt ttc tgg aac cgt gga atc tcc<br>Val Gly Ser Gly Glu Gly Ser Gly Gly Phe Trp Asn Arg Gly Ile Ser<br>130                         135                 140                 145 | 1989 |
| gct tgt gct gtt tgc gac gga gct gct ccg ata ttc cgt aac aaa cct<br>Ala Cys Ala Val Cys Asp Gly Ala Ala Pro Ile Phe Arg Asn Lys Pro<br>                150                 155                  160 | 2037 |
| ctt gcg gtg atc ggt gga ggc gat tca gca atg gaa gaa gca aac ttt<br>Leu Ala Val Ile Gly Gly Gly Asp Ser Ala Met Glu Glu Ala Asn Phe<br>           165                   170                 175 | 2085 |
| ctt aca aaa tat gga tct aaa gtg tat ata atc cat agg aga gat gct<br>Leu Thr Lys Tyr Gly Ser Lys Val Tyr Ile Ile His Arg Arg Asp Ala<br>      180                  185                 190 | 2133 |
| ttt aga gcg tct aag att atg cag cag cga gct ttg tct aat cct aag<br>Phe Arg Ala Ser Lys Ile Met Gln Gln Arg Ala Leu Ser Asn Pro Lys<br>195                         200                 205 | 2181 |
| att gat gtg att tgg aac tcg tct gtt gtg gaa gct tat gga gat gga<br>Ile Asp Val Ile Trp Asn Ser Ser Val Val Glu Ala Tyr Gly Asp Gly<br>210                         215                 220                 225 | 2229 |
| gaa aga gat gtg ctt gga gga ttg aaa gtg aag aat gtg gtt acc gga<br>Glu Arg Asp Val Leu Gly Gly Leu Lys Val Lys Asn Val Val Thr Gly<br>                230                 235                 240 | 2277 |
| gat gtt tct gat tta aaa gtt tct gga ttg ttc ttt gct att ggt cat<br>Asp Val Ser Asp Leu Lys Val Ser Gly Leu Phe Phe Ala Ile Gly His<br>           245                   250                 255 | 2325 |
| gag cca gct acc aag ttt ttg gat ggt ggt gtt gag tta gat tcg gat<br>Glu Pro Ala Thr Lys Phe Leu Asp Gly Gly Val Glu Leu Asp Ser Asp<br>      260                  265                 270 | 2373 |
| ggt tat gtt gtc acg aag cct ggt act aca cag act agc gtt ccc gga<br>Gly Tyr Val Val Thr Lys Pro Gly Thr Thr Gln Thr Ser Val Pro Gly<br>275                         280                 285 | 2421 |
| gtt ttc gct gcg ggt gat gtt cag gat aag aag tat agg caa gcc atc<br>Val Phe Ala Ala Gly Asp Val Gln Asp Lys Lys Tyr Arg Gln Ala Ile<br>290                         295                 300                 305 | 2469 |
| act gct gca gga act ggg tgc atg gca gct ttg gat gca gag cat tac<br>Thr Ala Ala Gly Thr Gly Cys Met Ala Ala Leu Asp Ala Glu His Tyr<br>                310                 315                 320 | 2517 |
| tta caa gag att gga tct cag caa ggt aag agt gat atg gcg gat aca<br>Leu Gln Glu Ile Gly Ser Gln Gln Gly Lys Ser Asp Met Ala Asp Thr<br>           325                   330                 335 | 2565 |
| gct aga gga acc cat cac gat atc atc ggc aga gac cag tac ccg atg<br>Ala Arg Gly Thr His His Asp Ile Ile Gly Arg Asp Gln Tyr Pro Met<br>      340                  345                 350 | 2613 |
| atg ggc cga gac cga gac cag tac cag atg tcc gga cga gga tct gac<br>Met Gly Arg Asp Arg Asp Gln Tyr Gln Met Ser Gly Arg Gly Ser Asp<br>355                         360                 365 | 2661 |
| tac tcc aag tct agg cag att gct aaa gct gca act gct gtc aca gct<br>Tyr Ser Lys Ser Arg Gln Ile Ala Lys Ala Ala Thr Ala Val Thr Ala<br>370                         375                 380                 385 | 2709 |
| ggt ggt tcc ctc ctt gtt ctc tcc agc ctt acc ctt gtt gga act gtc<br>Gly Gly Ser Leu Leu Val Leu Ser Ser Leu Thr Leu Val Gly Thr Val<br>                390                 395                 400 | 2757 |
| ata gct ttg act gtt gca aca cct ctg ctc gtt atc ttc agc cca atc<br>Ile Ala Leu Thr Val Ala Thr Pro Leu Leu Val Ile Phe Ser Pro Ile<br>           405                   410                 415 | 2805 |
| ctt gtc ccg gct ctc atc aca gtt gca ctc ctc atc acc ggt ttt ctt<br>Leu Val Pro Ala Leu Ile Thr Val Ala Leu Leu Ile Thr Gly Phe Leu<br>      420                  425                 430 | 2853 |

```
tcc tct gga ggg ttt ggc att gcc gct ata acc gtt ttc tct tgg att    2901
Ser Ser Gly Gly Phe Gly Ile Ala Ala Ile Thr Val Phe Ser Trp Ile
    435                 440                 445 tac aag taagcacaca tttatcatct tacttcataa ttttgtgcaa tatgtgcatg     2957
Tyr Lys
450 catgtgttga gccagtagct ttggatcaat ttttttggtc gaataacaaa tgtaacaata    3017 agaaattgca aattctaggg aacatttggt taactaaata cgaaatttga cctagctagc    3077 ttgaatgtgt ctgtgtatat catctatata ggtaaaatgc ttggtatgat acctattgat    3137 tgtgaatagg tac gca acg gga gag cac cca cag gga tca gac aag ttg     3186
            Tyr Ala Thr Gly Glu His Pro Gln Gly Ser Asp Lys Leu
                                    455                 460 gac agt gca agg atg aag ttg gga agc aaa gct cag gat ctg aaa gac    3234
Asp Ser Ala Arg Met Lys Leu Gly Ser Lys Ala Gln Asp Leu Lys Asp
465                 470                 475                 480 aga gct cag tac tac gga cag caa cat act ggt ggg gaa cat gac cgt    3282
Arg Ala Gln Tyr Tyr Gly Gln Gln His Thr Gly Gly Glu His Asp Arg
                    485                 490                 495 gac cgt act cgt ggt ggc cag cac act act taagcttaat aagtatgaac      3332
Asp Arg Thr Arg Gly Gly Gln His Thr Thr
                500                 505 taaaatgcat gtaggtgtaa gagctcatgg agagcatgga atattgtatc cgaccatgta    3392
acagtataat aactgagctc catctcactt cttctatgaa taaacaaagg atgttatgat    3452
atattaacac tctatctatg caccttattg ttctatgata aatttcctct tattattata    3512
aatcatctga atcgtgacgg cttatggaat gcttcaaata gtacaaaaac aaatgtgtac    3572
tataagactt tctaaacaat tctaacttta gcattgtgaa cgagacataa gtgttaagaa    3632
gacataacaa ttataatgga agaagtttgt ctccatttat atattatata ttacccactt    3692
atgtattata ttaggatgtt aaggagacat aacaattata aagagagaag tttgtatcca    3752
tttatatatt atatactacc catttatata ttatacttat ccacttattt aatgtctttta   3812 taaggtttga tccatgatat ttctaatatt ttagttgata tgtatatgaa agggtactat    3872
ttgaactctc ttactctgta taaaggttgg atcatcctta aagtgggtct atttaatttt    3932
attgcttctt acagataaaa aaaaaattat gagttggttt gataaaatat tgaaggattt    3992
aaaataataa taaataataa ataacatata atatatgtat ataaatttat tataatataa    4052
catttatcta taaaaaagta aatattgtca taaatctata caatcgttta gccttgctgg    4112
acgactctca attatttaaa cgagagtaaa catatttgac ttttttggtta tttaacaaat    4172 tattatttaa cactatatga aatttttttt tttttatcggc aaggaaataa aattaaatta    4232
ggagggacaa tggtgtgtcc caatccttat acaaccaact tccacaggaa ggtcaggtcg    4292
gggacaacaa aaaacaggc aagggaaatt ttttaatttg ggttgtcttg tttgctgcat    4352
aatttatgca gtaaaacact acacataacc cttttagcag tagagcaatg gttgaccgtg    4412
tgcttagctt cttttatttt attttttttat cagcaaagaa taaataaaat aaaatgagac    4472
acttcaggga tgtttcaacc cttatacaaa accccaaaaa caagtttcct agcaccctac    4532
caactaaggt acc                                                      4545

<210> SEQ ID NO 54
<211> LENGTH: 451
<212> TYPE: PRT
<213> ORGANISM: Artificial Sequence
<220> FEATURE:
```

-continued

<223> OTHER INFORMATION: Description of Artificial Sequence: Phaseolin
    promoter-thioredoxin reductase oleosin-phaseolin
    terminator

<400> SEQUENCE: 54

Met Asn Gly Leu Glu Thr His Asn Thr Arg Leu Cys Ile Val Gly Ser
 1               5                  10                  15

Gly Pro Ala Ala His Thr Ala Ala Ile Tyr Ala Ala Arg Ala Glu Leu
            20                  25                  30

Lys Pro Leu Leu Phe Glu Gly Trp Met Ala Asn Asp Ile Ala Pro Gly
        35                  40                  45

Gly Gln Leu Thr Thr Thr Thr Asp Val Glu Asn Phe Pro Gly Phe Pro
    50                  55                  60

Glu Gly Ile Leu Gly Val Glu Leu Thr Asp Lys Phe Arg Lys Gln Ser
65                  70                  75                  80

Glu Arg Phe Gly Thr Thr Ile Phe Thr Glu Thr Val Thr Lys Val Asp
                85                  90                  95

Phe Ser Ser Lys Pro Phe Lys Leu Phe Thr Asp Ser Lys Ala Ile Leu
            100                 105                 110

Ala Asp Ala Val Ile Leu Ala Thr Gly Ala Val Ala Lys Arg Leu Ser
        115                 120                 125

Phe Val Gly Ser Gly Glu Gly Ser Gly Gly Phe Trp Asn Arg Gly Ile
    130                 135                 140

Ser Ala Cys Ala Val Cys Asp Gly Ala Ala Pro Ile Phe Arg Asn Lys
145                 150                 155                 160

Pro Leu Ala Val Ile Gly Gly Gly Asp Ser Ala Met Glu Glu Ala Asn
                165                 170                 175

Phe Leu Thr Lys Tyr Gly Ser Lys Val Tyr Ile Ile His Arg Arg Asp
            180                 185                 190

Ala Phe Arg Ala Ser Lys Ile Met Gln Gln Arg Ala Leu Ser Asn Pro
        195                 200                 205

Lys Ile Asp Val Ile Trp Asn Ser Ser Val Val Glu Ala Tyr Gly Asp
    210                 215                 220

Gly Glu Arg Asp Val Leu Gly Gly Leu Lys Val Lys Asn Val Val Thr
225                 230                 235                 240

Gly Asp Val Ser Asp Leu Lys Val Ser Gly Leu Phe Phe Ala Ile Gly
                245                 250                 255

His Glu Pro Ala Thr Lys Phe Leu Asp Gly Gly Val Glu Leu Asp Ser
            260                 265                 270

Asp Gly Tyr Val Val Thr Lys Pro Gly Thr Thr Gln Thr Ser Val Pro
        275                 280                 285

Gly Val Phe Ala Ala Gly Asp Val Gln Asp Lys Lys Tyr Arg Gln Ala
    290                 295                 300

Ile Thr Ala Ala Gly Thr Gly Cys Met Ala Ala Leu Asp Ala Glu His
305                 310                 315                 320

Tyr Leu Gln Glu Ile Gly Ser Gln Gln Gly Lys Ser Asp Met Ala Asp
                325                 330                 335

Thr Ala Arg Gly Thr His His Asp Ile Ile Gly Arg Asp Gln Tyr Pro
            340                 345                 350

Met Met Gly Arg Asp Arg Asp Gln Tyr Gln Met Ser Gly Arg Gly Ser
        355                 360                 365

Asp Tyr Ser Lys Ser Arg Gln Ile Ala Lys Ala Ala Thr Ala Val Thr
    370                 375                 380

Ala Gly Gly Ser Leu Leu Val Leu Ser Ser Leu Thr Leu Val Gly Thr

-continued

```
385                 390                 395                 400
Val Ile Ala Leu Thr Val Ala Thr Pro Leu Leu Val Ile Phe Ser Pro
                405                 410                 415

Ile Leu Val Pro Ala Leu Ile Thr Val Ala Leu Leu Ile Thr Gly Phe
            420                 425                 430

Leu Ser Ser Gly Gly Phe Gly Ile Ala Ala Ile Thr Val Phe Ser Trp
        435                 440                 445

Ile Tyr Lys
    450

<210> SEQ ID NO 55
<211> LENGTH: 55
<212> TYPE: PRT
<213> ORGANISM: Artificial Sequence
<220> FEATURE:
<223> OTHER INFORMATION: Description of Artificial Sequence: Phaseolin
      promoter-thioredoxin reductase oleosin-phaseolin
      terminator

<400> SEQUENCE: 55

Tyr Ala Thr Gly Glu His Pro Gln Gly Ser Asp Lys Leu Asp Ser Ala
 1               5                  10                  15

Arg Met Lys Leu Gly Ser Lys Ala Gln Asp Leu Lys Asp Arg Ala Gln
            20                  25                  30

Tyr Tyr Gly Gln Gln His Thr Gly Gly Glu His Asp Arg Asp Arg Thr
        35                  40                  45

Arg Gly Gly Gln His Thr Thr
    50                  55
```

PREPARATION OF THIOREDOXIN AND THIOREDOXIN REDUCTASE PROTEINS ON OIL BODIES

CROSS-REFERENCE TO RELATED APPLICATIONS

The present application is a continuation-in-part of U.S. Ser. No. 09/210,843 that was filed Dec. 15, 1998 (now U.S. Pat. No. 6,288,304), which is a continuation-in-part of U.S. Ser. No. 08/846,021 that was filed Apr. 25, 1997 (now U.S. Pat. No. 5,948,682), which is a continuation-in-part of U.S. Ser. No. 08/366,783 that was filed on Dec. 30, 1994 (now U.S. Pat. No. 5,650,554), which is a continuation-in-part of U.S. Ser. No. 08/142,418 that was filed Nov. 16, 1993 (now abandoned), which is a continuation-in-part of U.S. Ser. No. 07/659,835 that was filed on Feb. 22, 1991 (now abandoned), all of which are incorporated by reference in their entirety.

FILED OF THE INVENTION

The present invention relates to the production of proteins such as thioredoxin and thioredoxin reductase on oil bodies.

BACKGROUND OF THE INVENTION

Many very diverse methods have been tested for the production of recombinant molecules of interest and commercial value. Different organisms that have been considered as hosts for foreign protein expression include single celled organisms such as bacteria and yeasts, cells and cell cultures of animals, fungi and plants and whole organisms such as plants, insects and transgenic animals.

The use of fermentation techniques for large-scale production of bacteria, yeasts and higher organism cell cultures is well established. The capital costs associated with establishment of the facility and the costs of maintenance are negative economic factors. Although the expression levels of proteins that can be achieved are high, energy inputs and protein purification costs can greatly increase the cost of recombinant protein production.

The production of a variety of proteins of therapeutic interest has been described in transgenic animals, however the cost of establishing substantial manufacturing is prohibitive for all but high value proteins. Numerous foreign proteins have been expressed in whole plants and selected plant organs. Methods of stably inserting recombinant DNA into plants have become routine and the number of species that are now accessible to these methods has increased greatly.

Plants represent a highly effective and economical means to produce recombinant proteins as they can be grown on a large scale with modest cost inputs and most commercially important species can now be transformed. Although the expression of foreign proteins has been clearly demonstrated, the development of systems with commercially viable levels of expression coupled with cost effective separation techniques has been limited.

The production of recombinant proteins and peptides in plants has been investigated using a variety of approaches including transcriptional fusions using a strong constitutive plant promoter (e.g., from cauliflower mosaic virus (Sijmons et al., 1990, Bio/Technology, 8:217–221); transcriptional fusions with organ specific promoter sequences (Radke etal., 1988, Theoret. Appl. Genet., 75:685–694); and translational fusions which require subsequent cleavage of a recombinant protein (Vanderkerckove et al., 1989, Bio/Technology, 7:929–932).

Foreign proteins that have been successfully expressed in plant cells include proteins from bacteria (Fraley et al., 1983, Proc. Natl. Acad. Sci. USA, 80:4803–4807), animals (Misra and Gedamu, 1989, Theor. Appl. Genet., 78:161–168), fungi and other plant species (Fraley et al., 1983, Proc. Natl. Acad. Sci. USA, 80:4803–4807). Some proteins, predominantly markers of DNA integration, have been expressed in specific cells and tissues including seeds (Sen Gupta-Gopalan et al., 1985, Proc. Natl. Acad. Sci. USA, 82:3320–3324); Radke et al., 1988, Theor. Appl. Genet., 75:685–694). Seed specific research has been focused on the use of seed-storage protein promoters as a means of deriving seed-specific expression. Using such a system, Vanderkerckove et al., (1989, Bio/Technol., 7:929–932) expressed the peptide leu-enkephalin in seeds of *Arabidopsis thaliana* and *Brassica napus*. The level of expression of this peptide was quite low and it appeared that expression of this peptide was limited to endosperm tissue.

It has been generally shown that the construction of chimeric genes which contain the promoter from a given regulated gene and a coding sequence of a reporter protein not normally associated with that promoter gives rise to regulated expression of the reporter. The use of promoters from seed-specific genes for the expression of recombinant sequences in seed that are not normally expressed in a seed-specific manner have been described.

Sengupta-Gopalan et al., (1985, Proc. Natl. Acad. Sci. USA, 82:3320–3324) reported expression of a major storage protein of french bean, called β-phaseolin, in tobacco plants. The gene expressed correctly in the seeds and only at very low levels elsewhere in the plant. However, the constructs used by Sengupta-Gopalan were not chimeric. The entire β-phaseolin gene including the native 5'-flanking sequences were used. Subsequent experiments with other species (Radke et al., 1988, Theor. App. Genet. 75:685–694) or other genes (Perez-Grau, L., Goldberg, R. B., 1989, Plant Cell, 1:1095–1109) showed the fidelity of expression in a seed-specific manner in both Arabidopsis and Brassica. Radke et al., (1988, vide supra), used a "tagged" gene i.e., one containing the entire napin gene plus a non-translated "tag".

The role of the storage proteins is to serve as a reserve of nitrogen during seed germination and growth. Although storage protein genes can be expressed at high levels, they represent a class of protein whose complete three-dimensional structure appears important for proper packaging and storage. The storage proteins generally assemble into multimeric units which are arranged in specific bodies in endosperm tissue. Perturbation of the structure by the addition of foreign peptide sequences leads to storage proteins unable to be packaged properly in the seed.

In addition to nitrogen, the seed also stores lipids. The storage of lipids occurs in oil or lipid bodies. Analysis of the contents of lipid bodies has demonstrated that in addition to triglyceride and membrane lipids, there are also several polypeptides/proteins associated with the surface or lumen of the oil body (Bowman-Vance and Huang, 1987, J. Biol. Chem., 262:11275–11279, Murphy et al., 1989, Biochem. J., 258:285–293, Taylor et al., 1990, Planta, 181:18–26). Oil-body proteins have been identified in a wide range of taxonomically diverse species (Moreau et al., 1980, Plant Physiol., 65:1176–1180; Qu et al., 1986, Biochem. J., 235:57–65) and have been shown to be uniquely localized in oil-bodies and not found in organelles of vegetative tissues. In *Brassica napus* (rapeseed, canola) there are at least three polypeptides associated with the oil-bodies of developing seeds (Taylor et al., 1990, Planta, 181:18–26).

The oil bodies that are produced in seeds are of a similar size (Huang A. H. C., 1985, in Modern Meths. Plant Analysis, Vol. 1:145–151 Springer-Verlag, Berlin). Electron microscopic observations have shown that the oil-bodies are surrounded by a membrane and are not freely suspended in the cytoplasm. These oil-bodies have been variously named by electron microscopists as oleosomes, lipid bodies and spherosomes (Gurr MI., 1980, in The Biochemistry of Plants, 4:205–248, Acad. Press, Orlando, Fla.). The oil-bodies of the species that have been studied are encapsulated by an unusual "half-unit" membrane comprising, not a classical lipid bilayer, but rather a single amphophilic layer with hydrophobic groups on the inside and hydrophillic groups on the outside (Huang A. H. C., 1985, in Modern Meths. Plant Analysis, Vol. 1:145–151 Springer-Verlag, Berlin).

The numbers and sizes of oil-body associated proteins may vary from species to species. In corn, for example, there are two immunologically distinct polypeptide classes found in oil-bodies (Bowman-Vance and Huang, 1988, J. Biol. Chem., 263:1476–1481). Oleosins have been shown to comprise alternate hydrophillic and hydrophobic regions (Bowman-Vance and Huang, 1987, J. Biol. Chem., 262:11275–11279). The amino acid sequences of oleosins from corn, rapeseed, and carrot have been obtained. See Qu and Huang, 1990, J. Biol. Chem., 265:2238–2243, Hatzopoulos et al., 1990, Plant Cell, 2:457–467, respectively. In an oilseed such as rapeseed, oleosin may comprise between 8% (Taylor et al., 1990, Planta, 181:18–26) and 20% (Murphy et al., 1989, Biochem. J., 258:285–293) of total seed protein. Such a level is comparable to that found for many seed storage proteins.

Genomic clones encoding oil-body proteins with their associated upstream regions have been reported for several species, including maize (Zea mays, Bowman-Vance and Huang, 1987, J. Biol. Chem., 262:11275–11279; and Qu Huang, 1990, J. Biol. Chem., 265:2238–2243) and carrot (Hatzopoulos et al., 1990, Plant Cell, 2:457–467). cDNAs and genomic clones have also been reported for cultivated oilseeds, Brassica napus (Murphy, et al., 1991, Biochem. Biophys. Acta, 1088:86–94; and Lee and Huang, 1991, Plant Physiol 96:1395–1397), sunflower (Cummins and Murphy, 1992, Plant Molec. Biol. 19:873–878) soybean (Kalinski et al., 1991, Plant Molec. Biol. 17: 1095–1098), and cotton (Hughes et al., 1993, Plant Physiol 101:697–698). Reports on the expression of these oil-body protein genes in developing seeds have varied. In the case of Zea mays, transcription of genes encoding oil-body protein isoforms began quite early in seed development and were easily detected 18 days after pollination. In non-endospermic seeds such as the dicotyledonous plant Brassica napus (canola, rapeseed), expression of oil-body protein genes seems to occur later in seed development (Murphy, et al., 1989, Biochem. J., 258:285–293) compared to corn.

A maize oleosin has been expressed in seed oil bodies in Brassica napus transformed with a Zea mays oleosin gene. The gene was expressed under the control of regulatory elements from a Brassica gene encoding napin, a major seed storage protein. The temporal regulation and tissue specificity of expression was reported to be correct for a napin gene promoter/terminator (Lee et al., 1991, Proc. Natl. Acad. Sci. USA, 88:6181–6185).

Thus the above demonstrates that oil body proteins (or oleosins) from various plant sources share a number of similarities in both structure and expression. However, at the time of the above references it was generally believed that modifications to oleosins or oil body proteins would likely lead to abherant targeting and instability of the protein product. (Vande Kerckhove et al., 1989. Bio/Technology, 7:929–932; Radke et al., 1988. Theor. and Applied Genetics, 75:685–694; and Hoffman et al., 1988. Plant Mol. Biol. 11:717–729).

Of particular relevance to the present invention are the redox proteins thioredoxin and its reductant thioredoxin reductase. Thioredoxins are relatively small proteins (typically approximately 12 kDa) that belong to the family of thioltransferases which catalyze oxido-reductions via the formation or hydrolysis of disulfide bonds and are widely, if not universally, distributed throughout the animal, plant and bacterial kingdom. In order to reduce the oxidized thioredoxin two cellular reductants provide the reduction equivalents, reduced ferredoxin and NADPH. These reduction equivalents are supplied via different thioredoxin reductases including the NADPH thioredoxin reductase and ferredoxin thioredoxin reductase. The latter thioredoxin reductase is involved in the reduction of plant thioredoxins designated as TRx and TRm, both of which are involved in the regulation of photosynthetic processes in the chloroplast. The NADPH/thioredoxin active in plant seeds is designated TRh and is capable of the reduction of a wide range of proteins thereby functioning as an important cellular redox buffer.

Thioredoxins have been obtained from several organisms including Arabidopsis thaliana (Riveira Madrid et al. (1995) Proc. Natl. Acad. Sci. 92: 5620–5624), wheat (Gautier et al. (1998) Eur. J. Biochem. 252: 314–324); Escherichia coli (Hoeoeg et al (1984) Biosci. Rep. 4: 917–923) and thermophylic microorganisms such as Methanococcus jannaschii and Archaeoglobus fulgidus (PCT Patent Application 00/36126). Thioredoxins have also been recombinantly expressed in several host systems including bacteria (Gautier et al. (1998) Eur J. Biochem. 252: 314–324) and plants (PCT Patent Application WO 00/58453) Commercial preparations of E. coli sourced thioredoxin are readily available from for example: Sigma Cat No. T 0910 Thioredoxin (E. coli, recombinant; expressed in E. coli).

NADPH-thioredoxin reductase is a cytosolic homodimeric enzyme comprising typically 300–500 amino acids. Crystal structures of both E. coli and plant NADPH-thioredoxin reductase have been obtained (Waksman et al. (1994) J. Mol. Biol. 236: 800–816; Dai et al. (1996) J. Allergy Clin. Immunol. 103: 690–697). NADPH-thioredoxin reductases have been expressed in heterologous hosts, for example the Arabidopsis NADPH-thioredoxin reductase has been expressed in E. coli (Jacquot et al. (1994) J. Mol. Biol. 235: 1357–1363) and wheat (PCT Patent Application 00/58453).

There is a need in the art to further improve the methods for the recombinant expression of thioredoxin and thioredoxin reductase in association with oil bodies.

SUMMARY OF THE INVENTION

The present invention describes the use of an oil body protein gene to target the expression of a heterologous polypeptide, to an oil body in a host cell. The unique features of both the oil body protein and the expression patterns are used in this invention to provide a means of synthesizing commercially important proteins on a scale that is difficult if not impossible to achieve using conventional systems of protein production. In a preferred embodiment of the present invention, the heterologous peptide is a thioredoxin or thioredoxin reductase.

In particular, the present invention provides a method for the expression of a thioredoxin or thioredoxin reductase by a host cell said method comprising:

a) introducing into a host cell a chimeric nucleic acid sequence comprising:
   1) a first nucleic acid sequence capable of regulating the transcription in said host cell of
   2) a second nucleic acid sequence, wherein said second sequence encodes a fusion polypeptide and comprises (i) a nucleic acid sequence encoding a sufficient portion of an oil body protein gene to provide targeting of the fusion polypeptide to a lipid phase linked in reading frame to (ii) a nucleic acid sequence encoding thioredoxin or thioredoxin reductase; and
   3) a third nucleic acid sequence encoding a termination region functional in the host cell; and
b) growing said host cell to produce the fusion polypeptide. In a preferred embodiment the oil body protein is an oleosin. Preferred host cells are plant cells, bacterial cells and yeast cells.

The present invention also provides a chimeric nucleic acid sequence encoding a fusion polypeptide, capable of being expressed in association with an oil body of a host cell comprising:
   1) a first nucleic acid sequence capable of regulating the transcription in said host cell of
   2) a second nucleic acid sequence, wherein said second sequence encodes a fusion polypeptide and comprises (i) a nucleic acid sequence encoding a sufficient portion of an oil body protein gene to provide targeting of the fusion polypeptide to a lipid phase linked in reading frame to (ii) a nucleic acid sequence encoding a thioredoxin or thioredoxin reductase; and
   3) a third nucleic acid sequence encoding a termination region functional in the host cell.

In a preferred embodiment the oil body protein is an oleosin. Preferred host cells are plant cells, bacterial cells and yeast cells.

The present invention also includes a fusion polypeptides encoded by a chimeric nucleic acid sequence comprising (i) a nucleic acid sequence encoding a sufficient portion of an oil body protein to provide targeting of the fusion polypeptide to an oil body linked in reading frame to (ii) a nucleic acid sequence encoding a thioredoxin or thioredoxin reductase.

The invention further provides methods for the separation of a thioredoxin or thioredoxin reductase from host cell components by partitioning of the oil body fraction and subsequent release of the thioredoxin or thioredoxin reductase via specific cleavage of the thioredoxin or thioredoxin reductase-oil body protein fusion. Optionally a cleavage site may be located prior to the N-terminus and after the C-terminus of the thioredoxin or thioredoxin reductase protein allowing the fusion polypeptide to be cleaved and separated by phase separation into its component peptides. This production system finds utility in the production of many proteins and peptides such as those with pharmaceutical, enzymic, rheological and adhesive properties.

The methods described above are not limited to thioredoxin or thioredoxin reductase produced in plant seeds as oil body proteins may also be found in association with oil bodies in other cells and tissues. Additionally the methods are not limited to the recovery of thioredoxin or thioredoxin reductase produced in plants because the extraction and release methods can be adapted to accommodate oil body protein-thioredoxin/thioredoxin reductase protein fusions produced in any cell type or organism. An extract containing the fusion protein is mixed with additional oleosins and appropriate tri-glycerides and physical conditions are manipulated to reconstitute the oil-bodies. The reconstituted oil-bodies are separated by floatation and the recombinant thioredoxin or thioredoxin reductase released by the cleavage of the junction with the oil body protein.

BRIEF DESCRIPTION OF THE DRAWINGS

FIG. 2 shows the nucleotide sequence (SEQ.ID.NO.1) and deduced amino acid sequence (SEQ.ID.NO.2 and NO.3) of an oil-body protein gene that codes for a 18 KDa oleosin from *Arabidopsis thaliana*. The intron sequence is printed in lower case. The predicted amino acid sequence is shown in single letter code.

FIG. 4 shows the nucleotide sequence (SEQ.ID.NO.4) of a *B. napus* oleosin cDNA clone and the predicted amino acid sequence (SEQ.ID.NO.5).

FIG. 6 shows the nucleotide sequence (SEQ.ID.NO.6) and deduced amino acid (SEQ.ID.NOS.7 and 8) sequence of the 2.7 kbp HindIII fragment of pSBSOTPTNT containing the oleosin-chymosin fusion gene. Indicated in bold (nt 1625–1631) is the NcoI site containing the methionine start codon of the prochymosin sequence. The preceding spacer sequence (nt 1608–1630), replacing the oleosin stopcodon is underlined.

FIG. 9 shows a comparison of the published NADPH thioredoxin reductase sequence (SEQ.ID.NO.36) (ATTHIREDB Jacquot et al. J. Mol. Biol. (1994) 235 (4):1357–63.) with the sequence isolated in this report (SEQ.ID.NO.37).

FIG. 10 shows a nucleotide sequence (SEQ.ID.NO.37) and deduced amino acid sequence (SEQ.ID.NO.38) of the NADPH thioredoxin reductase sequence isolated in this report.

FIG. 11 shows a comparison of the deduced amino acid sequence of the published NADPH thioredoxin reductase sequence (SEQ.ID.NO.39) (ATTHIREDB Jacquot et al. J. Mol. Biol. (1994) 235 (4):1357–63) with the sequence isolated in this report (TR) (SEQ.ID.NO.38).

FIG. 12 shows the nucleotide sequence of the phaseolin promoter-Arabidopsis Trxh-phaseolin terminator sequence (SEQ.ID.NO.40). The Trxh coding sequence and its deduced amino acid sequence is indicated (SEQ.ID.NO.41). The phaseolin promoter corresponds to nucleotide 6-1554, and the phaseolin terminator corresponds to nucleotide sequence 1905–3124. The promoter was furnished with a PstI site (nt 1–6) and the terminator was furnished with a HindIII site (nt 1898–1903) and a KpnI site (nt 3124–3129) to facilitate cloning.

FIG. 13 shows the nucleotide sequence (SEQ.ID.NO.42) of the phaseolin promoter-oleosin Trxh-phaseolin terminator sequence. The oleosin-Trxh coding sequence and its deduced amino acid sequence (SEQ.ID.NOS.:43 and 44) is indicated. As in FIG. 12, the phaseolin promoter corresponds to nucleotide 6-1554. The sequence encoding oleosin corresponds to nt 1555–2313, the intron in this sequence (nt 1908–2147) is indicated in italics. The Trxh coding sequence corresponds to nt 2314–2658. The phaseolin terminator corresponds to nucleotide sequence 2664–3884. As in FIG. 12 the synthetic PstI, HindIII and KpnI sites are also indicated.

FIG. 14 shows the nucleotide sequence of the phaseolin promoter—Trxh oleosin—phaseolin terminator sequence (SEQ.ID.NO.45). The Trxh oleosin—coding sequence and its deduced amino acid sequence are indicated (SEQ.ID.NOS.46 and 47). As in FIGS. 12 and 13, the phaseolin promoter corresponds to nucleotide 6-1554. The Trxh coding sequence corresponds to nt 1555–1896. The sequence encoding oleosin corresponds to nt 1897–2658, the intron in this sequence (nt 2250–2489) is indicated in italics. The phaseolin terminator corresponds to nucleotide sequence 2664–3884. As in FIGS. 12 and 13 the synthetic PstI, HindIII and KpnI sites are also indicated.

FIG. 15 shows the nucleotide sequence of the phaseolin promoter—thioredoxin reductase—phaseolin terminator sequence (SEQ.ID.NO.48). The thioredoxin reductase coding sequence and its deduced amino acid sequence is indicated (SEQ.ID.NO.49). The phaseolin promoter corresponds to nucleotide 6-1554. The thioredoxin reductase coding sequence corresponds to nt 1555–2556. The phaseolin terminator corresponds to nucleotide sequence 2563–3782. The synthetic PstI, HindIII and KpnI sites are also indicated.

FIG. 16 shows the nucleotide sequence of the phaseolin promoter-oleosin thioredoxin reductase-phaseolin terminator sequence (SEQ.ID.NO.50). The oleosin-thioredoxin reductase coding sequence and its deduced amino acid sequence is indicated (SEQ.ID.NOS.51 and 52). The phaseolin promoter corresponds to nucleotide 6-1554. The sequence encoding oleosin corresponds to nt 1555–2313, the intron in this sequence (nt 1980–2147) is indicated in italics. The thioredoxin reductase coding sequence corresponds to nt 2314–3315. The phaseolin terminator corresponds to nucleotide sequence 3321–4540. The synthetic PstI, HindIII and KpnI sites are also indicated.

FIG. 17 shows the nucleotide sequence of the phaseolin promoter—thioredoxin reductase oleosin—phaseolin terminator sequence (SEQ.ID.NO.53). The thioredoxin reductase coding sequence and its deduced amino acid sequence is indicated (SEQ.ID.NOS.54 and 55). The phaseolin promoter corresponds to nucleotide 6-1554. The thioredoxin reductase coding sequence corresponds to nt 1555–2553. The sequence encoding oleosin corresponds to nt 2554–3315, the intron in this sequence (nt 2751–3146) is indicated in italics. The phaseolin terminator corresponds to nucleotide sequence 3321–4540. The synthetic PstI, HindIII and KpnI sites are also indicated.

DETAILED DESCRIPTION OF THE INVENTION

Figure 1A:
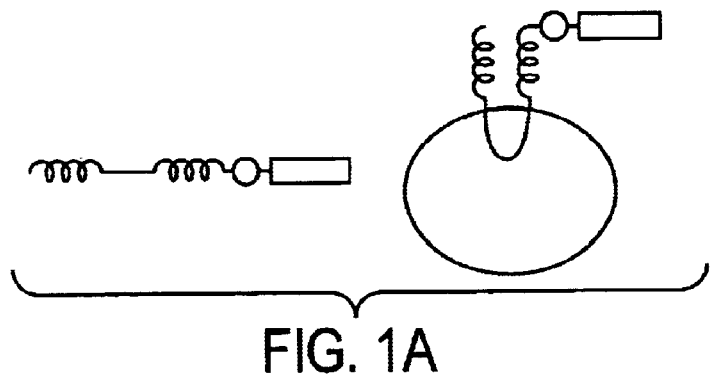
FIGS. 1A–1D show a schematic representation of the types of oil body protein fusions that are contemplated as methods of the invention for the fusion of oil-body protein genes with genes encoding foreign polypeptides. IA is a C-terminal fusion of a desired polypeptide to a oil body protein; IB is an N-terminal fusion of a desired polypeptide to oil body protein; IC is an internal fusion of a desired polypeptide within oil body protein; and ID is an inter-dimer translational fusion of desired polypeptide enclosed between two substantially complete oil body protein targeting sequences. Each fusion is shown in a linear diagrammatic form and in the configuration predicted when specifically associated with the oil body. In both the linear and oil body associated form, the oil body coding sequence that specifically targets the protein to the oil body is shown as a single thin line, a solid circle represents a protease recognition motif; a corkscrew line represents a native C- or N-terminal of a oil body protein and a inserted coding region is represented by an open box. The oil body is represented as a simple circle.
Figure 1B:
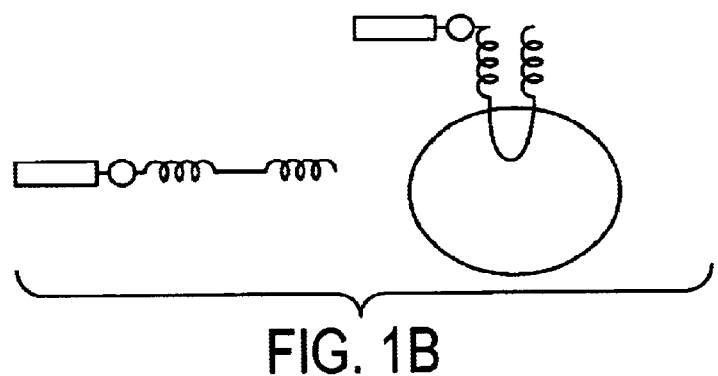
Figure 1C:
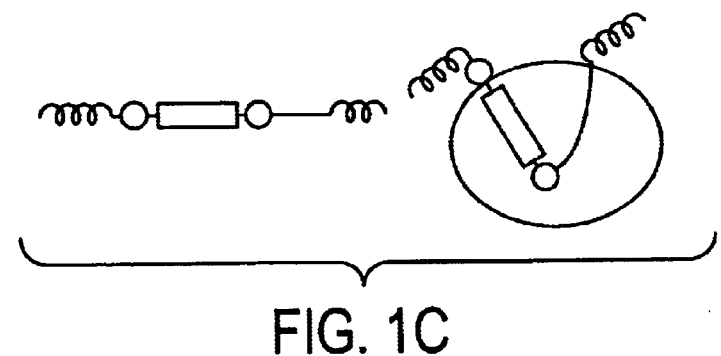
Figure 1D:
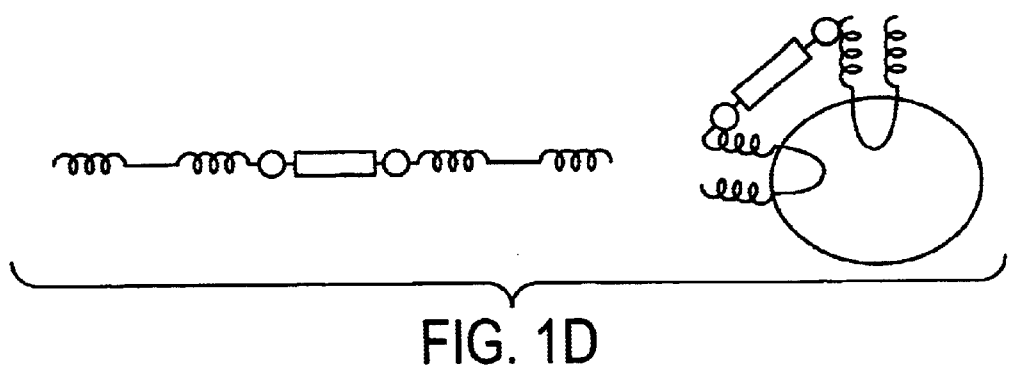

In accordance with the subject invention, methods and compositions are provided for a novel means of production of heterologous proteins and peptides that can be easily separated from host cell components. In accordance with further embodiments of the invention methods and compositions are provided for novel uses of recombinant proteins produced by said methods.

In accordance with one aspect of the subject invention, methods and compositions are provided for a novel means of production of heterologous proteins and peptides in host cells that are easily separated from other host cell components. Purification of the protein, if required, is greatly simplified. The nucleic acid encoding the heterologous peptide may be part or all of a naturally occurring gene from any source, it may be a synthetic nucleic acid sequence or it may be a combination of naturally occurring and synthetic sequences. The subject method includes the steps of preparing an expression cassette comprising a first nucleic acid sequence capable of regulating the transcription of a second nucleic acid sequence encoding a sufficient portion of an oil body protein gene to provide targeting to an oil body and fused to this second nucleic acid sequence a third nucleic acid sequence encoding the polypeptide of interest; delivery and incorporation of the expression cassette into a host cell; production of a transformed organism or cell population in which the chimeric gene product is expressed and recovery of a chimeric gene protein product through specific association with an oil body. The heterologous peptide is generally a foreign polypeptide normally not expressed in the host cell or found in association with the oil-body.

In particular, the present invention provides a method for the expression of a heterologous polypeptide by a host cell said method comprising:
a) introducing into a host cell a chimeric nucleic acid sequence comprising:
   1) a first nucleic acid sequence capable of regulating the transcription in said host cell of
   2) a second nucleic acid sequence, wherein said second sequence encodes a fusion polypeptide and comprises
      (i) a nucleic acid sequence encoding a sufficient portion of an oil body protein gene to provide targeting of the fusion polypeptide to a lipid phase linked in reading frame to (ii) a nucleic acid sequence encoding the heterologous polypeptide; and
   3) a third nucleic acid sequence encoding a termination region functional in the host cell; and
b) growing said host cell to produce the fusion polypeptide.

In a preferred embodiment the oil body protein is an oleosin.

In a further preferred embodiment, the present invention provides a method for the expression of a thioredoxin or thioredoxin reductase by a host cell said method comprising:
a) introducing into a host cell a chimeric nucleic acid sequence comprising:
   1) a first nucleic acid sequence capable of regulating the transcription in said host cell of
   2) a second nucleic acid sequence, wherein said second sequence encodes a fusion polypeptide and comprises
      (i) a nucleic acid sequence encoding a sufficient portion of an oil body protein gene to provide targeting of the fusion polypeptide to a lipid phase linked in reading frame to (ii) a nucleic acid sequence encoding a thioredoxin or thioredoxin reductase; and
   3) a third nucleic acid sequence encoding a termination region functional in the host cell; and
b) growing said host cell to produce the fusion polypeptide.

The term "oil body protein" as used herein means a protein that can naturally associate with oil bodies or can be isolated using a standard oil body preparation protocol. Examples of oil body proteins include oleosins and caleosins. An oil body preparation protocol is described in van Rooijen and Moloney, 1995, Bio/Technology, 13:72–77. The oil body protein may share sequence homology with other oil body proteins which may be oleosins known in the art.

In a preferred embodiment the oil body protein is a plant oleosin and shares sequence homology with other plant oleosins such as the oleosin isolated from *Arabidopsis thaliana* (FIG. 2 and SEQ.ID.NO.2) or *Brassica napus* (FIG. 4 and SEQ.ID.NO.5). In another embodiment, the oil body protein is a plant caleosin. Caleosin nucleic acid sequences are also known to the art (Naested et al (2000) Plant Mol Biol. 44(4):463–476; Chen et al (1999) Plant Cell Physiol. 40(10):1079–1086).

The term "heterologous polypeptide" as used herein means a polypeptide, peptide or protein that is not normally linked or fused to an oil body protein and is not normally expressed in association with oil bodies.

The host cell may be selected from a wide range of host cells including plants, bacteria, yeasts, insects and mammals. In one embodiment the host cell is a plant cell. The use of plants to produce proteins of interest allows exploitation of the ability of plants to capture energy and limited nutrient input to make proteins. The scale and yield of material afforded by production in plants allows adaptation of the technology for use in the production of a variety of polypeptides of commercial interest. The plant may be selected from various plant families including Brassicaceae, Compositae, Euphorbiaceae, Leguminosae, Linaceae, Malvaceae, Umbilliferae and Graminae.

In another embodiment the host cell is a bacterial cell. Bacterial host cells suitable for carrying out the present invention include *E. coli, B. subtilis, Salmonella typhimurium* and Staphylococcus, as well as many other bacterial species well known to one of ordinary skill in the art. Representative examples of bacterial host cells include JM109 ATCC No. 53323 and DH5 (Stratagene, Lajolla, Calif.). Suitable bacterial expression vectors preferably comprise a promoter which functions in the host cell, one or more selectable phenotypic markers, and a bacterial origin of replication. Representative promoters include the LacZ, the β-lactamase (penicillinase) and lactose promoter system (see Chang et al., Nature 275:615, 1978), the trp promoter (Nichols and Yanofsky, Meth in Enzymology 101:155, 1983) and the tac promoter (Russell et al., Gene 20:231, 1982).

In another embodiment, the host cell is a yeast cell. Yeast and fungi host cells suitable for carrying out the present invention include, among others *Saccharomyces cerevisae*, the genera Pichia or Kluyveromyces and various species of the genus Aspergillus. Suitable expression vectors for yeast and fungi include, among others, $YC_p50$ (ATCC No. 37419) for yeast, and the amdS cloning vector pV3 (Turnbull, Bio/Technology 7:169, 1989). Protocols for the transformation of yeast are also well known to those of ordinary skill in the art. For example, transformation may be readily accomplished either by preparation of spheroplasts of yeast with DNA (see Hinnen et al., PNAS USA 75:1929, 1978) or by treatment with alkaline salts such as LiCl (see Itoh et al., J. Bacteriology 153:163, 1983). Transformation of fungi may also be carried out using polyethylene glycol as described by Cullen et al. (Bio/Technology 5:369, 1987).

The host cell may also be a mammalian cell. Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter, as well as other transcriptional and translational control sequences. Suitable promoters include PMSG, pSVL, SV40, pCH 110, MMTV, metallothionein-1, adenovirus Ela, CMV, immediate early, immunoglobulin heavy chain promoter and enhancer, and RSV-LTR. Protocols for the transfection of mammalian cells are well known to those of ordinary skill in the art. Representative methods include calcium phosphate mediated electroporation, retroviral, and protoplast fusion-mediated transfection (see Sambrook et al., Molecular Cloning a Laboratory Manual, 2nd Edition, Cold Spring Harbour Laboratory Press, 1989).

The host cell may also be an insect cell. Insect cells suitable for carrying out the present invention include cells and cell lines from Bombyx or Spodotera species. Suitable expression vectors for directing expression in insect cells include Baculoviruses such as the *Autographa californica* nuclear polyhedrosis, virus (Miller et al. 1987, in *Genetic Engineering*, Vol. 8 ed. Setler, J. K. et al., Plenum Press, N.Y.) and the *Bombyx mori* nuclear polyhedrosis virus (Maeda et al., 1985, Nature 315:592).

The use of an oil body protein as a carrier or targeting means provides a simple mechanism to recover proteins. The chimeric protein associated with the oil body or reconstituted oil body fraction is separated away from the bulk of cellular components in a single step (such as centrifugation size exclusion or floatation); the protein is also protected from degradation during extraction as the separation also reduces contact of the proteins with non-specific proteases.

The invention contemplates the use of heterologous proteins, specifically enzymes, fused to oil body proteins and associated with oil bodies, or reconstituted oil bodies for conversion of substrates in aqueous solutions following mixing of oil body fractions and substrate solutions. Association of the enzyme with the oil body allows subsequent recovery of the enzyme by simple means (centrifugation and floatation) and repeated use thereafter.

In accordance with further embodiments of the invention methods and compositions are provided for the release of heterologous proteins and peptides fused to oleosin proteins specifically associated with isolated oil body or reconstituted oil body fractions. The subject method includes the steps of preparing an expression cassette comprising a first nucleic acid sequence capable of regulating the transcription of a second nucleic acid sequence encoding a sufficient portion of an oil body protein gene such as oleosin to provide targeting to an oil body and fused to this second nucleic acid sequence via a linker nucleic acid sequence encoding a amino acid sequence cleavable by a specific protease or chemical treatment a third nucleic acid sequence encoding the polypeptide of interest; such that the protein of interest can be cleaved from the isolated oil body fraction by the action of said specific chemical or protease.

For embodiments of the invention wherein the cleavage of heterologous proteins fused to oleosins associated with seed oil bodies is contemplated in germinating seed the expression cassette containing the heterologous protein gene so described above is modified to contain an additional second recombinant nucleic acid molecule comprising a first nucleic acid sequence capable of regulating expression in plants, particularly in germinating seed, more specifically seed embryo or other seed tissue containing oil bodies and under the control of this regulatory sequence a nucleic acid sequence encoding a protease enzyme, specifically a particular protease enzyme capable of cleavage of the fusion protein associated with said oil bodies to release a heterologous protein or peptide from the oil body, and a transcriptional and translational termination region functional in plants. It is desirable that the second recombinant nucleic acid molecule be so constructed such that the first and second recombinant nucleic acid sequences are linked by a multiple cloning site to allow for the convenient substitution of any one of a variety of proteolytic enzymes that may be used to cleave fusion proteins associated with oil bodies.

It is obvious to a person skilled in the art of plant molecular biology, genetics or plant breeding that the equivalent to the above modification to the expression cassette to allow release of proteins and peptides of interest in germinating seeds can be accomplished by other similar means. For example it is possible that the first recombinant nucleic acid molecule and the second recombinant nucleic acid molecule described above may be contained within two independent expression cassettes introduced into the genome of a plant independently. Additionally it is possible to sexually cross a first recombinant plant containing the first recombinant nucleic acid molecule integrated into its genome with a second recombinant plant with the second recombinant nucleic acid integrated into its genome to produce seed comprising both the first and second nucleic acid molecules.

For embodiments of the invention wherein the heterologous protein is to be produced in and potentially recovered from plant seeds the expression cassette will generally include, in the 5'-3' direction of transcription, a first recombinant nucleic add sequence comprising a transcriptional and translational regulatory region capable of expression in plants, particularly in developing seed, more specifically seed embryo or other seed tissue that has oil body or triglyceride storage such as pericarp or cuticle, and a second recombinant nucleic add sequence encoding a fusion peptide or protein comprising a sufficient portion of an oil body specific protein to provide targeting to an oil body, a heterologous protein of interest, and a transcriptional and translational termination region functional in plants. One or more introns may also be present within the oil body specific protein coding sequence or within the coding sequence of the heterologous protein of interest. The fusion peptide or protein may also comprise a peptide sequence linking the oil body specific portion and the peptide or protein of interest that can be specifically cleaved by chemical or enzymatic means. It is desirable that the nucleic acid expression cassette is constructed in such a fashion that the first and second recombinant nucleic acid sequences are linked by a multiple cloning site to allow for the convenient substitution of alternative second recombinant nucleic add sequences comprising the oil body targeting sequence and any one of a variety of proteins or peptides of interest to be expressed and targeted to oil bodies in seeds.

According to one embodiment of the invention the expression cassette is introduced into a host cell in a form where the expression cassette is stably incorporated into the genome of the host cell. Accordingly it is apparent that one may also introduce the expression cassette as part of a recombinant nucleic add sequence capable of replication and or expression in the host cell without the need to become integrated into the host chromosome. Examples of this are found in a variety of vectors such as viral or plasmid vectors capable of replication and expression of proteins in the host cell. One specific example are plasmids that carry an origin of replication that permit high copy number such as the pUC series of E. coli plasmids additionally said plasmids modified to contain an inducible promoter such as the LacZ promoter inducible by galactose or IPTG.

In an alternative embodiment of the invention nucleic acid is stably incorporated into the genome of the host cell by homologous recombination. Examples of gene targeting by homologous recombination have been described for various cell types including mammalian cells (Mansour et al., 1988, Nature, 336, 348–352) and plant cells (Miao and Lam, 1995, Plant Journal, 7: 359–365). Introduction into the host cell genome of the protein of interest may be accomplished by homologous recombination of the protein of interest in such a fashion that upon recombination an expression cassette is generated which will generally include, in the 5'–3' direction of transcription, a first nucleic acid sequence comprising a transcriptional and translational regulatory region capable of expression in the host cell, a second nucleic acid sequence encoding a fusion protein comprising a sufficient portion of an oil body protein to provide targeting to an oil body and a heterologous protein, and a transcriptional and translational termination region functional in plants.

For embodiments of the invention wherein the production and recovery of the heterologous protein is contemplated from non-plant cells the expression cassette so described above is modified to comprise a first recombinant nucleic acid sequence comprising a transcriptional and translational regulatory sequence capable of expression in the intended host production cell or organism. Promoter regions highly active in cells of microorganisms, fungi, insects and animals are well described in the literature of any contemplated host species and may be commercially available or can be obtained by standard methods known to a person skilled in the art. It is apparent that one means to introduce the recombinant molecule to the host cell is through specific infectious entities such as viruses capable of infection of the host modified to contain the recombinant nucleic acid to be expressed.

In a further embodiment of the invention it is contemplated that proteins other than plant oleosins and proteins with homology to plant oleosins that may specifically associate with triglycerides, oils, lipids, fat bodies or any hydrophobic cellular inclusions in the host organism or with reconstituted plant oil bodies may be fused to a recombinant protein and used in the manner contemplated. A system functionally equivalent to plant oleosins and oil bodies has been described in bacteria (Pieper-Fürst et al., 1994, J. Bacteriol. 176:4328–4337). Other proteins from additional sources such as, but not limited to; fungi, insects or animals, with equivalent regulatory and targeting properties may be known or discovered by a person skilled in the art.

Of particular interest for transcriptional and translational regulation in plants of the first recombinant nucleic acid molecule is a regulatory sequence (promoter) from an oil body protein gene, preferably an oil body protein gene expressed in dicotyledonous oil seeds. The expression of these genes in dicotyledonous oilseeds was found to occur much earlier than had hitherto been believed as reported in the literature. Thus, the promoters and upstream elements of these genes are valuable for a variety of uses including the modification of metabolism during phases of embryogenesis which precede the accumulation of storage proteins. Alternatively said promoter may also comprise a promoter capable of expression constitutively throughout the plant or a promoter which has enhanced expression within tissues or organs associated with oil synthesis. Of more particular interest is a promoter that expresses an oil body protein to a high level. Many plant species are tetraploid or hexaploid and may contain numerous copies of functional oil body protein genes. As it is preferable to obtain a gene that is controlled by a promoter that expresses at high levels when compared to other oil body protein genes within the same species it may be advantageous to choose a diploid species as a source of oil body protein genes. An example is the diploid cruciferous plant Arabidopsis thaliana, wherein only two or three oil body protein genes are detected by southern blot analysis whereas the seeds contain oil body proteins as a high percentage of total protein.

The degree of evolutionary relationship between the plant species chosen for isolation of a promoter and the plant species selected to carry out the invention may not be critical. The universality of most plant genes and promoter function within dicotyledonous species has been amply demonstrated in the literature. Additionally to a certain extent the conservation of function between monocot and dicot genes has also been shown. This is apparent to a person skilled in the art that the function of any given promoter in any chosen species may be tested prior to practising the invention by simple means such as transient expression of marker gene promoter fusions in isolated cells or intact tissues. The promoter region typically comprises minimally from 100 bp 5' to the translational start of the structural gene coding sequence, up to 2.5 kb 5' from the same translational start.

Examples of nucleic acid sequences encoding sequences capable of providing targeting to an oil body protein are oleosins genes obtainable from Arabidopsis thaliana or Brassica napus which provide for expression of the protein of interest in seed (See Taylor et al., 1990, Planta 181:18–26). The necessary regions and amino-acid sequences needed to provide targeting to the oil body reside in the highly hydrophobic central region of oil body proteins. The amino acid sequence necessary to provide targeting to the oil body for Arabidopsis thaliana oleosins contain amino acids 46–117 shown in SEQ.ID.NO.2. Similarly, the amino acid sequence necessary to provide targeting to the oil body for Brassica napus oleosins contains amino acids 60–132 shown in SEQ.ID.NO.5. In a preferred embodiment, the amino acid sequence necessary for targeting additionally contains the N-terminus of the oleosin which includes amino acids 1–45 (SEQ.ID.NO.2) and 1–60 (SEQ.ID.NO.5) for Arabidopis and Brassica, respectively.

To identify other oil body protein genes having the desired characteristics, where an oil body protein has been or is isolated, the protein may be partially sequenced, so that a probe may be designed for identifying mRNA. Such a probe is particularly valuable if it is designed to target the coding region of the central hydrophobic domain which is highly conserved among diverse species. In consequence, a nucleic acid or RNA probe for this region may be particularly useful for identifying coding sequences of oil body proteins from other plant species. To further enhance the concentration of the mRNA, cDNA may be prepared and the cDNA subtracted with mRNA or cDNA from non-oil body producing cells. The residual cDNA may then be used for probing the genome for complementary sequences, using an appropriate library prepared from plant cells. Sequences which hybridize to the cDNA under stringent conditions may then be isolated.

In some instances, as described above, the use of an oil body protein gene probe (conserved region), may be employed directly for screening a genomic library and identifying sequences which hybridize to the probe. The isolation may also be performed by a standard immunological screening technique of a seed-specific cDNA expression library. Antibodies may be obtained readily for oil-body proteins using the purification procedure and antibody preparation protocol described by Taylor et al. (1990, Planta, 181:18–26). cDNA expression library screening using antibodies is performed essentially using the techniques of Huynh et al. (1985, in DNA Cloning, Vol. 1, a Practical Approach, ed. D. M. Glover, IRL Press, pp. 49–78). Confirmation of sequence is facilitated by the highly conserved central hydrophobic region (see FIG. 1). DNA sequencing by the method of Sanger et al. (1977, Proc. Natl. Acad. Sci. USA, 74:5463–5467) or Maxam and Gilbert (1980, Meth. Enzymol., 65:497–560) may be performed on all putative clones and searches for homology performed. Homology of sequences encoding the central hydrophobic domain is typically 70%, both at the amino-acid and nucleotide level between diverse species. If an antibody is available, confirmation of sequence identity may also be performed by hybrid-select and translation experiments from seed mRNA preparations as described by Sambrook et al. (1990, Molecular Cloning, 2nd Ed., Cold Spring Harbour Press, pp. 8–49 to 8–51).

cDNA clones made from seed can be screened using cDNA probes made from the conserved coding regions of any available oil body protein gene (e.g., Bowman-Vance and Huang, 1987, J. Biol. Chem., 262:11275–11279). Clones are selected which have more intense hybridization with seed nucleic acidss as compared to seedling cDNAs. The screening is repeated to identify a particular cDNA associated with oil bodies of developing seeds using direct antibody screening or hybrid-select and translation. The mRNA complementary to the specific cDNA is absent in other tissues which are tested. The cDNA is then used for screening a genomic library and a fragment selected which hybridizes to the subject cDNA. Of particular interest for transcriptional and translational regulation in plants of said second recombinant nucleic acid molecule is a regulatory sequence (promoter) from a gene expressed during the germination of seeds and the early stages of growth of a seedling, specifically a gene showing high levels of expression during the stage of mobilization of stored seed reserves, more specifically the promoter sequence from the glyoxisomal enzymes iso-citrate lyase or malate synthase. Information concerning genomic clones of iso-citrate lyase and malate synthase from *Brassica napus* and Arabidopsis that have been isolated and described has been published (Comai et al., 1989, Plant Cell 1: 293–300) and can be used by a person skilled in the art, by the methods described above, to isolate a functional promoter fragment. Other enzymes involved in the metabolism of lipids or other seed reserves during germination may also serve as a source of equivalent regulatory regions.

In order to identify oil body proteins, other than oleosins, oil body preparations such as described in the art for the plants canola (Van Rooijen and Moloney, 1995, Bio/Technology 13: 72–77) and peanut (jacks et al., J.A.O.C.S., 1990, 67: 353–361) and such as described for oil body-like granules in the bacterial species *Rhodococcus ruber* (Pieper-Fürst et al., 1994, J. Bacteriol. 176: 4328–4337) may be performed. From such preparations, individual proteins may be readily identified upon electrophoresis on a SDS polyacrylamide gel. Proteins may be extracted from the polyacrylamide gel following the protocol of Weber and Osborn (J. Biol. Chem., 1969, 244: 4406–4412) and polyclonal antibodies against oil body proteins may be obtained using the protocol described by Taylor (1990, Planta, 181: 18–26). In order to isolate the corresponding cDNA clone, a cDNA expression library may then be screened with the antibody using techniques familiar to a skilled artisan (see for example: Huynh et al., 1985, in DNA cloning, Vol. 1, a Practical Approach, ed. D. M. Glover, IRL Press, pp 49–78).

For production of recombinant protein oleosin fusions in heterologous systems such as animal, insect or microbial species, promoters would be chosen for maximal expression in said cells, tissues or organs to be used for recombinant protein production. The invention is contemplated for use in a variety of organisms which can be genetically altered to express foreign proteins including animals, especially those producing milk such as cattle and goats, invertebrates such as insects, specifically insects that can be reared on a large scale, more specifically those insects which can be infected by recombinant baculoviruses that have been engineered to express oleosin fusion proteins, fungal cells such as yeasts and bacterial cells. Promoter regions highly active in viruses, microorganisms, fungi, insects and animals are well described in the literature and may be commercially available or can be obtained by standard methods known to a person skilled in the art. It is preferred that all of the transcriptional and translational functional elements of the initiation control region are derived from or obtained from the same gene.

For those applications where expression of the recombinant protein is derived from extrachromosomal elements, one may chose a replicon capable of maintaining a high copy number to maximize expression. Alternatively or in addition to high copy number replicons, one may further modify the recombinant nucleic acid sequence to contain specific transcriptional or translation enhancement sequences to assure maximal expression of the foreign protein in host cells.

The level of transcription should be sufficient to provide an amount of RNA capable of resulting in a modified seed, cell, tissue, organ or organism. The term "modified" is meant a detectably different phenotype of a seed, cell, tissue, organ or organism in comparison to the equivalent non-transformed material, for example one not having the expression cassette in question in its genome. It is noted that the RNA may also be an "antisense RNA" capable of altering a phenotype by inhibition of the expression of a particular gene.

Ligation of the nucleic acid sequence encoding the targeting sequence to the gene encoding the polypeptide of interest may take place in various ways including terminal fusions, internal fusions, and polymeric fusions. In all cases, the fusions are made to avoid disruption of the correct reading frame of the oil-body protein and to avoid inclusion of any translational stop signals in or near the junctions. The different types of terminal an internal fusions are shown in FIG. 1 along with a representation of configurations in vivo.

In many of the cases described, the ligation of the gene encoding the peptide preferably would include a linker encoding a protease target motif. This would permit the release of the peptide once extracted as a fusion protein. Potential cleavage sites which could be employed are recognition motifs for thrombin (Leu-Val-Pro-Arg-Gly, SEQ.ID.NO.9) (Fujikawa et al., 1972, Biochemistry 11:4892–4899), of factor Xa (Phe-Glu-Gly-Arg-aa, SEQ. ID NO.10) (Nagai et al., 1985, Proc. Natl Acad. Sci. USA, 82:7252–7255) collagenase (Pro-Leu-Gly-Pro, SEQ.ID.NO.11) (Scholtissek and Grosse, 1988, Gene 62:55–64) or Tobacco Etch Virus (TEV) protease (Glu-Asn-Leu-Tyr-Phe-Gln-Gly SEQ.ID.NO.12) (Dougherty et al., 1989, Virology, 172: 302). Additionally, for uses where the fusion protein contains a peptide hormone that is released upon ingestion, the protease recognition motifs may be chosen to reflect the specificity of gut proteases to simplify the release of the peptide.

For those uses where chemical cleavage of the polypeptide from the oil body protein fusion is to be employed, one may alter the amino acid sequence of the oil body protein to include or eliminate potential chemical cleavage sites. For example, one may eliminate the internal methionine residues in the Arabidopsis oleosin at positions 11 and 117 by site directed mutagenesis to construct a gene that encodes a oleosin that lacks internal methionine residues. By making a N-terminal fusion with the modified oleosin via the N-terminal methionine residue already present in the Arabidopsis oleosin, one may cleave the polypeptide of interest by the use of cyanogen bromide providing there are no internal methionines in said polypeptide. Similar strategies for other chemical cleavage agents may be employed. It should be noted that a variety of strategies for cleavage may be employed including a combination of chemical modification and enzymatic cleavage.

By appropriate manipulations, such as restriction, chewing back or filling in overhangs to provide blunt ends, ligation of linkers, or the like, complementary ends of the fragments can be provided for joining and ligation. In carrying out the various steps, cloning is employed, so as to amplify the amount of nucleic acid and to allow for analyzing the nucleic acid to ensure that the operations have occurred in proper manner. A wide variety of cloning vectors are available, where the cloning vector includes a replication system functional in *E. coli* and a marker which allows for selection of the transformed cells. Illustrative vectors include pBR332, pUC series, M13 mp series, pACYC184, etc for manipulation of the primary nucleic acid constructs. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the nucleic acid sequence to be used in the final construct may be restricted and joined to the next sequence, where each of the partial constructs may be cloned in the same or different plasmids.

The mode by which the oil body protein and the protein to be expressed are fused can be either a N-terminal, C-terminal or internal fusion. The choice is dependant upon the application. For example, C-terminal fusions can be made as follows: A genomic clone of an oil body protein gene preferably containing at least 100 bp 5' to the translational start is cloned into a plasmid vehicle capable of replication in a suitable bacterial host (e.g., pUC or pBR322 in *E. coli*). A restriction site is located in the region encoding the hydrophilic C-terminal portion of gene. In a plant oil body protein of approximately 18 KDa, such as the Arabidopsis oleosin, this region stretches typically from codons 125 to the end of the clone. The ideal restriction site is unique, but this is not absolutely essential. If no convenient restriction site is located in this region, one may be introduced by site-directed mutagenesis. The only major restriction on the introduction of this site is that it must be placed 5' to the translational stop signal of the OBP clone.

With this altered clone in place, a synthetic oligonucleotide adapter may be produced which contains coding sequence for a protease recognition site such as Pro-Leu-Gly-Pro (SEQ.ID.NO.11) or a multimer thereof. This is the recognition site for the protease collagenase. The adaptor would be synthesized in such a way as to provide a 4-base overhang at the 5' end compatible with the restriction site at the 3' end of the oil body protein done, a 4-base overhang at the 3' end of the adaptor to facilitate ligation to the foreign peptide coding sequence and additional bases, if needed, to ensure no frame shifts in the transition between the oil body protein coding sequence, the protease recognition site and the foreign peptide coding sequence. The final ligation product will contain an almost complete oil body protein gene, coding sequence for collagenase recognition motif and the desired polypeptide coding region all in a single reading frame.

A similar approach is used for N-terminal fusions. The hydrophilic N-terminal end of oil-body proteins permits the fusion of peptides to the N-terminal while still assuring that the foreign peptide would be retained on the outer surface of the oil body. This configuration can be constructed from similar starting materials as used for C-terminal fusions, but requires the identification of a convenient restriction site close to the translational start of the oil body protein gene. A convenient site may be created in many plant oil body protein genes without any alteration in coding sequence by the introduction of a single base change just 5' to the start codon (ATG). In plant oil body proteins thus far studied, the second amino acid is alanine whose codon begins with a "G". A-C transition at that particular "G" yields a Nco I site. As an illustration of such a modification, the context of the sequences is shown below:

```
3' TC TCA ACA ATG GCA Carrot Oil      (SEQ.ID.NO.13)
                     Body Protein 3' CG GCA GCA ATG GCG Maize 18KDa     (SEQ.ID.NO.14)
                     Oil Body
                     Protein
```

A single base change at the adenine prior to the 'ATG' would yield in both cases CCATGG which is an Nco I site. Thus, modification of this base using the site-directed mutagenesis will introduce a Nco I site which can be used directly for the insertion of a nucleic acid coding sequence assuming no other Nco I sites are present in the sequence. Alternatively other restriction sites may be used or introduced to obtain cassette vectors that provide a convenient means to introduce foreign nucleic acid.

The coding sequence for the foreign peptide may require preparation which will allow its ligation directly into the introduced restriction site. For example, introduction of a coding sequence into the Nco I site introduced into the oil body protein coding sequences described above may require the generation of compatible ends. This may typically require a single or two-base modification by site-directed mutagenesis to generate an Nco I site around the translational start of the foreign peptide. This peptide is then excised from its cloning vehicle using Nco I and a second enzyme which cuts close to the translational stop of the target. Again, using the methods described above, a second convenient site can be introduced by site-directed mutagenesis. It has been suggested by Qu and Huang (1990, supra) that the N-terminal methionine might be removed during processing of the plant oil body proteins protein in vivo and that the alanine immediately downstream of this might be acylated. To account for this possibility, it may be necessary to retain the Met-Ala sequence at the N-terminal end of the protein. This is easily accomplished using a variety of strategies which introduce a convenient restriction site into the coding sequence in or after the Ala codon.

The resultant constructs from these N-terminal fusions would contain an oil body protein promoter sequence, an in-frame fusion in the first few codons of the oil body protein gene of a high value peptide coding sequence with its own ATG as start signal if necessary and the remainder of the oil body protein gene and terminator.

A third type of fusion involves the placing of a high value peptide coding sequence internally to the coding sequence of the oil body protein. This type of fusion requires the same strategy as in N-terminal fusions, but may only be functional with modifications in regions of low conservation, as it is believed that regions of high conservation in these oil body proteins are essential for targeting of the mature protein. A primary difference in this kind of fusion is the necessity for flanking protease recognition sites for the release of the protein. This means that in place of the single protease recognition site thus far described, it is necessary to have the protein of interest flanked by one or more copies of the protease recognition site.

Various strategies are dependant on the particular use and nucleic acid sequence of the inserted coding region and would be apparent to those skilled in the art. The preferred method would be to use synthetic oligonucleotides as linkers to introduce the high value peptide coding sequence flanked by appropriate restriction sites or linkers. Orientation is checked by the use of an asymmetrically placed restriction site in the high-value peptide coding sequence.

The heterologous polypeptide of interest to be produced as an oleosin fusion by any of the specific methods described herein, may be any peptide or protein. For example, proteins that alter the amino acid content of seeds may be used. These include genes encoding proteins high in essential amino acids or amino acids that are limiting in diets, especially arginine, histidine, isoleucine, leucine, lysine, methionine, phenylalanine, threonine, tryptophan and valine. Storage proteins such as the high lysine 10 KDa zein from Zea mays or the 2S high methionine Brazil Nut storage protein may be used. Alternatively synthetic or modified storage proteins may be employed such as peptides encoding poly-lysine or poly-phenylalanine or fusions of one or more coding regions high in essential amino acids. Proteins may also encode useful additives for animal feeds. These proteins may be enzymes for modification of phytate content in meal such as phytase, more specifically phytase from novel sources and having novel activities. Proteins may also encode hormones useful for boosting productivity such as growth hormones or bovine somatotropin. Proteins may also encode peptides useful for aquaculture.

Proteins may also be those used for various industrial processes. Examples of such proteins include chitinase, glucose isomerase, collagenase, amylase, xylanase, cellulase, lipase, chymosin, renin or various proteases or protease inhibitors. One may also express proteins of interest to the cosmetic industry such as collagen, keratin or various other proteins for use in formulation of cosmetics. Proteins of use to the food industry may also be synthesized including sweetener proteins such as thaumatin, and other flavour enhancing proteins. Proteins that have adhesive properties may also be used.

Of particular interest are those proteins or peptides that may have a therapeutic or diagnostic value. These proteins include enzymes, antigens, such as viral coat proteins or microbial cell wall or toxin proteins or various other antigenic peptides, peptides of direct therapeutic value such as interleukin-1-β, the anticoagulant hirudin, blood clotting factors and bactericidal peptides, antibodies, specifically a single-chain antibody comprising a translational fusion of the VH or VL chains of an immunoglobulin. Human growth hormone may also be produced. The invention is not limited by the source or the use of the heterologous polypeptide.

Preferred heterologous proteins of the present application are thioredoxin or thioredoxin reductase.

Accordingly, the present invention provides a chimeric nucleic acid sequence, capable of being expressed in association with an oil body of a host cell comprising:

1) a first nucleic acid sequence capable of regulating the transcription in said host cell of
2) a second DNA sequence, wherein said second sequence encodes a fusion polypeptide and comprises (i) a nucleic sequence encoding a sufficient portion of an oil body protein gene to provide targeting of the fusion polypeptide to a lipid phase linked in reading frame to (ii) a nucleic sequence encoding a thioredoxin or thioredoxin reductase; and
3) a third nucleic acid sequence encoding a termination region functional in the host cell.

In the practice of the present invention any protein which is classified as a thioredoxin may be used, including the thioredoxin component of the NADPH thioredoxin system and the thioredoxin present in the ferredoxin/thioredoxin systems also known as TRx and TRm.

In the practice of the invention any protein which is capable of reducing thioredoxin may be used, including the NADPH thioredoxin reductase and the ferredoxin-thioredoxin reductase and any other proteins having the capability of reducing thioredoxin. In preferred embodiments the thioredoxin and thioredoxin reductase are plant derived.

The nucleic acid sequences encoding thioredoxin polypeptides from diverse biological sources including *E. coli* (Hoeoeg et al. (1984) Biosci. Rep.: 4 917–923); *Methanococcus jannaschii* and *Archaeoglobus fulgidus* (PCT Patent Application 00/36126); *Arabidopsis thaliana* (Rivera-Madrid (1995) Proc. Natl. Acad. Sci. 92: 5620–5624); wheat (Gautier et al (1998) Eur. J. Biochem. 252(2): 314–324); tobacco (Marty et al. (1991) Plant Mol. Biol. 17: 143–148); barley (PCT Patent Application 00/58352); rice (Ishiwatari et al. (1995) Planta 195: 456–463); soybean (Shi et al. (1996) Plant Mol. Biol. 32: 653–662); rapeseed (Bower et al. Plant Cell 8: 1641–1650) and calf (Terashima et al. (1999) DNA Seq. 10(3): 203–205) are available and may all be used in accordance with the present invention. Nucleic acid sequences encoding thioredoxin reductase proteins from Arabidopsis (Riveira Madrid et al. (1995) Proc. Natl. Acad. Sci. USA 92: 5620–5624), *E.* coli (Russel et al. (1988) J. Biol. Chem. 263: 9015–9019); barley (PCT Patent Application 00/58352 and wheat (Gautier et al., (1998) Eur. J. Biochem. 252: 314–324) are also known and may be used in accordance with the present invention.

Known nucleic acid sequences encoding thioredoxin and thioredoxin reductase proteins may be used to design and construct nucleic acid sequence based probes in order to uncover and identify previously undiscovered nucleic acid sequences encoding thioredoxin or thioredoxin reductase, for example by screening cDNA or genomic libraries. Thus additional nucleic acid sequences may be discovered and used in accordance with the present invention. In embodiments of the invention in which a thioredoxin and a thioredoxin reductase are used the nucleic acid sequence encoding the thioredoxin and thioredoxin reductase may be obtained from separate sources or may be obtained from the same source. In general however it is preferred that the nucleic acid sequence encoding the thioredoxin polypeptide and the nucleic acid sequence encoding the thioredoxin reductase are obtained from the same or a similar biological source. The nucleic acid sequences encoding the thioredoxin or thioredoxin reductase proteins may be altered to improve expression levels for example by optimizing the nucleic acids sequence in accordance with the preferred codon usage for the particular cell type which is selected for expression of the thioredoxin or thioredoxin reductase, or by altering of motifs known to destabilize mRNAs (see for example: PCT Patent Application 97/02352). Comparison of the codon usage of the thioredoxin or thioredoxin reductase with codon usage of the host will enable the identification of codons that may be changed. For example typically plant evolution has tended towards a preference for CG rich nucleotide sequences while bacterial evolution has resulted in bias towards AT rich nucleotide sequences. By modifying the nucleic acid sequences to incorporate nucleic acid sequences preferred by the host cell expression may be optimized. Construction of synthetic genes by altering codon usage is described in for example PCT patent Application 93/07278. The thioredoxin or thioredoxin reductase may be altered using for example targeted mutagenesis, random mutagenesis (Shiraishi et al. (1998) Arch. Biochem. Biophys. 358: 104–115; Galkin et al. (1997) Protein Eng. 10: 687–690; Carugo et al. (1997) Proteins 28: 10–28; Hurley et al. (1996) Biochemistry 35: 5670–5678) (and/or by the addition of organic solvent (Holmberg et al. (1999) Protein Eng. 12: 851–856). In embodiments of the invention in which a thioredoxin and thioredoxin reductase are used, the thioredoxin and thioredoxin reductase may be selected by developing a two-dimensional matrix and determining which combination of first and second redox protein is most effective in electron transport using for example a colorometric reduction assay (Johnson et al (1984) J. of Bact. Vol. 158 3:1061–1069, Luthman et al (1982) Biochemistry Vol 21 26:6628–2233). Combinations of thioredoxin and thioredoxin reductase may be tested by determining the reduction of wheat storage proteins and milk storage protein beta-lactoglobulin in vitro (Del Val et al. (1999) J. Allerg. Clin. Immunol. 103: 690–697).

The termination region which is employed will be primarily one of convenience, since in many cases termination regions appear to be relatively interchangeable. The termination region may be native to the transcriptional initiation region, may be native to the nucleic acid sequence encoding the polypeptide of interest, or may be derived from another source. Convenient termination regions for plant cell expression are available from the Ti-plasmid of *A. tumefaciens*, such as the octopine synthase and nopaline synthase termination regions. Termination signals for expression in other organisms are well known in the literature.

A variety of techniques are available for the introduction of nucleic acid into host cells. For example, the chimeric nucleic acid constructs may be introduced into host cells obtained from dicotyledonous plants, such as tobacco, and oleaginous species, such as *Brassica napus* using standard Agrobacterium vectors by a transformation protocol such as that described by Moloney et al., 1989, Plant Cell Rep., 8:238–242 or Hinchee et al., 1988, Bio/Technol., 6:915–922; or other techniques known to those skilled in the art. For example, the use of T-DNA for transformation of plant cells has received extensive study and is amply described in EPA Ser. No. 120,516; Hoekema et al., 1985, Chapter V, In: The Binary Plant Vector System Offsetdrukkerij Kanters B. V., Alblasserdam; Knauf, et al., 1983, Genetic Analysis of Host Range Expression by Agrobacterium, p. 245, In: Molecular Genetics of the Bacteria-Plant Interaction, Puhler, A. ed., Springer-Verlag, NY; and An et al., 1985, EMBO J., 4:277–284. Conveniently, explants may be cultivated with *A. tumefaciens* or *A. rhizogenes* to allow for transfer of the transcription construct to the plant cells. Following transformation using Agrobacterium the plant cells are dispersed in an appropriate medium for selection, subsequently callus, shoots and eventually plantlets are recovered. The Agrobacterium host will harbour a plasmid comprising the vir genes necessary for transfer of the T-DNA to the plant cells. For injection and electroporation, (see below) disarmed Ti-plasmids (lacking the tumour genes, particularly the T-DNA region) may be introduced into the plant cell.

The use of non-Agrobacterium techniques permits the use of the constructs described herein to obtain transformation and expression in a wide variety of monocotyledonous and dicotyledonous plants and other organisms. These techniques are especially useful for species that are intractable in an Agrobacterium transformation system. Other techniques for gene transfer include biolistics (Sanford, 1988, Trends in Biotech., 6:299–302), electroporation (Fromm et al., 1985, Proc. Natl. Acad. Sci. USA, 82:5824–5828; Riggs and Bates, 1986, Proc. Natl. Acad. Sci. USA 83 5602–5606 or PEG-mediated DNA uptake (Potrykus et al., 1985, Mol. Gen. Genet., 199:169–177).

In a specific application, such as to *Brassica napus*, the host cells targeted to receive recombinant nucleic acid constructs typically will be derived from cotyledonary petioles as described by Moloney et al., 1989, Plant Cell Rep., 8:238–242). Other examples using commercial oil seeds include cotyledon transformation in soybean explants (Hinchee etal., 1988, Bio/technology, 6:915–922) and stem transformation of cotton (Umbeck etal., 1981, Bio/technology, 5:263–266).

Following transformation, the cells, for example as leaf discs, are grown in selective medium. Once shoots begin to emerge, they are excised and placed onto rooting medium. After sufficient roots have formed, the plants are transferred to soil. Putative transformed plants are then tested for presence of a marker. Southern blotting is performed on genomic nucleic acid using an appropriate probe, for example an *A. thaliana* oleosin gene, to show that integration of the desired sequences into the host cell genome has occurred.

The expression cassette will normally be joined to a marker for selection in plant cells. Conveniently, the marker may be resistance to a herbicide, eg phosphinthricin or glyphosate, or more particularly an antibiotic, such as kanamycin, G418, bleomycin, hygromycin, chloramphenicol, or the like. The particular marker employed will be one which will allow for selection of transformed cells compared with cells lacking the introduced recombinant nucleic acid.

The fusion peptide in the expression cassette constructed as described above, expresses at least preferentially in developing seeds. Accordingly, transformed plants grown in accordance with conventional ways, are allowed to set seed. See, for example, McCormick et al. (1986, Plant Cell Reports, 5:81–84). Northern blotting can be carried out using an appropriate gene probe with RNA isolated from tissue in which transcription is expected to occur such as a seed embryo. The size of the transcripts can then be compared with the predicted size for the fusion protein transcript.

Oil-body proteins are then isolated from the seed and analyses performed to determine that the fusion peptide has been expressed. Analyses can be for example by SDS-PAGE. The fusion peptide can be detected using an antibody to the oleosin portion of the fusion peptide. The size of the fusion peptide obtained can then be compared with predicted size of the fusion protein.

Two or more generations of transgenic plants may be grown and either crossed or selfed to allow identification of plants and strains with desired phenotypic characteristics including production of recombinant proteins. It may be desirable to ensure homozygosity of the plants, strains or lines producing recombinant proteins to assure continued inheritance of the recombinant trait. Methods of selecting homozygous plants are well known to those skilled in the art of plant breeding and include recurrent selfing and selection and anther and microspore culture. Homozygous plants may also be obtained by transformation of haploid cells or tissues followed by regeneration of haploid plantlets subsequently converted to diploid plants by any number of known means, (eg: treatment with colchicine or other microtubule disrupting agents).

The desired protein can be extracted from seed that is preferably homozygous for the introduced trait by a variety of techniques, including use of an aqueous, buffered extraction medium and a means of grinding, breaking, pulverizing or otherwise disrupting the cells of the seeds. The extracted seeds can then be separated (for example, by centrifugation or sedimentation of the brei) into three fractions: a sediment or insoluble pellet, an aqueous supernatant, and a buoyant layer comprising seed storage lipid and oil bodies. These oil bodies contain both native oil body proteins and chimeric oil body proteins, the latter containing the foreign peptide. The oil bodies are separated from the water-soluble proteins and re-suspended in aqueous buffer.

If a linker comprising a protease recognition motif has been included in the expression cassette, a protease specific for the recognition motif is added to the resuspension buffer. This releases the required peptide into the aqueous phase. A second centrifugation step will now re-float the processed oil bodies with their attached proteins and leave an aqueous solution of the released peptide or protein. The foreign protein may also be released from the oil bodies by incubation of the oil body fraction with a different oil body fraction that contains the specific protease fused to oleosin. In this manner the protease cleavage enzyme is removed with the oil bodies that contained the fusion protein with the protease recognition site leaving a product uncontaminated by protease. The desired peptide may be precipitated, chemically modified or lyophilized according to its properties and desired applications.

In certain applications the protein may be capable of undergoing self-release. For example, the proteolytic enzyme chymosin undergoes self-activation from a precursor to an active protease by exposure of the precursor to low pH conditions. Expression of the chymosin precursor/oil body fusion protein to conditions of low pH will activate the chymosin. If a chymosin recognition site is included between the oil body protein and the chymosin protein sequences, the activated chymosin can then cleave the fusion proteins. This is an example of self release that can be controlled by manipulation of the conditions required for enzyme activity. Additional examples may be dependant on the requirement for specific co-factors that can be added when self-cleavage is desired. These may include ions, specific chemical co-factors such as NADH or FADH, ATP or other energy sources, or peptides capable of activation of specific enzymes. In certain applications it may not be necessary to remove the fusion protein from the oil-body protein. Such an application would include cases where the fusion peptide includes an enzyme which is tolerant to N or C-terminal fusions and retains its activity; such enzymes could be used without further cleavage and purification. The enzyme/oil body protein fusion would be contacted with substrate. It is also possible to re-use said oil bodies to process additional substrate as a form of an immobilized enzyme. This specific method finds utility in the batch processing of various substances. The process is also useful for enzymatic detoxification of contaminated water or bodies of water where introduction of freely diffusible enzyme may be undesirable. Said process allows recovery of the enzyme with removal of the oil bodies. It is also possible, if desired, to purify the enzyme-oil body protein fusion protein using an immunoaffinity column comprising an immobilized high titre antibody against the oil body protein.

Other uses for the subject invention are as follows. Oil body proteins comprise a high percentage of total seed protein, thus it is possible to enrich the seed for certain desirable properties such as high-lysine, high methionine, and the like, simply by making the fusion protein rich in the amino-acid(s) of interest could find utility of particular interest is the modification of grains and cereals which are used either directly or indirectly as food sources for livestock, including cattle, poultry, and humans. It may be possible to include, as the fusion peptide, an enzyme which may assist in subsequent processing of the oil or meal in conventional oilseed crushing and extraction, for example inclusion of a thermostable lipid-modifying enzyme which would remain active at the elevated crushing temperatures used to process seed and thus add value to the extracted triglyceride or protein product. Other uses of the fusion protein include improvement of the agronomic health of the crop. For example, an insecticidal protein or a portion of an immunoglobulin specific for an agronomic pest such as a fungal cell wall or membrane, could be coupled to the oil body protein thus reducing attack of the seed by a particular plant pest.

It is possible that the polypeptide/protein will itself be valuable and could be extracted and, if desired, further purified. Alternatively the polypeptide/protein or even the mRNA itself may be used to confer a new biochemical phenotype upon the developing seed. New phenotypes could include such modifications as altered seed-protein or seed oil composition, enhanced production of pre-existing desirable products or properties and the reduction or even suppression of an undesirable gene product using antisense, ribozyme or co-suppression technologies (Izant and Weintraub, 1984, Cell 36: 1007–1015, Hazelhoff and Gerlach, 1988, Nature 334:585–591, Napoli, et al., 1990, Plant Cell, 2:279–289). While one embodiment of the invention contemplates the use of the regulatory sequence in cruciferous plants, it is possible to use the promoter in a wide variety of plant species given the wide conservation of oleosin genes. For example, the promoter could be used in various other dicotyledonous species as well as monocotyledonous plant. A number of studies have shown the spatial and temporal regulation of dicot genes can be conserved when expressed in a monocotyledonous host. The tomato rbcS gene (Kyozuka et al, 1993, Plant Physiol. 102:991–1000) and the Pin2 gene of potato (Xu et al, 1993 Plant Physiol. 101:683–687) have been shown to function in a monocotyledonous host consistent with their expression pattern observed in the host from which they were derived. Studies have also indicated expression from some dicotyledonous promoters in monocotyledonous hosts can be enhanced by inclusion of an intron derived from a monocotyledonous gene in the coding region of the introduced gene (Xu et al, 1994, Plant Physiol. 106:459–467). Alternatively, given the wide conservation of oleosin genes, it is possible for the skilled artisan to readily isolate oleosin genes from a variety of host plants according to the methodology described within this specification.

It is expected that the desired proteins would be expressed in all embryonic tissue, although different cellular expression can be detected in different tissues of the embryonic axis and cotyledons. This invention has a variety of uses which include improving the intrinsic value of plant seeds by their accumulation of altered polypeptides or novel recombinant peptides or by the incorporation or elimination of a metabolic step. In its simplest embodiment, use of this invention may result in improved protein quality (for example, increased concentrations of essential or rare amino acids), improved lipid quality by a modification of fatty acid composition, or improved or elevated carbohydrate composition. The invention may also be used to control a seed phenotype such as seed coat color or even the development of seed. In some instances it may be advantageous to express a gene that arrests seed development at a particular stage, leading to the production of "seedless" fruit or seeds which contain large amounts of precursors of mature seed products. Extraction of these precursors may be simplified in this case.

Other uses include the inclusion of fusion proteins that contain antigens or vaccines against disease. This application may be particularly relevant to improvements in health care of fish or other wildlife that is not readily assessable by conventional means as the crushed seed can be converted directly into a convenient food source. Other uses include the addition of phytase to improve the nutritional properties of seed for monogastric animals through the release of phosphate from stored phytate, the addition of chlorophyllase to reduce undesirable chlorophyll contamination of seed oils, especially canola oil and addition of enzymes to reduce anti-metabolites, pigments or toxins from seeds. Additionally the fusion protein may comprise, an insecticidal or fungicidal protein such as magainin or secropin or a portion of an immunoglobulin specific for an agronomic pest, such as a fungal cell wall or membrane, coupled to the oil body protein thus improving seed resistance to pre and post harvest spoilage.

Applications for the use of chimeric proteins associated with the oil body fraction include as above enzymes that are tolerant of N or C-terminal fusions and retain activity. Enzymes associated with oil body suspensions can be mixed with simple or complex solutions containing enzyme substrates. After conversion of substrates to products the enzyme oleosin fusion is readily recovered by centrifugation and floatation and can be reused an indefinite number of times.

EXAMPLES

The following examples are offered by way of illustration and not by limitation.

Example 1

Isolation of Plant Oleosin Gene

Oil body proteins can be isolated from a variety of sources. The isolation of a oil body protein gene (oleosin) from the plant species *Arabidopsis thaliana* is described herein. Similar methods may be used by a person skilled in the art to isolate oil body proteins from other sources. In this example, a *Brassica napus* oleosin gene (described by Murphy et al, 1991, Biochim Biophys Acta 1088:86–94) was used to screen a genomic library of *A. thaliana* (cv. Columbia) constructed in the Lamda cloning vector EMBL3A (Obtained from Stratagene Laboratories) using standard techniques. The screening resulted in the isolation of a EMBL 3A clone (referred to as clone 12.1) containing a 15 kb genomic fragment which contains a oleosin gene from *A. thaliana*. The oleosin gene coding region is contained within a 6.6 kb Kpn I restriction fragment of this 15 kb fragment. The 6.6 kb KpnI restriction fragment was further mapped and a 1.8 kb Nco I/Kpn I fragment containing the oleosin gene including approximately 850 nucleotides of 5' sequence, the complete coding sequence and the 3' region was isolated. This 1.8 kb fragment was end filled and subcloned in the Sma I site of RFM13 mp19. The 1.8 kb insert was further digested with a number of standard restriction enzymes and subcloned in M13 mp19 for sequencing. Standard cloning procedures were carried out according to Sambrook et al. (*Molecular Cloning: A Laboratory Manual* 2nd ed., 1989, Cold Spring Harbour Laboratory Press.) The nucleotide sequence was determined and the 1.8 kb sequence of the *A. thaliana* oleosin gene is presented in FIG. 2 and SEQ.ID.NO.1. This particular DNA sequence codes for a 18 KDa *A. thaliana* oleosin gene. The coding region contains a single intron. This gene was used for the construction of recombinant protein expression vectors. The gene may also be used for screening of genomic libraries of other species.

Example 2

Modification of a Native Oleosin for Expression of Heterologous Proteins

The DNA fragment described in example 1 that contains the oleosin gene and regulatory elements was incorporated into an expression cassette for use with a variety of foreign/alternative genes. The following illustrates the modification made to the native *A. thaliana* oleosin gene, especially the promoter and coding region, in order to use this gene to illustrate the invention. It is contemplated that a variety of techniques can be used to obtain recombinant molecules, accordingly this example is offered by way of illustration and not limitation. The *A. thaliana* oleosin gene described in example 1 was cloned as a 1803 bp fragment flanked by Nco 1 and Kpn 1 sites in a vector called pPAW4. The plasmid pPAW4 is a cloning vehicle derived from the plasmid pPAW1 which is a Bluescript plasmid (Clonetech Laboratories) containing a *Brassica napus* Acetolactate synthase (ALS) gene (Wiersma et al., 1989, Mol Gen Genet.

219:413–420). To construct pPAW4, the plasmid pPAW1 was digested with Kpn I. The digested DNA was subjected to agarose gel electrophoresis and the fragment that contained the Bluescript plasmid vector backbone and a 677 base pair portion of the *B. napus* ALS gene was isolated and religated. This plasmid contains the following unique restriction sites within the insert: Pst I, Nco I, Hind III and Kpn I. This plasmid was called pPAW4. The 1803 bp Nco I-Kpn I Arabidopsis oleosin gene fragment was cloned between the Nco I and Kpn I sites in pPAW4. The resultant plasmid contained in addition to the Bluescript plasmid sequences, a 142 bp Pst I-Nco I fragment derived from the *B. napus* ALS gene and the entire 1803 bp Arabidopsis oleosin gene. The 142 bp Pst I-Nco I fragment is present only as a "stuffer" fragment as a result of the cloning approach and is not used in oleosin expression constructs.

Figure 3:
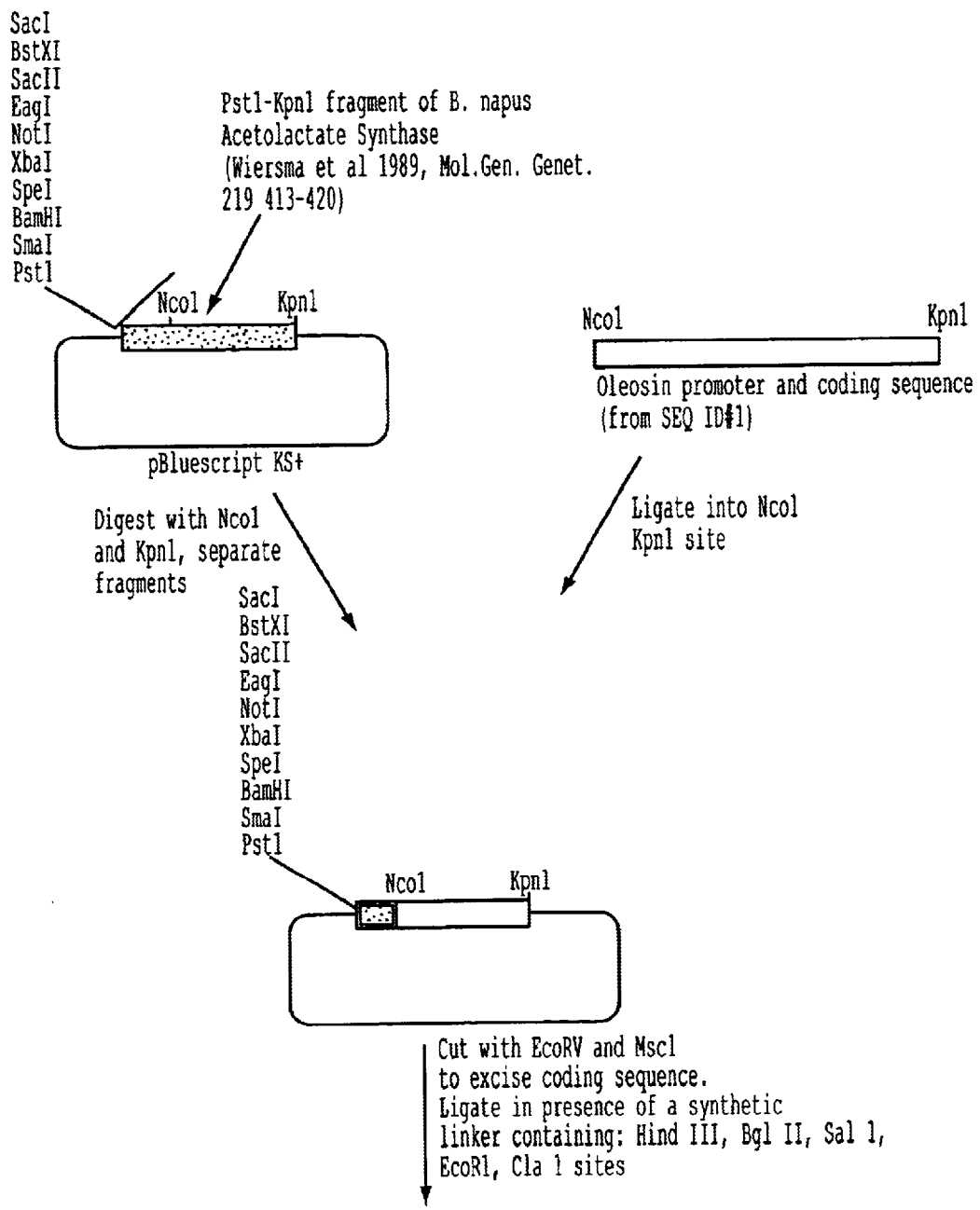
FIG. 3 shows a schematic representation of the construction of pOleoP1.
Figure 3A:
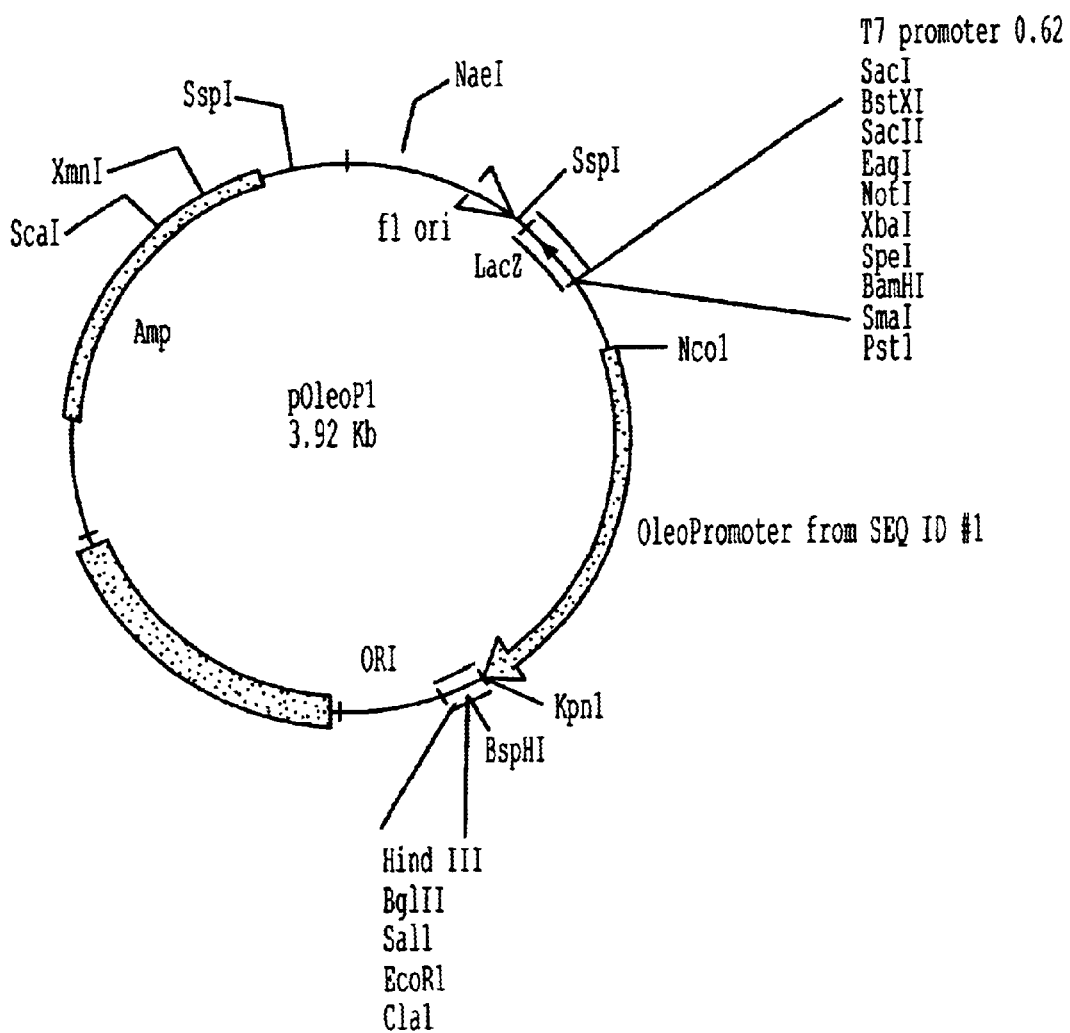

The resultant plasmid was used to further modify the Arabidopsis oleosin gene. Site-directed mutagenesis was used to introduce nucleotide changes at positions −2, −1 and +4 in the DNA sequence shown in FIG. 2. The changes made were: A to T (nucleotide position −2); A to C (nucleotide position−1) and G to A (nucleotide position +4). These nucleotide changes create a 6 nucleotide Bsp HI restriction endonuclease site at nucleotide positions −2 to +4. The Bsp H1 site (T/CATGA) encompasses the ATG initiation codon and provides a recessed end compatible with Nco 1. A second modification was made by digestion with the enzymes Eco RV and Ms c1 which released a 658 bp fragment containing most of the coding sequence of the native oleosin. This digestion left blunt ends at both the Eco RV and Ms c1 sites. The cut vector was recircularized in the presence of an oligonucleotide linker containing the following unique restriction sites: Hind III, Bgl II, Sal I, Eco RI and Cla I. The recircularized plasmid containing all the 5′ regulatory sequences of the oleosin gene, a transcriptional start site and an initiation codon embedded in a Bsp H1 site. Thirty-one bases downstream of this is a short polylinker containing unique restriction sites. This plasmid was called pOleoP1. The restriction map of this construct is shown in FIG. 3.

Introduction of any DNA sequence into pOleoP1, this particular cassette requires that the foreign DNA sequence may have, or be modified to have, a Bsp H1 or Nco 1 site at the initial ATG position. This will assure conservation of the distance between the "cap" site and the initiator codon. Alternatively restriction site linkers may be added to facilitate insertion into the cassette. The same restriction site can be chosen for the site of insertion of the 3′ end of the gene or linkers may be added to introduce appropriate sites. The complete chimeric construct is then excised using the appropriate restriction enzyme(s) and introduced into an appropriate plant transformation vector.

Example 3

Using the Arabidopsis Oleosin Promoter For Controlling Expression in Heterologous Plant Species To demonstrate expression of the oleosin promoter and to determine the amount of 5′ regulatory region required for expression in transgenic plants, a small number of DNA constructs were made that contain the 5′ transcriptional initiation region of the Arabidopsis oleosin gene joined to the coding region for βglucuronidase (GUS). These constructs were prepared using PCR. The constructs are designated according to the amount of the oleosin 5′ region contained, for example, the 2500 construct has approximately 2500 base pairs of the oleosin 5′ region. The constructs were introduced into *Brassica napus* and tobacco and the expression of the β-glucuronidase (GUS) gene was measured as described in detail below. The constructs were made using standard molecular biology techniques, including restriction enzyme digestion, ligation and polymerase chain reaction (PCR). As an illustration of the techniques employed, the construction of the 800 construct is described in detail.

In order to obtain a DNA fragment containing approximately 800 base pairs from the 5′ transcriptional initiation region of the Arabidopsis oleosin gene in a configuration suitable for ligation to a GUS coding sequence, PCR was used. To perform the necessary PCR amplification, two oligonucleotide primers were synthesized (Milligen-Biosearch, Cyclone DNA synthesizer). The first primer, the 5′ primer, was called GVR10 and had the following sequence (also shown in SEQ.ID.NO.15):

5'-CA*CTGCA*GGAACTCTCTGGTAA-3' (GVR10)

The italicized bases correspond to nucleotide positions −833 to −817 in the sequence reported in FIG. 2. The Pst 1 site is underlined. The additional nucleotides 5′ of this sequence in the primer are not identical to the oleosin gene, but were included in order to place a Pst I site at the 5′ end of the amplification product.

The second primer, the 3′ primer, is designated as ALP 1 and has the following sequence (also shown in SEQ.ID.NO.16):

5'-CTA*CCCGGGATCCT*GTTTACTAGAGAGAATG-3' (ALP 1)

This primer contains the precise complement (shown in italics) to the sequence reported in FIG. 2 from base −13 to −30. In addition, it contains a further 13 bases at the 5′ end added to provide two (overlapping) restriction sites, Sma 1 (recognition CCCGGG) and BamH1 (recognition GGATCC), at the 3′ end of the amplification product to facilitate cloning of the PCR fragment. Both the Sma 1 and Bam H1 sites are underlined, the Bam H1 site is delineated by a double underline.

These two primers were used in a PCR amplification reaction to produce DNA fragment containing the sequence between nucleotides −833 and −13 of the oleosin gene that now contains a Pst 1 site at the 5′ end and Sma 1 and Bam H1 sites at the 3′ end. The template was the oleosin genomic clone 12.1 described in example 1.

The amplification product was called OLEO p800 and was gel purified and digested with Pst 1. The digestion product was gel purified and end filled using DNA polymerase Klenow fragment then cut with Sma 1 to produce a blunt ended fragment. This fragment was cloned into the Sma 1 site of pUC19 to yield the plasmid pUC OLEOp800. This plasmid contained the insert oriented such that the end of the amplified fragment which contained the Pst 1 site is proximal to the unique Hind III site in the pUC19 cloning vector and the end of the amplified fragment that contains the Sma 1 and Bam H1 site is proximal to the unique Eco RI site in the pUC19. This subclone now contains approximately 800 base pairs of 5′ regulatory region from the Arabidopsis oleosin gene.

The promoter region contained within the plasmid pUC OLEOp800 was fused to the reporter gene GUS. This was accomplished by substituting the oleosin promoter region for a heat shock promoter fused to a GUS gene in the plasmid HspGUS1559. HspGUS1559 is a plasmid used as a binary vector in Agrobacterium, derived from the vector pCGN 1559 (MacBride and Summerfeldt, 1990, Plant Molecular Biology, 14, 269–276) with an insert containing heat shock promoter (flanked by Bam H1 sites), the β-glucuronidase open reading frame and a nopaline synthase terminator (derived from pBl221, Jefferson RA in Cloning Vectors 1988, Eds. Pouwels P., Enger-Valk BE, Brammer WJ., Elsevier Science Pub BV, Amsterdam section VII, Ai11). The binary plasmid HspGUS1559 was digested with BamH1 which resulted in the release of the heat shock promoter and permitted the insertion of a BamH1 fragment in its place. pUC OLEOp800 was then cut with Bam H1 to yield a promoter fragment flanked by Bam H1 sites. This fragment was cloned into the Bam H1 sites of the plasmid HspGUS1559 to yield the Agrobacterium binary transformation vector pOLEOp800GUS1559. The other constructs were prepared by the same PCR method described above using the appropriate primers for amplifying the –2500 fragment, the –1200 fragment, the –600 fragment or the –200 fragment. These plasmids was used to transform *Brassica napus* and tobacco. GUS expression assays (Jefferson R. A., 1987, Plant Mol. Biol. Rep. 5 387–405) were performed on the developing seeds and on non-reproductive plant parts as controls. The results in *Brassica napus* expressed as specific activity of GUS enzyme are shown in Table I. The results in tobacco are shown in Table II. GUS expression reported is an average obtained from approximately five seeds from each of approximately five different transgenic plants.

These results demonstrate that the oleosin fragment from –833 to –13 used in the 800 construct contains sufficient information to direct specific expression of a reporter gene in transgenic *Brassica napus* embryos as early as heart stage and that the Arabidopsis oleosin promoter is capable of directing transcription in plants other than Arabidopsis.

It should be noted that the specific expression demonstrated here does not depend on interactions with the native terminator of an oleosin gene 3' end. In this example, the 3' oleosin terminator was replaced by a terminator derived from the nopaline synthase gene of Agrobacterium. Thus, the sequence in the 800 construct is sufficient to achieve the desired expression profile independent of ancillary sequences.

Example 4

Use of Oleosin Promoter and Coding Sequences to Direct Fusion Proteins to the Oil Body Fraction of Seeds In this example, we have prepared a transgenic plant which expresses, under the control of the oil body promoter, fusion proteins which associate with oilbodies. The enzymatic properties of the inserted coding sequences are preserved while fused to the oleosin. In this example we use the β-glucuronidase enzyme derived from the microorganism *E. coli.* was fused to the oleosin coding region (referred to as a oleosin/GUS fusion) under the control of the Arabidopsis oleosin promoter. In order to create an in-frame GUS fusion with the Arabidopsis oleosin, two intermediate plasmids were constructed referred to as pOThromb and pGUSNOS.

The plasmid pOThromb comprises the oleosin 5' regulatory region, the oleosin coding sequence wherein the carboxy terminus of the protein has been modified by addition of a thrombin cleavage site. The plasmid pGUSNOS contains the GUS enzyme coding region followed by the nos terminator polyadenylation signal. These two plasmids were joined to make a fusion protein consisting of the oleosin protein fused to the GUS enzyme by way of a linker peptide that is recognized by the endoprotease thrombin.

These plasmids were constructed using PCR and the specific primers shown below. For the construction of pOThromb, a linker oligonucleotide named GVR01 was synthesized having the DNA sequence (shown in SEQ.ID.NO.17) of:

```
           10        20        30        40
5'AATCCCATGG ATCCTCGTGG AACGAGAGTA GTGTGCTGGC

CACCACGAGT ACGGTCACGG TC 3'(GVR01)
           50        60
```

This DNA sequence contains from nucleotides 27–62 sequences complementary to the 3' end of the Arabidopsis oleosin coding sequence, from nucleotides 12–26 sequences encoding amino acids that comprise the coding region for a thrombin cleavage site, LVPRGS, and from nucleotides 5–14, the sequence for the restriction sites Bam HI and Nco I. A second primer referred to as GVR10 was also synthesized and consisting of the following DNA sequence (also shown in SEQ.ID.NO.18):

```
             10        20
 5'-CACTGCAGGAACTCTCTGGTAAGC-3'(GVR10)
```

This DNA sequence contains from nucleotides 5–24 sequences homologous to the oleosin 5' flanking sequence –834 and –814. These two primers were used to amplify the promoter region (0.8 kb) of the Arabidopsis oleosin gene contained in the clone 12.1 described in example 1. The resultant fragment was endfilled and cloned in the Sma I site of pUC19. This plasmid was called pOThrom which contained the oleosin promoter region, the oleosin coding sequence followed by a cleavage site for the enzyme thrombin and restriction sites for the insertion of the β-glucuronidase (hereinafter GUS).

In order to create an in frame GUS fusion with the Arabidopsis oleosin coding region now contained in pOThrom, a GUS gene with the appropriate restriction site was constructed by the use of PCR. An oligonucleotide referred to as GVR20 was synthesized and containing the following DNA sequence (also shown in SEQ.ID.NO.19):

```
             10        20
 5'-GAGGATCCATGGTACGTCCTGTAGAAACC-3'(GVR20)
```

This oligonucleotide contains from nucleotides 9–29, sequences complementary to the GUS gene and from nucleotides 3–12 the sequence for the restriction sites Bam HI and Nco I to facilitate cloning. In order to create these restriction sites the fourth nucleotide of the GUS sequence was changed from T to G changing the TTA codon (Leu) into GTA (Val). The second primer used was the universal sequencing primer comprising the DNA sequence (also shown in SEQ.ID.NO.20):

```
             10
5'-GTAAAACGACGGCCAGT-3'    (Universal Sequencing
                            Primer)
```

The GVR20 and the Universal Sequencing Primer were used to amplify the GUS-nopaline synthase terminator region from the plasmid pBI121 (Clontech Laboratories). This fragment was endfilled and cloned in the Sma I site of pUC19. This plasmid was called pGUSNOS.

The plasmid pOThromb was digested with Pst I and Nco I, pGUSNOS was digested with Nco 1 and Xba I. The inserts of both these plasmids were ligated simultaneously into pCGN1559 cut with Xba I and Pst I to generate plasmid pCGOBPGUS. The plasmid pCGOBPGUS contained in the following order, the Arabidopsis oleosin 5' regulatory region, the oleosin coding region, a short amino acid sequence at the carboxy end of the oleosin coding sequence comprising a thrombin protease recognition site, the coding region for the β-glucuronidase gene followed by the nos terminator polyadenylation signal. The fusion protein coded for by this particular DNA construct is designated as an oleosin/GUS fusion protein.

This plasmid pCGOBPGUS was digested with Pst I and Kpn I cloned into the PstI and Kpn I sites of pCGN1559 resulting in plasmid pCGOBPGUS which was used as a binary vector in Agrobacterium transformation experiments to produce transgenic B. napus. Seeds from transgenic Brassica napus were obtained and tested for GUS activity. The transformed seeds showed GUS activity specifically associated with the oil body fraction. The results of these experiments are shown in Table III. The data demonstrate specific fractionation of the GUS enzyme to the oil body fraction. This example illustrates the expression and targeting of a bacterial derived enzyme specifically to the oil body fraction of transgenic plants.

One skilled in the art would realize that various modifications can be made to the above method. For example, a constitutive promoter may be used to control the expression of a oleosin/GUS fusion protein. In particular, the 35S promoter may also be used to control the expression of the oleosin/GUS fusion described above by replacing the Arabidopsis oleosin promoter with the 35S promoter from CaMV (available from the vector pBI 221.1, Clonetech Laboratories) in the vector pCGOBPGUS. The resultant vector can contain in the following order, the CaMV 35S promoter, the oleosin coding region, a short amino acid sequence at the carboxy end of the oleosin coding sequence comprising a thrombin protease recognition site, the coding region for the β-glucuronidase gene followed by the nos terminator polyadenylation signal. This plasmid can be inserted into Bin 19 and the resultant plasmid may be introduced into Agrobacterium. The resulting strain can be used to transform B. napus. GUS activity can be measured in the oil body fraction.

Example 5

Cleavage of Oleosin-Fusion Proteins

In example 4 it was demonstrated that the targeting information contained within the oleosin is sufficient to target the protein oleosin/GUS fusion to the oil body. The oleosin/GUS fusion protein contains an amino acid sequence (LVPRGS SEQ.ID.NO.21), which separates the oleosin from GUS. This sequence is recognized by the protease thrombin, which cleaves this peptide sequence after the arginine (R) amino acid residue. The transgenic seeds containing these oleosin/GUS fusions, were used to demonstrate the general utility of such a method of cleavage of a foreign peptide from intact oil bodies containing oleosin/foreign peptide-fusions. The oil body fraction that contained the oleosin/GUS fusion was resuspended in thrombin cleavage buffer which consisted of 50 mM Tris (pH 8.0), 150 mM NaCl, 2.5 mM $CaCl_2$ 2% Triton X-100 and 0.5% sarcosyl. Thrombin enzyme was added and the sample was placed for 30 minutes each at 45° C., 50° C. and 55° C. Following this incubation oil bodies were recovered and tested for GUS activity. GUS enzymatic activity was found in the aqueous phase following this cleavage and removal of the oil bodies. This is shown in table IV. Western blot analysis confirmed the cleavage of GUS enzyme from the oleosin/GUS fusion protein. This example illustrates the cleavage and recovery of a active enzyme from a oleosin/enzyme fusion following biosynthesis and recovery of the enzyme in the oil body fraction of transgenic seeds.

Example 6

Use of Fusion Proteins as Reusable Immobilized Enzymes

In this example, oleosin/GUS fusion proteins that were associated with oilbodies were used as immobilized enzymes for bioconversion of substrates. Advantage was taken of the fact that enzymatic properties are preserved while fused to the oleosin and the oleosin is very specifically and strongly associated with the oil bodies even when the oil bodies are extracted from seeds. In this example it is demonstrated that said fusion enzymes can be used repeatedly and recovered easily by their association with the oil bodies. In order to demonstrate the reusable and stable GUS activity of the transgenic seeds, transgenic oil bodies were isolated from mature dry seeds as follows. The Brassica napus transgenic seeds containing a oleosin/GUS fusion protein were ground in extraction buffer A which consists of 0.15 M Tricine-KOH pH 7.5, 10 mM KCl, 1 mM $MgCl_2$ and 1 mM EDTA, 4° C. to which sucrose to a final concentration of 0.6M was added just before use. The ground seeds in extraction buffer were filtered through four layers of cheesecloth before centrifugation for 10 minutes at 5000×g at 4° C. The oil bodies present as a surface layer were recovered and resuspended in buffer A containing 0.6M sucrose. This solution was overlaid with an equal volume of Buffer A containing 0.1M sucrose and centrifuged at 18,000×g for 20 minutes. This procedure was repeated twice with the purified oil body fraction (which contained the oilbodies and oleosin/GUS fusion proteins) and was resuspended in buffer A containing 1 mM p-nitrophenyl β-D-glucuronide, a substrate for the GUS enzyme. After incubation, the conversion of the colorless substrate to the yellow p-nitrophenol was used as an indication of GUS activity in the suspensions of transgenic oil bodies. This illustrated the activity of the enzyme is maintained while fused to the oleosin protein and the enzyme is accessible to substrate while attached to the oil bodies. The oil bodies were recovered as described above. No GUS enzyme remained in the aqueous phase after removal of the oil bodies. The oil bodies were then added to fresh substrate. When the oil bodies were allowed to react with fresh substrate, conversion of substrate was demonstrated. This process was repeated four times with no loss of GUS activity. In parallel quantitative experiments, the amount of methyl umbelliferyl glucuronide (MUG) converted to methyl umbelliferone was determined by fluorimetry, and the oil bodies were recovered by flotation centrifugation and added to a new test tube containing MUG. The remaining buffer was tested for residual GUS activity. This procedure was repeated several times. The GUS enzyme showed 100% activity after using four uses and remained stably associated with the oil body fraction. These results are shown in table V. These experiments illustrate the immobilization and recovery of the active enzyme following substrate conversion. The stability of the GUS activity in partially purified oil bodies was established by measuring the GUS activity of the oil body suspension several weeks in a row. The half-life of the GUS activity when the oil-bodies are stored in extraction buffer at 4° C. is more than 3 weeks.

Expression of Oleosin Fusion Proteins

Example 7

Expression of an Oleosin/IL-1-β as a Fusion Protein

To further illustrate the utility of the invention, the human protein interleukin 1-β (IL-1-β) was chosen for biosynthesis according the method. IL-1-β consists of 9 amino acids (aa); Val-Gln-Gly-Glu-Glu-Ser-Asn-Asp-Lys (Antoni et al., 1986, J. Immunol. 137:3201–3204 SEQ.ID.NO.22). The strategy for biosynthesis was to place this nine amino acid protein at the carboxy terminus of the native oleosin protein. The strategy further employed the inclusion of a protease recognition site to permit the cleavage of the Il-1-β from the oleosin protein while fused to the oil bodies. In order to accomplish this, a recognition site for the endoprotease Factor Xa was incorporated into the construct. The protease Factor Xa can cleave a protein sequence which contains amino acid sequence ile-glu-gly-arg. Cleavage takes place after the arginine residue. Based on these sequences, an oligonucleotide was synthesized which contained 18 nucleotides of the 3' coding region of the A. thaliana oleosin (base position 742–759, coding for the last six amino acids of the native protein), an alanine residue (as a result of replacing the TAA stop codon of the native oleosin with a GCT codon for alanine), the coding sequence for the Factor Xa cleavage (four codons for the amino acids ile-glu-gly-arg) followed by the coding sequence for IL-1-β. The oligonucleotide further comprised a TAA stop coding after the carboxy terminus lysine residue of IL-1-β and adjacent to this stop codon, a Sal 1 restriction site was added. The IL-1-β coding sequence was designed using optimal codon usage for the B. napus and A. thaliana oleosin. It is apparent to those skilled in the art that maximal expression is expected when the codon usage of the recombinant protein matches that of other genes expressed in the same plant or plant tissue. This oligonucleotide was inserted into the Arabidopsis oleosin gene. The modified oleosin gene was cut with Pst 1 and Sal 1 and joined to the nos terminator to obtain the plasmid called pCGOBPILT. This plasmid contains, in the following order, the Arabidopsis oleosin promoter, the oleosin coding sequence, including the intron, and the IL-1-β coding region joined at the carboxy terminus of the oleosin protein through a Factor Xa protease recognition site and the nos terminator polyadenylation signal. This construct was inserted into the binary plasmid Bin 19 (Bevan, M., 1984, Nucl. Acids Res. 12:8711–8721) and the resultant plasmid was introduced into Agrobacterium. The resulting strain was used to transform B. napus and tobacco plants.

The Arabidopsis oleosin/IL-1-β fusion was stably integrated into the genomes of tobacco and B. napus. Northern analysis of embryo RNA isolated from different transformed tobacco plants showed the accumulation of Arabidopsis oleosin/IL-1-β mRNA.

Oil body proteins from transformed tobacco seeds were prepared, and western blotting was performed. An antibody raised against a 22 KDa oleosin of B. napus, was used to detect the Arabidopsis oleosin/IL-1-β fusion in the tobacco seeds. This antibody recognizes all the major oleosins in B. napus and A. thaliana. In addition, this antibody recognizes the tobacco oleosins. In oleosins extracted from transformed tobacco seeds the antibody recognized a 20 KDa-protein, which represents oleosin/IL-1-β fusion oleosin. This fusion protein was not present in the untransformed tobacco seed. These results demonstrate the accumulation of oleosin/IL-1-β fusion in tobacco. Similar expression and accumulation is seen in Brassica napus transformed with the oleosin/IL-1-β fusion gene. These results further exemplify the utility of the method for the expression of heterologous proteins in plants.

Example 8

Expression of Oleosin/Hirudin Gene Fusion in B. napus

As a further example of the invention, the protein hirudin, derived from the leech (a segmented worm) was synthesized and fused to oleosin. Hirudin is an anti-coagulant which is produced in the salivary glands of the leech Hirudo medicinalis (Dodt et al., 1984, FEBS Lett., 65:180–183). The protein is synthesized as a precursor protein (Harvey et al., 1986, Proc. Natl. Acad. Sci. USA 83: 1084–1088) and processed into a 65 amino acid mature protein. The hirudin gene was resynthesized to reflect the codon usage of Brassica and Arabidopsis oleosin genes and a gene fusion was made with the C-terminal end of the Arabidopsis oleosin gene. The gene sequences for oleosin and huridin were separated by codons for an amino acid sequence encoding a Factor Xa endoprotease cleavage site. The resulting plasmid was called pCGOBHIRT. This plasmid contains, in the following order, the promoter region of the Arabidopsis oleosin gene, the coding sequence of the oleosin protein including the intron, a factor Xa cleavage site and the resynthesized huridin gene followed by the nos terminator polyadenylation signal. This construct was inserted into the binary plasmid Bin 19 and the resultant plasmid was introduced into Agrobacterium. The resulting strain was used to transform B. napus and tobacco.

The Arabidopsis oleosin/hirudin fusion (OBPHIR) was stably integrated into the genomes of N. tabacum and B. napus respectively. Northern analysis of embryo RNA isolated from different OBPHIR transformed plants showed the accumulation OBPHIR mRNA in B. napus seeds. Monoclonal antibodies raised against hirudin confirmed the stable accumulation of the oleosin/hirudin fusion in the seeds of transformed plants. Transgenic seeds containing an oleosin/hirudin were assayed after a year of storage at room temperature. No degradation of the oleosin/hirudin protein could be observed demonstrating the stability of the huridin in intact seeds.

The huridin can be cleaved from the oleosin by the use of the Factor Xa cleavage site built into the fusion protein. Upon treatment of the oilbody fraction of transgenic Brassica napus seeds, active huridin was released. These results are shown in Table VI. This example illustrates the utility of the invention for the production of heterologous proteins with therapeutic value from non-plant sources.

Example 9

Fusion of Foreign Proteins to the N-terminus of Oleosin

In this example, a foreign protein was joined to the oleosin coding region via fusion to the N-terminus of the oleosin. As an illustration of the method, the GUS enzyme was fused in-frame to the Arabidopsis oleosin coding region described in example 1. In order to accomplish this, four DNA components were ligated to yield a GUS-oleosin fusion under the control of the oleosin promoter. These were: The oleosin 5' regulatory region, the GUS coding region, the oleosin coding region, and the nos ter transcription termination region. These four DNA components were constructed as follows:

The first of these components comprised the oleosin promoter isolated by PCR using primers that introduced convenient restriction sites. The 5' primer was called OleoPromK and comprised the sequence (also shown as SEQ.ID.NO.23):

```
            Nco1
5'-CGC GGT ACC ATGG CTA TAC CCA ACC TCG-3'
        Kpn1
```

This primer creates a convenient Kpn 1 site in the 5' region of the promoter. The 3' primer comprised the sequence (also shown as SEQ.ID.NO.24):

```
5'-CGC ATCGATGTTCTTGTTTACTAGAGAG-3'
        Cla1
```

This primer creates a convenient Cla 1 site at the end of the untranslated leader sequence of the oleosin transcribed sequence just prior to the ATG initiation codon in the native oleosin sequence. These two primers were used to amplify a modified promoter region from the native Arabidopsis oleosin gene. Following the reaction, the amplification product was digested with Kpn 1 and Cla 1 to yield a 870 bp fragment containing the oleosin promoter and the 5' untranslated leader sequence. This promoter fragment is referred to as Kpn-OleoP-Cla and was ligated in the Kpn 2-Cla 1 sites of a standard subcloning vector referred to as pBS.

The second DNA component constructed was the GUS coding region modified to introduce the appropriate restriction sites and a Factor Xa cleavage site. In order to accomplish this, the GUS coding region in the vector PBI221 was used as a template in a PCR reaction using the following primers. The 5' primer was called 5'-GUS-Cla which comprised the following sequence (also shown as SEQ.ID.NO.25):

```
5'-        Nde 1
GCC ATCGATCAT ATG TTA CGT CCT GTA GAA ACC CCA-3'
        Cla 1
```

The 3' primer was referred to as 3'-GUS-FX-Bam and comprised the following nucleotide sequence (also shown as SEQ.ID.NO.26):

```
5'CGC GGATCC TCT TCC TTC GAT TTG TTT GCC TCC CTG
C-3'
      Bam H1    Factor Xa
                encoding DNA sequence
                shown in boldface
```

This second oligonucleotide also encodes four amino acids specifying the amino acid sequence I-E-G-R, the recognition site for the endoprotease activity of factor Xa. The amplification product of approximately 1.8 kb comprises a GUS coding region flanked by a Cla 1 site at the 5' end and in place of the GUS termination codon, a short nucleotide sequence encoding the four amino acids that comprise the Factor Xa endoprotease activity cleavage site. Following these amino acid codons is a restriction site for BamH1.

The isolation of the oleosin coding region was also performed using PCR. To isolate this third DNA component, the Arabidopsis oleosin genomic clone was used as a template in a reaction that contained the following two primers. The first of these primers is referred to as 5'-Bam-Oleo and has the following sequence (also shown as SEQ.ID.NO.27):

```
5'CGC GGATCC ATG GCG GAT ACA GCT AGA 3'
        Bam H1
```

The second primer is referred to as 3'-Oleo-Xba and has the following sequence (also shown as SEQ.ID.NO.28):

```
5'TGC TCTAGA CGA TGA CAT CAG TGG GGT AAC TTA AGT3'
        Xba 1
```

PCR amplification of the genomic clone yielded an oleosin coding region flanked by a Bam H1 site at the 5' end and a Xba 1 site at the 3' end. This coding sequence was subcloned into the Bam Hi and Xba 1 site of the subcloning vector pBS.

The fourth DNA component comprised the nopaline synthetase transcriptional termination region (nos ter) isolated from the vector pBI 221 as a blunt-ended Sst 1-EcoRI fragment cloned into the blunt-ended Hind III site of pUC 19. This subclone has a Xba 1 site at the 5' end and a Hind III site at the 3' end.

As a first step to assemble these four DNA components, the oleosin coding region and nos ter were first jointed by ligation of the Bam H1-Xba 1 fragment of the oleosin coding region with the Xba 1-Hind III fragment of the nos ter into Bam H1-Hind III digested pUC 19. This construct yielded a subclone that comprised the oleosin coding region joined to the nos ter. As a second step in the assembly of the DNA components, the oleosin promoter region was then joined to the modified GUS coding region by ligation of the Kpn 1-Cla 1 oleosin promoter fragment to the Cla 1-Bam H1 fragment of the GUS coding region modified to contain the Factor Xa recognition site and subcloning these ligated fragments into pUC 19 cut with Kpn 1 and Bam H1.

To assemble all four DNA components, the Kpn 1-Bam H1 oleosin promoter fused to the GUS coding region was ligated with the Bam H1-Hind III oleosin coding region-nos ter fragment in a tripartite ligation with Kpn1-Hind III digested Agrobacterium binary transformation vector PCGN1559. The resultant transformation vector was called pCGYGON1 and was mobilized into *Agrobacterium tumefaciens* EHA 101 and used to transform *B. napus*. Transformed plants were obtained, transferred to the greenhouses and allowed to set seed. Seeds were analyzed as described by Holbrook et al (1991, Plant Physiology 97:1051–1058) and oil bodies were obtained. Western blotting was used to demonstrate the insertion of the GUS oleosin fusion protein into the oil body membranes. In these experiments, more that 80% of the GUS oleosin fusion protein was associated with the oil body fraction. No degradation of the fusion protein was observed. This example illustrates the utility of the method for the expression and recovery of foreign proteins fused to the N-terminus of oleosin.

Example 10

Expression of an Oleosin/Chymosin Fusion Protein

As a further example of the invention, the bovine aspartic protease, chymosin—which is also frequently referred to in the art as rennin—was expressed as an oleosin fusion. Also exemplified here is the cleavage of an oleosin fusion protein by chemical means.

A complementary DNA clone containing a gene of interest may be obtained by any standard technique. For the purpose of this experiment, reverse transcription PCR was used to obtain a full length pre-prochymosin cDNA clone. RNA isolated from calf abomasum was used as the source material for the PCR and primers were designed in accordance with the sequence described by Harris et al. (1982, Nucl. Acids Res., 10: 2177–2187). Subsequently, prochymosin was furnished with an NcoI recognition sequence (CCATGG) in such a way that the initiating methionine codon was in frame with the prochymosin cDNA. The Met-prochymosin sequence was ligated in frame to the 3' coding sequence of an A. thaliana oleosin genomic sequence oleosin in which the TAA stopcodon had been replaced by a short spacer sequence (encoding LVPRGS SEQ.ID.NO.29) and an NcoI site. The complete sequence of a HindIII fragment containing the oleosin-spacer-Met-prochymosin sequence is shown in FIG. 6 and SEQ.ID.NO.6. This HindIII fragment was joined to a nopaline synthase terminator and cloned into the binary vector pCGN1559 (McBride and Summerfelt, 1990, Plant Mol. Biol. 14: 269–276). The resulting plasmid was called pSB-SOTPTNT and introduced in A. tumefaciens. The resulting bacterial strain was used to transform B. napus plants.

Oil bodies from transformed B. napus plants were prepared and resuspended in 100 mM Tris-Cl, pH 8.0. In order to demonstrate chemical cleavage of chymosin from the oleosin-spacer-Met-prochymosin fusion, the pH of the oil body suspension was lowered into two steps to pH 5.5 and pH 3.0, respectively using HCl. Oil bodies were subjected to these acidic conditions for several hours prior to Western blotting. Western blotting was performed using polyclonal antibodies raised against bovine chymosin and using commercially available chymosin (Sigma) as a positive control. The oleosin-spacer-Met-prochymosin fusion protein (approximately 62 kDa) could only be detected in oil body protein extracts obtained from transgenic B. napus seeds incubated at pH 8.0 and pH 5.0. No mature chymosin (35 kDa) was detected in protein extracts incubated under these conditions. The mature chymosin polypeptide was detected as the predominant molecular species in oil body protein extracts incubated at pH 3.0. In addition, oil body protein extracts incubated at pH 3.0 were the only extracts exhibiting chymosin activity as measured by milk-clotting assay. In protein extracts isolated from untransformed control plants no specific cross-reactivity with anti-chymosin antibodies was detected.

Example 11

Expression of an Oleosin/Cystatin Fusion Protein

As a further example of the present invention, the expression of a protein that is toxic to insects is illustrated. The cysteine protease inhibitor, cystatin (OC-I), from Oryza sativa was expressed in a germination-specific manner in Brassica napus cv. Westar. The strategy for biosynthesis was to place the coding sequence for the complete 11.5 kDa OC-I protein downstream of the isocitrate lysase (ICL) promoter, isolated from Brassica napus (Comai et al., 1989, Plant Cell 1: 293–300). The ICL promoter has been shown to be functional for several days directly after germination of the seeds. Thus, this will allow for the pulse release of cystatin only for several days after germination when seedlings are most susceptible to the feeding of insects such as the flea beetle (Phyllotreta cruciferae) or the red turnip beetle (Entomoscelis americana).

The 313 bp sequence, encoding OC-I, from the cDNA clone OC 9b (Chen et al., 1992, Prot. Expr. and Purif., 3: 41–49) was amplified by PCR, using 5' and 3' specific primers, designed to introduce BspHI and BamHI sites for cloning purposes. The resulting fragment was cloned into pITG7, a vector containing the nos terminator of transcription. OC-I-nos was amplified from this plasmid by PCR, using the 5' primer specific to the OC-I coding sequence and the Universal primer (Stratagene). The resulting OC-I-nos fragment was cloned into the SmaI site of pBS(KS), excised with BspHI and KpnI and introduced into pUC18-ICL (plasmid containing the ICL promoter) at the NcoI and KpnI sites. The entire ICL-OC-I-nos cassette was removed by digestion with PstI, cloned into the plant binary vector pCGN 1547 (McBride and Summerfelt, 1990, Plant Mol. Biol. 14: 269–276) and designated pCGN-ICLOC. This plasmid was introduced into Agrobacterium tumefaciens EHA101 and the resulting strain was used to transform Brassica napus cv. Westar, using the cut petiole transformation method (Moloney et al., 1989, Plant Cell Reports 8: 238–242). Transformation resulted in the stable integration of the ICL-OC-I-nos construct into the genome of Brassica napus. Northern blot analysis of poly-$A^+$ mRNA isolated from seedlings showed the accumulation of OC-I mRNA transcripts between one (1) to four (4) days after germination.

Protein extracts from the cotyledons of transformed Brassica napus seedlings were prepared using standard techniques (Sambrook et al., 1989, Molecular Cloning: a laboratory manual 2nd ed, Cold Spring Harbor Laboratory Press) and Western blot analysis was performed in order to determine if OC-I protein was produced. A polyclonal antibody raised against the truncated 10 kDa recombinant form of OC-I (Chen et al., 1992) was produced and allowed the detection of the complete OC-I protein (11.5 kDa) in extracts prepared from transformed Brassica napus seedlings. The OC-I protein was not detected in ungerminated seeds or in untransformed seeds or seedlings. The expression of OC-I was also found to be tissue specific, with the protein being found in cotyledons and hypocotyls but absent from roots and the first true leaves.

In order to prove functionality of the OC-I protein produced in the Brassica napus seedlings, a proteinase inhibitor assay (Rymerson et al., manuscript in preparation) was performed, using the proteinase papain. OC-I produced in the seedlings was shown to significantly inhibit the activity of papain. The experiments described here, indicate that OC-I protein, cystatin, is produced in a germination and tissue specific manner and acts as a functional proteinase inhibitor in this system.

Example 12

Expression of an Oleosin/Xylanase Fusion Protein

As a further example of the present invention, the production of an industrial enzyme, xylanase, is illustrated. A variety of industrial applications have been reported for xylananes (Jeffries et al., 1994, TAPPI 77: 173–179; Biely, 1985, Trends Biotechnol. 3: 286–290), including the conversion of the pulp and paper industry waste product xylan to useful monosaccharides.

The xynC gene encoding a highly active xylanase from the rumen fungus Neocallimastix patriciarum (Selinger et al., 1995, Abstract, 23rd Biennial Conference on Rumen Function, Chicago, Ill.) was joined in-frame to oleosin via a fusion to the C-terminus of the Arabidopsis oleosin coding region described in example 1. The xynC gene consists of an N-terminal catalytic domain preceded by a signal peptide. The xylanase gene lacking the ATG startcodon and partial signal peptide coding sequence was first amplified by PCR using the following 2 primers (also shown in SEQ.ID.NO.30 and SEQ.ID.NO.31):

```
         10        20        30
5'-ATCTCTAGAATTCAACTACTCTTGCTCAAAG-3'
``` and

```
         10        20
5'-GGGTTGCTCGAGATTTCTAATCAATTTAT-3'
```

The PCR product was digested with EcoRI and XhoI and cloned into the *E. coli* expression vector pGEX4T-3 (Pharmacia) and designated pGEXxyn. Following expression and purification of the xylanase-glutathion-S-transferase fusion protein according to the protocol provided by the manufacturer, polyclonal antibodies against xylanase were obtained from rabbits immunized with thrombin-cleaved, purified recombinant xylanase.

In order to obtain the 1608 bp fragment containing the oleosin promoter and oleosin coding region, the construct pCGYOBPGUSA (van Rooijen and Moloney, 1995, Plant Physiol. 109: 1353–1361) was digested with PstI and BamHI. The xylanase coding region was obtained by digestion of pGEXxyn with EcoRI and XhoI. The oleosin fragment and xylanase fragment were cloned into pBluescript (pBS), previously digested with EcoRI and XhoI, resulting in pBSOleXyn. In order to isolate the nopaline synthase (NOS) terminator region containing XbaI and XhoI cloning sites, the BamHI-HindIII fragment from pCGYOBPGUSA containing the NOS terminator sequence was subcloned in pBS to yield the intermediate plasmid pBSNos. Digestion of pBSNos with XbaI and XhoI and digestion of pBSOleXyn with PstI and XhoI yielded fragments containing the NOS terminator and the oleosin-xylanase fusion respectively and were ligated into the binary vector pCGN1559 which was digested with PstI and XhoI. The resulting binary vector containing the recombinant oleosin-xylanase fusion was named pCGOleXyn. Following introduction of pCGO-LeXyn into *A. tumefaciens, B. napus* cv Westar plants were transformed using the method of Moloney et al. (1989, Plant Cell Rep. 8: 238–242).

Accumulation of oleosin-XynC fusion protein in oil-bodies of transgenic canola plants was assessed by Western analysis. Probing of total seed protein extracts and oil body protein extracts with anti-XynC antiserum revealed the presence of a predominant band of 70 kDa on Western blots in both extracts. The predicted molecular weight of the oleosin-XynC fusion protein (68.2 kDa) and hence is in good agreement with the observed band. The fusion protein was absent in extracts from untransformed plants.

In order to evaluate functional activity of the oleosin-xylanase fusion proteins, xylanase enzyme assays using remazol brilliant blue-xylan (RBB-xylan) as described by Biely et al. (1988, Methods Enzymol. 160: 536–542) were carried out using oilbody immobilized xylanase. Xylanase activity was found to be associated almost exclusively with the oil body fraction and kinetic parameters were comparable to those of microbially expressed xylanase.

Example 13

Expression of an Oleosin/Carp Growth Hormone Fusion Protein

As a further example of this invention, the production of carp growth hormone (cGH) as an oleosin fusion protein is described. A DNA fragment containing the cGH coding region lacking its 22 amino acid signal sequence was amplified from a plasmid containing on an insert a common carp (*Cyprinus carpio*) growth hormone cDNA (Koren et al., 1989, Gene 67: 309–315) using the PCR in combination with two cGH-specific primers. The amplified cGH fragment was fused in the correct reading frame and 3' to the *A. thaliana* oleosin using pOThromb (van Rooijen, 1993, PhD Thesis, University of Calgary) as a parent plasmid and employing cloning strategies similar to those outlined in the present application in e.g. examples 9 to 11 and well known to a person skilled in the art. In pOThromb a thrombin cleavage site was engineered 3' to the oleosin coding sequence. The oleosin-cGH fusion was introduced into the binary vector pCGN1559 (McBride and Summerfelt, 1990, Plant Mol. Biol. 14: 269–276) and the resulting construct was used to transform *A. tumefaciens*. The Agrobacterium strain was employed to transform *B. napus* cv Westar seedlings.

Seeds from transgenic *B. napus* plants were analysed for cGH expression by Western blotting using monoclonal antibodies against cGH. The expected 40 kDa oleosin-cGH fusion protein was specifically detected in oil body protein extracts containing the oleosin-cGH fusion protein. A 22 kDa polypeptide corresponding with cGH could be released from oil bodies upon treatment with thrombin, while no cGH was detected in oil body protein extracts from untransformed control plants.

Example 14

Expression of an Oleosin/Zein Fusion Protein

In order to demonstrate the utility of the instant invention for the production of improved meal, a gene specifying high levels of methionine residues, was expressed as an oleosin fusion in *B. napus* seeds. For the purpose of this experiment the gene encoding the corn seed storage protein zein (Kirihara et al., 1988, Gene 71: 359–370) was used. The zein gene was fused 3' of the oleosin coding sequence and introduced in the binary vector pCGN1559 (McBride and Summerfelt, 1990, Plant Mol. Biol. 14: 269–276) employing cloning strategies similar to those described in the present application in e.g. examples 9 to 11 and well known to the skilled artisan. The resulting recombinant plasmid was introduced in *A. tumefaciens* and used to transform *B. napus* cotyledonary explants. Amino acid analyses of canola meal of plants transformed with the oleosin-zein fusion construct indicated a significant increase in the levels of methionine in the meal when compared to untransformed plants.

Example 15

Construction of an Oleosin/Collagenase Protein Vector

As a further example of the invention, a vector containing an oleosin-collagenase fusion was constructed.

A 2.2 kbp fragment containing the collagenase gene from *vibrio alginolyticus* was PCR amplified from genomic bacterial DNA using primers in accordance with the published sequence (Takeuchi et al., 1992, Biochem. Journal, 281: 703–708). The fragment 2.2 kbp was then subcloned into pUC19 yielding pZAP1. Subsequently, the collagenase gene was introduced into pNOS8 containing the NOS terminator. The collagenase gene was ligated to the oleosin promoter and coding sequence of pThromb (van Rooijen, 1993, PhD Thesis, University of Calgary) containing a thrombin cleavage site and introduced into the binary vector pCGN1559 (McBride and Summerfelt, 1990, Plant Mol. Biol. 14: 269–276).

The collagenase construct may be introduced in a transgenic plant containing a second oleosin gene fusion to, for example, a gene encoding the enzyme chitinase isolated from tobacco (Melchers et al., 1994, Plant Journal 5: 469–480) and containing a collagenase recognition sequence engineered between the oleosin sequence and the second fusion protein. Introduction of the two fusion genes may be accomplished by sexual crossing of two lines which each contain one of the fusion genes or by transformation of a plant containing the first construct the second construct.

Expression in Plant Hosts

Example 16

Expression of Oleosin/GUS Fusions in Various Plant Species

It is a feature of the present invention that a wide variety of host cells may be employed. In order to illustrate the expression of oleosin fusions in a number of plant species, the expression of the A. thaliana oleosin fused to the reporter gene GUS was assessed in the embryos of nine different plant species, including the monocotelydenous plant species Zea mays (corn).

Plasmid pCGYOBPGUS containing the intact A. thaliana oleosin gene with a carboxyl terminal fused GUS gene (van Rooijen et al., 1995, Plant Physiol. 109: 1353–1361) was used to transform oilseed embryos of the following plant species: *Brassica napus* (canola), *Helianthus anuus* (sunflower), *Carthamus tinctorius* (safflower), *Glycine max* (soybean), *Ricinus communis* (castor bean), *Linum usitatissimum* (flax), *Gossypium hirsutum* (cotton), *Coriandrum sativum* (coriander) and *Zea mays* (corn). Transformation was accomplished by particle bombardment (Klein et al., 1987, Nature, 327: 70–73) and plasmid pGN, containing a promoterless GUS gene was used as a control. Histochemical GUS staining (Klein et al., 1988, Proc. Natl. Acad. Sci. 85: 8502–8505) of the embryos was used to assess GUS expression.

The embryos of the 9 species transformed with plasmid pCGTYOBPGUS containing the oleosin-GUS fusion gene all exhibited substantial GUS expression as judged by histochemical staining. In contrast, no appreciable levels of GUS activity was detected in embryos transformed with the promoterless GUS construct.

Expression in Prokaryotes

Example 17

Isolation of a *B. napus* Oleosin cDNA

The Arabidopsis oleosin gene described in Example 1 contains an intron, and as such is not suitable for use in a prokaryotic expression system. In order to express oleosin fusions in a microorganism such as bacteria, a coding sequence devoid of introns must be used. To accomplish this, a *B. napus* cDNA library was made using standard techniques and was used to isolate oleosin cDNAs. Four clones were obtained and were called pcDNA#7, pcDNA#8, pcDNA#10 and pcDNA#12. These cDNA clones were partly sequenced, and one clone pcDNA#8, was sequenced completely. All the clones showed high levels of identity to oleosins. pcDNA#10 was identical to pcDNA#12, but different from pcDNA#8 and pcDNA#7. The deduced amino add sequence of the insert of pcDNA#8 is very similar to the Arabidopsis oleosin and is shown in FIG. 4. This coding region of oleosin can be used to isolate other oleosin genes or for expression of oleosin fusions in prokaryotic systems. It also provides a convenient coding region for fusion with various other promoters for heterologous expression of foreign proteins due to the ability of the protein (oleosin) to specifically interact with the oilbody fraction of plant extracts.

Example 18

Expression of a Oleosin/GUS Fusion in the Heterologous Host *E. coli*

Figure 5:
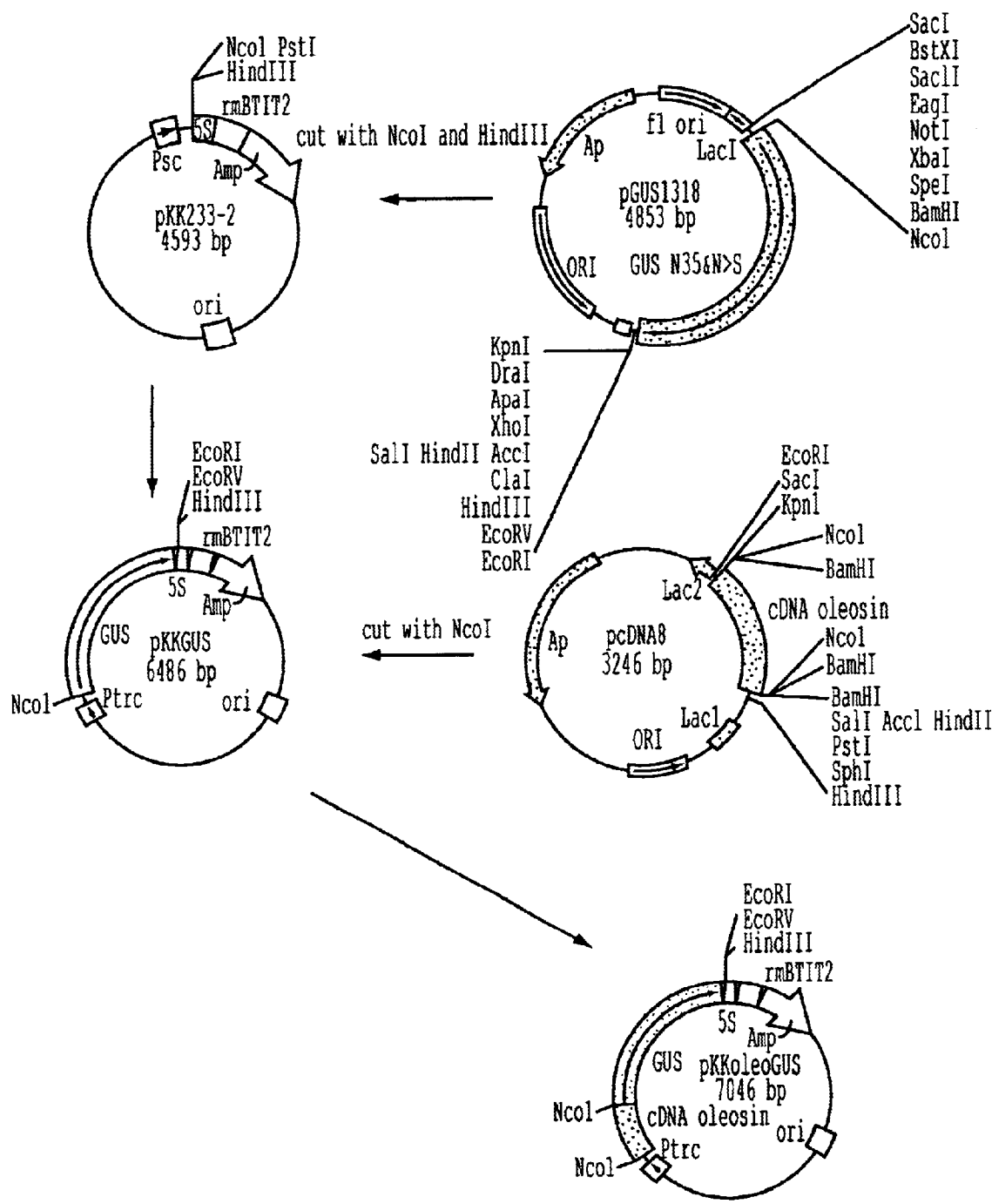
FIG. 5 describes the construction of a oleosin/GUS fusion for expression in *E. coli*.

In order to further illustrate the invention, an oleosin/GUS gene fusion was expressed in *E. coli* strain JM109. The oleosin cDNA pcDNA#8 described in example 17 was digested with Nco I and ligated into the Nco I site of pKKGUS, an expression vector containing the LacZ promoter fused to GUS. The plasmid pKKGUS was constructed by adding the GUS coding region to the vector pKK233 (Pharmacia) to generate the plasmid pKKoleoGUS and the anti-sense construct pKKoeloGUS. This construct is shown in FIG. 5. These plasmids were introduced into *E. coli* strain JM109 and expression was induced by IPTG. The *E. coli* cells were prepared for GUS activity measurements. In bacterial cells containing the vector pKKGUS, strong induction of GUS activity is observed following addition of ITPG. In cells containing pKKoleoGUS similar strong induction of GUS activity was seen following addition of IPTG. In cells containing pKKoeloGUS (GUS in the antisense orientation) no induction over background was observed following the addition of IPTG. These results suggest that the oleosin/GUS fusion is active in bacteria. Although that activity observed for the fusion product is less than the unfused product, the oleosin coding sequence was not optimized for expression in bacteria. It is apparent to those skilled in the art that simple modification of codons or other sequences such as ribosome binding sites could be employed to increase expression. The results are summarized in Table VII.

The fusion protein can be isolated from the bulk of the cellular material by utilizing the ability of the oleosin portion of the fusion proteins to specifically associate with oil bodies.

Expression in Fungi

Example 19

Expression of an Oleosin/GUS Fusion in the Heterologous Host *Saccharomyces cerevisiae*

Figure 7:
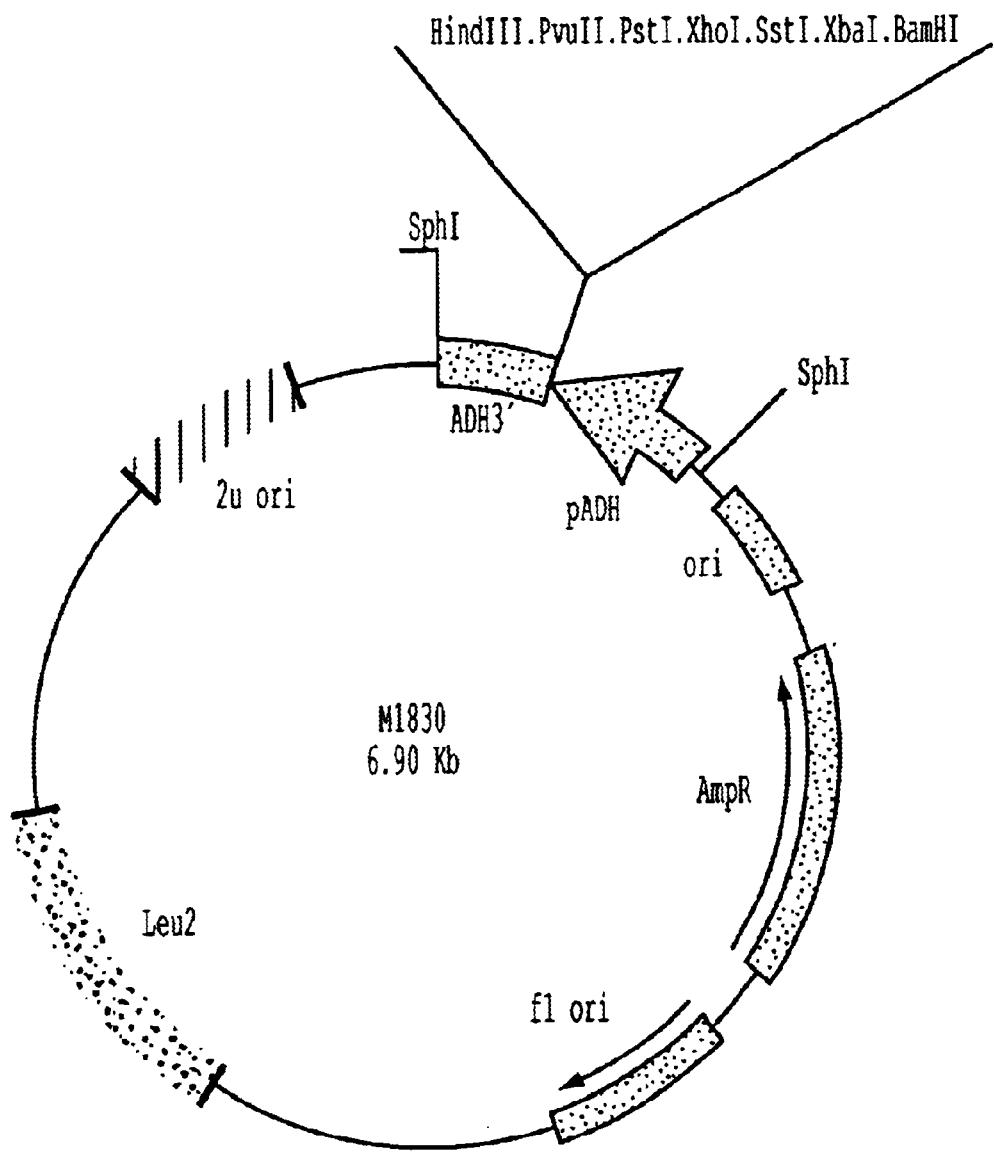
FIG. 7 shows a schematic drawing of plasmid M1830. The plasmid was constructed by replacing the Ura3 gene from pVT102-U (Gene 52: 225–233, 1987) with the Leu2 gene.
Figure 8:
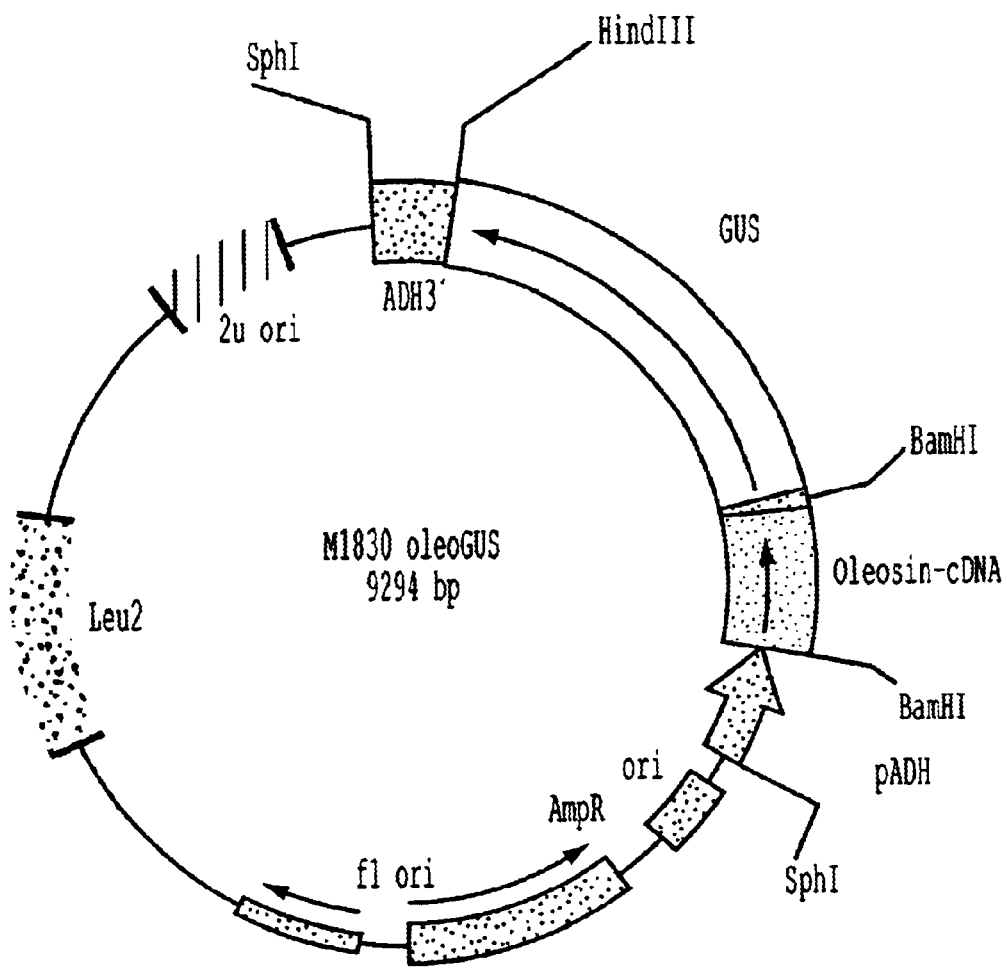
FIG. 8 shows a schematic drawing of plasmid M1830oleoGUS. A BamHI-GUS-hindIII fragment was inserted into the multiple cloning site of M1830, resulting in M1830GUS. A *B. napus* oleosin cDNA was furnished with BamHI sites at the 5' and 3' ends of the gene and inserted in frame and in the right orientation in the BamHI site of M1830GUS yielding plasmid M1830oleoGUS.
Figure 18A:
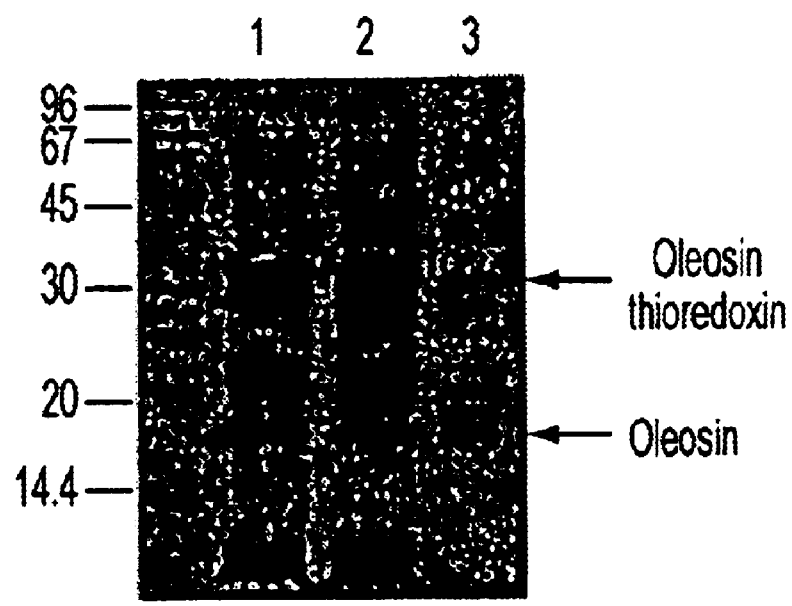
FIGS. 18A and B are a gel and Western blot, respectively, showing the analysis of total seed extracts (Lane 1 and 2) and oil body protein extract (Lane 3) of wt Arabidopsis (Lane 1) and Arabidopsis transformed with pSBS2510 (oleosin-thioredoxin). Panel A; coomassie stained gel, Panel B; Western blot treated with a monoclonal antibody raised against Arabidopsis oleosin followed by an alkaline phosphatase linked secondary antibody and NBT/BCIP color reaction. Indicated are the most abundant native oleosin (red arrow) and the oleosin-thioredoxin fusion protein (green arrow).
Figure 18B:
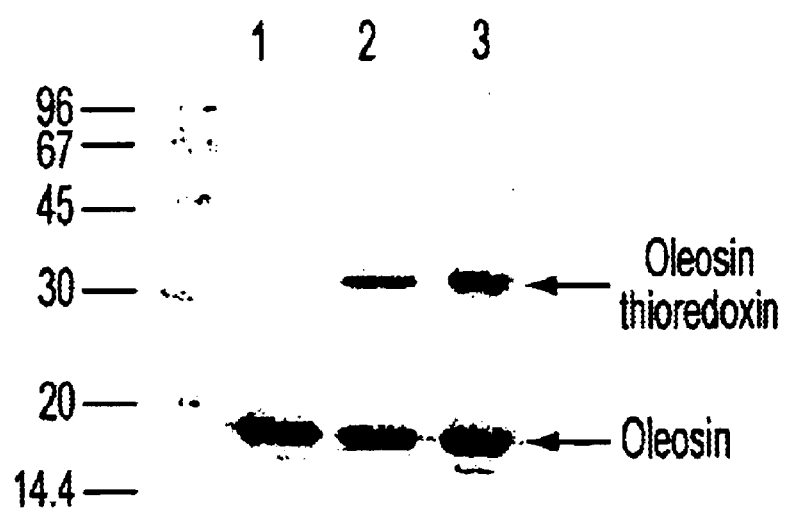

As an example of the utility of the disclosed invention for expression in fungal systems, an oleosin-GUS fusion was expressed in *S. cerevisiae*. Plasmids pM18300leoGUS, containing an oleosin-GUS fusion, and control plasmid pM1830 (FIGS. 7 and 8) were used to transform *S. cerevisiae* strain 1788 (Mata/Matα) an isogenic diploid of EG123 (MATα leu2-3,112 ura3-52trp1his4canI$^r$; Kyung and Levin, 1992, Mol. Cel. Biol. 12: 172–182) according to the method of Elbe (1992, Biotechniques: 13: 18–19). Briefly, strain 1788 was grown on YPD (1% yeast extract, 2% peptone, 2% dextrose; Sherman et al., methods in yeast genetics, Cold Spring Harbor Laboratory Press) at 30° C. for 1 day. The strain was then transformed with plasmids pM1830 and pM1830OleoGUS. Transformants were selected on synthetic media (SC, Sherman et al. Methods in yeast genetics, Cold Spring Harbor Laboratory Press), lacking leucine at 30° C. for 3 days. Individual colonies were grown in SC (minus leucine) for 1 day, reinoculated into fresh medium at equal starting densities ($OD_{600}$=0.05), then grown to mid-log phase ($OD_{600}$)=2.0–3.0). Cultures were centrifuged at 4,000 rpm for 5 min and the supernatant was removed. The pellet was resuspended in 100 mM Tris-Cl (pH 7.5), 1 mM PMSF (phenyl methyl sulphonyl fluoride) and the cells were lysed using a French Press. GUS activity measurements were done according to Jefferson (1987) and protein determination was done as described by Bradford et al. (1976, Anal. Biochem. 72: 248–254).

Western blotting using a polyclonal anti-oleosin antibody revealed the presence of a 90 kDa polypeptide, which is in agreement with the molecular weight deduced from the amino acid sequence of the fusion protein (89.7 kDa). No cross-reactivity was observed in extracts from the untransformed strain or in extract transformed with the control plasmid pM1830. Significant GUS activity could be detected in S. cerevisiae cells transformed with pM1830OleoGUS, while no appriciable levels of GUS activity were measured in untransformed cells or cells transformed with pM1830 (table VIII).

Example 20

Isolation of Thioredoxin and NADPH Thioredoxin Reductase Genes

An Arabidopsis silique cDNA library CD4-12 was obtained from the Arabidopsis Biological Resource Centre (ABRC, http://aims.cps.msu.edu) Arabidopsis stock centre and used as a template for the isolation of the thioredoxin h (Trxh) and thioredoxin reductase genes from Arabidopsis. For the isolation of the Trxh gene the following primers were synthesized:

```
GVR833:
5' TACCATGGCTTCGGAAGAAGGA 3'         (SEQ.ID.NO.32)
```

The sequence identical to the 5' end of the Trxh gene as published in Rivera-Madrid et al, (1993) Plant Physiol 102: 327–328, is indicated in bold. Underlined is an NcoI restriction site to facilitate cloning.

```
GVR834:
5' GAAAGCTTAAGCCAAGTGTTTG 3'         (SEQ.ID.NO.33)
```

The sequence complementary to the 3' end of the Trxh gene as published in Rivera-Madrid et al, (1993) Plant Physiol 102: 327–328, is indicated in bold. Underlined is an HindIII restriction site to facilitate cloning.

A Polymerase Chain Reaction (PCR) was carried out using GVR833 and GVR834 as primers and the cDNA library CD4-12 as a template. The resulted PCR fragment was isolated, cloned into pBluescript and sequenced. The isolated sequence encoding Trxh was identical to the published Trxh gene sequence (Rivera-Madrid et al, (1993) Plant Physiol 102: 327–328). The pBluescript vector containing the Trxh gene is called pSBS2500

For the isolation of the thioredoxin reductase gene the following primers were synthesized:

```
GVR836:                              (SEQ.ID.NO.34)
5' GGCCAGCACACTACCATGAATGGTCTCGAAACTCAC 3'.
```

The sequence identical to the 5' end of the thioredoxin reductase gene as published (ATTHIREDB Jacquot et al, J Mol Biol. (1994) 235 (4):1357–63), is indicated in bold.

```
GVR837:
5' TTAAGCTTCAATCACTCTTACCTTGCTG 3'    (SEQ.ID.NO.35)
```

A Polymerase Chain Reaction (PCR) was carried out using GVR836 and GVR837 as primers and the cDNA library CD4-12 as a template. The resulted PCR fragment was isolated, cloned into pBluescript and sequenced. The pBluescript vector containing the thioredoxin reductase gene is called pSBS2502.

A total of three clones were sequenced, the sequence of each of the three clones were identical to each other. However, as depicted in FIG. 9 this sequence indicated several nucleotide differences compared to the published thioredoxin reductase gene sequence published (ATTHIREDB Jacquot et al, J Mol Biol. (1994) 235 (4):1357–63). The complete coding sequence and its deduced aminoacid sequence is shown in FIG. 10. As a result of the nucleotide differences between the published sequence and the sequence isolated in this report, several amino acid changes are also predicted. A comparison of the deduced amino acid sequence of the published NADPH thioredoxin reductase sequence thioredoxin (ATTHIREDB, Jacquot et al, J Mol Biol. (1994) 235 (4):1357–63.) with the sequence isolated in this report (TR) is shown in FIG. 11.

Example 21

Construction of Plant Expression Vectors

Expression vectors were constructed to allow for the seed specific over-expression of thioredoxin and NADPH thioredoxin reductase in seeds. Vectors were constructed to allow for over-expression in its natural subcellular location and for accumulation on oilbodies.

Construction of plant transformation vector pSBS2520. The Arabidopsis thioredoxin h gene as described in Example 20 was placed under the regulatory control of the phaseolin promoter and the phaseolin terminator derived from the common bean Phaseolus vulgaris (Slightom et al (1983) Proc. Natl Acad Sc USA 80: 1897–1901; Sengupta-Gopalan et al., (1985) PNAS USA 82: 3320–3324)). A gene splicing by overlap extension technique (Horton et al (1989) 15: 61–68) was used to fuse the phaseolin promoter to the Trxh gene. Standard molecular biology laboratory techniques (see eg: Sambrook et al. (1990) Molecular Cloning, $2^{nd}$ ed. Cold Spring Harbor Press) were used to furnish the phaseolin promoter and terminator with Pst I and HindIII/KpnI sites respectively (see FIG. 12). Standard molecular biology laboratory techniques were also used to place the phaseolin terminator dowstream from the Trxh gene. The PstI-phaseolin promoter-Trxh-phaseolin terminator-KpnI insert sequence was cloned into the PstI-KpnI sites of pSBS3000 (pSBS3000 is a derivative from the Agrobacterium binary plasmid pPZP221 (Hajdukiewicz et al., 1994, Plant Molec. Biol. 25: 989–994). In pSBS3000, the CaMV35S promoter-gentamycin resistance gene-CAMV 35S terminator of pPZP221 was replaced with parsley ubiquitin promoter-phosphinothricin acetyl transferase gene-parsley ubiquitin termination sequence to confer resistance to the herbicide glufosinate ammonium.) The resulting plasmid is called pSBS2520. The sequence of the phaseolin promoter-Arabidopsis Trxh-phaseolin terminator sequence is shown in FIG. 12.

Construction of plant transformation vector pSBS2510. The 3' coding sequence of an Arabidopsis oleosin gene (Van Rooijen et al (1992) Plant Mol. Biol.18: 1177–1179). was altered to contain an NcoI site. The NcoI-HindIII fragment from vector pSBS2500 (Example 20) containing the Trxh was ligated to the coding sequence of this Arabidopsis oleosin utilizing this NcoI restriction site. A gene splicing by overlap extension technique (Horton et al (1989) 15: 61--68) was used to fuse the phaseolin promoter (Slightom et al (1983) Proc. Natl Acad Sc USA 80: 1897–1901; Sengupta-Gopalan et al., (1985) PNAS USA 82: 3320–3324) containing a synthetic PstI site (see construction of pSBS2520)) to the coding sequence of the Arabidopsis oleosin. Standard molecular biology laboratory techniques (see eg: Sambrook et al. (1990) Molecular Cloning, $2^{nd}$ ed. Cold Spring Harbor Press) were again used to clone the HindIII KpnI fragment containing the phaseolin terminator (see construction of pSBS2520) downstream of the Trxh gene. The PstI-phaseolin promoter-oleosin-Trxh-phaseolin terminator-KpnI insert sequence was cloned into the PstI-KpnI sites of pSBS3000. The resulting plasmid is called pSBS2510. The sequence of the phaseolin promoter-oleosin Trxh-phaseolin terminator sequence is shown in FIG. 13.

Construction of plant transformation vector pSBS2521. This vector contains the same genetic elements as the insert of pSBS2510 except the Trxh gene is fused to the 5' end of the oleosin gene. The 3' oleosin coding sequence including its native stopcodon (Van Rooijen et al (1992) Plant Mol. Biol.18: 1177–1179) was furnished with a HindIII cloning site. Again a gene splicing by overlap extension technique (Horton et al (1989) 15: 61–68) was used to fuse the phaseolin promoter to the Trxh gene and to fuse the Trxh gene to the oleosin sequence. Standard molecular biology laboratory techniques (see eg: Sambrook et al. (1990) Molecular Cloning, $2^{nd}$ ed. Cold Spring Harbor Press) were again used to clone the HindIII KpnI fragment containing the phaseolin terminator (see construction of pSBS2520) dowstream of the oleosin gene. The PstI-phaseolin promoter-Trxh oleosin-phaseolin terminator-KpnI insert sequence was cloned into the PstI-KpnI sites of pSBS3000. The resulting plasmid is called pSBS2521. The sequence of the phaseolin promoter-Trxh oleosin-phaseolin terminator sequence is shown in FIG. 14.

Construction of plant transformation vector pSBS2527. The Arabidopsis NADPH thioredoxin reductase gene as described in Example 20 was placed under the regulatory control of the phaseolin promoter and the phaseolin terminator derived from the common bean *Phaseolus vulgaris* (Slightom et al (1983) Proc. Natl Acad Sc USA 80: 1897–1901; Sengupta-Gopalan et al., (1985) PNAS USA 82: 3320–3324). A gene splicing by overlap extension technique (Horton et al (1989) 15: 61--68) was used to fuse the phaseolin promoter to the thioredoxin reductase gene. Standard molecular biology laboratory techniques (see eg: Sambrook et al. (1990) Molecular Cloning, $2^{nd}$ ed. Cold Spring Harbor Press) were used to furnish the phaseolin promoter and terminator with PstI and HindIII/KpnI sites respectively (see FIG. 12). Standard molecular biology laboratory techniques were also used to place the phaseolin terminator downstream from the thioredoxin reductase gene. The PstI-phaseolin promoter-thioredoxin reductase-phaseolin terminator-KpnI insert sequence was cloned into the PstI-KpnI sites of pSBS3000 The resulting plasmid is called pSBS2527. The sequence of the phaseolin promoter-Arabidopsis thioredoxin reductase-phaseolin terminator sequence is shown in FIG. 15.

Construction of plant transformation vector pSBS2531. A gene splicing by overlap extension technique (Horton et al (1989) 15: 61–68) was used to fuse the phaseolin promoter (Slightom et al (1983) Proc. Natl Acad Sc USA 80: 1897–1901; Sengupta-Gopalan et al., (1985) PNAS USA 82: 3320–3324 to the coding sequence of the Arabidopsis oleosin. The same gene splicing technique was used to fuse the oleosin gene to the thioredoxin reductase coding sequence. Standard molecular biology laboratory techniques (see eg: Sambrook et al. (1990) Molecular Cloning, $2^{nd}$ ed. Cold Spring Harbor Press) were again used to clone the HindIII KpnI fragment containing the phaseolin dowstream of the thioredoxin reductase gene. The PstI-phaseolin promoter—oleosin-thioredoxin reductase—phaseolin terminator KpnI insert sequence was cloned into the PstI-KpnI sites of pSBS3000. The resulting plasmid is called pSBS2531. The sequence of the phaseolin promoter—oleosin thioredoxin reductase—phaseolin terminator sequence is shown in FIG. 16.

Construction of plant transformation vector pSBS2529. This vector contains the same genetic elements as the insert of pSBS2531 except the thioredoxin gene is fused to the 5' end of the oleosin gene. The 3' oleosin coding sequence including its native stopcodon (Van Rooijen et al. (1992) Plant Mol. Biol.18: 1177–1179) was furnished with a Hin-dIII cloning site. Again a gene splicing by overlap extension technique (Horton et al (1989) 15: 61–68) was used to fuse the phaseolin promoter to the thioredoxin reductase gene and to fuse the thioredoxin reductase gene to the oleosin sequence. Standard molecular biology laboratory techniques (see eg: Sambrook et al. (1990) Molecular Cloning, $_2$nd ed. Cold Spring Harbor Press) were again used to clone the HindIII KpnI fragment containing the phaseolin terminator (see construction of pSBS2520) downstream of the oleosin gene. The PstI-phaseolin promoter—thioredoxin reductase oleosin—phaseolin terminator KpnI insert sequence was cloned into the PstI-KpnI sites of pSBS3000. The resulting plasmid is called pSBS2529. The sequence of the phaseolin promoter—thioredoxin reductase oleosin—phaseolin terminator sequence is shown in FIG. 17.

Plasmids pSBS2510, pSBS2520, pSBS2521, pSBS2527, pSBS2529 and pSBS2531 and were electroporated into Agrobacterium strain EHA101. These Agrobacterium strains were used to transform Arabidopsis. Arabidopsis transformation was done essentially as described in "Arabidopsis Protocols; Methods in molecular biology Vol 82. Edited by Martinez-Zapater JM and Salinas J. ISBN 0-89603-391-0 pg 259–266 (1998) except the putative transgenic plants were selected on agarose plates containing 80 $\mu$M L-phosphinothricine, after they were transplanted to soil and allowed to set seed.

Example 22

Polyacrylamide Gel Electrophoresis and Immunoblotting of Transgenic Seed Extracts Source of Arabidopsis thioredoxin, thioredoxin reductase and oleosin antibodies. The Arabidopsis thioredoxin and thioredoxin reductase genes were cloned in frame in bacterial expression vector pRSETB (Invitrogen) to allow for the overexpression of Arabidopsis thioredoxin and thioredoxin reductase proteins. These proteins were purified using standard protocols (see eg Invitrogen protocol) and used to raise antibodies in rabbits using standard biochemical techniques (See eg Current Protocols in Molecular Biology, John Wiley & Sons, N.Y. (1989). The Arabidopsis oleosin gene genes was cloned in frame in bacterial expression vector pRSETB (Invitrogen) to allow for the overexpression Arabidopsis oleosin protein. This protein was purified using standard protocols (see eg Invitrogen protocol) and used to prepare mouse monoclonal antibodies using standard biochemical techniques (See eg Current Protocols in Molecular Biology, John Wiley & Sons, N.Y. (1989).

Preparation of total Arabidopsis seed extracts for PAGE. Arabidopsis seeds were ground in approximately 20 volumes of 2% SDS, 50 mM Tris-Cl, this extract was boiled, spun and the supernatant was prepared for polyacrylamide gelelectrophoresis (PAGE) using standard protocols.

Preparation of Arabidopsis oil body protein extracts. Arabidopsis seeds were ground in approximately 20 volumes of water and spun in a microfuge. The oilbodies were recovered and washed sequentially with approximately 20 volumes of water, a high stringency wash buffer, containing 8M urea and 100 mM sodiumcarbonate and water. After this last wash the oilbodies are prepared for poly acrylamide gelelectrophoresis (PAGE) using standard protocols.

Figure 19A:
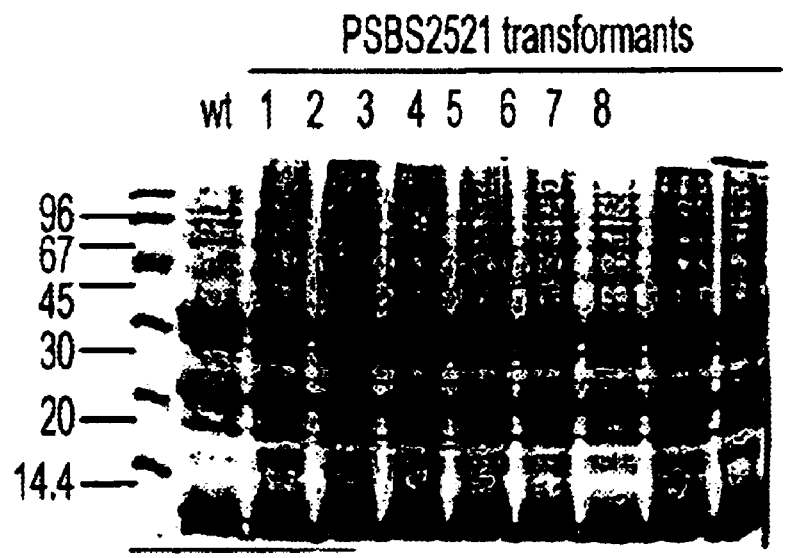
FIGS. 19A and B are a gel and Western blot, respectively, showing the analysis of total seed extracts (Lane 2) and oilbody protein extract (Lane 1 and 3) of wt Arabidopsis (Lane 1) and Arabidopsis transformed with pSBS2521 (thioredoxin-oleosin, lane 2 and 3). Panel A; coomassie stained gel, Panel B; Western blot treated with a polyclonal antibody raised against Arabidopsis thioredoxin protein followed by an alkaline phosphatase linked secondary antibody and NBT/BCIP color reaction. Panel C; Western blot treated with a monoclonal antibody raised against Arabidopsis oleosin followed by an alkaline phosphatase linked secondary antibody and NBT/BCIP color reaction. Indicated is the most abundant native oleosin (red arrow) and the thoredoxin oleosin fusion protein (blue arrow).
Figure 19B:
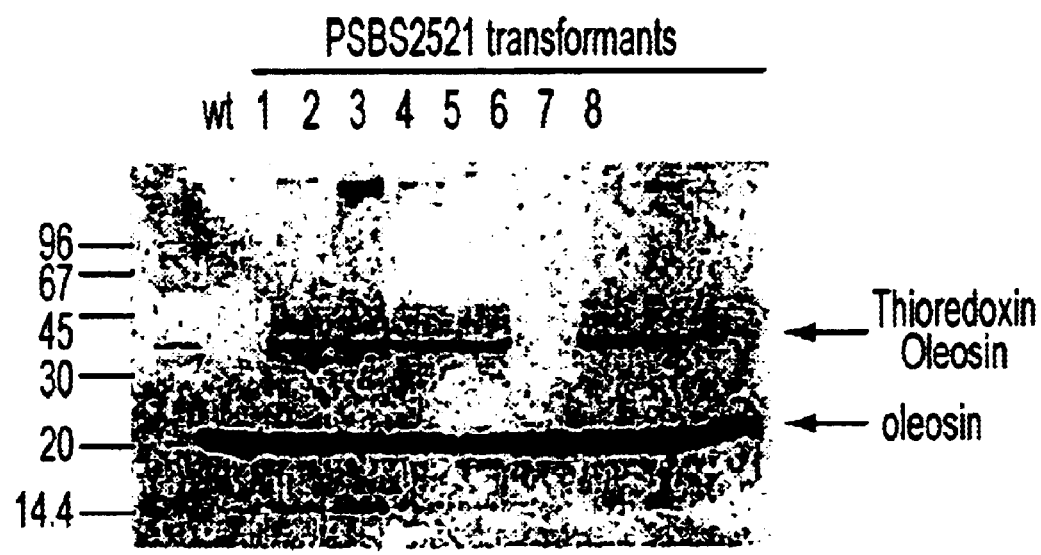

Analysis of seed and oil body extracts from plants transformed with pSBS2510. Total seed and oilbody protein extracts from plants transformed with pSBS2510 were loaded onto polyacrylamide gels and either stained with coomassie brilliant blue or electroblotted onto PVDF membranes. The membranes were challenged with a polyclonal antibody raised against Arabidopsis thioredoxin, or a monoclonal antibody raised against the Arabidopsis 18.5 kDa oleosin and visualized using alkaline phosphatase. Expression of the oleosin-thioredoxin results in an additional band of 31.2 kDa. The results are shown in FIG. 19. The thioredoxin antibodies are immunologically reactive with a band of the right predicted molecular weight (31.2 kDa), the oleosin antibodies are also immunologically reactive with a band of the right predicted molecular weight for the fusion protein (31.2 kDa) in addition to a band corresponding to the native Arabidopsis oleosin (18.5 kDa). This indicates that oleosin-thioredoxin is expressed in Arabidopsis seeds and is correctly targeted to oilbodies.

Analysis of seed and oil body extracts from plants transformed with pSBS2521. Total seed and oilbody protein extracts from plants transformed with pSBS25121 were loaded onto polyacrylamide gels and either stained with coomassie brilliant blue or electroblotted onto PVDF membranes. The membranes were challenged with a polyclonal antibody raised against Arabidopsis thioredoxin, or a monoclonal antibody raised against the Arabidopsis 18.5 kDa oleosin and visualized using alkaline phosphatase. Expression of the thioredoxin-oleosin results in an additional band of 31.2 kDa. The results are shown in FIG. 19. The thioredoxin antibodies are immunologically reactive with a band of the right predicted molecular weight (31.2 kDa), the oleosin antibodies are also immunologically reactive with a band of the right predicted molecular weight for the fusion protein (31.2 kDa) in addition to a band corresponding to the native Arabidopsis oleosin (18.5 kDa). This indicates that thioredoxin-oleosin is expressed in Arabidopsis seeds and is correctly targeted to oilbodies.

Figure 20A:
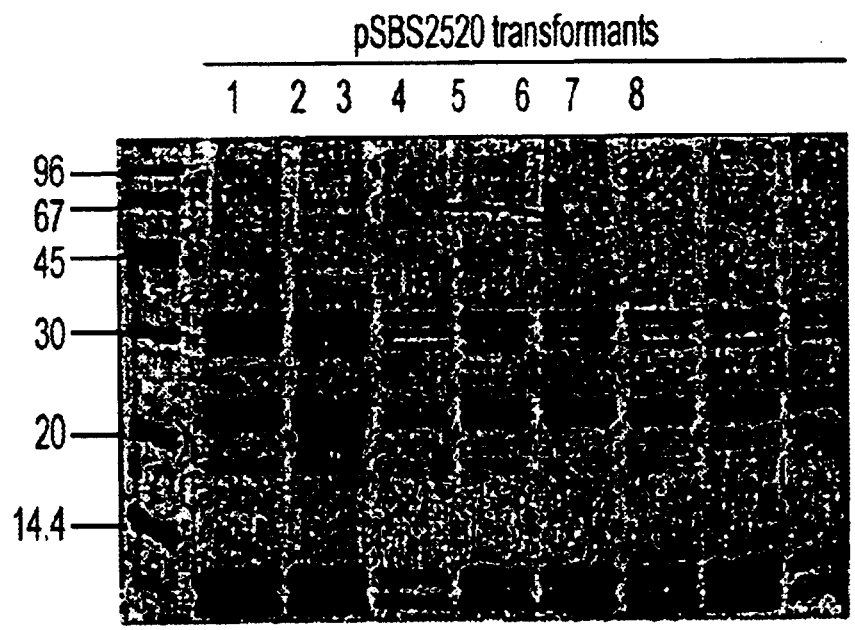
FIGS. 20A and B are a gel and Western blot, respectively, showing the analysis of total seed extracts of wt Arabidopsis (lane 1) and Arabidopsis transformed with pSBS2520 ("free" thioredoxin, lane 2, 3, 4, 5, 6, 7, 8) Panel A; coomassie stained gel, Panel B; Western blot treated with a polyclonal antibody raised against Arabidopsis thioredoxin protein followed by an alkaline phosphatase linked secondary antibody and NBT/BCIP color reaction. Indicated is the band reacting with the anti-thioredoxin antibody. A strong signal can be detected in lane 3, 5, 6, 7, 8 and no signal can be detected in the wt extract (Lane 1) and two seed extracts derived from 2 different transgenic lines (lane 2, 4). The lack of detectable thioredoxin expression (as shown in lane 2, 4) could be due to either a position effect or we are looking or these seeds could be derived from a non-trangenic (escape or false-positive) plant.
Figure 20B:
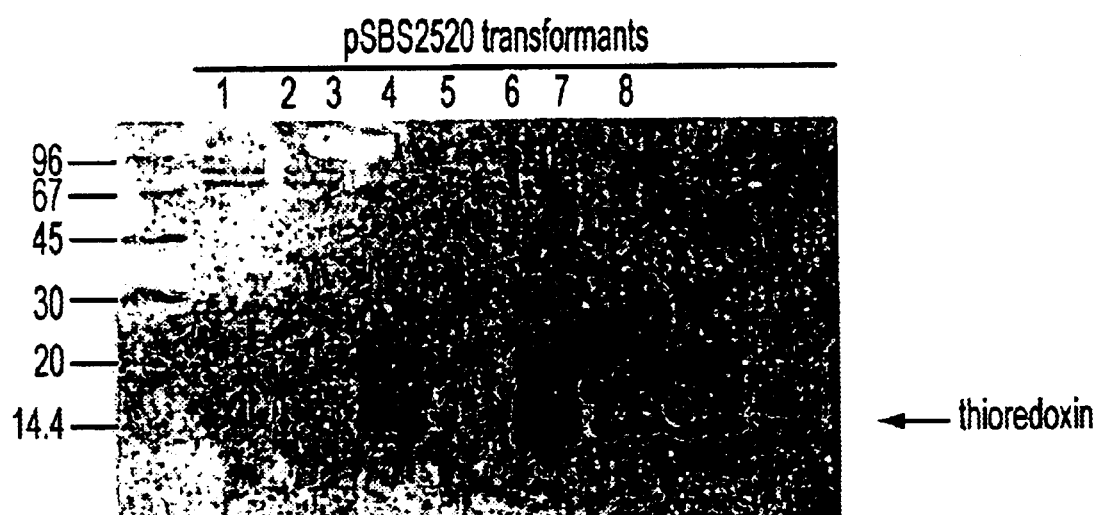

Analysis of seed extracts from plants transformed with pSBS2520. Total seed extracts from plants transformed with pSBS2520 were loaded onto polyacrylamide gels and either stained with coomassie brilliant blue or electroblotted onto PVDF membranes. The membranes were challenged with a polyclonal antibody raised against Arabidosis thioredoxin and visualized using alkaline phosphatase. The thioredoxin antibodies are immunologically reactive with a band of approximately the right predicted molecular weight (12 kDa). Untransformed seeds do not show a detectable thioredoxin band (results not shown). The results of this analysis are shown in FIG. 20.

Figure 21A:
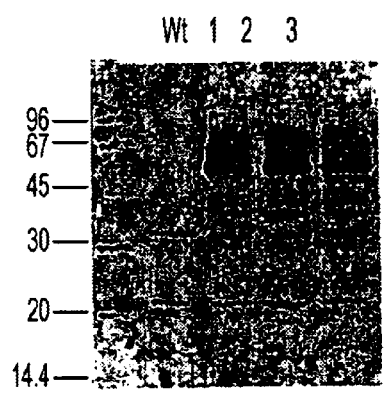
FIGS. 21A and B are Western blots showing the analysis of total seed of wt Arabidopsis (wt) and Arabidopsis transformed with pSBS2529 (thioredoxin reductase-oleosin, lane 1, 2 and 3). Panel A; Western blot treated with a polyclonal antibody raised against Arabidopsis thioredoxin reductase protein followed by an alkaline phosphatase linked secondary antibody and NBT/BCIP color reaction. Panel B; Western blot treated with a monoclonal antibody raised against Arabidopsis oleosin followed by an alkaline phosphatase linked secondary antibody and NBT/BCIP color reaction. Indicated is the most abundant native oleosin and the thoredoxin reductase oleosin fusion protein (blue arrow).
Figure 21B:
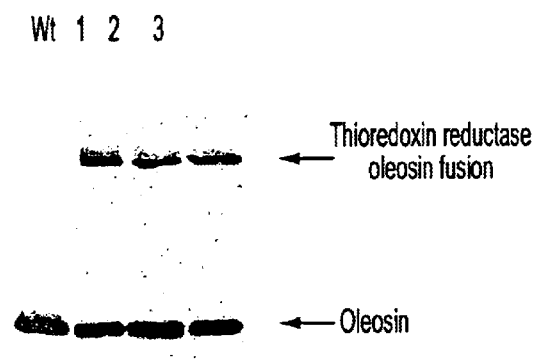

Analysis of seed and oil body extracts from plants transformed with pSBS2529. Total seed and oilbody protein extracts from plants transformed with pSBS2529 were loaded onto polyacrylamide gels and electroblotted onto PVDF membranes. The membranes were challenged with a polyclonal antibody raised against Arabidopsis thioredoxin reductase, or a monoclonal antibody raised against the Arabidopsis 18.5 kDa oleosin and visualized using alkaline phosphatase. Expression of the thioredoxin reductase-oleosin results in an additional band of 53.8 kDa. The results are shown in FIG. 21. The thioredoxin reductase antibodies are immunologically reactive with a band of the right predicted molecular weight for the fusion protein (53.8 kDa), the oleosin antibodies are also immunologically reactive with a band of the right predicted molecular weight (53.8 kDa) in addition to a band corresponding to the native Arabidopsis oleosin (18.5 kDa). This indicates that thioredoxin reductase-oleosin is expressed in Arabidopsis seeds.

Figure 22:
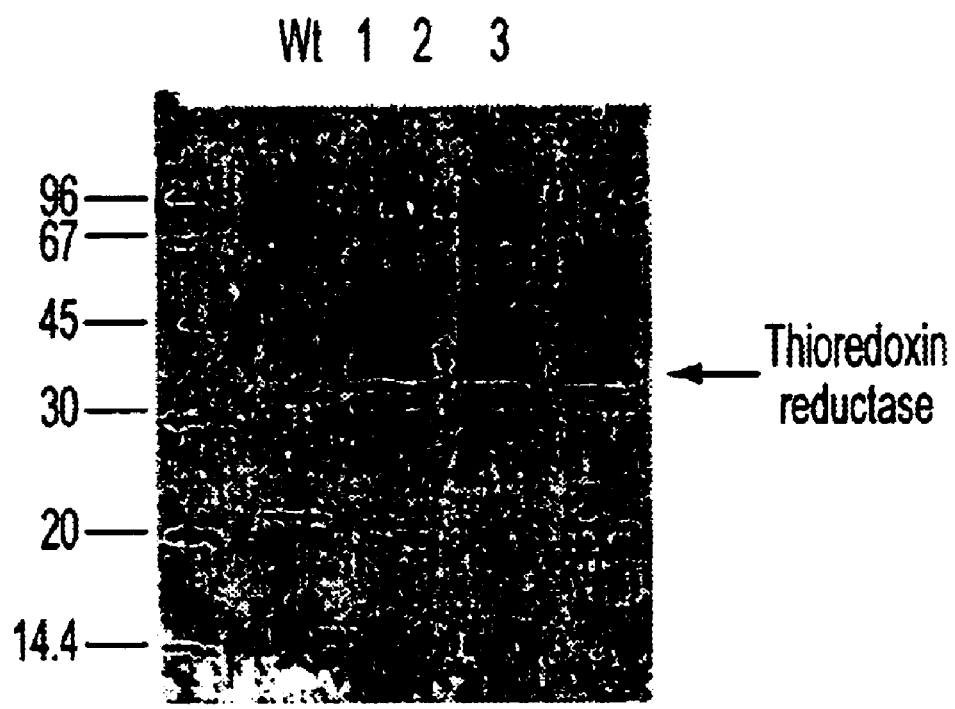
FIG. 22 is a Western blot showing the analysis of total seed extracts of wt Arabidopsis (wt) and Arabidopsis transformed with pSBS2527 ("free" thioredoxin reductase, Lane 1, 2, 3). Indicated is a Western blot treated with a polyclonal antibody raised against Arabidopsis thioredoxin reductase protein followed by an alkaline phosphatase linked secondary antibody and NBT/BCIP color reaction. Indicated is the overexpressed thioredoxin reductase in Lane 1, 2 and 3.

Analysis of seed extracts from plants transformed with pSBS2527. Total seed extracts from plants transformed with pSBS2527 were loaded onto polyacrylamide gels and electroblotted onto PVDF membranes. The membranes were challenged with a polyclonal antibody raised against Arabidopsis thioredoxin reductase and visualized using alkaline phosphatase. The thioredoxin reductase antibodies are immunologically reactive with a band of approximately the right predicted molecular weight for the (35.3 kDa). Untransformed seeds do not show a detectable thioredoxin band. The results of this analysis are shown in FIG. 22.

Figure 23A:
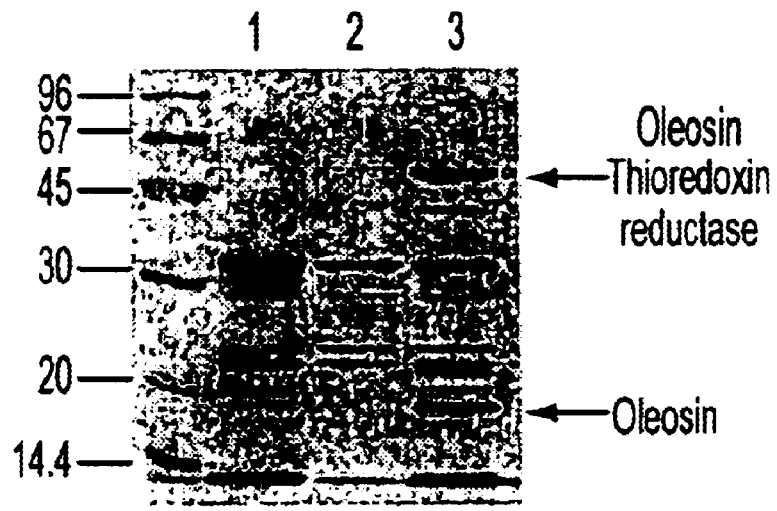
FIGS. 23A and B are a gel and Western blot, respectively, showing the analysis of total seed extracts (Lane 1 and 2) and oilbody protein extract (Lane 3) of wt Arabidopsis (Lane 1) and Arabidopsis transformed with pSBS2531 (oleosin-Thioreoxin reductase Panel A; Coomassie stained gel, Panel B; Western blot treated with a monoclonal antibody raised against Arabidopsis oleosin followed by an alkaline phosphatase-linked secondary antibody and NBT/BCIP color reaction. Indicated are the most abundant native oleosin (red arrow) and the oleosin-DMSR fusion protein (green arrow). The oilbodies as shown in lane 3 were not washed. As a result some (contaminating) seed proteins can be seen in the oilbody extract as well. However the most abundant proteins in this extract are native oleosin and oleosin-DMSR fusion protein. As expected the wt seed extract (lane 1) showed reactivity only with the native oleosin.
Figure 23B:
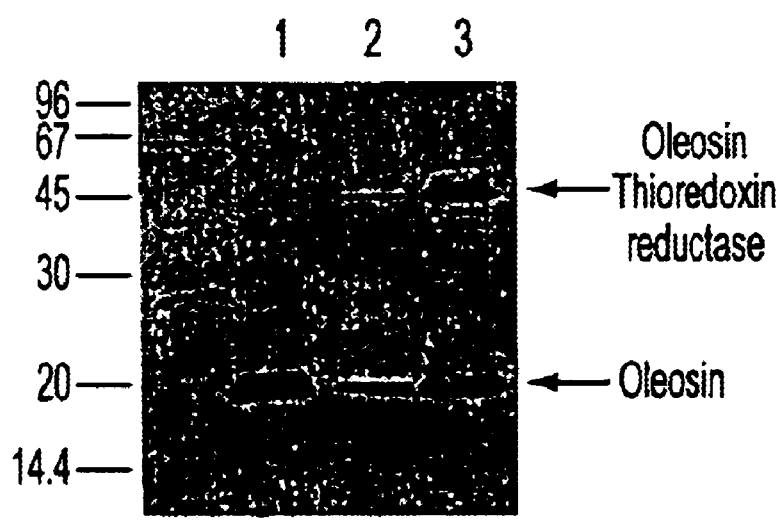

Analysis of seed extracts from plants transformed with pSBS2531. FIG. 23 shows a protein gel and immunoblot of the expression of oleosin-DMSR in Arabidopsis T2 seeds and correct targeting to Arabidopsis oilbodies. The expected molecular weight based on the deduced amino acid sequence is calculated to be 53,817 Da. In the oilbody extract of the putative transgenic oleosin-thioredoxin reductase sample an extra band of approximately 54 kDa can be seen (Panel A). This band is confirmed to be oleosin-thioredoxin reductase by immunoblotting (Panel B). From the polyacrylamide gel it can be seen that the expression of the oleosin-Thioredoxin reductase is about double compared to the expression of the major 18.5 kDa Arabidopsis oleosin. This represents approximately 2–4% of total seed protein.

Additional Applications of the Invention

The above examples describe various proteins that can be fused to an oil body protein and expressed in oil bodies in plants, bacteria and yeast. The above also provides the methodology to prepare such transgenic plants. Therefore one skilled in the art can readily modify the above in order to prepare fusion proteins containing any desired protein or polypeptide fused to an oil body protein in a variety of host systems. Several examples of other applications of the present invention are provided below.

a) Construction of an Oleosin/Single Chain Antibody Fusion Protein

As a further example of the invention, an antibody may be expressed in *B. napus*. Prior to the construction of an oleosin gene fusion, the deduced amino acid sequence of the coding region for the antibody may be back-translated using a *B. napus* codon usage table derived from several known *B. napus* genes and 'inside-out' recursive PCR (Prodomou & Pearl, 1992, Protein Eng. 5: 827–829) and yielding a synthetic scFv gene.

Gene fusion between the oleosin gene and the antibody gene can be accomplished by joining the synthetic antibody gene to the 5' end of the oleosin gene in a plasmid using cloning strategies well known to a person skilled in the art and similar to those outlined in the subject application in e.g. Examples 9 to 11. The insert from the plasmid may be cloned into the binary vector pCGN1559 and used to transform *A. tumefaciens*. Cotelydonary petioles of *B. napus* may be transformed with the recombinant binary vector as described in Moloney et al. (1989, Plant Cell Reports, 8: 238–242).

Oil body extracts from transgenic *B. napus* plants may analysed by Western blotting using an anti oleosin antibody for the presence of the fusion protein.

b) Combination of Two Oleosin Fusion Proteins to Release a Protein Product from Oil Bodies Two different oil body protein fusions associated with oil bodies can be used as a means to obtain a final product. For example, a transgenic *B. napus* may be obtained which contains a gene that comprises the GUS enzyme fused to the 3' coding sequence of oleosin separated by a collagenase protease recognition site. Oil bodies may be obtained from the seed of this plant. These oil bodies can be mixed with the oil bodies described above, which contains collagenase fused to oleosin. The collagenase activity of the oleosin/collagenase fusion protein oil bodies can release the GUS enzyme from the oleosin/GUS fusion proteins oil bodies. The GUS enzyme remains in the aqueous phase after removal of the oil bodies. No collagenase enzyme or contaminating oleosins will remain associated with the purified GUS enzyme illustrating the utility of the invention in obtaining easily purified proteins.

c) Expression of a Oleosin/Phytase fusion protein in *B. napus*

A microbial phytase from a Aspergillus may be isolated based on the published sequence (van Gorcom et al, European Patent Application 90202565.9, publication number 0 420 358 A1). This gene can be fused to the carboxy terminus of the oleosin protein using techniques described above and a collagenase recognition protease cleave site may be included to allow for separation of the phytase from the oil body if desired. The construct may contain, in the following order, the promoter region of the Arabidopsis oleosin gene, the coding sequence of the oleosin protein including the intron, a collagenase cleavage site and the phytase gene followed by the nos terminator polyadenylation signal. The construct can be inserted into the binary plasmid Bin 19 and the resultant plasmid introduced into Agrobacterium. The resulting strain can be used to transform *B. napus*. The seed of the transgenic plants will contain phytase activity. The phytase activity will be associated with the oil body fraction. The phytase activity is useful for the enhancement of meal for monogastric animal feed. The phytase may be purified by treatment with collagenase as described in a), or the transgenic seed may be used as a feed additive.

d) Expression of a Oleosin/Glucose Isomerase

The enzyme glucose isomerase can be expressed as a oleosin fusion protein by joining the coding sequence for the enzyme, (for example, described by Wilhelm Hollenberg, 1985, Nucl. Acid. Res. 13:5717–5722) to the oleosin protein as described above. The construct may be used to transform *B. napus*.

e) Expression of a Oleosin/High Lysine Fusion Protein

In order to increase the lysine content of transgenic seeds, a polylysine oligonucleotide may be added to the 3' coding region of the oleosin gene. For example, a repetitive oligonucleotide encoding a polylysine coding sequence can be made by synthesizing a $(AAG)_{20}$ oligonucleotide that is joined to the 3' coding region of the oleosin gene by replacement of the hirudin coding sequence contained within pCBOGHIRT plasmid described above in example 8 with the polylysine oligonucleotide through the use of cohesive restriction termini. The construct may contain, in the following order, the promoter region of the Arabidopsis oleosin gene, the coding sequence of the oleosin protein including the intron, 20 codons for the amino acid lysine followed by the nos terminator polyadenylation signal. The construct may be inserted into the binary plasmid Bin 19 and the resultant plasmid may be introduced into the Agrobacterium. The resulting strain can be used to transform *B. napus*.

f) Expression of a Fungicidal Protein as an Oleosin Fusion Protein

As a further example of the invention, an oleosin fusion protein may be constructed which encodes a protein that is toxic to fungi. For example, the gene for the enzyme chitinase isolated from tobacco (Melchers et al, 1994, Plant Journal 5:469–480) may be fused to the 3' coding region of oleosin under the control of the native oleosin promoter. Included in this construct may be an oligonucleotide that encodes a collagenase recognition site located between the oleosin and chitinase coding regions. The expression of this construct will result in the production of a oleosin/chitinase fusion protein from which the chitinase enzyme can be released from the oleosin by treatment with collagenase. To this construct may be added a second chimeric gene capable of expression of a collagenase enzyme during seed germination. This second gene can comprise approximately 1.5 Kb of the 5' promoter region for isocitrate lyase, the collagenase coding sequence of *Vibrio alginolyticus* (Takeuchi et al., 1992, Biochemical Journal, 281:703–708) and the nos terminator. Isocitrate lyase is a glyoxysomal enzyme expressed under transcriptional control during early stages of seed germination (Comai et al., 1989, The Plant Cell, 1:293–300). This second construct therefore will express collagenase during the germination of the seed and mobilization of the oil body reserves. Expression of isocitrate lyase is restricted to germination and is not expressed in developing seeds. This second gene, joined to the oleosin/chitinase gene can be inserted into the binary vector Bin 19. The resultant vector may be introduced into Agrobacterium and used to transform *Brassica napus* plants. It is noted that the two genes may also be introduced independently or in two different plants which are then combined through sexual crossing. Seed from transgenic plants would be collected and tested for resistance to fungi.

g) Expression of an Oleosin Fusion Protein that Provides Protection from Insect Predation As a further example of the invention, a fusion oleosin protein may be constructed which encodes a protein toxic to foraging insects. For example, the gene for cowpea trypsin inhibitor (Hilder et al., 1987, Nature, 330:160–163) may be used to replace the chitinase gene described in e). The expression of this construct will result in the production of a oleosin/trypsin inhibitor fusion protein from which the trypsin inhibitor can be released from the oleosin by treatment with collagenase. By replacement of the chitinase gene in e) with the trypsin inhibitor, the construct also contains the collagenase gene under control of the germination specific promoter from the isocitrate lyase gene. This construct may be inserted into the binary vector Bin 19. The resultant vector can be introduced into Agrobacterium and used to transform *Brassica napus* plants. Seed from transgenic plants were collected and tested for resistance to insect predation.

h) Expression of an Enzyme to Alter Secondary Metabolites in Seeds

In order to alter specific secondary metabolites in the seed, an enzyme encoding tryptophan decarboxylase (TDC) can be expressed in the seed as a fusion to oleosin. This particular enzyme (DeLuca et al., 1989, Proc. Natl. Acad. Sci. USA, 86:2582–2586), redirects tryptophan into tryptamine and causes a depletion of tryptophan derived glucosinolates. This lowers the amount of the antinutritional glucosinolates in the seed and provides a means to further reduce glucosinolate production in crucifer plant species. To accomplish this, a fusion protein may be constructed between the TDC gene and the oleosin coding region. The construct may contain, in the following order, the promoter region of the Arabidopsis oleosin gene, the coding sequence of the oleosin protein including the intron, the TDC gene followed by the nos terminator polyadenylation signal. The construct may be inserted into the binary plasmid Bin 19 and the resultant plasmid introduced into Agrobacterium. The resulting strain can be used to transform *B. napus*.

i) Expression of Heterologous Proteins in Mammalian Cells

The oil body protein—heterologous protein fusion may also be prepared in mammalian host cells. For example, an oleosin/GUS fusion may be inserted into a mammalian expression vector and introduced into mammalian cells as described below.

Expression of an oleosin/GUS fusion in mammalian cells would require the cloning of the GUS gene as described in example 17 in commercially available mammalian expression vectors. For example, mammalian expression vectors pMSG, pSVL SV40, pCH 110, (all available from Pharmacia code No. 27-4506-01, 27-4509-01 and 27-4508-1 respectively) may be used. The oleosin/GUS fusion gene may be fused in the plasmid. These plasmids can be introduced into mammalian cells using established protocols (See eg. Introduction of DNA into mammalian cells (1995) Current Protocols in Molecular Biology, Ausubel et al. (ed) Supplement 29, Section 9). Accumulation of the oleosin/GUS transcript in mammalian cells can be determined after preparation of mammalian cell RNA (See eg. Direct analysis of RNA after transfection (1995) Current Protocols in Molecular Biology, Ausubel et al. (ed) Supplement 29, Section 9.8), northern blotting, and hybridization of this northern blot to a $^{32}$P labelled Brassica oleosin cDNA as described in Example 18. After preparation of a total protein extract from the transfected mammalian cell culture, GUS activity can be measured, demonstrating the accumulation of the oleosin/GUS protein. Alternatively, immunoblotting can be performed on this protein extract using commercially available GUS antibodies and/or oleosin antibodies.

TABLE I

Expression of Arabidopsis oleosin chimearic promoter constructs in transgenic *Brassica napus*.

| Promoter Construct (GUS fusion) | Expression of GUS Activity (pmol/MU/mg protein/min) | | | | |
|---|---|---|---|---|---|
| | Early Seed (torpedo) | Root | Leaf | Stem | Late Seed (cotyledon) |
| 2500 | 7709 | 444 | 47 | 88 | 11607 |
| 1200 | 1795 | — | — | — | 8980 |
| 800 | 475 | — | — | — | 7130 |
| 600 | 144 | — | — | — | 1365 |
| 200 | 65 | 260 | 6 | 26 | 11 |
| control | 14 | 300 | 6 | 30 | 14 |

Oleosin promoter-GUS fusions were constructed as described in example 3. Included are GUS values obtained from a control non-transformed plant. A (–) indicated the tissue was not tested. Units are picomoles of methyl umbelliferone (product) per mg protein per minute.

TABLE II

Expression of Arabidopsis oleosin chimearic promoter constructs in transgenic tobacco (*Nicotiana tabacum*).

| Promoter Constructs (GUS fusions) | GUS Activity in Seeds (pmol/MU/mg protein/min) |
|---|---|
| 2500 | 11330 |
| 800 | 10970 |
| Control | 0 |

Oleosin promoter-GUS fusions were constructed as described in example 3. Included are GUS values obtained from a control non-transformed plant. Units are picomoles of methyl umbelliferone (product) per mg protein per minute.

TABLE III

Specific partitioning of GUS/oleosin fusions into oil bodies when expressed in transgenic *Brassica napus* plants.

| Plant Number | Percent GUS Activity in Oil Bodies (%) | GUS Activity in Oil bodies | GUS Activity 100,000 × g Supernatant | GUS Activity in 100,000 × g Pellet |
|---|---|---|---|---|
| A1 | 88 | 493 | 1 | 67 |
| B7 | 90 | 243 | 5 | 22 |
| control | 0 | 0 | 0 | 0 |

Plants were transformed with an oleosin/GUS fusion protein under the control of the Arabidopsis oleosin promoter. Transformed seeds were obtained and fractionated. The initial fractionation consisted of grinding the seeds in 1.5 mL of buffer A consisting of 15 mM Tricine-KOH, pH 7.5, 10 mM KCl, 1 mM Mg Cl$_2$, 1 mM EDTA, 100 mM sucrose followed by centrifugation at 14,000×g for 15 minutes at 4° C. From this three fractions were obtained consisting of a floating oil body layer, an aqueous layer and a pellet. The oil body fraction was recovered and assayed for GUS activity. The remaining aqueous phase was further centrifuged for 2 hours at 100,000×g. The pellet and supernatant from this centrifugation was also tested for GUS activity. Units are nmol MU per mg protein per min.

TABLE IV

Cleavage of GUS enzyme from oleosin/GUS fusions associated with oil bodies derived from transgenic *Brassica napus* containing an oleosin/GUS fusion protein.

| Fraction | GUS Activity (nmol product/mg protein/min) | | |
|---|---|---|---|
| | Before Cleavage | After Cleavage | % Activity |
| Oil bodies | 113 | 26.4 | 24 |
| 100,000 × g supernatant | 14.3 | 83.6 | 76 |
| 100,000 × g pellet | 15.7 | — | — |

Oil bodies containing an oleosin/GUS fusion protein were subjected to cleavage using the endopeptidase thrombin as described in example 5. Values shown are GUS activities before and after cleavage with thrombin. The values are also expressed as a percentage of total GUS activity released following enzyme fusion. Units are nmol methyl umbelliferone per mg protein/min.

TABLE V

Reuse of oil body associated enzymatic activities.

| | % GUS Activity | |
|---|---|---|
| # Times Oil Bodies Washed | Oil bodies | Supernatant |
| 1 | 100 | 8 ± 5 |
| 2 | 118 ± 7 | 5 ± 3 |
| 3 | 115 ± 8 | 3 ± 4 |
| 4 | 119 ± 8 | 1 ± 20 |

Oil bodies containing an oleosin/GUS protein were isolated from the seeds of transgenic *Brassica napus*. The oil bodies were added to the fluorometric GUS substrate MUG and allowed to react for one hour. The oil bodies were then recovered and added to a new tube containing the substrate and allowed to react for one hour again. This process was repeated a total of four times. The table illustrates the reusable activity of the GUS enzyme while still associated with the oil bodies. Values are normalized to 100% as the GUS activity of original oil body isolates.

TABLE VI

Recovery of active hirudin following synthesis of hirudin in plant seeds.

| Treatment | Thrombin Units Per Assay | Antithrombin Units per mg Oil Body Proteins |
|---|---|---|
| Buffer only | 0.143 | 0 |
| Wild-type seed | 0.146 | 0 |
| Wild-type seed + factor Xa | 0.140 | <0.001 |
| Transformed (uncut) | 0.140 | <0.001 |
| Transformed + factor Xa | 0.0065 | 0.55 |

Oil bodies containing a hirudin/GUS fusion protein were isolated according to the method and treated with the endoprotease Factor Xa inhibition assay using N-p tosyl-gly-pro-arg-p-nitro anilide (Sigma). Hirudin activity was measured by the use of a thrombin in the method of Dodt et al (1984, FEBS Lett. 65, 180–183). Hirudin activity is expressed as thrombin units per assay in presence of 255 μg of oil body proteins, and also as antithrombin units per mg oil body protein.

TABLE VII

Expression of active oleosin/GUS fusions in *E. coli*.

| Plasmid | Gus Activity |
|---|---|
| pKK233-2 | 2.5 |
| pKKoeloGUS | 3.1 |
| pKKo1eoGUS | 28.1 |
| pkkGUS | 118.2 |

As described in example 22, oleosin/GUS fusions were expressed in *E. coli*. Cells were grown, induced with ITPG and GUS activity measured.

TABLE VIII

GUS activity of total extracts of untransformed *S. Cerevisiae* strain 1788, transformed with M1830 and M1830oleoGUS

| *S. Cerevisiae* strain 1788 | Specific Activity (pmol MU · min$^{-1}$ · μg prot$^{-1}$) |
|---|---|
| untransformed | 0.001 |
| transformed with M1830 | 0.001 |
| Transformed with M1830 OleosinGUS | 41.3 |

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What we claim as our invention is:

1. A method for the expression of a thioredoxin or thioredoxin reductase by a host cell said method comprising:
   a) introducing into a plant, bacterial or yeast host cell a chimeric nucleic acid sequence comprising:
      1) a first nucleic acid sequence capable of regulating the transcription in said host cell of
      2) a second nucleic acid sequence, wherein said second sequence encodes a fusion polypeptide and comprises (i) a nucleic acid sequence encoding a sufficient portion of an oleosin gene to provide targeting of the fusion polypeptide to a lipid phase linked in reading frame to (ii) a nucleic acid sequence encoding a thioredoxin or thioredoxin reductase; and
      3) a third nucleic acid sequence encoding a termination region functional in the host cell; and
   b) growing said host cell to produce the fusion polypeptide.

2. The method according to claim 1 further including separating the recombinant fusion polypeptide from cellular host cell components by selective partitioning into a lipid phase.

3. The method according to claim 2 wherein said selective partitioning comprises centrifugation, floatation or size exclusion.

4. The method according to claim 1 further including separating the recombinant fusion polypeptide from cellular host components by selective partitioning into a lipid phase comprising oil bodies.

5. The method according to claim 4 wherein said recombinant fusion polypeptide is separated by addition of oil body components and reconstitution of the oil bodies.

6. The method according to claim 2 further comprising releasing the heterologous polypeptide from the fusion polypeptide associated with the lipid phase, said method comprising:
   c) including in said second DNA sequence (2) between said DNA sequence (i) encoding the oil body protein and the DNA sequence (ii) encoding the thioredoxin or thioredoxin reductase, a linker DNA sequence (iii) encoding an amino acid sequence that is specifically cleavable by enzymatic or chemical means; and
   d) contacting the lipid phase with said enzymatic or chemical means such that said thioredoxin or thioredoxin reductase is released from the fusion polypeptide.

7. The method according to claim 6 wherein said linker DNA sequence encodes an amino acid sequence that is recognizable by the proteolytic action of an enzyme selected from the group consisting of thrombin, factor Xa, collagenase, chymosin, clostrapain and viral protease.

8. The method according to claim 6 wherein said enzymatic means comprises an enzyme that is immobilized.

9. The method according to claim 8 wherein said enzyme is immobilized by attachment to an oleosin that is associated with an oil body.

10. The method according to claim 1 wherein said plant host cell is obtainable from a dicotyledonous plant.

11. The method according to claim 1 wherein said plant cell is obtainable from a monocotelydenous plant.

12. The method according to claim 1 wherein said plant cell is obtainable from the species *Carthamus tinctorius* (safflower).

13. A chimeric nucleic acid sequence, capable of being expressed in association with an oil body of a host cell comprising:

1) a first nucleic acid sequence capable of regulating the transcription in said host cell of
2) a second DNA sequence, wherein said second sequence encodes a fusion polypeptide and comprises (i) a nucleic sequence encoding a sufficient portion of an oleosin gene to provide targeting of the fusion polypeptide to a lipid phase linked in reading frame to (ii) a nucleic sequence encoding a thioredoxin or thioredoxin reductase; and
3) a third nucleic acid sequence encoding a termination region functional in the host cell.

14. The chimeric nucleic acid sequence according to claim 13 further including (iii) a linker nucleic acid sequence encoding an amino acid sequence that is specifically cleavable by enzymatic means wherein said linker nucleic acid sequence (iii) is located between said (i) nucleic acid sequence encoding the oil body protein and said (ii) nucleic acid sequence encoding the thioredoxin or thioredoxin reductase.

15. The chimeric nucleic acid according to claim 14 wherein said nucleic acid linker sequence (iii) encodes a cleavage site for an enzyme selected from the group consisting of thrombin, factor Xa, collagenase chymosin and viral protease.

16. An expression cassette comprising a chimeric nucleic acid sequence according to claim 13.

17. A plant transformed with a chimeric nucleic acid sequence according to claim 13.

18. A plant according to claim 17 wherein said plant is *Carthamus tinctorius* (safflower).

19. A plant cell culture containing a chimeric nucleic acid sequence according to claim 13.

20. A plant seed containing a chimeric nucleic acid sequence according to claim 13.

21. A plant seed according to claim 20 wherein said plant seed is *Carthamus tinctorius* (safflower) plant seed.

* * * * *